(12) United States Patent
Alekshun et al.

(10) Patent No.: US 7,075,582 B2
(45) Date of Patent: Jul. 11, 2006

(54) METHODS FOR IDENTIFYING AND USING MARR FAMILY POLYPEPTIDE BINDING COMPOUNDS

(75) Inventors: Michael N. Alekshun, Wakefield, MA (US); Stuart B. Levy, Boston, MA (US); Brent L. Podlogar, Hamden, CT (US); Roger Frechette, Reading, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 328 days.

(21) Appl. No.: 10/196,672

(22) Filed: Jul. 15, 2002

(65) Prior Publication Data

US 2003/0215873 A1 Nov. 20, 2003

Related U.S. Application Data

(60) Provisional application No. 60/388,618, filed on Jun. 13, 2002, provisional application No. 60/305,322, filed on Jul. 13, 2001.

(51) Int. Cl.
*C07D 209/04* (2006.01)
(52) U.S. Cl. .................. 348/469; 548/503; 548/494
(58) Field of Classification Search ............... 548/503, 548/469
See application file for complete search history.

(56) References Cited

U.S. PATENT DOCUMENTS

| 5,817,793 | A | 10/1998 | Levy |
| 6,346,391 | B1 | 2/2002 | Oethinger et al. |
| 6,391,545 | B1 | 5/2002 | Levy |
| 6,448,006 | B1 | 9/2002 | Levy |

FOREIGN PATENT DOCUMENTS

WO WO 03/006626 A2 7/2003

OTHER PUBLICATIONS

Alekshun, M.N. et al. "Regulation of charomosomally mediated multiple antibiotic resistance: the mar regulon." *Antimicrob. Agents Chemother.* Oct. 1997;41(10):2067-75.
Alekshun, M.N. et al. "Characterization of MarR super-repressor mutants." *J. Bacteriol.* May 1999;181(10):3303-6.
Alekshun, M.N. et al. "Alteration of the repressor activity of MarR, the negative regulator of the *Escherichia coli* marRAB locus, by multiple chemicals *in vitro*." *J. Bacteriol.* Aug. 1999; 181(15):4669-72.
Alekshun, M.N. et al. "The mar regulon: multiple resistance to antibiotics and other toxic chemicals." *Trends Microbiol.* Oct. 1999;7(10):410-3.
Alekshun, M.N. et al., "Mutational analysis of MarR, the negative regulator of marRAB expression in *Escherichia coli*, suggests the presence of two regions required for DNA binding." *Mol. Microbiol.* Mar. 2000;35(6):1394-404.
Barbosa, T.M. et al. "Differential expression of over 60 chromosomal genes in *Escherichia coli* by constitutive expression of MarA." *J. Bacteriol.* Jun. 2000;182(12):3467-74.
Brooun, A. et al. "Purification and ligand binding of EmrR, a regulator of a multidrug transporter." *J. Bacteriol.* Aug. 1999;181(16):5131-3.
Drenth, J. "Chapter 1: Crystallizing a protein." from *Principles of Protein X-ray Crystallography* pp. 1-18, 1994 Springer-Verlag New York, Inc.
Gajiwala, K.S. et al. "Winged helix proteins." *Curr. Opin. Struct. Biol.* Feb. 2000;10(1):110-6.
Gajiwala, K.S. et al. "Structure of the winged-helix protein hRFX1 reveals a new mode of DNA binding." *Nature* Feb. 24, 2000;403(6772):916-21.
Kem. W.V. et al. "Non-target gene mutations in the development of fluoroquinolone resistance in *Escherichia coli*." *Antimicrob. Agents Chemother.* Apr. 2000;44(4):814-20.
Koutsolioutsou, A. et al. "A soxRS-constitutive mutation contributing to antibotic resistance in a clinical isolate of *Salmonella enterica* (Serovar typhimurium)." *Antimicrob. Agents Chemother.* Jan. 2001;45(1):38-43.
Linde, H.J. et al. "*In vivo* increase in resistance to ciprofloxacin in *Escherichia coli* associated with deletion of the C-terminal part of MarR." *Antimicrob. Agents Chemother.* Jul. 2000;44(7):1865-8.
Maneewannakul, K. et al. "Identification for mar mutants among quinolone-resistant clinical isolates of *Escherichia coli*." *Antimicrob. Agents Chemother.* Jul. 1996;40(7):1695-8.
Martin, R.G. et al. "Binding of purified multiple antibiotic-resistance repressor protein (MarR) to mar operator sequences." *Proc. Natl. Acad. Sci. U.S.A.* Jun. 6, 1995;92(12):5456-60.
Martin, R.G. et al. "Autoactivation of the marRAB multiple antibiotic resistance operon by the MarA transcriptional activator in *Escherichia coli*." *J. Bateriol.* Apr. 1996;178(8):2216-23.

(Continued)

*Primary Examiner*—Taofiq Solola
*Assistant Examiner*—Robert Shiao
(74) *Attorney, Agent, or Firm*—Lahive & Cockfield, LLP; Elizabeth A. Hanley, Esq.; Cynthia M. Soroos, Esq.

(57) ABSTRACT

Methods for identifying MarR family inhibiting compounds are described. The methods include the use of computer aided rational based drug design programs and three dimensional structures of MarR family polypeptides.

7 Claims, 57 Drawing Sheets

OTHER PUBLICATIONS

Martin, R.G. et al. "Binding of purified multiple antibiotic-resistance repressor protein (MarR) to mar operator sequences." *Proc. Natl. Acad. Sci. U.S.A.* Jun. 1995; 92:5456-5460.

Nikaido, H. "Multiple antibiotic resistance and efflux." *Curr. Opin. Microbiol.* Oct. 1998;1(5):516-23.

Oethinger, M. et al. "Overexpression of the marA or soxS regulatory gene in clinical topoisomerase mutants of *Escherichia coli*." *Antimicrob. Agents Chemother.* Aug. 1998;42(8):2089-94.

Pohl, E. et al. "Motion of the DNA-binding domain with respect to the core of the diphtheria toxin repressor (DtxR) revealed in the crystal structures of apo- and holo-DtxR." *J. Biol. Chem.* Aug. 28, 1998;273(35):22420-7.

Providenti, M.A. et al. "Indentification and functional characterization of CbaR, a MarR-like modulator of the cbaABC-encoded chlorobenzoate catabolism pathway." *Applied and Environmental Microbiology* Aug. 2001: 67(8):3530-41.

Randall, L.P. et al. "Multiple antibiotic resistance (mar) locus in *Salmonella enterica* serovar typhimurium DT104." *Applied and Experimental Microbiology.* Mar. 2001;67(3):1190-1197.

Sulavik, M.C. et al. "The MarR repressor of the multiple antibiotic resistance (mar) operon in *Escherichia coli*: prototypic member of a family of bacterial regulatory proteins involved in sensing phenolic compounds." May 1995; 1(4):436-446.

Sulavik, M.C. et al. "The *Salmonella typhimurium* mar locus: molecular and genetic analyses and assessment of its role in virulence." *J. Bateriol.* Mar. 1997;179(6):1857-66.

White, A. et al. "Structure of the metal-ion-activated diphtheria toxin repressor/tox operator complex." *Nature* Jul. 30, 1998;394(6692):502-6.

Zheng, N. et al. "Structural basis of DNA recognition by the heterodimeric cell cycle transcription factor E2F-DP." *Genes Dev.* Mar. 15, 1999;13(6):666-74.

Ziha-Zarifi, I. et al. "*In vivo* emergence of multidrug-resistant mutants of *Pseudomonas aeruginosa* overexpressing the active efflux system MexA-MexB-OprM." *Antimicrob. Agents Chemother.* Feb. 1999;43(2)287-91.

Alekshun, et al. The crystal structure of MarR, a regulator of multiple antibiotic resistance, at 2.3 A resolution.: *Nat Struct Biol.* Aug. 2001; 8(8):710-4.

Geneseq__101002 database, AAR4977, dated Oct. 14, 1994; Result #1.

```
HEADER    TRANSCRIPTION                           26-JUN-01   1JGS
TITLE     MULTIPLE ANTIBIOTIC RESISTANCE REPRESSOR, MARR WITH SALICYLATE
COMPND    MOL_ID: 1;
COMPND   2 MOLECULE: MULTIPLE ANTIBIOTIC RESISTANCE PROTEIN MARR;
COMPND   3 CHAIN: A;
COMPND   4 ENGINEERED: YES
SOURCE    MOL_ID: 1;
SOURCE   2 ORGANISM_SCIENTIFIC: ESCHERICHIA COLI;
SOURCE   3 ORGANISM_COMMON: BACTERIA;
SOURCE   4 EXPRESSION_SYSTEM: ESCHERICHIA COLI;
SOURCE   5 EXPRESSION_SYSTEM_COMMON: BACTERIA;
SOURCE   6 EXPRESSION_SYSTEM_STRAIN: BL21(DE3)
KEYWDS    TRANSCRIPTION REGULATION, DNA-BINDING, REPRESSOR,
KEYWDS   2 ANTIBIOTIC RESISTANCE
EXPDTA    X-RAY DIFFRACTION
AUTHOR    M.N.ALEKSHUN,S.B.LEVY,T.R.MEALY,B.A.SEATON,J.F.HEAD
REVDAT   1   28-DEC-01 1JGS    0
JRNL        AUTH   M.N.ALEKSHUN,S.B.LEVY,T.R.MEALY,B.A.SEATON,J.F.HEAD
JRNL        TITL   THE CRYSTAL STRUCTURE OF MARR, A REGULATOR OF
JRNL        TITL 2 MULTIPLE ANTIBIOTIC RESISTANCE, AT 2.3 A
JRNL        TITL 3 RESOLUTION.
JRNL        REF    NAT.STRUCT.BIOL.              V.  8   710 2001
JRNL        REFN   ASTM NSBIEW  US ISSN 1072-8368
REMARK   1
REMARK   2
REMARK   2 RESOLUTION. 2.30 ANGSTROMS.
REMARK   3
REMARK   3 REFINEMENT.
REMARK   3   PROGRAM     : CNS 1.0
REMARK   3   AUTHORS     : BRUNGER,ADAMS,CLORE,DELANO,GROS,GROSSE-
REMARK   3               : KUNSTLEVE,JIANG,KUSZEWSKI,NILGES, PANNU,
REMARK   3               : READ,RICE,SIMONSON,WARREN
REMARK   3
REMARK   3   REFINEMENT TARGET : NULL
REMARK   3
REMARK   3  DATA USED IN REFINEMENT.
REMARK   3   RESOLUTION RANGE HIGH (ANGSTROMS) : 2.30
REMARK   3   RESOLUTION RANGE LOW  (ANGSTROMS) : 50.00
REMARK   3   DATA CUTOFF            (SIGMA(F)) : NULL
REMARK   3   OUTLIER CUTOFF HIGH (RMS(ABS(F))) : NULL
REMARK   3   COMPLETENESS (WORKING+TEST)   (%) : NULL
REMARK   3   NUMBER OF REFLECTIONS             : 5968
REMARK   3
REMARK   3  FIT TO DATA USED IN REFINEMENT.
REMARK   3   CROSS-VALIDATION METHOD          : THROUGHOUT
REMARK   3   FREE R VALUE TEST SET SELECTION  : RANDOM
REMARK   3   R VALUE            (WORKING SET) : 0.247
REMARK   3   FREE R VALUE                     : 0.287
REMARK   3   FREE R VALUE TEST SET SIZE   (%) : NULL
REMARK   3   FREE R VALUE TEST SET COUNT      : 506
REMARK   3   ESTIMATED ERROR OF FREE R VALUE  : NULL
REMARK   3
REMARK   3  FIT IN THE HIGHEST RESOLUTION BIN.
REMARK   3   TOTAL NUMBER OF BINS USED            : NULL
REMARK   3   BIN RESOLUTION RANGE HIGH       (A)  : NULL
REMARK   3   BIN RESOLUTION RANGE LOW        (A)  : NULL
REMARK   3   BIN COMPLETENESS (WORKING+TEST) (%)  : NULL
REMARK   3   REFLECTIONS IN BIN    (WORKING SET)  : NULL
REMARK   3   BIN R VALUE           (WORKING SET)  : NULL
REMARK   3   BIN FREE R VALUE                     : NULL
REMARK   3   BIN FREE R VALUE TEST SET SIZE  (%)  : NULL
REMARK   3   BIN FREE R VALUE TEST SET COUNT      : NULL
REMARK   3   ESTIMATED ERROR OF BIN FREE R VALUE  : NULL
REMARK   3
REMARK   3  NUMBER OF NON-HYDROGEN ATOMS USED IN REFINEMENT.
REMARK   3   PROTEIN ATOMS           : 1078
REMARK   3   NUCLEIC ACID ATOMS      : 0
REMARK   3   HETEROGEN ATOMS         : 20
REMARK   3   SOLVENT ATOMS           : 0
REMARK   3
REMARK   3  B VALUES.
REMARK   3   FROM WILSON PLOT          (A**2) : NULL
REMARK   3   MEAN B VALUE   (OVERALL, A**2) : NULL
```

FIGURE 1-1

```
REMARK   3    OVERALL ANISOTROPIC B VALUE.
REMARK   3     B11 (A**2) : NULL
REMARK   3     B22 (A**2) : NULL
REMARK   3     B33 (A**2) : NULL
REMARK   3     B12 (A**2) : NULL
REMARK   3     B13 (A**2) : NULL
REMARK   3     B23 (A**2) : NULL
REMARK   3
REMARK   3   ESTIMATED COORDINATE ERROR.
REMARK   3    ESD FROM LUZZATI PLOT        (A) : NULL
REMARK   3    ESD FROM SIGMAA              (A) : NULL
REMARK   3    LOW RESOLUTION CUTOFF        (A) : NULL
REMARK   3
REMARK   3   CROSS-VALIDATED ESTIMATED COORDINATE ERROR.
REMARK   3    ESD FROM C-V LUZZATI PLOT    (A) : NULL
REMARK   3    ESD FROM C-V SIGMAA          (A) : NULL
REMARK   3
REMARK   3   RMS DEVIATIONS FROM IDEAL VALUES.
REMARK   3    BOND LENGTHS                 (A) : 0.007
REMARK   3    BOND ANGLES            (DEGREES) : NULL
REMARK   3    DIHEDRAL ANGLES        (DEGREES) : NULL
REMARK   3    IMPROPER ANGLES        (DEGREES) : NULL
REMARK   3
REMARK   3   ISOTROPIC THERMAL MODEL : NULL
REMARK   3
REMARK   3   ISOTROPIC THERMAL FACTOR RESTRAINTS.   RMS    SIGMA
REMARK   3    MAIN-CHAIN BOND             (A**2) : NULL  ; NULL
REMARK   3    MAIN-CHAIN ANGLE            (A**2) : NULL  ; NULL
REMARK   3    SIDE-CHAIN BOND             (A**2) : NULL  ; NULL
REMARK   3    SIDE-CHAIN ANGLE            (A**2) : NULL  ; NULL
REMARK   3
REMARK   3   BULK SOLVENT MODELING.
REMARK   3    METHOD USED : NULL
REMARK   3    KSOL        : NULL
REMARK   3    BSOL        : NULL
REMARK   3
REMARK   3   NCS MODEL : NULL
REMARK   3
REMARK   3   NCS RESTRAINTS.                        RMS    SIGMA/WEIGHT
REMARK   3    GROUP  1  POSITIONAL        (A)    : NULL  ; NULL
REMARK   3    GROUP  1  B-FACTOR          (A**2) : NULL  ; NULL
REMARK   3
REMARK   3   PARAMETER FILE  1  : NULL
REMARK   3   TOPOLOGY FILE   1  : NULL
REMARK   3
REMARK   3   OTHER REFINEMENT REMARKS: NULL
REMARK   4
REMARK   4 1JGS COMPLIES WITH FORMAT V. 2.3, 09-JULY-1998
REMARK 100
REMARK 100 THIS ENTRY HAS BEEN PROCESSED BY RCSB ON 15-JUL-2001.
REMARK 100 THE RCSB ID CODE IS RCSB013753.
REMARK 200
REMARK 200 EXPERIMENTAL DETAILS
REMARK 200  EXPERIMENT TYPE                : X-RAY DIFFRACTION
REMARK 200  DATE OF DATA COLLECTION        : NULL
REMARK 200  TEMPERATURE           (KELVIN) : 100.0
REMARK 200  PH                             : 5.50
REMARK 200  NUMBER OF CRYSTALS USED        : 1
REMARK 200
REMARK 200  SYNCHROTRON              (Y/N) : Y
REMARK 200  RADIATION SOURCE               : NSLS X8C
REMARK 200  BEAMLINE                       : NULL
REMARK 200  X-RAY GENERATOR MODEL          : NULL
REMARK 200  MONOCHROMATIC OR LAUE    (M/L) : M
REMARK 200  WAVELENGTH OR RANGE        (A) : 1.072
REMARK 200  MONOCHROMATOR                  : NULL
REMARK 200  OPTICS                         : NULL
REMARK 200
REMARK 200  DETECTOR TYPE                  : CCD
REMARK 200  DETECTOR MANUFACTURER          : ADSC QUANTUM 4
REMARK 200  INTENSITY-INTEGRATION SOFTWARE : DENZO
REMARK 200  DATA SCALING SOFTWARE          : SCALEPACK
REMARK 200
```

FIGURE 1-2

```
REMARK 200  NUMBER OF UNIQUE REFLECTIONS      : 6069
REMARK 200  RESOLUTION RANGE HIGH      (A)    : 2.300
REMARK 200  RESOLUTION RANGE LOW       (A)    : 50.000
REMARK 200  REJECTION CRITERIA   (SIGMA(I))   : NULL
REMARK 200
REMARK 200  OVERALL.
REMARK 200   COMPLETENESS FOR RANGE    (%)    : 99.5
REMARK 200   DATA REDUNDANCY                  : 9.500
REMARK 200   R MERGE                   (I)    : 0.06000
REMARK 200   R SYM                     (I)    : NULL
REMARK 200   <I/SIGMA(I)> FOR THE DATA SET    : 21.1000
REMARK 200
REMARK 200  IN THE HIGHEST RESOLUTION SHELL.
REMARK 200   HIGHEST RESOLUTION SHELL, RANGE HIGH (A) : 2.30
REMARK 200   HIGHEST RESOLUTION SHELL, RANGE LOW  (A) : 2.38
REMARK 200   COMPLETENESS FOR SHELL    (%)    : 100.0
REMARK 200   DATA REDUNDANCY IN SHELL         : NULL
REMARK 200   R MERGE FOR SHELL         (I)    : 0.20000
REMARK 200   R SYM FOR SHELL           (I)    : NULL
REMARK 200   <I/SIGMA(I)> FOR SHELL           : 12.000
REMARK 200
REMARK 200  DIFFRACTION PROTOCOL: MAD
REMARK 200  METHOD USED TO DETERMINE THE STRUCTURE: MAD
REMARK 200  SOFTWARE USED: SOLVE
REMARK 200  STARTING MODEL: NULL
REMARK 200
REMARK 200 REMARK: NULL
REMARK 280
REMARK 280 CRYSTAL
REMARK 280  SOLVENT CONTENT, VS   (%): NULL
REMARK 280  MATTHEWS COEFFICIENT, VM (ANGSTROMS**3/DA): NULL
REMARK 280
REMARK 280 CRYSTALLIZATION CONDITIONS: PEG MME 5000, AMMONIUM SULFATE,
REMARK 280  SODIUM SALICYLATE, HEPTANETRIOL, GLYCEROL, DTT
REMARK 290
REMARK 290 CRYSTALLOGRAPHIC SYMMETRY
REMARK 290 SYMMETRY OPERATORS FOR SPACE GROUP: I 41 2 2
REMARK 290
REMARK 290      SYMOP   SYMMETRY
REMARK 290      NNNMMM  OPERATOR
REMARK 290       1555   X,Y,Z
REMARK 290       2555   1/2-X,1/2-Y,1/2+Z
REMARK 290       3555   -Y,1/2+X,1/4+Z
REMARK 290       4555   1/2+Y,-X,3/4+Z
REMARK 290       5555   1/2-X,Y,3/4-Z
REMARK 290       6555   X,1/2-Y,1/4-Z
REMARK 290       7555   1/2+Y,1/2+X,1/2-Z
REMARK 290       8555   -Y,-X,-Z
REMARK 290       9555   1/2+X,1/2+Y,1/2+Z
REMARK 290      10555   1/1-X,1/1-Y,1/1+Z
REMARK 290      11555   1/2-Y,1/1+X,3/4+Z
REMARK 290      12555   1/1+Y,1/2-X,5/4+Z
REMARK 290      13555   1/1-X,1/2+Y,5/4-Z
REMARK 290      14555   1/2+X,1/1-Y,3/4-Z
REMARK 290      15555   1/1+Y,1/1+X,1/1-Z
REMARK 290      16555   1/2-Y,1/2-X,1/2-Z
REMARK 290
REMARK 290     WHERE NNN -> OPERATOR NUMBER
REMARK 290           MMM -> TRANSLATION VECTOR
REMARK 290
REMARK 290 CRYSTALLOGRAPHIC SYMMETRY TRANSFORMATIONS
REMARK 290 THE FOLLOWING TRANSFORMATIONS OPERATE ON THE ATOM/HETATM
REMARK 290 RECORDS IN THIS ENTRY TO PRODUCE CRYSTALLOGRAPHICALLY
REMARK 290 RELATED MOLECULES.
REMARK 290    SMTRY1   1  1.000000  0.000000  0.000000        0.00000
REMARK 290    SMTRY2   1  0.000000  1.000000  0.000000        0.00000
REMARK 290    SMTRY3   1  0.000000  0.000000  1.000000        0.00000
REMARK 290    SMTRY1   2 -1.000000  0.000000  0.000000       31.00000
REMARK 290    SMTRY2   2  0.000000 -1.000000  0.000000       31.00000
REMARK 290    SMTRY3   2  0.000000  0.000000  1.000000       66.44500
REMARK 290    SMTRY1   3  0.000000 -1.000000  0.000000        0.00000
REMARK 290    SMTRY2   3  1.000000  0.000000  0.000000       31.00000
REMARK 290    SMTRY3   3  0.000000  0.000000  1.000000       33.22250
```

FIGURE 1-3

```
REMARK 290   SMTRY1   4    0.000000   1.000000   0.000000       31.00000
REMARK 290   SMTRY2   4   -1.000000   0.000000   0.000000        0.00000
REMARK 290   SMTRY3   4    0.000000   0.000000   1.000000       99.66750
REMARK 290   SMTRY1   5   -1.000000   0.000000   0.000000       31.00000
REMARK 290   SMTRY2   5    0.000000   1.000000   0.000000        0.00000
REMARK 290   SMTRY3   5    0.000000   0.000000  -1.000000       99.66750
REMARK 290   SMTRY1   6    1.000000   0.000000   0.000000        0.00000
REMARK 290   SMTRY2   6    0.000000  -1.000000   0.000000       31.00000
REMARK 290   SMTRY3   6    0.000000   0.000000  -1.000000       33.22250
REMARK 290   SMTRY1   7    0.000000   1.000000   0.000000       31.00000
REMARK 290   SMTRY2   7    1.000000   0.000000   0.000000       31.00000
REMARK 290   SMTRY3   7    0.000000   0.000000  -1.000000       66.44500
REMARK 290   SMTRY1   8    0.000000  -1.000000   0.000000        0.00000
REMARK 290   SMTRY2   8   -1.000000   0.000000   0.000000        0.00000
REMARK 290   SMTRY3   8    0.000000   0.000000  -1.000000        0.00000
REMARK 290   SMTRY1   9    1.000000   0.000000   0.000000       31.00000
REMARK 290   SMTRY2   9    0.000000   1.000000   0.000000       31.00000
REMARK 290   SMTRY3   9    0.000000   0.000000   1.000000       66.44500
REMARK 290   SMTRY1  10   -1.000000   0.000000   0.000000       62.00000
REMARK 290   SMTRY2  10    0.000000  -1.000000   0.000000       62.00000
REMARK 290   SMTRY3  10    0.000000   0.000000   1.000000      132.89000
REMARK 290   SMTRY1  11    0.000000  -1.000000   0.000000       31.00000
REMARK 290   SMTRY2  11    1.000000   0.000000   0.000000       62.00000
REMARK 290   SMTRY3  11    0.000000   0.000000   1.000000       99.66750
REMARK 290   SMTRY1  12    0.000000   1.000000   0.000000       62.00000
REMARK 290   SMTRY2  12   -1.000000   0.000000   0.000000       31.00000
REMARK 290   SMTRY3  12    0.000000   0.000000   1.000000      166.11250
REMARK 290   SMTRY1  13   -1.000000   0.000000   0.000000       62.00000
REMARK 290   SMTRY2  13    0.000000   1.000000   0.000000       31.00000
REMARK 290   SMTRY3  13    0.000000   0.000000  -1.000000      166.11250
REMARK 290   SMTRY1  14    1.000000   0.000000   0.000000       31.00000
REMARK 290   SMTRY2  14    0.000000  -1.000000   0.000000       62.00000
REMARK 290   SMTRY3  14    0.000000   0.000000  -1.000000       99.66750
REMARK 290   SMTRY1  15    0.000000   1.000000   0.000000       62.00000
REMARK 290   SMTRY2  15    1.000000   0.000000   0.000000       62.00000
REMARK 290   SMTRY3  15    0.000000   0.000000  -1.000000      132.89000
REMARK 290   SMTRY1  16    0.000000  -1.000000   0.000000       31.00000
REMARK 290   SMTRY2  16   -1.000000   0.000000   0.000000       31.00000
REMARK 290   SMTRY3  16    0.000000   0.000000  -1.000000       66.44500
REMARK 290
REMARK 290 REMARK: NULL
REMARK 300
REMARK 300 BIOMOLECULE: 1
REMARK 300 THIS ENTRY CONTAINS THE CRYSTALLOGRAPHIC ASYMMETRIC UNIT
REMARK 300 WHICH CONSISTS OF 1 CHAIN(S). SEE REMARK 350 FOR
REMARK 300 INFORMATION ON GENERATING THE BIOLOGICAL MOLECULE(S).
REMARK 350
REMARK 350 GENERATING THE BIOMOLECULE
REMARK 350 COORDINATES FOR A COMPLETE MULTIMER REPRESENTING THE KNOWN
REMARK 350 BIOLOGICALLY SIGNIFICANT OLIGOMERIZATION STATE OF THE
REMARK 350 MOLECULE CAN BE GENERATED BY APPLYING BIOMT TRANSFORMATIONS
REMARK 350 GIVEN BELOW.  BOTH NON-CRYSTALLOGRAPHIC AND
REMARK 350 CRYSTALLOGRAPHIC OPERATIONS ARE GIVEN.
REMARK 350
REMARK 350 BIOMOLECULE: 1
REMARK 350 APPLY THE FOLLOWING TO CHAINS: A
REMARK 350   BIOMT1   1    1.000000   0.000000   0.000000        0.00000
REMARK 350   BIOMT2   1    0.000000   1.000000   0.000000        0.00000
REMARK 350   BIOMT3   1    0.000000   0.000000   1.000000        0.00000
REMARK 350   BIOMT1   2   -1.000000   0.000000   0.000000       62.00000
REMARK 350   BIOMT2   2    0.000000  -1.000000   0.000000       62.00000
REMARK 350   BIOMT3   2    0.000000   0.000000   1.000000      132.89000
REMARK 500
REMARK 500 GEOMETRY AND STEREOCHEMISTRY
REMARK 500 SUBTOPIC: COVALENT BOND LENGTHS
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,2(A3,1X,A1,I4,A1,1X,A4,3X),F6.3)
```

FIGURE 1-4

```
REMARK 500
REMARK 500 EXPECTED VALUES: ENGH AND HUBER, 1991
REMARK 500
REMARK 500   M RES CSSEQI ATM1   RES CSSEQI ATM2    DEVIATION
REMARK 500     MET A  74   CE    MET A  74   SD      0.043
REMARK 500     GLU A 131   CA    GLU A 131   N       0.046
REMARK 500
REMARK 500 GEOMETRY AND STEREOCHEMISTRY
REMARK 500 SUBTOPIC: COVALENT BOND ANGLES
REMARK 500
REMARK 500 THE STEREOCHEMICAL PARAMETERS OF THE FOLLOWING RESIDUES
REMARK 500 HAVE VALUES WHICH DEVIATE FROM EXPECTED VALUES BY MORE
REMARK 500 THAN 6*RMSD (M=MODEL NUMBER; RES=RESIDUE NAME; C=CHAIN
REMARK 500 IDENTIFIER; SSEQ=SEQUENCE NUMBER; I=INSERTION CODE).
REMARK 500
REMARK 500 STANDARD TABLE:
REMARK 500 FORMAT: (10X,I3,1X,A3,1X,A1,I4,A1,3(1X,A4,2X),12X,F5.1)
REMARK 500
REMARK 500 EXPECTED VALUES: ENGH AND HUBER, 1991
REMARK 500
REMARK 500   M RES CSSEQI ATM1   ATM2    ATM3
REMARK 500     LEU A  97   N   -  CA  -  C    ANGL. DEV. = -8.4 DEGREES
REMARK 500     THR A 101   N   -  CA  -  C    ANGL. DEV. = -8.9 DEGREES
REMARK 500     GLU A 131   N   -  CA  -  C    ANGL. DEV. =  9.5 DEGREES
REMARK 500     LEU A 143   N   -  CA  -  C    ANGL. DEV. =  8.6 DEGREES
REMARK 500
REMARK 500 GEOMETRY AND STEREOCHEMISTRY
REMARK 500 SUBTOPIC: TORSION ANGLES
REMARK 500
REMARK 500 TORSION ANGLES OUTSIDE THE EXPECTED RAMACHANDRAN REGIONS:
REMARK 500 (M=MODEL NUMBER; RES=RESIDUE NAME; C=CHAIN IDENTIFIER;
REMARK 500 SSEQ=SEQUENCE NUMBER; I=INSERTION CODE).
REMARK 500
REMARK 500 STANDARD TABLE:
REMARK 500 FORMAT:(10X,I3,1X,A3,1X,A1,I4,A1,4X,F7.2,3X,F7.2)
REMARK 500
REMARK 500   M RES CSSEQI        PSI       PHI
REMARK 500     ALA A  53      -60.18     70.65
DBREF  1JGS A    7   144  SWS    P27245   MARR_ECOLI       7    144
SEQRES   1 A  138  LEU PHE ASN GLU ILE ILE PRO LEU GLY ARG LEU ILE HIS
SEQRES   2 A  138  MET VAL ASN GLN LYS LYS ASP ARG LEU LEU ASN GLU TYR
SEQRES   3 A  138  LEU SER PRO LEU ASP ILE THR ALA ALA GLN PHE LYS VAL
SEQRES   4 A  138  LEU CYS SER ILE ARG CYS ALA ALA CYS ILE THR PRO VAL
SEQRES   5 A  138  GLU LEU LYS LYS VAL LEU SER VAL ASP LEU GLY ALA LEU
SEQRES   6 A  138  THR ARG MET LEU ASP ARG LEU VAL CYS LYS GLY TRP VAL
SEQRES   7 A  138  GLU ARG LEU PRO ASN PRO ASN ASP LYS ARG GLY VAL LEU
SEQRES   8 A  138  VAL LYS LEU THR THR GLY GLY ALA ALA ILE CYS GLU GLN
SEQRES   9 A  138  CYS HIS GLN LEU VAL GLY GLN ASP LEU HIS GLN GLU LEU
SEQRES  10 A  138  THR LYS ASN LEU THR ALA ASP GLU VAL ALA THR LEU GLU
SEQRES  11 A  138  TYR LEU LEU LYS LYS VAL LEU PRO
HET    SAL    256      10
HET    SAL    257      10
HETNAM     SAL 2-HYDROXYBENZOIC ACID
HETSYN     SAL SALICYLIC ACID
FORMUL   2  SAL    2(C7 H6 O3)
HELIX    1   1 PRO A   13  SER A   34  1                                  22
HELIX    2   2 THR A   39  ALA A   53  1                                  15
HELIX    3   3 THR A   56  SER A   65  1                                  10
HELIX    4   4 ASP A   67  LYS A   81  1                                  15
HELIX    5   5 THR A  101  LYS A  125  1                                  25
HELIX    6   6 GLU A  131  LYS A  141  1                                  11
SHEET    1   A 2 VAL A  84  PRO A  88  0
SHEET    2   A 2 VAL A  96  LEU A 100 -1  N  LEU A  97   O  LEU A  87
CRYST1   62.000   62.000  132.890  90.00  90.00  90.00 I 41 2 2      16
ORIGX1      1.000000  0.000000  0.000000        0.00000
ORIGX2      0.000000  1.000000  0.000000        0.00000
ORIGX3      0.000000  0.000000  1.000000        0.00000
SCALE1      0.016129  0.000000  0.000000        0.00000
SCALE2      0.000000  0.016129  0.000000        0.00000
SCALE3      0.000000  0.000000  0.007525        0.00000
ATOM      1  N   LEU A   7      36.956  -0.266  22.798  1.00 63.50           N
ATOM      2  CA  LEU A   7      36.482   0.956  22.088  1.00 63.50           C
ATOM      3  C   LEU A   7      37.614   1.498  21.226  1.00 63.50           C
```

FIGURE 1-5

| | | | | | | | | | |
|---|---|---|---|---|---|---|---|---|---|
| ATOM | 4 | O | LEU | A | 7 | 37.388 | 1.940 | 20.097 | 1.00 63.50 | O |
| ATOM | 5 | CB | LEU | A | 7 | 36.033 | 2.021 | 23.097 | 1.00 65.57 | C |
| ATOM | 6 | CG | LEU | A | 7 | 35.117 | 3.140 | 22.579 | 1.00 65.57 | C |
| ATOM | 7 | CD1 | LEU | A | 7 | 33.812 | 2.545 | 22.096 | 1.00 65.57 | C |
| ATOM | 8 | CD2 | LEU | A | 7 | 34.848 | 4.157 | 23.684 | 1.00 65.57 | C |
| ATOM | 9 | N | PHE | A | 8 | 38.833 | 1.465 | 21.760 | 1.00 68.87 | N |
| ATOM | 10 | CA | PHE | A | 8 | 40.004 | 1.938 | 21.022 | 1.00 68.87 | C |
| ATOM | 11 | C | PHE | A | 8 | 40.644 | 0.777 | 20.278 | 1.00 68.87 | C |
| ATOM | 12 | O | PHE | A | 8 | 41.758 | 0.889 | 19.768 | 1.00 68.87 | O |
| ATOM | 13 | CB | PHE | A | 8 | 41.034 | 2.571 | 21.964 | 1.00 79.70 | C |
| ATOM | 14 | CG | PHE | A | 8 | 40.611 | 3.901 | 22.524 | 1.00 79.70 | C |
| ATOM | 15 | CD1 | PHE | A | 8 | 39.571 | 3.988 | 23.450 | 1.00 79.70 | C |
| ATOM | 16 | CD2 | PHE | A | 8 | 41.249 | 5.072 | 22.122 | 1.00 79.70 | C |
| ATOM | 17 | CE1 | PHE | A | 8 | 39.174 | 5.220 | 23.967 | 1.00 79.70 | C |
| ATOM | 18 | CE2 | PHE | A | 8 | 40.858 | 6.311 | 22.634 | 1.00 79.70 | C |
| ATOM | 19 | CZ | PHE | A | 8 | 39.820 | 6.383 | 23.557 | 1.00 79.70 | C |
| ATOM | 20 | N | ASN | A | 9 | 39.933 | -0.344 | 20.236 | 1.00 96.16 | N |
| ATOM | 21 | CA | ASN | A | 9 | 40.416 | -1.528 | 19.540 | 1.00 96.16 | C |
| ATOM | 22 | C | ASN | A | 9 | 39.437 | -1.875 | 18.426 | 1.00 96.16 | C |
| ATOM | 23 | O | ASN | A | 9 | 39.503 | -2.953 | 17.833 | 1.00 96.16 | O |
| ATOM | 24 | CB | ASN | A | 9 | 40.551 | -2.706 | 20.510 | 1.00 93.11 | C |
| ATOM | 25 | CG | ASN | A | 9 | 41.643 | -2.489 | 21.548 | 1.00 93.11 | C |
| ATOM | 26 | OD1 | ASN | A | 9 | 41.894 | -3.351 | 22.395 | 1.00 93.11 | O |
| ATOM | 27 | ND2 | ASN | A | 9 | 42.298 | -1.333 | 21.486 | 1.00 93.11 | N |
| ATOM | 28 | N | GLU | A | 10 | 38.530 | -0.944 | 18.143 | 1.00 59.45 | N |
| ATOM | 29 | CA | GLU | A | 10 | 37.525 | -1.142 | 17.105 | 1.00 59.45 | C |
| ATOM | 30 | C | GLU | A | 10 | 37.512 | 0.040 | 16.141 | 1.00 59.45 | C |
| ATOM | 31 | O | GLU | A | 10 | 37.604 | 1.191 | 16.561 | 1.00 59.45 | O |
| ATOM | 32 | CB | GLU | A | 10 | 36.143 | -1.305 | 17.747 | 1.00 65.56 | C |
| ATOM | 33 | CG | GLU | A | 10 | 35.257 | -2.304 | 17.033 | 1.00 65.56 | C |
| ATOM | 34 | CD | GLU | A | 10 | 35.908 | -3.673 | 16.912 | 1.00 65.56 | C |
| ATOM | 35 | OE1 | GLU | A | 10 | 36.330 | -4.238 | 17.943 | 1.00 65.56 | O |
| ATOM | 36 | OE2 | GLU | A | 10 | 35.995 | -4.186 | 15.778 | 1.00 65.56 | O |
| ATOM | 37 | N | ILE | A | 11 | 37.403 | -0.247 | 14.847 | 1.00 60.35 | N |
| ATOM | 38 | CA | ILE | A | 11 | 37.383 | 0.812 | 13.846 | 1.00 60.35 | C |
| ATOM | 39 | C | ILE | A | 11 | 35.962 | 1.288 | 13.573 | 1.00 60.35 | C |
| ATOM | 40 | O | ILE | A | 11 | 35.271 | 0.780 | 12.687 | 1.00 60.35 | O |
| ATOM | 41 | CB | ILE | A | 11 | 38.020 | 0.354 | 12.519 | 1.00 49.41 | C |
| ATOM | 42 | CG1 | ILE | A | 11 | 39.485 | -0.019 | 12.752 | 1.00 49.41 | C |
| ATOM | 43 | CG2 | ILE | A | 11 | 37.925 | 1.470 | 11.475 | 1.00 49.41 | C |
| ATOM | 44 | CD1 | ILE | A | 11 | 40.133 | -0.692 | 11.564 | 1.00 49.41 | C |
| ATOM | 45 | N | ILE | A | 12 | 35.537 | 2.270 | 14.357 | 1.00 57.24 | N |
| ATOM | 46 | CA | ILE | A | 12 | 34.213 | 2.852 | 14.227 | 1.00 57.24 | C |
| ATOM | 47 | C | ILE | A | 12 | 34.362 | 4.041 | 13.286 | 1.00 57.24 | C |
| ATOM | 48 | O | ILE | A | 12 | 35.210 | 4.918 | 13.503 | 1.00 57.24 | O |
| ATOM | 49 | CB | ILE | A | 12 | 33.697 | 3.328 | 15.609 | 1.00 44.12 | C |
| ATOM | 50 | CG1 | ILE | A | 12 | 33.711 | 2.147 | 16.591 | 1.00 44.12 | C |
| ATOM | 51 | CG2 | ILE | A | 12 | 32.294 | 3.907 | 15.481 | 1.00 44.12 | C |
| ATOM | 52 | CD1 | ILE | A | 12 | 33.624 | 2.551 | 18.061 | 1.00 44.12 | C |
| ATOM | 53 | N | PRO | A | 13 | 33.559 | 4.074 | 12.208 | 1.00 56.35 | N |
| ATOM | 54 | CA | PRO | A | 13 | 33.607 | 5.166 | 11.228 | 1.00 56.35 | C |
| ATOM | 55 | C | PRO | A | 13 | 33.175 | 6.508 | 11.834 | 1.00 56.35 | C |
| ATOM | 56 | O | PRO | A | 13 | 32.278 | 6.558 | 12.678 | 1.00 56.35 | O |
| ATOM | 57 | CB | PRO | A | 13 | 32.659 | 4.679 | 10.134 | 1.00 44.76 | C |
| ATOM | 58 | CG | PRO | A | 13 | 31.628 | 3.905 | 10.919 | 1.00 44.76 | C |
| ATOM | 59 | CD | PRO | A | 13 | 32.497 | 3.110 | 11.868 | 1.00 44.76 | C |
| ATOM | 60 | N | LEU | A | 14 | 33.816 | 7.583 | 11.384 | 1.00 50.54 | N |
| ATOM | 61 | CA | LEU | A | 14 | 33.547 | 8.938 | 11.865 | 1.00 50.54 | C |
| ATOM | 62 | C | LEU | A | 14 | 32.060 | 9.240 | 12.081 | 1.00 50.54 | C |
| ATOM | 63 | O | LEU | A | 14 | 31.652 | 9.658 | 13.179 | 1.00 50.54 | O |
| ATOM | 64 | CB | LEU | A | 14 | 34.145 | 9.947 | 10.880 | 1.00 41.30 | C |
| ATOM | 65 | CG | LEU | A | 14 | 34.006 | 11.443 | 11.136 | 1.00 41.30 | C |
| ATOM | 66 | CD1 | LEU | A | 14 | 34.719 | 11.839 | 12.423 | 1.00 41.30 | C |
| ATOM | 67 | CD2 | LEU | A | 14 | 34.603 | 12.185 | 9.952 | 1.00 41.30 | C |
| ATOM | 68 | N | GLY | A | 15 | 31.260 | 9.028 | 11.034 | 1.00 49.82 | N |
| ATOM | 69 | CA | GLY | A | 15 | 29.829 | 9.276 | 11.115 | 1.00 49.82 | C |
| ATOM | 70 | C | GLY | A | 15 | 29.180 | 8.770 | 12.390 | 1.00 49.82 | C |
| ATOM | 71 | O | GLY | A | 15 | 28.489 | 9.521 | 13.080 | 1.00 49.82 | O |
| ATOM | 72 | N | ARG | A | 16 | 29.389 | 7.496 | 12.708 | 1.00 56.39 | N |
| ATOM | 73 | CA | ARG | A | 16 | 28.807 | 6.925 | 13.917 | 1.00 56.39 | C |
| ATOM | 74 | C | ARG | A | 16 | 29.406 | 7.557 | 15.172 | 1.00 56.39 | C |
| ATOM | 75 | O | ARG | A | 16 | 28.698 | 7.776 | 16.154 | 1.00 56.39 | O |
| ATOM | 76 | CB | ARG | A | 16 | 29.013 | 5.409 | 13.947 | 1.00100.64 | C |

FIGURE 1-6

```
ATOM    77  CG  ARG A  16      28.044   4.622  13.073  1.00100.64           C
ATOM    78  CD  ARG A  16      28.476   3.163  12.974  1.00100.64           C
ATOM    79  NE  ARG A  16      28.621   2.532  14.287  1.00100.64           N
ATOM    80  CZ  ARG A  16      29.280   1.395  14.502  1.00100.64           C
ATOM    81  NH1 ARG A  16      29.861   0.758  13.492  1.00100.64           N
ATOM    82  NH2 ARG A  16      29.360   0.893  15.727  1.00100.64           N
ATOM    83  N   LEU A  17      30.707   7.853  15.147  1.00 42.87           N
ATOM    84  CA  LEU A  17      31.341   8.466  16.308  1.00 42.87           C
ATOM    85  C   LEU A  17      30.735   9.844  16.572  1.00 42.87           C
ATOM    86  O   LEU A  17      30.456  10.187  17.716  1.00 42.87           O
ATOM    87  CB  LEU A  17      32.859   8.587  16.115  1.00 41.77           C
ATOM    88  CG  LEU A  17      33.683   7.296  16.205  1.00 41.77           C
ATOM    89  CD1 LEU A  17      35.166   7.592  15.962  1.00 41.77           C
ATOM    90  CD2 LEU A  17      33.487   6.677  17.571  1.00 41.77           C
ATOM    91  N   ILE A  18      30.558  10.634  15.516  1.00 40.19           N
ATOM    92  CA  ILE A  18      29.959  11.962  15.643  1.00 40.19           C
ATOM    93  C   ILE A  18      28.557  11.779  16.234  1.00 40.19           C
ATOM    94  O   ILE A  18      28.113  12.567  17.072  1.00 40.19           O
ATOM    95  CB  ILE A  18      29.821  12.662  14.270  1.00 50.02           C
ATOM    96  CG1 ILE A  18      31.203  13.011  13.716  1.00 50.02           C
ATOM    97  CG2 ILE A  18      29.008  13.933  14 409  1.00 50.02           C
ATOM    98  CD1 ILE A  18      31.156  13.614  12.312  1.00 50.02           C
ATOM    99  N   HIS A  19      27.875  10.726  15.792  1.00 61.33           N
ATOM   100  CA  HIS A  19      26.534  10.419  16.262  1.00 61.33           C
ATOM   101  C   HIS A  19      26.592  10.158  17.755  1.00 61.33           C
ATOM   102  O   HIS A  19      26.050  10.922  18.557  1.00 61.33           O
ATOM   103  CB  HIS A  19      26.007   9.186  15.532  1.00 71.93           C
ATOM   104  CG  HIS A  19      24.670   8.715  16.009  1.00 71.93           C
ATOM   105  ND1 HIS A  19      23.556   9.526  16.029  1.00 71.93           N
ATOM   106  CD2 HIS A  19      24.257   7.501  16.445  1.00 71.93           C
ATOM   107  CE1 HIS A  19      22.515   8.833  16.454  1.00 71.93           C
ATOM   108  NE2 HIS A  19      22.913   7.600  16.712  1.00 71.93           N
ATOM   109  N   MET A  20      27.264   9.072  18.116  1.00 42.03           N
ATOM   110  CA  MET A  20      27.426   8.676  19.511  1.00 42.03           C
ATOM   111  C   MET A  20      27.796   9.844  20.414  1.00 42.03           C
ATOM   112  O   MET A  20      27.316   9.923  21.535  1.00 42.03           O
ATOM   113  CB  MET A  20      28.515   7.608  19.634  1.00 67.14           C
ATOM   114  CG  MET A  20      28.159   6.249  19.067  1.00 67.14           C
ATOM   115  SD  MET A  20      29.602   5.147  19.075  1.00 67.14           S
ATOM   116  CE  MET A  20      29.707   4.719  20.836  1.00 67.14           C
ATOM   117  N   VAL A  21      28.664  10.735  19.938  1.00 52.70           N
ATOM   118  CA  VAL A  21      29.092  11.885  20.733  1.00 52.70           C
ATOM   119  C   VAL A  21      28.002  12.948  20.875  1.00 52.70           C
ATOM   120  O   VAL A  21      27.875  13.592  21.933  1.00 52.70           O
ATOM   121  CB  VAL A  21      30.346  12.560  20.137  1.00 37.15           C
ATOM   122  CG1 VAL A  21      30.727  13.763  20.989  1.00 37.15           C
ATOM   123  CG2 VAL A  21      31.517  11.556  20.086  1.00 37.15           C
ATOM   124  N   ASN A  22      27.231  13.149  19.810  1.00 51.65           N
ATOM   125  CA  ASN A  22      26.161  14.131  19.863  1.00 51.65           C
ATOM   126  C   ASN A  22      25.157  13.551  20.836  1.00 51.65           C
ATOM   127  O   ASN A  22      24.591  14.263  21.671  1.00 51.65           O
ATOM   128  CB  ASN A  22      25.502  14.323  18.497  1.00 36.79           C
ATOM   129  CG  ASN A  22      24.601  15.544  18.465  1.00 36.79           C
ATOM   130  OD1 ASN A  22      25.067  16.671  18.633  1.00 36.79           O
ATOM   131  ND2 ASN A  22      23.304  15.326  18.257  1.00 36.79           N
ATOM   132  N   GLN A  23      24.957  12.241  20.723  1.00 53.66           N
ATOM   133  CA  GLN A  23      24.040  11.521  21.592  1.00 53.66           C
ATOM   134  C   GLN A  23      24.419  11.899  23.018  1.00 53.66           C
ATOM   135  O   GLN A  23      23.649  12.543  23.728  1.00 53.66           O
ATOM   136  CB  GLN A  23      24.205  10.015  21.384  1.00 84.11           C
ATOM   137  CG  GLN A  23      23.100   9.154  21.974  1.00 84.11           C
ATOM   138  CD  GLN A  23      22.270   8.458  20.903  1.00 84.11           C
ATOM   139  OE1 GLN A  23      22.789   7.665  20.109  1.00 84.11           O
ATOM   140  NE2 GLN A  23      20.972   8.752  20.877  1.00 84.11           N
ATOM   141  N   LYS A  24      25.631  11.519  23.412  1.00 47.08           N
ATOM   142  CA  LYS A  24      26.142  11.801  24.746  1.00 47.08           C
ATOM   143  C   LYS A  24      25.873  13.245  25.140  1.00 47.08           C
ATOM   144  O   LYS A  24      25.342  13.516  26.213  1.00 47.08           O
ATOM   145  CB  LYS A  24      27.651  11.540  24.817  1.00 49.11           C
ATOM   146  CG  LYS A  24      28.214  11.723  26.218  1.00 49.11           C
ATOM   147  CD  LYS A  24      29.725  11.840  26.227  1.00 49.11           C
ATOM   148  CE  LYS A  24      30.273  12.007  27.651  1.00 49.11           C
ATOM   149  NZ  LYS A  24      30.669  10.711  28.286  1.00 49.11           N
```

FIGURE 1-7

| | | | | | | | | | |
|---|---|---|---|---|---|---|---|---|---|
| ATOM | 150 | N | LYS | A | 25 | 26.253 | 14.161 | 24.260 | 1.00 49.08 | N |
| ATOM | 151 | CA | LYS | A | 25 | 26.082 | 15.592 | 24.491 | 1.00 49.08 | C |
| ATOM | 152 | C | LYS | A | 25 | 24.650 | 15.955 | 24.881 | 1.00 49.08 | C |
| ATOM | 153 | O | LYS | A | 25 | 24.428 | 16.784 | 25.767 | 1.00 49.08 | O |
| ATOM | 154 | CB | LYS | A | 25 | 26.504 | 16.365 | 23.235 | 1.00 88.21 | C |
| ATOM | 155 | CG | LYS | A | 25 | 26.525 | 17.878 | 23.381 | 1.00 88.21 | C |
| ATOM | 156 | CD | LYS | A | 25 | 25.257 | 18.516 | 22.837 | 1.00 88.21 | C |
| ATOM | 157 | CE | LYS | A | 25 | 25.373 | 20.036 | 22.832 | 1.00 88.21 | C |
| ATOM | 158 | NZ | LYS | A | 25 | 24.213 | 20.700 | 22.173 | 1.00 88.21 | N |
| ATOM | 159 | N | ASP | A | 26 | 23.677 | 15.331 | 24.227 | 1.00 49.82 | N |
| ATOM | 160 | CA | ASP | A | 26 | 22.291 | 15.635 | 24.539 | 1.00 49.82 | C |
| ATOM | 161 | C | ASP | A | 26 | 21.908 | 15.027 | 25.873 | 1.00 49.82 | C |
| ATOM | 162 | O | ASP | A | 26 | 21.190 | 15.650 | 26.661 | 1.00 49.82 | O |
| ATOM | 163 | CB | ASP | A | 26 | 21.356 | 15.137 | 23.432 | 1.00 69.22 | C |
| ATOM | 164 | CG | ASP | A | 26 | 21.429 | 15.997 | 22.174 | 1.00 69.22 | C |
| ATOM | 165 | OD1 | ASP | A | 26 | 21.641 | 17.227 | 22.294 | 1.00 69.22 | O |
| ATOM | 166 | OD2 | ASP | A | 26 | 21.259 | 15.444 | 21.065 | 1.00 69.22 | O |
| ATOM | 167 | N | ARG | A | 27 | 22.403 | 13.819 | 26.129 | 1.00 55.02 | N |
| ATOM | 168 | CA | ARG | A | 27 | 22.117 | 13.123 | 27.381 | 1.00 55.02 | C |
| ATOM | 169 | C | ARG | A | 27 | 22.570 | 13.967 | 28.562 | 1.00 55.02 | C |
| ATOM | 170 | O | ARG | A | 27 | 21.902 | 14.023 | 29.590 | 1.00 55.02 | O |
| ATOM | 171 | CB | ARG | A | 27 | 22.823 | 11.765 | 27.426 | 1.00107.80 | C |
| ATOM | 172 | CG | ARG | A | 27 | 22.687 | 11.072 | 28.770 | 1.00107.80 | C |
| ATOM | 173 | CD | ARG | A | 27 | 23.372 | 9.722 | 28.799 | 1.00107.80 | C |
| ATOM | 174 | NE | ARG | A | 27 | 23.381 | 9.171 | 30.151 | 1.00107.80 | N |
| ATOM | 175 | CZ | ARG | A | 27 | 23.926 | 8.005 | 30.485 | 1.00107.80 | C |
| ATOM | 176 | NH1 | ARG | A | 27 | 24.513 | 7.256 | 29.559 | 1.00107.80 | N |
| ATOM | 177 | NH2 | ARG | A | 27 | 23.884 | 7.585 | 31.746 | 1.00107.80 | N |
| ATOM | 178 | N | LEU | A | 28 | 23.715 | 14.619 | 28.410 | 1.00 41.40 | N |
| ATOM | 179 | CA | LEU | A | 28 | 24.232 | 15.464 | 29.469 | 1.00 41.40 | C |
| ATOM | 180 | C | LEU | A | 28 | 23.314 | 16.674 | 29.610 | 1.00 41.40 | C |
| ATOM | 181 | O | LEU | A | 28 | 23.000 | 17.105 | 30.720 | 1.00 41.40 | O |
| ATOM | 182 | CB | LEU | A | 28 | 25.662 | 15.913 | 29.142 | 1.00 54.85 | C |
| ATOM | 183 | CG | LEU | A | 28 | 26.672 | 14.768 | 29.009 | 1.00 54.85 | C |
| ATOM | 184 | CD1 | LEU | A | 28 | 28.074 | 15.320 | 28.812 | 1.00 54.85 | C |
| ATOM | 185 | CD2 | LEU | A | 28 | 26.629 | 13.914 | 30.259 | 1.00 54.85 | C |
| ATOM | 186 | N | LEU | A | 29 | 22.887 | 17.207 | 28.472 | 1.00 46.97 | N |
| ATOM | 187 | CA | LEU | A | 29 | 22.001 | 18.359 | 28.432 | 1.00 46.97 | C |
| ATOM | 188 | C | LEU | A | 29 | 20.738 | 18.053 | 29.245 | 1.00 46.97 | C |
| ATOM | 189 | O | LEU | A | 29 | 20.399 | 18.793 | 30.172 | 1.00 46.97 | O |
| ATOM | 190 | CB | LEU | A | 29 | 21.639 | 18.670 | 26.982 | 1.00 54.42 | C |
| ATOM | 191 | CG | LEU | A | 29 | 20.751 | 19.884 | 26.737 | 1.00 54.42 | C |
| ATOM | 192 | CD1 | LEU | A | 29 | 21.413 | 21.122 | 27.319 | 1.00 54.42 | C |
| ATOM | 193 | CD2 | LEU | A | 29 | 20.510 | 20.042 | 25.250 | 1.00 54.42 | C |
| ATOM | 194 | N | ASN | A | 30 | 20.043 | 16.965 | 28.903 | 1.00 36.87 | N |
| ATOM | 195 | CA | ASN | A | 30 | 18.849 | 16.583 | 29.648 | 1.00 36.87 | C |
| ATOM | 196 | C | ASN | A | 30 | 19.174 | 16.503 | 31.144 | 1.00 36.87 | C |
| ATOM | 197 | O | ASN | A | 30 | 18.399 | 16.977 | 31.981 | 1.00 36.87 | O |
| ATOM | 198 | CB | ASN | A | 30 | 18.302 | 15.220 | 29.189 | 1.00 52.27 | C |
| ATOM | 199 | CG | ASN | A | 30 | 17.560 | 15.296 | 27.862 | 1.00 52.27 | C |
| ATOM | 200 | OD1 | ASN | A | 30 | 18.148 | 15.107 | 26.795 | 1.00 52.27 | O |
| ATOM | 201 | ND2 | ASN | A | 30 | 16.259 | 15.583 | 27.925 | 1.00 52.27 | N |
| ATOM | 202 | N | GLU | A | 31 | 20.320 | 15.905 | 31.474 | 1.00 57.43 | N |
| ATOM | 203 | CA | GLU | A | 31 | 20.733 | 15.760 | 32.874 | 1.00 57.43 | C |
| ATOM | 204 | C | GLU | A | 31 | 20.946 | 17.092 | 33.588 | 1.00 57.43 | C |
| ATOM | 205 | O | GLU | A | 31 | 20.661 | 17.214 | 34.776 | 1.00 57.43 | O |
| ATOM | 206 | CB | GLU | A | 31 | 22.004 | 14.908 | 32.981 | 1.00 80.57 | C |
| ATOM | 207 | CG | GLU | A | 31 | 21.742 | 13.406 | 32.919 | 1.00 80.57 | C |
| ATOM | 208 | CD | GLU | A | 31 | 23.005 | 12.566 | 33.095 | 1.00 80.57 | C |
| ATOM | 209 | OE1 | GLU | A | 31 | 23.742 | 12.795 | 34.081 | 1.00 80.57 | O |
| ATOM | 210 | OE2 | GLU | A | 31 | 23.253 | 11.672 | 32.253 | 1.00 80.57 | O |
| ATOM | 211 | N | TYR | A | 32 | 21.436 | 18.090 | 32.863 | 1.00 46.41 | N |
| ATOM | 212 | CA | TYR | A | 32 | 21.676 | 19.408 | 33.446 | 1.00 46.41 | C |
| ATOM | 213 | C | TYR | A | 32 | 20.393 | 20.212 | 33.627 | 1.00 46.41 | C |
| ATOM | 214 | O | TYR | A | 32 | 20.319 | 21.063 | 34.511 | 1.00 46.41 | O |
| ATOM | 215 | CB | TYR | A | 32 | 22.622 | 20.219 | 32.565 | 1.00 77.48 | C |
| ATOM | 216 | CG | TYR | A | 32 | 23.960 | 19.576 | 32.316 | 1.00 77.48 | C |
| ATOM | 217 | CD1 | TYR | A | 32 | 24.590 | 19.716 | 31.080 | 1.00 77.48 | C |
| ATOM | 218 | CD2 | TYR | A | 32 | 24.610 | 18.853 | 33.315 | 1.00 77.48 | C |
| ATOM | 219 | CE1 | TYR | A | 32 | 25.834 | 19.154 | 30.838 | 1.00 77.48 | C |
| ATOM | 220 | CE2 | TYR | A | 32 | 25.859 | 18.285 | 33.089 | 1.00 77.48 | C |
| ATOM | 221 | CZ | TYR | A | 32 | 26.465 | 18.441 | 31.845 | 1.00 77.48 | C |
| ATOM | 222 | OH | TYR | A | 32 | 27.703 | 17.894 | 31.601 | 1.00 77.48 | O |

FIGURE 1-8

```
ATOM    223  N    LEU A   33      19.393  19.955  32.784  1.00 41.53           N
ATOM    224  CA   LEU A   33      18.120  20.684  32.858  1.00 41.53           C
ATOM    225  C    LEU A   33      17.058  19.961  33.689  1.00 41.53           C
ATOM    226  O    LEU A   33      15.980  20.502  33.943  1.00 41.53           O
ATOM    227  CB   LEU A   33      17.566  20.931  31.450  1.00 35.85           C
ATOM    228  CG   LEU A   33      18.493  21.636  30.462  1.00 35.85           C
ATOM    229  CD1  LEU A   33      17.719  21.961  29.198  1.00 35.85           C
ATOM    230  CD2  LEU A   33      19.038  22.907  31.080  1.00 35.85           C
ATOM    231  N    SER A   34      17.385  18.740  34.102  1.00 49.29           N
ATOM    232  CA   SER A   34      16.500  17.900  34.892  1.00 49.29           C
ATOM    233  C    SER A   34      15.924  18.583  36.131  1.00 49.29           C
ATOM    234  O    SER A   34      14.755  18.387  36.458  1.00 49.29           O
ATOM    235  CB   SER A   34      17.240  16.623  35.304  1.00 54.11           C
ATOM    236  OG   SER A   34      16.391  15.733  36.002  1.00 54.11           O
ATOM    237  N    PRO A   35      16.733  19.374  36.853  1.00 36.68           N
ATOM    238  CA   PRO A   35      16.216  20.049  38.054  1.00 36.68           C
ATOM    239  C    PRO A   35      15.460  21.353  37.760  1.00 36.68           C
ATOM    240  O    PRO A   35      14.772  21.893  38.638  1.00 36.68           O
ATOM    241  CB   PRO A   35      17.481  20.331  38.883  1.00 44.90           C
ATOM    242  CG   PRO A   35      18.530  19.429  38.291  1.00 44.90           C
ATOM    243  CD   PRO A   35      18.204  19.432  36.823  1.00 44.90           C
ATOM    244  N    LEU A   36      15.618  21.868  36.543  1.00 37.76           N
ATOM    245  CA   LEU A   36      14.978  23.120  36.141  1.00 37.76           C
ATOM    246  C    LEU A   36      13.610  22.879  35.491  1.00 37.76           C
ATOM    247  O    LEU A   36      13.374  21.840  34.862  1.00 37.76           O
ATOM    248  CB   LEU A   36      15.889  23.882  35.170  1.00 41.54           C
ATOM    249  CG   LEU A   36      17.362  24.080  35.557  1.00 41.54           C
ATOM    250  CD1  LEU A   36      18.086  24.902  34.476  1.00 41.54           C
ATOM    251  CD2  LEU A   36      17.451  24.788  36.901  1.00 41.54           C
ATOM    252  N    ASP A   37      12.721  23.857  35.630  1.00 31.59           N
ATOM    253  CA   ASP A   37      11.368  23.757  35.090  1.00 31.59           C
ATOM    254  C    ASP A   37      11.369  24.064  33.583  1.00 31.59           C
ATOM    255  O    ASP A   37      10.747  25.019  33.109  1.00 31.59           O
ATOM    256  CB   ASP A   37      10.469  24.730  35.856  1.00 32.69           C
ATOM    257  CG   ASP A   37       8.990  24.479  35.628  1.00 32.69           C
ATOM    258  OD1  ASP A   37       8.186  25.361  35.988  1.00 32.69           O
ATOM    259  OD2  ASP A   37       8.619  23.420  35.101  1.00 32.69           O
ATOM    260  N    ILE A   38      12.089  23.245  32.832  1.00 37.25           N
ATOM    261  CA   ILE A   38      12.169  23.417  31.392  1.00 37.25           C
ATOM    262  C    ILE A   38      12.734  22.157  30.781  1.00 37.25           C
ATOM    263  O    ILE A   38      13.564  21.488  31.402  1.00 37.25           O
ATOM    264  CB   ILE A   38      13.100  24.574  31.018  1.00 29.59           C
ATOM    265  CG1  ILE A   38      13.047  24.798  29.502  1.00 29.59           C
ATOM    266  CG2  ILE A   38      14.536  24.258  31.500  1.00 29.59           C
ATOM    267  CD1  ILE A   38      13.782  26.019  29.034  1.00 29.59           C
ATOM    268  N    THR A   39      12.308  21.844  29.559  1.00 37.34           N
ATOM    269  CA   THR A   39      12.798  20.656  28.875  1.00 37.34           C
ATOM    270  C    THR A   39      13.852  20.986  27.800  1.00 37.34           C
ATOM    271  O    THR A   39      13.901  22.097  27.270  1.00 37.34           O
ATOM    272  CB   THR A   39      11.648  19.897  28.216  1.00 28.45           C
ATOM    273  OG1  THR A   39      11.152  20.664  27.114  1.00 28.45           O
ATOM    274  CG2  THR A   39      10.502  19.671  29.227  1.00 28.45           C
ATOM    275  N    ALA A   40      14.693  20.001  27.489  1.00 40.45           N
ATOM    276  CA   ALA A   40      15.741  20.147  26.487  1.00 40.45           C
ATOM    277  C    ALA A   40      15.144  20.691  25.198  1.00 40.45           C
ATOM    278  O    ALA A   40      15.680  21.623  24.601  1.00 40.45           O
ATOM    279  CB   ALA A   40      16.406  18.789  26.227  1.00 37.38           C
ATOM    280  N    ALA A   41      14.024  20.112  24.774  1.00 36.96           N
ATOM    281  CA   ALA A   41      13.368  20.562  23.555  1.00 36.96           C
ATOM    282  C    ALA A   41      12.948  22.027  23.647  1.00 36.96           C
ATOM    283  O    ALA A   41      13.127  22.777  22.686  1.00 36.96           O
ATOM    284  CB   ALA A   41      12.164  19.677  23.237  1.00 24.45           C
ATOM    285  N    GLN A   42      12.386  22.434  24.790  1.00 35.44           N
ATOM    286  CA   GLN A   42      11.981  23.836  24.971  1.00 35.44           C
ATOM    287  C    GLN A   42      13.219  24.723  24.874  1.00 35.44           C
ATOM    288  O    GLN A   42      13.185  25.786  24.247  1.00 35.44           O
ATOM    289  CB   GLN A   42      11.303  24.050  26.334  1.00 33.78           C
ATOM    290  CG   GLN A   42       9.873  23.514  26.443  1.00 33.78           C
ATOM    291  CD   GLN A   42       9.324  23.554  27.870  1.00 33.78           C
ATOM    292  OE1  GLN A   42       9.838  24.264  28.735  1.00 33.78           O
ATOM    293  NE2  GLN A   42       8.270  22.801  28.111  1.00 33.78           N
ATOM    294  N    PHE A   43      14.316  24.280  25.484  1.00 35.55           N
ATOM    295  CA   PHE A   43      15.562  25.053  25.453  1.00 35.55           C
```

FIGURE 1-9

```
ATOM    296  C   PHE A  43      16.062  25.332  24.013  1.00 35.55           C
ATOM    297  O   PHE A  43      16.431  26.337  23.606  1.00 35.55           O
ATOM    298  CB  PHE A  43      16.633  24.365  26.299  1.00 45.48           C
ATOM    299  CG  PHE A  43      17.937  25.100  26.337  1.00 45.48           C
ATOM    300  CD1 PHE A  43      17.973  26.470  26.599  1.00 45.48           C
ATOM    301  CD2 PHE A  43      19.134  24.426  26.127  1.00 45.48           C
ATOM    302  CE1 PHE A  43      19.180  27.163  26.652  1.00 45.48           C
ATOM    303  CE2 PHE A  43      20.351  25.110  26.178  1.00 45.48           C
ATOM    304  CZ  PHE A  43      20.372  26.486  26.441  1.00 45.48           C
ATOM    305  N   LYS A  44      16.049  24.149  23.241  1.00 38.60           N
ATOM    306  CA  LYS A  44      16.479  24.191  21.844  1.00 38.60           C
ATOM    307  C   LYS A  44      15.600  25.174  21.054  1.00 38.60           C
ATOM    308  O   LYS A  44      16.107  26.007  20.297  1.00 38.60           O
ATOM    309  CB  LYS A  44      16.379  22.794  21.222  1.00 82.69           C
ATOM    310  CG  LYS A  44      17.267  21.744  21.877  1.00 82.69           C
ATOM    311  CD  LYS A  44      16.994  20.355  21.302  1.00 82.69           C
ATOM    312  CE  LYS A  44      17.924  19.296  21.891  1.00 82.69           C
ATOM    313  NZ  LYS A  44      19.348  19.510  21.502  1.00 82.69           N
ATOM    314  N   VAL A  45      14.284  25.078  21.221  1.00 34.06           N
ATOM    315  CA  VAL A  45      13.396  25.997  20.517  1.00 34.06           C
ATOM    316  C   VAL A  45      13.710  27.448  20.877  1.00 34.06           C
ATOM    317  O   VAL A  45      13.619  28.324  20.019  1.00 34.06           O
ATOM    318  CB  VAL A  45      11.913  25.708  20.829  1.00 30.26           C
ATOM    319  CG1 VAL A  45      11.034  26.859  20.357  1.00 30.26           C
ATOM    320  CG2 VAL A  45      11.490  24.411  20.137  1.00 30.26           C
ATOM    321  N   LEU A  46      14.085  27.710  22.129  1.00 42.08           N
ATOM    322  CA  LEU A  46      14.408  29.086  22.530  1.00 42.08           C
ATOM    323  C   LEU A  46      15.721  29.573  21.899  1.00 42.08           C
ATOM    324  O   LEU A  46      15.816  30.704  21.423  1.00 42.08           O
ATOM    325  CB  LEU A  46      14.529  29.228  24.059  1.00 33.35           C
ATOM    326  CG  LEU A  46      13.316  29.155  24.989  1.00 33.35           C
ATOM    327  CD1 LEU A  46      13.772  29.485  26.416  1.00 33.35           C
ATOM    328  CD2 LEU A  46      12.243  30.120  24.554  1.00 33.35           C
ATOM    329  N   CYS A  47      16.734  28.720  21.903  1.00 47.51           N
ATOM    330  CA  CYS A  47      18.015  29.103  21.334  1.00 47.51           C
ATOM    331  C   CYS A  47      17.874  29.371  19.841  1.00 47.51           C
ATOM    332  O   CYS A  47      18.515  30.275  19.303  1.00 47.51           O
ATOM    333  CB  CYS A  47      19.045  28.004  21.577  1.00 47.01           C
ATOM    334  SG  CYS A  47      19.407  27.720  23.319  1.00 47.01           S
ATOM    335  N   SER A  48      17.029  28.590  19.176  1.00 42.18           N
ATOM    336  CA  SER A  48      16.814  28.747  17.737  1.00 42.18           C
ATOM    337  C   SER A  48      16.060  30.018  17.367  1.00 42.18           C
ATOM    338  O   SER A  48      16.352  30.638  16.356  1.00 42.18           O
ATOM    339  CB  SER A  48      16.047  27.547  17.180  1.00 30.64           C
ATOM    340  OG  SER A  48      16.769  26.345  17.382  1.00 30.64           O
ATOM    341  N   ILE A  49      15.068  30.390  18.171  1.00 41.78           N
ATOM    342  CA  ILE A  49      14.287  31.585  17.893  1.00 41.78           C
ATOM    343  C   ILE A  49      15.181  32.789  18.171  1.00 41.78           C
ATOM    344  O   ILE A  49      15.177  33.767  17.427  1.00 41.78           O
ATOM    345  CB  ILE A  49      13.039  31.650  18.796  1.00 41.13           C
ATOM    346  CG1 ILE A  49      12.068  30.527  18.418  1.00 41.13           C
ATOM    347  CG2 ILE A  49      12.363  33.009  18.671  1.00 41.13           C
ATOM    348  CD1 ILE A  49      10.746  30.559  19.184  1.00 41.13           C
ATOM    349  N   ARG A  50      15.948  32.692  19.253  1.00 49.26           N
ATOM    350  CA  ARG A  50      16.858  33.747  19.644  1.00 49.26           C
ATOM    351  C   ARG A  50      17.766  34.163  18.479  1.00 49.26           C
ATOM    352  O   ARG A  50      17.680  35.299  17.978  1.00 49.26           O
ATOM    353  CB  ARG A  50      17.712  33.279  20.827  1.00 66.71           C
ATOM    354  CG  ARG A  50      18.819  34.249  21.219  1.00 66.71           C
ATOM    355  CD  ARG A  50      19.567  33.783  22.449  1.00 66.71           C
ATOM    356  NE  ARG A  50      20.818  34.514  22.581  1.00 66.71           N
ATOM    357  CZ  ARG A  50      21.761  34.242  23.476  1.00 66.71           C
ATOM    358  NH1 ARG A  50      21.606  33.248  24.344  1.00 66.71           N
ATOM    359  NH2 ARG A  50      22.879  34.953  23.485  1.00 66.71           N
ATOM    360  N   CYS A  51      18.626  33.232  18.062  1.00 56.95           N
ATOM    361  CA  CYS A  51      19.585  33.437  16.975  1.00 56.95           C
ATOM    362  C   CYS A  51      19.000  34.159  15.790  1.00 56.95           C
ATOM    363  O   CYS A  51      19.623  35.058  15.216  1.00 56.95           O
ATOM    364  CB  CYS A  51      20.128  32.096  16.499  1.00 55.83           C
ATOM    365  SG  CYS A  51      21.019  31.209  17.754  1.00 55.83           S
ATOM    366  N   ALA A  52      17.799  33.746  15.421  1.00 43.02           N
ATOM    367  CA  ALA A  52      17.107  34.328  14.295  1.00 43.02           C
ATOM    368  C   ALA A  52      16.401  35.650  14.628  1.00 43.02           C
```

FIGURE 1-10

| | | | | | | | | | | |
|---|---|---|---|---|---|---|---|---|---|---|
| ATOM | 369 | O | ALA | A | 52 | 15.889 | 36.319 | 13.718 | 1.00 43.02 | O |
| ATOM | 370 | CB | ALA | A | 52 | 16.112 | 33.325 | 13.764 | 1.00 30.40 | C |
| ATOM | 371 | N | ALA | A | 53 | 16.373 | 36.025 | 15.914 | 1.00 45.66 | N |
| ATOM | 372 | CA | ALA | A | 53 | 15.711 | 37.257 | 16.362 | 1.00 45.66 | C |
| ATOM | 373 | C | ALA | A | 53 | 14.196 | 37.112 | 16.249 | 1.00 45.66 | C |
| ATOM | 374 | O | ALA | A | 53 | 13.465 | 37.222 | 17.239 | 1.00 45.66 | O |
| ATOM | 375 | CB | ALA | A | 53 | 16.166 | 38.446 | 15.526 | 1.00 34.46 | C |
| ATOM | 376 | N | CYS | A | 54 | 13.749 | 36.877 | 15.021 | 1.00 42.13 | N |
| ATOM | 377 | CA | CYS | A | 54 | 12.347 | 36.690 | 14.686 | 1.00 42.13 | C |
| ATOM | 378 | C | CYS | A | 54 | 12.290 | 35.612 | 13.605 | 1.00 42.13 | C |
| ATOM | 379 | O | CYS | A | 54 | 13.032 | 35.672 | 12.626 | 1.00 42.13 | O |
| ATOM | 380 | CB | CYS | A | 54 | 11.741 | 37.976 | 14.119 | 1.00 63.33 | C |
| ATOM | 381 | SG | CYS | A | 54 | 11.425 | 39.280 | 15.311 | 1.00 63.33 | S |
| ATOM | 382 | N | ILE | A | 55 | 11.407 | 34.636 | 13.765 | 1.00 45.27 | N |
| ATOM | 383 | CA | ILE | A | 55 | 11.300 | 33.580 | 12.771 | 1.00 45.27 | C |
| ATOM | 384 | C | ILE | A | 55 | 9.881 | 33.051 | 12.687 | 1.00 45.27 | C |
| ATOM | 385 | O | ILE | A | 55 | 9.140 | 33.064 | 13.681 | 1.00 45.27 | O |
| ATOM | 386 | CB | ILE | A | 55 | 12.243 | 32.408 | 13.102 | 1.00 41.76 | C |
| ATOM | 387 | CG1 | ILE | A | 55 | 12.130 | 31.329 | 12.018 | 1.00 41.76 | C |
| ATOM | 388 | CG2 | ILE | A | 55 | 11.902 | 31.846 | 14.481 | 1.00 41.76 | C |
| ATOM | 389 | CD1 | ILE | A | 55 | 13.119 | 30.197 | 12.173 | 1.00 41.76 | C |
| ATOM | 390 | N | THR | A | 56 | 9.500 | 32.596 | 11.500 | 1.00 37.37 | N |
| ATOM | 391 | CA | THR | A | 56 | 8.161 | 32.049 | 11.302 | 1.00 37.37 | C |
| ATOM | 392 | C | THR | A | 56 | 8.092 | 30.637 | 11.890 | 1.00 37.37 | C |
| ATOM | 393 | O | THR | A | 56 | 9.103 | 29.929 | 11.974 | 1.00 37.37 | O |
| ATOM | 394 | CB | THR | A | 56 | 7.799 | 31.988 | 9.811 | 1.00 68.07 | C |
| ATOM | 395 | OG1 | THR | A | 56 | 8.687 | 31.086 | 9.137 | 1.00 68.07 | O |
| ATOM | 396 | CG2 | THR | A | 56 | 7.901 | 33.371 | 9.189 | 1.00 68.07 | C |
| ATOM | 397 | N | PRO | A | 57 | 6.904 | 30.212 | 12.327 | 1.00 37.02 | N |
| ATOM | 398 | CA | PRO | A | 57 | 6.837 | 28.864 | 12.887 | 1.00 37.02 | C |
| ATOM | 399 | C | PRO | A | 57 | 7.275 | 27.811 | 11.870 | 1.00 37.02 | C |
| ATOM | 400 | O | PRO | A | 57 | 8.020 | 26.875 | 12.208 | 1.00 37.02 | O |
| ATOM | 401 | CB | PRO | A | 57 | 5.379 | 28.741 | 13.290 | 1.00 39.03 | C |
| ATOM | 402 | CG | PRO | A | 57 | 5.043 | 30.143 | 13.708 | 1.00 39.03 | C |
| ATOM | 403 | CD | PRO | A | 57 | 5.662 | 30.958 | 12.596 | 1.00 39.03 | C |
| ATOM | 404 | N | VAL | A | 58 | 6.847 | 27.973 | 10.619 | 1.00 50.69 | N |
| ATOM | 405 | CA | VAL | A | 58 | 7.218 | 27.019 | 9.579 | 1.00 50.69 | C |
| ATOM | 406 | C | VAL | A | 58 | 8.726 | 26.999 | 9.335 | 1.00 50.69 | C |
| ATOM | 407 | O | VAL | A | 58 | 9.318 | 25.929 | 9.193 | 1.00 50.69 | O |
| ATOM | 408 | CB | VAL | A | 58 | 6.503 | 27.324 | 8.267 | 1.00 56.43 | C |
| ATOM | 409 | CG1 | VAL | A | 58 | 6.909 | 26.304 | 7.223 | 1.00 56.43 | C |
| ATOM | 410 | CG2 | VAL | A | 58 | 4.990 | 27.308 | 8.484 | 1.00 56.43 | C |
| ATOM | 411 | N | GLU | A | 59 | 9.349 | 28.175 | 9.280 | 1.00 44.74 | N |
| ATOM | 412 | CA | GLU | A | 59 | 10.796 | 28.248 | 9.087 | 1.00 44.74 | C |
| ATOM | 413 | C | GLU | A | 59 | 11.443 | 27.568 | 10.299 | 1.00 44.74 | C |
| ATOM | 414 | O | GLU | A | 59 | 12.412 | 26.816 | 10.176 | 1.00 44.74 | O |
| ATOM | 415 | CB | GLU | A | 59 | 11.251 | 29.707 | 9.008 | 1.00 89.17 | C |
| ATOM | 416 | CG | GLU | A | 59 | 12.746 | 29.900 | 8.766 | 1.00 89.17 | C |
| ATOM | 417 | CD | GLU | A | 59 | 13.151 | 29.678 | 7.319 | 1.00 89.17 | C |
| ATOM | 418 | OE1 | GLU | A | 59 | 12.953 | 28.557 | 6.803 | 1.00 89.17 | O |
| ATOM | 419 | OE2 | GLU | A | 59 | 13.671 | 30.630 | 6.696 | 1.00 89.17 | O |
| ATOM | 420 | N | LEU | A | 60 | 10.892 | 27.837 | 11.478 | 1.00 41.66 | N |
| ATOM | 421 | CA | LEU | A | 60 | 11.405 | 27.241 | 12.702 | 1.00 41.66 | C |
| ATOM | 422 | C | LEU | A | 60 | 11.215 | 25.721 | 12.625 | 1.00 41.66 | C |
| ATOM | 423 | O | LEU | A | 60 | 12.053 | 24.940 | 13.088 | 1.00 41.66 | O |
| ATOM | 424 | CB | LEU | A | 60 | 10.651 | 27.817 | 13.907 | 1.00 44.47 | C |
| ATOM | 425 | CG | LEU | A | 60 | 11.044 | 27.322 | 15.300 | 1.00 44.47 | C |
| ATOM | 426 | CD1 | LEU | A | 60 | 12.533 | 27.525 | 15.539 | 1.00 44.47 | C |
| ATOM | 427 | CD2 | LEU | A | 60 | 10.219 | 28.080 | 16.333 | 1.00 44.47 | C |
| ATOM | 428 | N | LYS | A | 61 | 10.101 | 25.314 | 12.028 | 1.00 54.28 | N |
| ATOM | 429 | CA | LYS | A | 61 | 9.778 | 23.902 | 11.863 | 1.00 54.28 | C |
| ATOM | 430 | C | LYS | A | 61 | 10.870 | 23.222 | 11.028 | 1.00 54.28 | C |
| ATOM | 431 | O | LYS | A | 61 | 11.294 | 22.102 | 11.319 | 1.00 54.28 | O |
| ATOM | 432 | CB | LYS | A | 61 | 8.413 | 23.769 | 11.165 | 1.00 53.54 | C |
| ATOM | 433 | CG | LYS | A | 61 | 7.943 | 22.338 | 10.945 | 1.00 53.54 | C |
| ATOM | 434 | CD | LYS | A | 61 | 7.356 | 22.167 | 9.548 | 1.00 53.54 | C |
| ATOM | 435 | CE | LYS | A | 61 | 7.057 | 20.693 | 9.231 | 1.00 53.54 | C |
| ATOM | 436 | NZ | LYS | A | 61 | 8.259 | 19.782 | 9.328 | 1.00 53.54 | N |
| ATOM | 437 | N | LYS | A | 62 | 11.324 | 23.919 | 9.992 | 1.00 55.89 | N |
| ATOM | 438 | CA | LYS | A | 62 | 12.359 | 23.401 | 9.103 | 1.00 55.89 | C |
| ATOM | 439 | C | LYS | A | 62 | 13.716 | 23.356 | 9.784 | 1.00 55.89 | C |
| ATOM | 440 | O | LYS | A | 62 | 14.466 | 22.396 | 9.624 | 1.00 55.89 | O |
| ATOM | 441 | CB | LYS | A | 62 | 12.473 | 24.267 | 7.843 | 1.00 90.82 | C |

FIGURE 1-11

```
ATOM    442  CG   LYS A  62      11.240  24.274   6.954  1.00 90.82           C
ATOM    443  CD   LYS A  62      11.501  25.040   5.654  1.00 90.82           C
ATOM    444  CE   LYS A  62      12.551  24.348   4.783  1.00 90.82           C
ATOM    445  NZ   LYS A  62      12.107  22.996   4.325  1.00 90.82           N
ATOM    446  N    VAL A  63      14.035  24.403  10.539  1.00 51.21           N
ATOM    447  CA   VAL A  63      15.317  24.473  11.228  1.00 51.21           C
ATOM    448  C    VAL A  63      15.476  23.407  12.302  1.00 51.21           C
ATOM    449  O    VAL A  63      16.573  22.915  12.532  1.00 51.21           O
ATOM    450  CB   VAL A  63      15.508  25.834  11.897  1.00 72.29           C
ATOM    451  CG1  VAL A  63      16.841  25.867  12.624  1.00 72.29           C
ATOM    452  CG2  VAL A  63      15.427  26.933  10.854  1.00 72.29           C
ATOM    453  N    LEU A  64      14.379  23.063  12.967  1.00 55.82           N
ATOM    454  CA   LEU A  64      14.419  22.074  14.034  1.00 55.82           C
ATOM    455  C    LEU A  64      14.203  20.642  13.548  1.00 55.82           C
ATOM    456  O    LEU A  64      14.568  19.695  14.249  1.00 55.82           O
ATOM    457  CB   LEU A  64      13.359  22.413  15.088  1.00 42.64           C
ATOM    458  CG   LEU A  64      13.549  23.683  15.926  1.00 42.64           C
ATOM    459  CD1  LEU A  64      12.256  23.980  16.678  1.00 42.64           C
ATOM    460  CD2  LEU A  64      14.727  23.505  16.898  1.00 42.64           C
ATOM    461  N    SER A  65      13.616  20.490  12.358  1.00 57.55           N
ATOM    462  CA   SER A  65      13.320  19.167  11.793  1.00 57.55           C
ATOM    463  C    SER A  65      12.399  18.480  12.783  1.00 57.55           C
ATOM    464  O    SER A  65      12.774  17.504  13.423  1.00 57.55           O
ATOM    465  CB   SER A  65      14.596  18.336  11.626  1.00 69.01           C
ATOM    466  OG   SER A  65      15.462  18.903  10.657  1.00 69.01           O
ATOM    467  N    VAL A  66      11.185  18.998  12.900  1.00 48.95           N
ATOM    468  CA   VAL A  66      10.221  18.464  13.850  1.00 48.95           C
ATOM    469  C    VAL A  66       8.820  18.454  13.262  1.00 48.95           C
ATOM    470  O    VAL A  66       8.541  19.120  12.254  1.00 48.95           O
ATOM    471  CB   VAL A  66      10.229  19.329  15.144  1.00 70.40           C
ATOM    472  CG1  VAL A  66       9.074  18.956  16.050  1.00 70.40           C
ATOM    473  CG2  VAL A  66      11.561  19.155  15.879  1.00 70.40           C
ATOM    474  N    ASP A  67       7.944  17.676  13.885  1.00 54.83           N
ATOM    475  CA   ASP A  67       6.558  17.592  13.455  1.00 54.83           C
ATOM    476  C    ASP A  67       5.940  18.961  13.731  1.00 54.83           C
ATOM    477  O    ASP A  67       6.140  19.539  14.807  1.00 54.83           O
ATOM    478  CB   ASP A  67       5.821  16.516  14.259  1.00 69.23           C
ATOM    479  CG   ASP A  67       4.334  16.480  13.963  1.00 69.23           C
ATOM    480  OD1  ASP A  67       3.572  15.961  14.803  1.00 69.23           O
ATOM    481  OD2  ASP A  67       3.922  16.962  12.891  1.00 69.23           O
ATOM    482  N    LEU A  68       5.187  19.475  12.767  1.00 57.37           N
ATOM    483  CA   LEU A  68       4.567  20.776  12.933  1.00 57.37           C
ATOM    484  C    LEU A  68       3.620  20.750  14.123  1.00 57.37           C
ATOM    485  O    LEU A  68       3.573  21.694  14.913  1.00 57.37           O
ATOM    486  CB   LEU A  68       3.799  21.175  11.668  1.00 70.92           C
ATOM    487  CG   LEU A  68       3.297  22.624  11.655  1.00 70.92           C
ATOM    488  CD1  LEU A  68       4.489  23.553  11.713  1.00 70.92           C
ATOM    489  CD2  LEU A  68       2.473  22.900  10.410  1.00 70.92           C
ATOM    490  N    GLY A  69       2.871  19.661  14.249  1.00 42.69           N
ATOM    491  CA   GLY A  69       1.921  19.541  15.341  1.00 42.69           C
ATOM    492  C    GLY A  69       2.550  19.715  16.711  1.00 42.69           C
ATOM    493  O    GLY A  69       2.001  20.399  17.577  1.00 42.69           O
ATOM    494  N    ALA A  70       3.714  19.107  16.907  1.00 34.08           N
ATOM    495  CA   ALA A  70       4.401  19.180  18.192  1.00 34.08           C
ATOM    496  C    ALA A  70       5.008  20.556  18.412  1.00 34.08           C
ATOM    497  O    ALA A  70       5.237  20.961  19.549  1.00 34.08           O
ATOM    498  CB   ALA A  70       5.484  18.120  18.259  1.00 29.39           C
ATOM    499  N    LEU A  71       5.265  21.272  17.320  1.00 36.90           N
ATOM    500  CA   LEU A  71       5.846  22.605  17.401  1.00 36.90           C
ATOM    501  C    LEU A  71       4.790  23.591  17.883  1.00 36.90           C
ATOM    502  O    LEU A  71       5.045  24.420  18.768  1.00 36.90           O
ATOM    503  CB   LEU A  71       6.368  23.040  16.030  1.00 46.47           C
ATOM    504  CG   LEU A  71       7.126  24.370  16.062  1.00 46.47           C
ATOM    505  CD1  LEU A  71       8.395  24.172  16.864  1.00 46.47           C
ATOM    506  CD2  LEU A  71       7.444  24.845  14.654  1.00 46.47           C
ATOM    507  N    THR A  72       3.603  23.477  17.296  1.00 33.18           N
ATOM    508  CA   THR A  72       2.467  24.323  17.620  1.00 33.18           C
ATOM    509  C    THR A  72       2.140  24.230  19.093  1.00 33.18           C
ATOM    510  O    THR A  72       1.956  25.249  19.761  1.00 33.18           O
ATOM    511  CB   THR A  72       1.210  23.895  16.825  1.00 64.50           C
ATOM    512  OG1  THR A  72       1.554  23.697  15.448  1.00 64.50           O
ATOM    513  CG2  THR A  72       0.129  24.965  16.921  1.00 64.50           C
ATOM    514  N    ARG A  73       2.048  23.003  19.600  1.00 32.09           N
```

FIGURE 1-12

| | | | | | | | | | |
|---|---|---|---|---|---|---|---|---|---|
| ATOM | 515 | CA | ARG A | 73 | 1.749 | 22.803 | 21.016 | 1.00 32.09 | C |
| ATOM | 516 | C | ARG A | 73 | 2.917 | 23.358 | 21.808 | 1.00 32.09 | C |
| ATOM | 517 | O | ARG A | 73 | 2.734 | 23.989 | 22.834 | 1.00 32.09 | O |
| ATOM | 518 | CB | ARG A | 73 | 1.558 | 21.309 | 21.343 | 1.00 47.77 | C |
| ATOM | 519 | CG | ARG A | 73 | 0.393 | 20.651 | 20.620 | 1.00 47.77 | C |
| ATOM | 520 | CD | ARG A | 73 | -0.084 | 19.386 | 21.337 | 1.00 47.77 | C |
| ATOM | 521 | NE | ARG A | 73 | 0.966 | 18.382 | 21.494 | 1.00 47.77 | N |
| ATOM | 522 | CZ | ARG A | 73 | 1.445 | 17.634 | 20.504 | 1.00 47.77 | C |
| ATOM | 523 | NH1 | ARG A | 73 | 0.973 | 17.766 | 19.269 | 1.00 47.77 | N |
| ATOM | 524 | NH2 | ARG A | 73 | 2.399 | 16.747 | 20.748 | 1.00 47.77 | N |
| ATOM | 525 | N | MET A | 74 | 4.122 | 23.114 | 21.312 | 1.00 37.17 | N |
| ATOM | 526 | CA | MET A | 74 | 5.341 | 23.599 | 21.954 | 1.00 37.17 | C |
| ATOM | 527 | C | MET A | 74 | 5.328 | 25.131 | 22.049 | 1.00 37.17 | C |
| ATOM | 528 | O | MET A | 74 | 5.598 | 25.709 | 23.109 | 1.00 37.17 | O |
| ATOM | 529 | CB | MET A | 74 | 6.566 | 23.155 | 21.144 | 1.00 41.38 | C |
| ATOM | 530 | CG | MET A | 74 | 7.852 | 23.892 | 21.493 | 1.00 41.38 | C |
| ATOM | 531 | SD | MET A | 74 | 8.444 | 23.481 | 23.126 | 1.00 41.38 | S |
| ATOM | 532 | CE | MET A | 74 | 9.524 | 22.058 | 22.712 | 1.00 41.38 | C |
| ATOM | 533 | N | LEU A | 75 | 5.021 | 25.787 | 20.934 | 1.00 30.84 | N |
| ATOM | 534 | CA | LEU A | 75 | 5.001 | 27.240 | 20.930 | 1.00 30.84 | C |
| ATOM | 535 | C | LEU A | 75 | 3.944 | 27.762 | 21.910 | 1.00 30.84 | C |
| ATOM | 536 | O | LEU A | 75 | 4.182 | 28.744 | 22.628 | 1.00 30.84 | O |
| ATOM | 537 | CB | LEU A | 75 | 4.770 | 27.755 | 19.506 | 1.00 25.28 | C |
| ATOM | 538 | CG | LEU A | 75 | 5.960 | 27.583 | 18.535 | 1.00 25.28 | C |
| ATOM | 539 | CD1 | LEU A | 75 | 5.565 | 28.044 | 17.136 | 1.00 25.28 | C |
| ATOM | 540 | CD2 | LEU A | 75 | 7.150 | 28.427 | 19.001 | 1.00 25.28 | C |
| ATOM | 541 | N | ASP A | 76 | 2.795 | 27.084 | 21.971 | 1.00 31.28 | N |
| ATOM | 542 | CA | ASP A | 76 | 1.734 | 27.500 | 22.888 | 1.00 31.28 | C |
| ATOM | 543 | C | ASP A | 76 | 2.203 | 27.312 | 24.323 | 1.00 31.28 | C |
| ATOM | 544 | O | ASP A | 76 | 1.954 | 28.161 | 25.167 | 1.00 31.28 | O |
| ATOM | 545 | CB | ASP A | 76 | 0.445 | 26.703 | 22.661 | 1.00 35.21 | C |
| ATOM | 546 | CG | ASP A | 76 | -0.433 | 27.287 | 21.544 | 1.00 35.21 | C |
| ATOM | 547 | OD1 | ASP A | 76 | -0.126 | 28.381 | 21.008 | 1.00 35.21 | O |
| ATOM | 548 | OD2 | ASP A | 76 | -1.451 | 26.643 | 21.211 | 1.00 35.21 | O |
| ATOM | 549 | N | ARG A | 77 | 2.874 | 26.205 | 24.618 | 1.00 31.46 | N |
| ATOM | 550 | CA | ARG A | 77 | 3.355 | 26.008 | 25.980 | 1.00 31.46 | C |
| ATOM | 551 | C | ARG A | 77 | 4.351 | 27.119 | 26.322 | 1.00 31.46 | C |
| ATOM | 552 | O | ARG A | 77 | 4.332 | 27.665 | 27.422 | 1.00 31.46 | O |
| ATOM | 553 | CB | ARG A | 77 | 4.031 | 24.640 | 26.134 | 1.00 37.99 | C |
| ATOM | 554 | CG | ARG A | 77 | 4.678 | 24.387 | 27.497 | 1.00 37.99 | C |
| ATOM | 555 | CD | ARG A | 77 | 3.701 | 24.641 | 28.652 | 1.00 37.99 | C |
| ATOM | 556 | NE | ARG A | 77 | 2.503 | 23.796 | 28.598 | 1.00 37.99 | N |
| ATOM | 557 | CZ | ARG A | 77 | 2.490 | 22.492 | 28.858 | 1.00 37.99 | C |
| ATOM | 558 | NH1 | ARG A | 77 | 3.617 | 21.869 | 29.192 | 1.00 37.99 | N |
| ATOM | 559 | NH2 | ARG A | 77 | 1.353 | 21.809 | 28.799 | 1.00 37.99 | N |
| ATOM | 560 | N | LEU A | 78 | 5.221 | 27.462 | 25.380 | 1.00 29.78 | N |
| ATOM | 561 | CA | LEU A | 78 | 6.216 | 28.507 | 25.645 | 1.00 29.78 | C |
| ATOM | 562 | C | LEU A | 78 | 5.564 | 29.868 | 25.889 | 1.00 29.78 | C |
| ATOM | 563 | O | LEU A | 78 | 6.054 | 30.661 | 26.695 | 1.00 29.78 | O |
| ATOM | 564 | CB | LEU A | 78 | 7.228 | 28.574 | 24.494 | 1.00 25.32 | C |
| ATOM | 565 | CG | LEU A | 78 | 8.171 | 27.356 | 24.470 | 1.00 25.32 | C |
| ATOM | 566 | CD1 | LEU A | 78 | 9.043 | 27.324 | 23.235 | 1.00 25.32 | C |
| ATOM | 567 | CD2 | LEU A | 78 | 9.009 | 27.399 | 25.725 | 1.00 25.32 | C |
| ATOM | 568 | N | VAL A | 79 | 4.460 | 30.145 | 25.199 | 1.00 31.60 | N |
| ATOM | 569 | CA | VAL A | 79 | 3.759 | 31.412 | 25.412 | 1.00 31.60 | C |
| ATOM | 570 | C | VAL A | 79 | 3.161 | 31.379 | 26.815 | 1.00 31.60 | C |
| ATOM | 571 | O | VAL A | 79 | 3.244 | 32.367 | 27.536 | 1.00 31.60 | O |
| ATOM | 572 | CB | VAL A | 79 | 2.641 | 31.623 | 24.370 | 1.00 28.89 | C |
| ATOM | 573 | CG1 | VAL A | 79 | 1.816 | 32.851 | 24.709 | 1.00 28.89 | C |
| ATOM | 574 | CG2 | VAL A | 79 | 3.271 | 31.765 | 22.982 | 1.00 28.89 | C |
| ATOM | 575 | N | CYS A | 80 | 2.588 | 30.235 | 27.214 | 1.00 35.75 | N |
| ATOM | 576 | CA | CYS A | 80 | 2.011 | 30.091 | 28.560 | 1.00 35.75 | C |
| ATOM | 577 | C | CYS A | 80 | 3.069 | 30.345 | 29.628 | 1.00 35.75 | C |
| ATOM | 578 | O | CYS A | 80 | 2.763 | 30.825 | 30.722 | 1.00 35.75 | O |
| ATOM | 579 | CB | CYS A | 80 | 1.448 | 28.686 | 28.787 | 1.00 46.08 | C |
| ATOM | 580 | SG | CYS A | 80 | -0.183 | 28.381 | 28.120 | 1.00 46.08 | S |
| ATOM | 581 | N | LYS A | 81 | 4.311 | 29.996 | 29.331 | 1.00 40.46 | N |
| ATOM | 582 | CA | LYS A | 81 | 5.372 | 30.215 | 30.299 | 1.00 40.46 | C |
| ATOM | 583 | C | LYS A | 81 | 5.877 | 31.658 | 30.213 | 1.00 40.46 | C |
| ATOM | 584 | O | LYS A | 81 | 6.719 | 32.082 | 31.014 | 1.00 40.46 | O |
| ATOM | 585 | CB | LYS A | 81 | 6.518 | 29.233 | 30.057 | 1.00 28.93 | C |
| ATOM | 586 | CG | LYS A | 81 | 6.207 | 27.809 | 30.479 | 1.00 28.93 | C |
| ATOM | 587 | CD | LYS A | 81 | 7.410 | 26.901 | 30.212 | 1.00 28.93 | C |

FIGURE 1-13

```
ATOM    588  CE  LYS A  81       7.281  25.556  30.910  1.00 28.93           C
ATOM    589  NZ  LYS A  81       8.603  24.910  31.080  1.00 28.93           N
ATOM    590  N   GLY A  82       5.350  32.406  29.244  1.00 34.82           N
ATOM    591  CA  GLY A  82       5.755  33.794  29.074  1.00 34.82           C
ATOM    592  C   GLY A  82       7.146  33.950  28.468  1.00 34.82           C
ATOM    593  O   GLY A  82       7.778  34.999  28.604  1.00 34.82           O
ATOM    594  N   TRP A  83       7.632  32.914  27.786  1.00 32.56           N
ATOM    595  CA  TRP A  83       8.956  32.985  27.198  1.00 32.56           C
ATOM    596  C   TRP A  83       8.961  33.366  25.730  1.00 32.56           C
ATOM    597  O   TRP A  83       9.981  33.799  25.209  1.00 32.56           O
ATOM    598  CB  TRP A  83       9.683  31.649  27.365  1.00 37.53           C
ATOM    599  CG  TRP A  83       9.919  31.242  28.782  1.00 37.53           C
ATOM    600  CD1 TRP A  83       9.854  32.040  29.884  1.00 37.53           C
ATOM    601  CD2 TRP A  83      10.243  29.929  29.253  1.00 37.53           C
ATOM    602  NE1 TRP A  83      10.111  31.307  31.018  1.00 37.53           N
ATOM    603  CE2 TRP A  83      10.353  30.006  30.660  1.00 37.53           C
ATOM    604  CE3 TRP A  83      10.448  28.696  28.625  1.00 37.53           C
ATOM    605  CZ2 TRP A  83      10.658  28.897  31.454  1.00 37.53           C
ATOM    606  CZ3 TRP A  83      10.755  27.584  29.415  1.00 37.53           C
ATOM    607  CH2 TRP A  83      10.856  27.695  30.817  1.00 37.53           C
ATOM    608  N   VAL A  84       7.822  33.218  25.062  1.00 30.33           N
ATOM    609  CA  VAL A  84       7.727  33.519  23.640  1.00 30.33           C
ATOM    610  C   VAL A  84       6.473  34.323  23.329  1.00 30.33           C
ATOM    611  O   VAL A  84       5.472  34.212  24.034  1.00 30.33           O
ATOM    612  CB  VAL A  84       7.703  32.198  22.825  1.00 28.67           C
ATOM    613  CG1 VAL A  84       7.370  32.466  21.374  1.00 28.67           C
ATOM    614  CG2 VAL A  84       9.051  31.487  22.946  1.00 28.67           C
ATOM    615  N   GLU A  85       6.532  35.145  22.287  1.00 32.27           N
ATOM    616  CA  GLU A  85       5.373  35.931  21.891  1.00 32.27           C
ATOM    617  C   GLU A  85       5.314  35.967  20.373  1.00 32.27           C
ATOM    618  O   GLU A  85       6.344  35.837  19.694  1.00 32.27           O
ATOM    619  CB  GLU A  85       5.428  37.355  22.470  1.00 48.71           C
ATOM    620  CG  GLU A  85       6.386  38.324  21.809  1.00 48.71           C
ATOM    621  CD  GLU A  85       6.466  39.642  22.578  1.00 48.71           C
ATOM    622  OE1 GLU A  85       6.858  39.604  23.753  1.00 48.71           O
ATOM    623  OE2 GLU A  85       6.134  40.719  22.031  1.00 48.71           O
ATOM    624  N   ARG A  86       4.101  36.129  19.862  1.00 41.63           N
ATOM    625  CA  ARG A  86       3.823  36.156  18.436  1.00 41.63           C
ATOM    626  C   ARG A  86       3.509  37.557  17.913  1.00 41.63           C
ATOM    627  O   ARG A  86       2.742  38.307  18.525  1.00 41.63           O
ATOM    628  CB  ARG A  86       2.625  35.255  18.156  1.00 42.32           C
ATOM    629  CG  ARG A  86       2.826  34.245  17.066  1.00 42.32           C
ATOM    630  CD  ARG A  86       1.630  33.345  17.037  1.00 42.32           C
ATOM    631  NE  ARG A  86       1.424  32.786  18.363  1.00 42.32           N
ATOM    632  CZ  ARG A  86       1.572  31.503  18.679  1.00 42.32           C
ATOM    633  NH1 ARG A  86       1.923  30.627  17.753  1.00 42.32           N
ATOM    634  NH2 ARG A  86       1.377  31.105  19.932  1.00 42.32           N
ATOM    635  N   LEU A  87       4.095  37.909  16.775  1.00 39.77           N
ATOM    636  CA  LEU A  87       3.826  39.209  16.180  1.00 39.77           C
ATOM    637  C   LEU A  87       3.519  39.000  14.703  1.00 39.77           C
ATOM    638  O   LEU A  87       3.853  37.963  14.131  1.00 39.77           O
ATOM    639  CB  LEU A  87       5.018  40.151  16.333  1.00 48.09           C
ATOM    640  CG  LEU A  87       6.305  39.730  15.630  1.00 48.09           C
ATOM    641  CD1 LEU A  87       7.061  40.968  15.171  1.00 48.09           C
ATOM    642  CD2 LEU A  87       7.156  38.884  16.578  1.00 48.09           C
ATOM    643  N   PRO A  88       2.860  39.983  14.070  1.00 54.80           N
ATOM    644  CA  PRO A  88       2.522  39.864  12.649  1.00 54.80           C
ATOM    645  C   PRO A  88       3.785  39.853  11.804  1.00 54.80           C
ATOM    646  O   PRO A  88       4.753  40.548  12.119  1.00 54.80           O
ATOM    647  CB  PRO A  88       1.661  41.101  12.392  1.00 66.77           C
ATOM    648  CG  PRO A  88       1.049  41.386  13.751  1.00 66.77           C
ATOM    649  CD  PRO A  88       2.235  41.180  14.661  1.00 66.77           C
ATOM    650  N   ASN A  89       3.785  39.046  10.748  1.00 61.50           N
ATOM    651  CA  ASN A  89       4.938  38.963   9.860  1.00 61.50           C
ATOM    652  C   ASN A  89       4.808  40.089   8.839  1.00 61.50           C
ATOM    653  O   ASN A  89       3.838  40.145   8.089  1.00 61.50           O
ATOM    654  CB  ASN A  89       4.973  37.609   9.139  1.00 63.20           C
ATOM    655  CG  ASN A  89       6.230  37.427   8.298  1.00 63.20           C
ATOM    656  OD1 ASN A  89       6.643  38.335   7.585  1.00 63.20           O
ATOM    657  ND2 ASN A  89       6.837  36.249   8.372  1.00 63.20           N
ATOM    658  N   PRO A  90       5.779  41.015   8.815  1.00 66.40           N
ATOM    659  CA  PRO A  90       5.762  42.142   7.878  1.00 66.40           C
ATOM    660  C   PRO A  90       5.812  41.709   6.415  1.00 66.40           C
```

FIGURE 1-14

```
ATOM    661  O    PRO A  90       4.973  42.114   5.613  1.00 66.40           O
ATOM    662  CB   PRO A  90       6.993  42.944   8.288  1.00 66.93           C
ATOM    663  CG   PRO A  90       7.079  42.679   9.759  1.00 66.93           C
ATOM    664  CD   PRO A  90       6.854  41.187   9.805  1.00 66.93           C
ATOM    665  N    ASN A  91       6.794  40.881   6.074  1.00 79.71           N
ATOM    666  CA   ASN A  91       6.944  40.391   4.705  1.00 79.71           C
ATOM    667  C    ASN A  91       5.781  39.490   4.271  1.00 79.71           C
ATOM    668  O    ASN A  91       5.840  38.856   3.216  1.00 79.71           O
ATOM    669  CB   ASN A  91       8.266  39.628   4.556  1.00119.06           C
ATOM    670  CG   ASN A  91       9.477  40.490   4.867  1.00119.06           C
ATOM    671  OD1  ASN A  91       9.685  41.537   4.251  1.00119.06           O
ATOM    672  ND2  ASN A  91      10.284  40.051   5.826  1.00119.06           N
ATOM    673  N    ASP A  92       4.736  39.430   5.093  1.00 89.89           N
ATOM    674  CA   ASP A  92       3.551  38.631   4.792  1.00 89.89           C
ATOM    675  C    ASP A  92       2.332  39.408   5.282  1.00 89.89           C
ATOM    676  O    ASP A  92       2.299  40.635   5.183  1.00 89.89           O
ATOM    677  CB   ASP A  92       3.627  37.262   5.483  1.00 66.82           C
ATOM    678  CG   ASP A  92       2.587  36.275   4.955  1.00 66.82           C
ATOM    679  OD1  ASP A  92       2.716  35.061   5.229  1.00 66.82           O
ATOM    680  OD2  ASP A  92       1.637  36.709   4.272  1.00 66.82           O
ATOM    681  N    LYS A  93       1.339  38.700   5.813  1.00 72.63           N
ATOM    682  CA   LYS A  93       0.124  39.337   6.317  1.00 72.63           C
ATOM    683  C    LYS A  93      -0.865  38.247   6.700  1.00 72.63           C
ATOM    684  O    LYS A  93      -1.854  38.496   7.387  1.00 72.63           O
ATOM    685  CB   LYS A  93      -0.486  40.247   5.244  1.00 83.15           C
ATOM    686  CG   LYS A  93      -1.673  41.088   5.699  1.00 83.15           C
ATOM    687  CD   LYS A  93      -1.307  42.071   6.811  1.00 83.15           C
ATOM    688  CE   LYS A  93      -1.321  41.416   8.191  1.00 83.15           C
ATOM    689  NZ   LYS A  93      -1.016  42.381   9.286  1.00 83.15           N
ATOM    690  N    ARG A  94      -0.581  37.034   6.240  1.00 58.78           N
ATOM    691  CA   ARG A  94      -1.414  35.878   6.527  1.00 58.78           C
ATOM    692  C    ARG A  94      -0.651  35.036   7.546  1.00 58.78           C
ATOM    693  O    ARG A  94      -1.072  33.943   7.913  1.00 58.78           O
ATOM    694  CB   ARG A  94      -1.639  35.066   5.246  1.00 92.71           C
ATOM    695  CG   ARG A  94      -2.651  33.937   5.385  1.00 92.71           C
ATOM    696  CD   ARG A  94      -4.081  34.467   5.370  1.00 92.71           C
ATOM    697  NE   ARG A  94      -4.493  34.880   4.032  1.00 92.71           N
ATOM    698  CZ   ARG A  94      -4.746  34.035   3.039  1.00 92.71           C
ATOM    699  NH1  ARG A  94      -4.634  32.728   3.236  1.00 92.71           N
ATOM    700  NH2  ARG A  94      -5.091  34.497   1.844  1.00 92.71           N
ATOM    701  N    GLY A  95       0.479  35.562   8.005  1.00 44.29           N
ATOM    702  CA   GLY A  95       1.294  34.827   8.954  1.00 44.29           C
ATOM    703  C    GLY A  95       1.842  35.630  10.111  1.00 44.29           C
ATOM    704  O    GLY A  95       1.608  36.836  10.228  1.00 44.29           O
ATOM    705  N    VAL A  96       2.580  34.949  10.978  1.00 40.14           N
ATOM    706  CA   VAL A  96       3.159  35.592  12.143  1.00 40.14           C
ATOM    707  C    VAL A  96       4.587  35.156  12.346  1.00 40.14           C
ATOM    708  O    VAL A  96       5.074  34.230  11.689  1.00 40.14           O
ATOM    709  CB   VAL A  96       2.387  35.253  13.441  1.00 35.66           C
ATOM    710  CG1  VAL A  96       0.964  35.734  13.329  1.00 35.66           C
ATOM    711  CG2  VAL A  96       2.439  33.759  13.718  1.00 35.66           C
ATOM    712  N    LEU A  97       5.256  35.838  13.263  1.00 30.82           N
ATOM    713  CA   LEU A  97       6.631  35.530  13.591  1.00 30.82           C
ATOM    714  C    LEU A  97       6.568  35.265  15.078  1.00 30.82           C
ATOM    715  O    LEU A  97       5.615  35.665  15.752  1.00 30.82           O
ATOM    716  CB   LEU A  97       7.560  36.736  13.335  1.00 43.64           C
ATOM    717  CG   LEU A  97       7.811  37.285  11.917  1.00 43.64           C
ATOM    718  CD1  LEU A  97       8.354  38.693  12.030  1.00 43.64           C
ATOM    719  CD2  LEU A  97       8.795  36.407  11.137  1.00 43.64           C
ATOM    720  N    VAL A  98       7.570  34.577  15.590  1.00 40.02           N
ATOM    721  CA   VAL A  98       7.614  34.333  17.007  1.00 40.02           C
ATOM    722  C    VAL A  98       8.980  34.805  17.425  1.00 40.02           C
ATOM    723  O    VAL A  98       9.962  34.607  16.704  1.00 40.02           O
ATOM    724  CB   VAL A  98       7.442  32.836  17.356  1.00 33.09           C
ATOM    725  CG1  VAL A  98       6.027  32.355  16.945  1.00 33.09           C
ATOM    726  CG2  VAL A  98       8.519  32.015  16.669  1.00 33.09           C
ATOM    727  N    LYS A  99       9.035  35.472  18.568  1.00 35.95           N
ATOM    728  CA   LYS A  99      10.295  35.956  19.100  1.00 35.95           C
ATOM    729  C    LYS A  99      10.212  35.734  20.593  1.00 35.95           C
ATOM    730  O    LYS A  99       9.127  35.487  21.137  1.00 35.95           O
ATOM    731  CB   LYS A  99      10.461  37.444  18.793  1.00 43.93           C
ATOM    732  CG   LYS A  99       9.512  38.352  19.556  1.00 43.93           C
ATOM    733  CD   LYS A  99       9.590  39.769  19.029  1.00 43.93           C
```

FIGURE 1-15

```
ATOM    734  CE  LYS A  99       9.757  40.761  20.153  1.00 43.93           C
ATOM    735  NZ  LYS A  99      11.015  40.516  20.922  1.00 43.93           N
ATOM    736  N   LEU A 100      11.349  35.823  21.262  1.00 44.66           N
ATOM    737  CA  LEU A 100      11.378  35.640  22.696  1.00 44.66           C
ATOM    738  C   LEU A 100      10.928  36.902  23.401  1.00 44.66           C
ATOM    739  O   LEU A 100      11.148  38.006  22.914  1.00 44.66           O
ATOM    740  CB  LEU A 100      12.791  35.312  23.158  1.00 32.99           C
ATOM    741  CG  LEU A 100      13.480  34.081  22.554  1.00 32.99           C
ATOM    742  CD1 LEU A 100      14.715  33.774  23.409  1.00 32.99           C
ATOM    743  CD2 LEU A 100      12.517  32.864  22.532  1.00 32.99           C
ATOM    744  N   THR A 101      10.276  36.737  24.543  1.00 38.68           N
ATOM    745  CA  THR A 101       9.871  37.886  25.332  1.00 38.68           C
ATOM    746  C   THR A 101      11.131  38.172  26.167  1.00 38.68           C
ATOM    747  O   THR A 101      12.059  37.348  26.179  1.00 38.68           O
ATOM    748  CB  THR A 101       8.708  37.523  26.256  1.00 35.09           C
ATOM    749  OG1 THR A 101       9.092  36.406  27.073  1.00 35.09           O
ATOM    750  CG2 THR A 101       7.474  37.153  25.449  1.00 35.09           C
ATOM    751  N   THR A 102      11.183  39.310  26.857  1.00 50.83           N
ATOM    752  CA  THR A 102      12.364  39.638  27.673  1.00 50.83           C
ATOM    753  C   THR A 102      12.678  38.510  28.647  1.00 50.83           C
ATOM    754  O   THR A 102      13.816  38.061  28.745  1.00 50.83           O
ATOM    755  CB  THR A 102      12.168  40.931  28.506  1.00 38.42           C
ATOM    756  OG1 THR A 102      11.800  42.012  27.645  1.00 38.42           O
ATOM    757  CG2 THR A 102      13.470  41.293  29.231  1.00 38.42           C
ATOM    758  N   GLY A 103      11.665  38.065  29.381  1.00 42.94           N
ATOM    759  CA  GLY A 103      11.872  36.976  30.312  1.00 42.94           C
ATOM    760  C   GLY A 103      12.371  35.723  29.602  1.00 42.94           C
ATOM    761  O   GLY A 103      13.289  35.053  30.082  1.00 42.94           O
ATOM    762  N   GLY A 104      11.762  35.404  28.459  1.00 38.70           N
ATOM    763  CA  GLY A 104      12.178  34.234  27.707  1.00 38.70           C
ATOM    764  C   GLY A 104      13.656  34.336  27.384  1.00 38.70           C
ATOM    765  O   GLY A 104      14.398  33.359  27.510  1.00 38.70           O
ATOM    766  N   ALA A 105      14.076  35.534  26.979  1.00 47.24           N
ATOM    767  CA  ALA A 105      15.471  35.799  26.634  1.00 47.24           C
ATOM    768  C   ALA A 105      16.390  35.514  27.812  1.00 47.24           C
ATOM    769  O   ALA A 105      17.438  34.893  27.650  1.00 47.24           O
ATOM    770  CB  ALA A 105      15.634  37.256  26.183  1.00 42.30           C
ATOM    771  N   ALA A 106      15.989  35.967  28.997  1.00 52.11           N
ATOM    772  CA  ALA A 106      16.778  35.763  30.201  1.00 52.11           C
ATOM    773  C   ALA A 106      16.876  34.267  30.503  1.00 52.11           C
ATOM    774  O   ALA A 106      17.966  33.730  30.719  1.00 52.11           O
ATOM    775  CB  ALA A 106      16.141  36.505  31.372  1.00 50.48           C
ATOM    776  N   ILE A 107      15.735  33.592  30.519  1.00 47.20           N
ATOM    777  CA  ILE A 107      15.731  32.160  30.772  1.00 47.20           C
ATOM    778  C   ILE A 107      16.728  31.464  29.818  1.00 47.20           C
ATOM    779  O   ILE A 107      17.558  30.652  30.241  1.00 47.20           O
ATOM    780  CB  ILE A 107      14.325  31.563  30.528  1.00 46.42           C
ATOM    781  CG1 ILE A 107      13.312  32.166  31.507  1.00 46.42           C
ATOM    782  CG2 ILE A 107      14.380  30.052  30.642  1.00 46.42           C
ATOM    783  CD1 ILE A 107      13.619  31.905  32.956  1.00 46.42           C
ATOM    784  N   CYS A 108      16.637  31.789  28.531  1.00 55.20           N
ATOM    785  CA  CYS A 108      17.508  31.187  27.526  1.00 55.20           C
ATOM    786  C   CYS A 108      18.981  31.472  27.763  1.00 55.20           C
ATOM    787  O   CYS A 108      19.839  30.689  27.346  1.00 55.20           O
ATOM    788  CB  CYS A 108      17.126  31.665  26.125  1.00 50.25           C
ATOM    789  SG  CYS A 108      18.283  31.139  24.836  1.00 50.25           S
ATOM    790  N   GLU A 109      19.275  32.590  28.425  1.00 53.61           N
ATOM    791  CA  GLU A 109      20.660  32.952  28.708  1.00 53.61           C
ATOM    792  C   GLU A 109      21.128  32.294  30.007  1.00 53.61           C
ATOM    793  O   GLU A 109      22.275  31.864  30.109  1.00 53.61           O
ATOM    794  CB  GLU A 109      20.813  34.472  28.795  1.00109.75           C
ATOM    795  CG  GLU A 109      22.263  34.944  28.795  1.00109.75           C
ATOM    796  CD  GLU A 109      23.044  34.423  27.598  1.00109.75           C
ATOM    797  OE1 GLU A 109      22.620  34.679  26.453  1.00109.75           O
ATOM    798  OE2 GLU A 109      24.084  33.759  27.799  1.00109.75           O
ATOM    799  N   GLN A 110      20.253  32.211  31.002  1.00 70.78           N
ATOM    800  CA  GLN A 110      20.635  31.560  32.249  1.00 70.78           C
ATOM    801  C   GLN A 110      21.020  30.123  31.918  1.00 70.78           C
ATOM    802  O   GLN A 110      22.045  29.621  32.382  1.00 70.78           O
ATOM    803  CB  GLN A 110      19.476  31.522  33.240  1.00 56.91           C
ATOM    804  CG  GLN A 110      19.214  32.789  34.020  1.00 56.91           C
ATOM    805  CD  GLN A 110      17.892  32.707  34.780  1.00 56.91           C
ATOM    806  OE1 GLN A 110      17.620  31.722  35.481  1.00 56.91           O
```

FIGURE 1-16

| | | | | | | | | | |
|---|---|---|---|---|---|---|---|---|---|
| ATOM | 807 | NE2 | GLN | A | 110 | 17.063 | 33.738 | 34.640 | 1.00 56.91 | N |
| ATOM | 808 | N | CYS | A | 111 | 20.180 | 29.471 | 31.116 | 1.00 60.37 | N |
| ATOM | 809 | CA | CYS | A | 111 | 20.397 | 28.087 | 30.714 | 1.00 60.37 | C |
| ATOM | 810 | C | CYS | A | 111 | 21.614 | 27.911 | 29.822 | 1.00 60.37 | C |
| ATOM | 811 | O | CYS | A | 111 | 22.456 | 27.047 | 30.077 | 1.00 60.37 | O |
| ATOM | 812 | CB | CYS | A | 111 | 19.177 | 27.546 | 29.964 | 1.00 52.09 | C |
| ATOM | 813 | SG | CYS | A | 111 | 17.688 | 27.268 | 30.941 | 1.00 52.09 | S |
| ATOM | 814 | N | HIS | A | 112 | 21.693 | 28.716 | 28.767 | 1.00 61.76 | N |
| ATOM | 815 | CA | HIS | A | 112 | 22.801 | 28.632 | 27.818 | 1.00 61.76 | C |
| ATOM | 816 | C | HIS | A | 112 | 24.160 | 28.735 | 28.502 | 1.00 61.76 | C |
| ATOM | 817 | O | HIS | A | 112 | 25.108 | 28.032 | 28.138 | 1.00 61.76 | O |
| ATOM | 818 | CB | HIS | A | 112 | 22.663 | 29.727 | 26.762 | 1.00 68.17 | C |
| ATOM | 819 | CG | HIS | A | 112 | 23.616 | 29.585 | 25.617 | 1.00 68.17 | C |
| ATOM | 820 | ND1 | HIS | A | 112 | 24.964 | 29.851 | 25.730 | 1.00 68.17 | N |
| ATOM | 821 | CD2 | HIS | A | 112 | 23.416 | 29.199 | 24.335 | 1.00 68.17 | C |
| ATOM | 822 | CE1 | HIS | A | 112 | 25.552 | 29.637 | 24.567 | 1.00 68.17 | C |
| ATOM | 823 | NE2 | HIS | A | 112 | 24.634 | 29.240 | 23.704 | 1.00 68.17 | N |
| ATOM | 824 | N | GLN | A | 113 | 24.243 | 29.603 | 29.503 | 1.00 60.30 | N |
| ATOM | 825 | CA | GLN | A | 113 | 25.480 | 29.792 | 30.240 | 1.00 60.30 | C |
| ATOM | 826 | C | GLN | A | 113 | 25.812 | 28.603 | 31.125 | 1.00 60.30 | C |
| ATOM | 827 | O | GLN | A | 113 | 26.940 | 28.117 | 31.105 | 1.00 60.30 | O |
| ATOM | 828 | CB | GLN | A | 113 | 25.406 | 31.059 | 31.093 | 1.00102.85 | C |
| ATOM | 829 | CG | GLN | A | 113 | 25.241 | 32.328 | 30.281 | 1.00102.85 | C |
| ATOM | 830 | CD | GLN | A | 113 | 25.367 | 33.575 | 31.125 | 1.00102.85 | C |
| ATOM | 831 | OE1 | GLN | A | 113 | 24.708 | 33.707 | 32.155 | 1.00102.85 | O |
| ATOM | 832 | NE2 | GLN | A | 113 | 26.212 | 34.503 | 30.689 | 1.00102.85 | N |
| ATOM | 833 | N | LEU | A | 114 | 24.836 | 28.132 | 31.896 | 1.00 64.71 | N |
| ATOM | 834 | CA | LEU | A | 114 | 25.057 | 27.001 | 32.798 | 1.00 64.71 | C |
| ATOM | 835 | C | LEU | A | 114 | 25.417 | 25.713 | 32.056 | 1.00 64.71 | C |
| ATOM | 836 | O | LEU | A | 114 | 26.468 | 25.123 | 32.295 | 1.00 64.71 | O |
| ATOM | 837 | CB | LEU | A | 114 | 23.819 | 26.766 | 33.671 | 1.00 66.45 | C |
| ATOM | 838 | CG | LEU | A | 114 | 23.238 | 28.013 | 34.349 | 1.00 66.45 | C |
| ATOM | 839 | CD1 | LEU | A | 114 | 22.189 | 27.587 | 35.387 | 1.00 66.45 | C |
| ATOM | 840 | CD2 | LEU | A | 114 | 24.353 | 28.830 | 35.002 | 1.00 66.45 | C |
| ATOM | 841 | N | VAL | A | 115 | 24.545 | 25.272 | 31.160 | 1.00115.02 | N |
| ATOM | 842 | CA | VAL | A | 115 | 24.811 | 24.054 | 30.412 | 1.00115.02 | C |
| ATOM | 843 | C | VAL | A | 115 | 26.134 | 24.163 | 29.661 | 1.00115.02 | C |
| ATOM | 844 | O | VAL | A | 115 | 26.908 | 23.206 | 29.606 | 1.00115.02 | O |
| ATOM | 845 | CB | VAL | A | 115 | 23.670 | 23.755 | 29.420 | 1.00 64.88 | C |
| ATOM | 846 | CG1 | VAL | A | 115 | 24.073 | 22.627 | 28.477 | 1.00 64.88 | C |
| ATOM | 847 | CG2 | VAL | A | 115 | 22.409 | 23.383 | 30.194 | 1.00 64.88 | C |
| ATOM | 848 | N | GLY | A | 116 | 26.393 | 25.335 | 29.089 | 1.00119.74 | N |
| ATOM | 849 | CA | GLY | A | 116 | 27.629 | 25.538 | 28.358 | 1.00119.74 | C |
| ATOM | 850 | C | GLY | A | 116 | 28.847 | 25.403 | 29.253 | 1.00119.74 | C |
| ATOM | 851 | O | GLY | A | 116 | 29.936 | 25.088 | 28.779 | 1.00119.74 | O |
| ATOM | 852 | N | GLN | A | 117 | 28.661 | 25.636 | 30.549 | 1.00 73.12 | N |
| ATOM | 853 | CA | GLN | A | 117 | 29.750 | 25.546 | 31.523 | 1.00 73.12 | C |
| ATOM | 854 | C | GLN | A | 117 | 29.944 | 24.137 | 32.084 | 1.00 73.12 | C |
| ATOM | 855 | O | GLN | A | 117 | 31.019 | 23.815 | 32.587 | 1.00 73.12 | O |
| ATOM | 856 | CB | GLN | A | 117 | 29.504 | 26.520 | 32.678 | 1.00 96.60 | C |
| ATOM | 857 | CG | GLN | A | 117 | 29.577 | 27.984 | 32.282 | 1.00 96.60 | C |
| ATOM | 858 | CD | GLN | A | 117 | 29.080 | 28.919 | 33.374 | 1.00 96.60 | C |
| ATOM | 859 | OE1 | GLN | A | 117 | 29.094 | 30.141 | 33.215 | 1.00 96.60 | O |
| ATOM | 860 | NE2 | GLN | A | 117 | 28.632 | 28.347 | 34.488 | 1.00 96.60 | N |
| ATOM | 861 | N | ASP | A | 118 | 28.905 | 23.308 | 32.006 | 1.00 69.89 | N |
| ATOM | 862 | CA | ASP | A | 118 | 28.981 | 21.937 | 32.507 | 1.00 69.89 | C |
| ATOM | 863 | C | ASP | A | 118 | 29.402 | 20.966 | 31.416 | 1.00 69.89 | C |
| ATOM | 864 | O | ASP | A | 118 | 30.112 | 19.995 | 31.680 | 1.00 69.89 | O |
| ATOM | 865 | CB | ASP | A | 118 | 27.632 | 21.487 | 33.070 | 1.00 86.01 | C |
| ATOM | 866 | CG | ASP | A | 118 | 27.261 | 22.204 | 34.348 | 1.00 86.01 | C |
| ATOM | 867 | OD1 | ASP | A | 118 | 26.218 | 21.849 | 34.935 | 1.00 86.01 | O |
| ATOM | 868 | OD2 | ASP | A | 118 | 28.004 | 23.117 | 34.767 | 1.00 86.01 | O |
| ATOM | 869 | N | LEU | A | 119 | 28.947 | 21.223 | 30.194 | 1.00 80.62 | N |
| ATOM | 870 | CA | LEU | A | 119 | 29.285 | 20.368 | 29.065 | 1.00 80.62 | C |
| ATOM | 871 | C | LEU | A | 119 | 30.769 | 20.458 | 28.772 | 1.00 80.62 | C |
| ATOM | 872 | O | LEU | A | 119 | 31.467 | 19.448 | 28.731 | 1.00 80.62 | O |
| ATOM | 873 | CB | LEU | A | 119 | 28.499 | 20.784 | 27.819 | 1.00 80.69 | C |
| ATOM | 874 | CG | LEU | A | 119 | 27.053 | 20.307 | 27.695 | 1.00 80.69 | C |
| ATOM | 875 | CD1 | LEU | A | 119 | 26.407 | 20.940 | 26.465 | 1.00 80.69 | C |
| ATOM | 876 | CD2 | LEU | A | 119 | 27.029 | 18.790 | 27.586 | 1.00 80.69 | C |
| ATOM | 877 | N | HIS | A | 120 | 31.244 | 21.680 | 28.569 | 1.00 76.91 | N |
| ATOM | 878 | CA | HIS | A | 120 | 32.647 | 21.911 | 28.275 | 1.00 76.91 | C |
| ATOM | 879 | C | HIS | A | 120 | 33.491 | 21.044 | 29.192 | 1.00 76.91 | C |

FIGURE 1-17

```
ATOM    880  O   HIS A 120      34.372  20.317  28.734  1.00 76.91           O
ATOM    881  CB  HIS A 120      32.998  23.384  28.494  1.00119.42           C
ATOM    882  CG  HIS A 120      34.363  23.758  28.006  1.00119.42           C
ATOM    883  ND1 HIS A 120      35.504  23.094  28.401  1.00119.42           N
ATOM    884  CD2 HIS A 120      34.770  24.736  27.162  1.00119.42           C
ATOM    885  CE1 HIS A 120      36.555  23.646  27.821  1.00119.42           C
ATOM    886  NE2 HIS A 120      36.137  24.644  27.065  1.00119.42           N
ATOM    887  N   GLN A 121      33.207  21.118  30.489  1.00 79.07           N
ATOM    888  CA  GLN A 121      33.940  20.340  31.480  1.00 79.07           C
ATOM    889  C   GLN A 121      33.760  18.848  31.239  1.00 79.07           C
ATOM    890  O   GLN A 121      34.724  18.140  30.952  1.00 79.07           O
ATOM    891  CB  GLN A 121      33.458  20.685  32.889  1.00 96.87           C
ATOM    892  CG  GLN A 121      33.479  22.169  33.202  1.00 96.87           C
ATOM    893  CD  GLN A 121      34.837  22.800  32.959  1.00 96.87           C
ATOM    894  OE1 GLN A 121      35.846  22.357  33.510  1.00 96.87           O
ATOM    895  NE2 GLN A 121      34.870  23.843  32.134  1.00 96.87           N
ATOM    896  N   GLU A 122      32.523  18.375  31.349  1.00 53.54           N
ATOM    897  CA  GLU A 122      32.235  16.958  31.158  1.00 53.54           C
ATOM    898  C   GLU A 122      32.783  16.358  29.873  1.00 53.54           C
ATOM    899  O   GLU A 122      33.365  15.271  29.897  1.00 53.54           O
ATOM    900  CB  GLU A 122      30.729  16.703  31.233  1.00 88.00           C
ATOM    901  CG  GLU A 122      30.187  16.610  32.650  1.00 88.00           C
ATOM    902  CD  GLU A 122      30.991  15.657  33.510  1.00 88.00           C
ATOM    903  OE1 GLU A 122      32.017  16.091  34.076  1.00 88.00           O
ATOM    904  OE2 GLU A 122      30.604  14.472  33.606  1.00 88.00           O
ATOM    905  N   LEU A 123      32.596  17.056  28.756  1.00 72.38           N
ATOM    906  CA  LEU A 123      33.074  16.579  27.460  1.00 72.38           C
ATOM    907  C   LEU A 123      34.593  16.554  27.402  1.00 72.38           C
ATOM    908  O   LEU A 123      35.199  15.644  26.829  1.00 72.38           O
ATOM    909  CB  LEU A 123      32.564  17.484  26.331  1.00 59.40           C
ATOM    910  CG  LEU A 123      31.065  17.540  26.049  1.00 59.40           C
ATOM    911  CD1 LEU A 123      30.789  18.535  24.929  1.00 59.40           C
ATOM    912  CD2 LEU A 123      30.580  16.147  25.675  1.00 59.40           C
ATOM    913  N   THR A 124      35.195  17.573  28.000  1.00 64.43           N
ATOM    914  CA  THR A 124      36.641  17.737  28.022  1.00 64.43           C
ATOM    915  C   THR A 124      37.288  17.074  29.234  1.00 64.43           C
ATOM    916  O   THR A 124      38.507  17.043  29.341  1.00 64.43           O
ATOM    917  CB  THR A 124      36.984  19.256  28.002  1.00 67.40           C
ATOM    918  OG1 THR A 124      36.866  19.751  26.663  1.00 67.40           O
ATOM    919  CG2 THR A 124      38.376  19.527  28.528  1.00 67.40           C
ATOM    920  N   LYS A 125      36.470  16.523  30.129  1.00 52.23           N
ATOM    921  CA  LYS A 125      36.966  15.900  31.358  1.00 52.23           C
ATOM    922  C   LYS A 125      38.170  14.973  31.201  1.00 52.23           C
ATOM    923  O   LYS A 125      39.044  14.944  32.068  1.00 52.23           O
ATOM    924  CB  LYS A 125      35.846  15.127  32.065  1.00 85.46           C
ATOM    925  CG  LYS A 125      35.460  13.806  31.400  1.00 85.46           C
ATOM    926  CD  LYS A 125      34.492  13.017  32.281  1.00 85.46           C
ATOM    927  CE  LYS A 125      34.044  11.712  31.633  1.00 85.46           C
ATOM    928  NZ  LYS A 125      33.098  10.969  32.515  1.00 85.46           N
ATOM    929  N   ASN A 126      38.224  14.215  30.108  1.00 50.93           N
ATOM    930  CA  ASN A 126      39.333  13.295  29.917  1.00 50.93           C
ATOM    931  C   ASN A 126      40.208  13.447  28.682  1.00 50.93           C
ATOM    932  O   ASN A 126      41.262  12.826  28.604  1.00 50.93           O
ATOM    933  CB  ASN A 126      38.833  11.844  30.023  1.00 72.05           C
ATOM    934  CG  ASN A 126      37.528  11.609  29.285  1.00 72.05           C
ATOM    935  OD1 ASN A 126      36.929  10.535  29.393  1.00 72.05           O
ATOM    936  ND2 ASN A 126      37.080  12.610  28.530  1.00 72.05           N
ATOM    937  N   LEU A 127      39.824  14.263  27.714  1.00113.27           N
ATOM    938  CA  LEU A 127      40.699  14.382  26.560  1.00113.27           C
ATOM    939  C   LEU A 127      41.620  15.594  26.688  1.00113.27           C
ATOM    940  O   LEU A 127      42.582  15.727  25.931  1.00113.27           O
ATOM    941  CB  LEU A 127      39.882  14.443  25.260  1.00 65.66           C
ATOM    942  CG  LEU A 127      39.297  15.758  24.754  1.00 65.66           C
ATOM    943  CD1 LEU A 127      40.410  16.733  24.365  1.00 65.66           C
ATOM    944  CD2 LEU A 127      38.436  15.466  23.538  1.00 65.66           C
ATOM    945  N   THR A 128      41.333  16.458  27.662  1.00 81.99           N
ATOM    946  CA  THR A 128      42.112  17.679  27.901  1.00 81.99           C
ATOM    947  C   THR A 128      43.609  17.562  27.596  1.00 81.99           C
ATOM    948  O   THR A 128      44.210  18.480  27.029  1.00 81.99           O
ATOM    949  CB  THR A 128      41.964  18.170  29.361  1.00 99.66           C
ATOM    950  OG1 THR A 128      40.575  18.315  29.685  1.00 99.66           O
ATOM    951  CG2 THR A 128      42.649  19.523  29.537  1.00 99.66           C
ATOM    952  N   ALA A 129      44.212  16.445  27.987  1.00102.35           N
```

FIGURE 1-18

```
ATOM    953  CA   ALA A 129      45.628  16.228  27.731  1.00102.35           C
ATOM    954  C    ALA A 129      45.851  16.337  26.228  1.00102.35           C
ATOM    955  O    ALA A 129      46.619  17.183  25.764  1.00102.35           O
ATOM    956  CB   ALA A 129      46.048  14.850  28.225  1.00 76.05           C
ATOM    957  N    ASP A 130      45.198  15.448  25.473  1.00 89.67           N
ATOM    958  CA   ASP A 130      45.262  15.470  24.013  1.00 89.67           C
ATOM    959  C    ASP A 130      44.908  16.860  23.521  1.00 89.67           C
ATOM    960  O    ASP A 130      45.261  17.257  22.398  1.00 89.67           O
ATOM    961  CB   ASP A 130      44.285  14.455  23.410  1.00103.50           C
ATOM    962  CG   ASP A 130      44.420  13.104  24.094  1.00103.50           C
ATOM    963  OD1  ASP A 130      44.236  13.026  25.328  1.00103.50           O
ATOM    964  OD2  ASP A 130      44.715  12.125  23.377  1.00103.50           O
ATOM    965  N    GLU A 131      44.167  17.618  24.366  1.00 61.61           N
ATOM    966  CA   GLU A 131      43.848  19.075  24.175  1.00 61.61           C
ATOM    967  C    GLU A 131      42.658  19.507  23.329  1.00 61.61           C
ATOM    968  O    GLU A 131      42.751  19.518  22.098  1.00 61.61           O
ATOM    969  CB   GLU A 131      45.075  19.734  23.589  1.00 59.54           C
ATOM    970  CG   GLU A 131      44.935  21.220  23.744  1.00 59.54           C
ATOM    971  CD   GLU A 131      44.602  21.536  25.176  1.00 59.54           C
ATOM    972  OE1  GLU A 131      43.619  22.275  25.430  1.00 59.54           O
ATOM    973  OE2  GLU A 131      45.308  21.040  26.070  1.00 59.54           O
ATOM    974  N    VAL A 132      41.502  19.874  23.920  1.00 61.80           N
ATOM    975  CA   VAL A 132      40.251  20.217  23.175  1.00 61.80           C
ATOM    976  C    VAL A 132      40.452  21.036  21.890  1.00 61.80           C
ATOM    977  O    VAL A 132      39.666  20.967  20.961  1.00 61.80           O
ATOM    978  CB   VAL A 132      39.280  20.917  24.135  1.00 77.83           C
ATOM    979  CG1  VAL A 132      37.860  20.909  23.588  1.00 77.83           C
ATOM    980  CG2  VAL A 132      39.321  20.254  25.499  1.00 77.83           C
ATOM    981  N    ALA A 133      41.519  21.812  21.920  1.00 74.99           N
ATOM    982  CA   ALA A 133      41.904  22.678  20.812  1.00 74.99           C
ATOM    983  C    ALA A 133      42.214  21.873  19.546  1.00 74.99           C
ATOM    984  O    ALA A 133      41.925  22.323  18.441  1.00 74.99           O
ATOM    985  CB   ALA A 133      43.099  23.540  21.186  1.00 70.55           C
ATOM    986  N    THR A 134      42.808  20.694  19.703  1.00 59.60           N
ATOM    987  CA   THR A 134      43.129  19.845  18.557  1.00 59.60           C
ATOM    988  C    THR A 134      41.852  19.236  17.961  1.00 59.60           C
ATOM    989  O    THR A 134      41.649  19.255  16.747  1.00 59.60           O
ATOM    990  CB   THR A 134      44.076  18.714  18.978  1.00 48.57           C
ATOM    991  OG1  THR A 134      45.208  19.286  19.647  1.00 48.57           O
ATOM    992  CG2  THR A 134      44.550  17.909  17.765  1.00 48.57           C
ATOM    993  N    LEU A 135      40.997  18.687  18.818  1.00 52.11           N
ATOM    994  CA   LEU A 135      39.748  18.106  18.357  1.00 52.11           C
ATOM    995  C    LEU A 135      38.950  19.211  17.683  1.00 52.11           C
ATOM    996  O    LEU A 135      38.387  19.019  16.604  1.00 52.11           O
ATOM    997  CB   LEU A 135      38.953  17.542  19.532  1.00 28.91           C
ATOM    998  CG   LEU A 135      37.563  16.938  19.216  1.00 28.91           C
ATOM    999  CD1  LEU A 135      37.675  15.855  18.148  1.00 28.91           C
ATOM   1000  CD2  LEU A 135      36.964  16.366  20.504  1.00 28.91           C
ATOM   1001  N    GLU A 136      38.922  20.379  18.315  1.00 51.30           N
ATOM   1002  CA   GLU A 136      38.188  21.509  17.766  1.00 51.30           C
ATOM   1003  C    GLU A 136      38.750  21.874  16.396  1.00 51.30           C
ATOM   1004  O    GLU A 136      38.007  22.136  15.458  1.00 51.30           O
ATOM   1005  CB   GLU A 136      38.282  22.704  18.716  1.00 50.36           C
ATOM   1006  CG   GLU A 136      37.995  22.341  20.160  1.00 50.36           C
ATOM   1007  CD   GLU A 136      37.849  23.550  21.070  1.00 50.36           C
ATOM   1008  OE1  GLU A 136      38.667  24.495  20.971  1.00 50.36           O
ATOM   1009  OE2  GLU A 136      36.915  23.542  21.904  1.00 50.36           O
ATOM   1010  N    TYR A 137      40.070  21.871  16.286  1.00 48.14           N
ATOM   1011  CA   TYR A 137      40.728  22.197  15.038  1.00 48.14           C
ATOM   1012  C    TYR A 137      40.267  21.258  13.934  1.00 48.14           C
ATOM   1013  O    TYR A 137      39.753  21.704  12.908  1.00 48.14           O
ATOM   1014  CB   TYR A 137      42.244  22.088  15.199  1.00 62.08           C
ATOM   1015  CG   TYR A 137      42.995  22.317  13.914  1.00 62.08           C
ATOM   1016  CD1  TYR A 137      43.121  23.595  13.380  1.00 62.08           C
ATOM   1017  CD2  TYR A 137      43.543  21.247  13.209  1.00 62.08           C
ATOM   1018  CE1  TYR A 137      43.774  23.810  12.172  1.00 62.08           C
ATOM   1019  CE2  TYR A 137      44.200  21.444  11.996  1.00 62.08           C
ATOM   1020  CZ   TYR A 137      44.310  22.732  11.483  1.00 62.08           C
ATOM   1021  OH   TYR A 137      44.939  22.938  10.274  1.00 62.08           O
ATOM   1022  N    LEU A 138      40.468  19.958  14.138  1.00 37.88           N
ATOM   1023  CA   LEU A 138      40.059  18.962  13.150  1.00 37.88           C
ATOM   1024  C    LEU A 138      38.554  19.022  12.848  1.00 37.88           C
ATOM   1025  O    LEU A 138      38.146  18.864  11.700  1.00 37.88           O
```

FIGURE 1-19

```
ATOM   1026  CB   LEU A 138     40.439  17.555  13.624  1.00 65.29           C
ATOM   1027  CG   LEU A 138     41.937  17.223  13.657  1.00 65.29           C
ATOM   1028  CD1  LEU A 138     42.152  15.798  14.136  1.00 65.29           C
ATOM   1029  CD2  LEU A 138     42.513  17.393  12.266  1.00 65.29           C
ATOM   1030  N    LEU A 139     37.731  19.256  13.868  1.00 37.74           N
ATOM   1031  CA   LEU A 139     36.291  19.329  13.654  1.00 37.74           C
ATOM   1032  C    LEU A 139     35.939  20.500  12.749  1.00 37.74           C
ATOM   1033  O    LEU A 139     34.915  20.479  12.068  1.00 37.74           O
ATOM   1034  CB   LEU A 139     35.547  19.468  14.987  1.00 35.40           C
ATOM   1035  CG   LEU A 139     35.320  18.190  15.805  1.00 35.40           C
ATOM   1036  CD1  LEU A 139     34.645  18.554  17.126  1.00 35.40           C
ATOM   1037  CD2  LEU A 139     34.461  17.208  15.019  1.00 35.40           C
ATOM   1038  N    LYS A 140     36.778  21.529  12.750  1.00 53.22           N
ATOM   1039  CA   LYS A 140     36.527  22.689  11.900  1.00 53.22           C
ATOM   1040  C    LYS A 140     36.822  22.323  10.459  1.00 53.22           C
ATOM   1041  O    LYS A 140     36.089  22.718   9.554  1.00 53.22           O
ATOM   1042  CB   LYS A 140     37.392  23.883  12.319  1.00 43.83           C
ATOM   1043  CG   LYS A 140     36.966  24.525  13.634  1.00 43.83           C
ATOM   1044  CD   LYS A 140     37.829  25.733  13.976  1.00 43.83           C
ATOM   1045  CE   LYS A 140     37.341  26.425  15.238  1.00 43.83           C
ATOM   1046  NZ   LYS A 140     38.091  27.695  15.494  1.00 43.83           N
ATOM   1047  N    LYS A 141     37.889  21.554  10.251  1.00 43.02           N
ATOM   1048  CA   LYS A 141     38.279  21.133   8.910  1.00 43.02           C
ATOM   1049  C    LYS A 141     37.210  20.276   8.245  1.00 43.02           C
ATOM   1050  O    LYS A 141     37.316  19.946   7.063  1.00 43.02           O
ATOM   1051  CB   LYS A 141     39.609  20.366   8.939  1.00 56.38           C
ATOM   1052  CG   LYS A 141     40.801  21.198   9.383  1.00 56.38           C
ATOM   1053  CD   LYS A 141     42.119  20.601   8.900  1.00 56.38           C
ATOM   1054  CE   LYS A 141     42.286  20.774   7.384  1.00 56.38           C
ATOM   1055  NZ   LYS A 141     43.556  20.185   6.830  1.00 56.38           N
ATOM   1056  N    VAL A 142     36.178  19.918   9.001  1.00 64.66           N
ATOM   1057  CA   VAL A 142     35.081  19.119   8.470  1.00 64.66           C
ATOM   1058  C    VAL A 142     33.940  20.008   7.952  1.00 64.66           C
ATOM   1059  O    VAL A 142     33.198  19.611   7.053  1.00 64.66           O
ATOM   1060  CB   VAL A 142     34.502  18.170   9.556  1.00 36.71           C
ATOM   1061  CG1  VAL A 142     33.236  17.503   9.044  1.00 36.71           C
ATOM   1062  CG2  VAL A 142     35.533  17.118   9.945  1.00 36.71           C
ATOM   1063  N    LEU A 143     33.815  21.212   8.504  1.00 55.78           N
ATOM   1064  CA   LEU A 143     32.736  22.126   8.125  1.00 55.78           C
ATOM   1065  C    LEU A 143     32.745  22.784   6.733  1.00 55.78           C
ATOM   1066  O    LEU A 143     31.732  22.766   6.021  1.00 55.78           O
ATOM   1067  CB   LEU A 143     32.591  23.210   9.202  1.00 39.23           C
ATOM   1068  CG   LEU A 143     32.052  22.650  10.517  1.00 39.23           C
ATOM   1069  CD1  LEU A 143     31.874  23.748  11.529  1.00 39.23           C
ATOM   1070  CD2  LEU A 143     30.736  21.952  10.247  1.00 39.23           C
ATOM   1071  N    PRO A 144     33.874  23.375   6.323  1.00 58.86           N
ATOM   1072  CA   PRO A 144     33.870  24.001   4.997  1.00 58.86           C
ATOM   1073  C    PRO A 144     33.622  23.019   3.840  1.00 58.86           C
ATOM   1074  O    PRO A 144     33.792  21.797   4.034  1.00 58.86           O
ATOM   1075  CB   PRO A 144     35.250  24.659   4.928  1.00 69.58           C
ATOM   1076  CG   PRO A 144     36.096  23.742   5.760  1.00 69.58           C
ATOM   1077  CD   PRO A 144     35.207  23.454   6.945  1.00 69.58           C
ATOM   1078  OXT  PRO A 144     33.265  23.490   2.742  1.00 69.58           O
TER    1079       PRO A 144
HETATM 1080  C1'  SAL   256      1.600  28.984  14.971  1.00 44.77           C
HETATM 1081  O1'  SAL   256      1.140  30.228  15.037  1.00 44.77           O
HETATM 1082  O2'  SAL   256      1.829  28.336  16.002  1.00 44.77           O
HETATM 1083  C1   SAL   256      1.818  28.433  13.617  1.00 44.77           C
HETATM 1084  C2   SAL   256      2.324  27.078  13.453  1.00 44.77           C
HETATM 1085  C3   SAL   256      2.546  26.526  12.169  1.00 44.77           C
HETATM 1086  C4   SAL   256      2.286  27.268  11.019  1.00 44.77           C
HETATM 1087  C5   SAL   256      1.734  28.740  11.167  1.00 44.77           C
HETATM 1088  C6   SAL   256      1.535  29.234  12.452  1.00 44.77           C
HETATM 1089  O2   SAL   256      2.610  26.273  14.510  1.00 44.77           O
HETATM 1090  C1'  SAL   257      6.631  20.720  25.251  1.00 42.17           C
HETATM 1091  O1'  SAL   257      7.014  21.247  26.407  1.00 42.17           O
HETATM 1092  O2'  SAL   257      5.545  21.061  24.701  1.00 42.17           O
HETATM 1093  C1   SAL   257      7.558  19.723  24.673  1.00 42.17           C
HETATM 1094  C2   SAL   257      7.247  19.073  23.396  1.00 42.17           C
HETATM 1095  C3   SAL   257      8.133  18.108  22.827  1.00 42.17           C
HETATM 1096  C4   SAL   257      9.326  17.754  23.481  1.00 42.17           C
HETATM 1097  C5   SAL   257      9.668  18.454  24.869  1.00 42.17           C
HETATM 1098  C6   SAL   257      8.767  19.390  25.369  1.00 42.17           C
```

FIGURE 1-20

```
HETATM 1099  O2  SAL   257       6.103  19.348  22.680  1.00 42.17           O
CONECT 1080 1081 1082 1083
CONECT 1081 1080
CONECT 1082 1080
CONECT 1083 1080 1084 1088
CONECT 1084 1083 1085 1089
CONECT 1085 1084 1086
CONECT 1086 1085 1087
CONECT 1087 1086 1088
CONECT 1088 1083 1087
CONECT 1089 1084
CONECT 1090 1091 1092 1093
CONECT 1091 1090
CONECT 1092 1090
CONECT 1093 1090 1094 1098
CONECT 1094 1093 1095 1099
CONECT 1095 1094 1096
CONECT 1096 1095 1097
CONECT 1097 1096 1098
CONECT 1098 1093 1097
CONECT 1099 1094
MASTER      306    0    2    6    2    0    0    6 1098    1   20   11
END
```

FIGURE 1-21

```
REMARK  Apo-MarR
REMARK  Written by O version 6.2.1
REMARK  DATE:10-May-02  11:21:32
CRYST1   65.8    137.7    96.4   90.00   90.00   90.00  C222
ATOM      1   CB  ILE A  12      59.905  14.106  45.475  1.00 67.94      A
ATOM      2   CG2 ILE A  12      59.418  13.830  44.055  1.00 67.94      A
ATOM      3   CG1 ILE A  12      58.771  13.864  46.472  1.00 67.94      A
ATOM      4   CD1 ILE A  12      58.227  12.461  46.458  1.00 67.94      A
ATOM      5   C   ILE A  12      61.444  13.384  47.291  1.00123.94      A
ATOM      6   O   ILE A  12      61.003  12.599  48.130  1.00123.94      A
ATOM      7   N   ILE A  12      60.812  11.760  45.543  1.00123.94      A
ATOM      8   CA  ILE A  12      61.114  13.198  45.814  1.00123.94      A
ATOM      9   N   PRO A  13      62.238  14.420  47.627  1.00130.37      A
ATOM     10   CD  PRO A  13      62.932  15.390  46.760  1.00 80.29      A
ATOM     11   CA  PRO A  13      62.578  14.645  49.035  1.00130.37      A
ATOM     12   CB  PRO A  13      63.297  15.990  49.002  1.00 80.29      A
ATOM     13   CG  PRO A  13      64.011  15.937  47.685  1.00 80.29      A
ATOM     14   C   PRO A  13      61.294  14.670  49.862  1.00130.37      A
ATOM     15   O   PRO A  13      60.232  15.061  49.371  1.00130.37      A
ATOM     16   N   LEU A  14      61.396  14.254  51.115  1.00 79.03      A
ATOM     17   CA  LEU A  14      60.236  14.183  51.985  1.00 79.03      A
ATOM     18   CB  LEU A  14      60.652  13.546  53.315  1.00 46.83      A
ATOM     19   CG  LEU A  14      59.567  13.009  54.251  1.00 46.83      A
ATOM     20   CD1 LEU A  14      58.532  12.213  53.467  1.00 46.83      A
ATOM     21   CD2 LEU A  14      60.223  12.134  55.316  1.00 46.83      A
ATOM     22   C   LEU A  14      59.542  15.528  52.206  1.00 79.03      A
ATOM     23   O   LEU A  14      58.310  15.596  52.261  1.00 79.03      A
ATOM     24   N   GLY A  15      60.332  16.593  52.312  1.00 52.34      A
ATOM     25   CA  GLY A  15      59.775  17.919  52.530  1.00 52.34      A
ATOM     26   C   GLY A  15      58.591  18.254  51.642  1.00 52.34      A
ATOM     27   O   GLY A  15      57.551  18.705  52.138  1.00 52.34      A
ATOM     28   N   ARG A  16      58.741  18.039  50.335  1.00 52.47      A
ATOM     29   CA  ARG A  16      57.664  18.331  49.393  1.00 52.47      A
ATOM     30   CB  ARG A  16      58.173  18.263  47.949  1.00111.16      A
ATOM     31   CG  ARG A  16      58.538  19.623  47.367  1.00111.16      A
ATOM     32   CD  ARG A  16      58.915  19.527  45.896  1.00111.16      A
ATOM     33   NE  ARG A  16      60.105  18.707  45.692  1.00111.16      A
ATOM     34   CZ  ARG A  16      61.304  18.988  46.193  1.00111.16      A
ATOM     35   NH1 ARG A  16      61.485  20.073  46.933  1.00111.16      A
ATOM     36   NH2 ARG A  16      62.324  18.179  45.957  1.00111.16      A
ATOM     37   C   ARG A  16      56.482  17.393  49.561  1.00 52.47      A
ATOM     38   O   ARG A  16      55.330  17.786  49.361  1.00 52.47      A
ATOM     39   N   LEU A  17      56.765  16.154  49.939  1.00 37.85      A
ATOM     40   CA  LEU A  17      55.706  15.175  50.117  1.00 37.85      A
ATOM     41   CB  LEU A  17      56.315  13.788  50.319  1.00 47.48      A
ATOM     42   CG  LEU A  17      55.704  12.665  49.481  1.00 47.48      A
ATOM     43   CD1 LEU A  17      55.356  13.152  48.075  1.00 47.48      A
ATOM     44   CD2 LEU A  17      56.702  11.515  49.432  1.00 47.48      A
ATOM     45   C   LEU A  17      54.832  15.562  51.303  1.00 37.85      A
ATOM     46   O   LEU A  17      53.600  15.578  51.199  1.00 37.85      A
ATOM     47   N   ILE A  18      55.475  15.889  52.423  1.00 32.29      A
ATOM     48   CA  ILE A  18      54.749  16.282  53.628  1.00 32.29      A
ATOM     49   CB  ILE A  18      55.715  16.537  54.819  1.00 22.79      A
ATOM     50   CG2 ILE A  18      54.938  17.003  56.048  1.00 22.79      A
ATOM     51   CG1 ILE A  18      56.487  15.247  55.131  1.00 22.79      A
ATOM     52   CD1 ILE A  18      57.543  15.383  56.248  1.00 22.79      A
ATOM     53   C   ILE A  18      53.983  17.550  53.307  1.00 32.29      A
ATOM     54   O   ILE A  18      52.900  17.792  53.836  1.00 32.29      A
ATOM     55   N   HIS A  19      54.545  18.353  52.416  1.00 38.61      A
ATOM     56   CA  HIS A  19      53.893  19.587  52.022  1.00 38.61      A
ATOM     57   CB  HIS A  19      54.837  20.437  51.178  1.00 36.15      A
ATOM     58   CG  HIS A  19      54.378  21.850  51.011  1.00 36.15      A
ATOM     59   CD2 HIS A  19      53.819  22.714  51.890  1.00 36.15      A
ATOM     60   ND1 HIS A  19      54.490  22.534  49.819  1.00 36.15      A
ATOM     61   CE1 HIS A  19      54.019  23.758  49.971  1.00 36.15      A
ATOM     62   NE2 HIS A  19      53.606  23.892  51.217  1.00 36.15      A
ATOM     63   C   HIS A  19      52.613  19.294  51.235  1.00 38.61      A
ATOM     64   O   HIS A  19      51.550  19.822  51.567  1.00 38.61      A
ATOM     65   N   MET A  20      52.706  18.447  50.208  1.00 40.71      A
ATOM     66   CA  MET A  20      51.529  18.134  49.397  1.00 40.71      A
ATOM     67   CB  MET A  20      51.932  17.320  48.167  1.00 37.11      A
ATOM     68   CG  MET A  20      52.702  18.147  47.140  1.00 37.11      A
ATOM     69   SD  MET A  20      53.466  17.123  45.859  1.00 37.11      A
```

FIGURE 2-1

| | | | | | | | | | | |
|---|---|---|---|---|---|---|---|---|---|---|
| ATOM | 70 | CE | MET | A | 20 | 54.894 | 16.449 | 46.755 | 1.00 37.11 | A |
| ATOM | 71 | C | MET | A | 20 | 50.455 | 17.415 | 50.201 | 1.00 40.71 | A |
| ATOM | 72 | O | MET | A | 20 | 49.265 | 17.732 | 50.088 | 1.00 40.71 | A |
| ATOM | 73 | N | VAL | A | 21 | 50.873 | 16.456 | 51.020 | 1.00 34.62 | A |
| ATOM | 74 | CA | VAL | A | 21 | 49.920 | 15.737 | 51.845 | 1.00 34.62 | A |
| ATOM | 75 | CB | VAL | A | 21 | 50.623 | 14.669 | 52.700 | 1.00 33.69 | A |
| ATOM | 76 | CG1 | VAL | A | 21 | 49.651 | 14.074 | 53.696 | 1.00 33.69 | A |
| ATOM | 77 | CG2 | VAL | A | 21 | 51.181 | 13.583 | 51.798 | 1.00 33.69 | A |
| ATOM | 78 | C | VAL | A | 21 | 49.240 | 16.760 | 52.755 | 1.00 34.62 | A |
| ATOM | 79 | O | VAL | A | 21 | 48.009 | 16.759 | 52.909 | 1.00 34.62 | A |
| ATOM | 80 | N | ASN | A | 22 | 50.041 | 17.652 | 53.336 | 1.00 31.08 | A |
| ATOM | 81 | CA | ASN | A | 22 | 49.489 | 18.656 | 54.230 | 1.00 31.08 | A |
| ATOM | 82 | CB | ASN | A | 22 | 50.576 | 19.546 | 54.827 | 1.00 26.87 | A |
| ATOM | 83 | CG | ASN | A | 22 | 50.032 | 20.418 | 55.951 | 1.00 26.87 | A |
| ATOM | 84 | OD1 | ASN | A | 22 | 49.760 | 19.919 | 57.052 | 1.00 26.87 | A |
| ATOM | 85 | ND2 | ASN | A | 22 | 49.830 | 21.713 | 55.672 | 1.00 26.87 | A |
| ATOM | 86 | C | ASN | A | 22 | 48.457 | 19.556 | 53.555 | 1.00 31.08 | A |
| ATOM | 87 | O | ASN | A | 22 | 47.397 | 19.850 | 54.130 | 1.00 31.08 | A |
| ATOM | 88 | N | GLN | A | 23 | 48.765 | 20.015 | 52.349 | 1.00 22.48 | A |
| ATOM | 89 | CA | GLN | A | 23 | 47.828 | 20.871 | 51.670 | 1.00 22.48 | A |
| ATOM | 90 | CB | GLN | A | 23 | 48.401 | 21.383 | 50.354 | 1.00 42.54 | A |
| ATOM | 91 | CG | GLN | A | 23 | 49.576 | 22.309 | 50.520 | 1.00 42.54 | A |
| ATOM | 92 | CD | GLN | A | 23 | 49.739 | 23.255 | 49.337 | 1.00 42.54 | A |
| ATOM | 93 | OE1 | GLN | A | 23 | 49.522 | 22.876 | 48.173 | 1.00 42.54 | A |
| ATOM | 94 | NE2 | GLN | A | 23 | 50.132 | 24.498 | 49.629 | 1.00 42.54 | A |
| ATOM | 95 | C | GLN | A | 23 | 46.528 | 20.110 | 51.432 | 1.00 22.48 | A |
| ATOM | 96 | O | GLN | A | 23 | 45.447 | 20.683 | 51.600 | 1.00 22.48 | A |
| ATOM | 97 | N | LYS | A | 24 | 46.616 | 18.829 | 51.064 | 1.00 27.17 | A |
| ATOM | 98 | CA | LYS | A | 24 | 45.393 | 18.068 | 50.835 | 1.00 27.17 | A |
| ATOM | 99 | CB | LYS | A | 24 | 45.693 | 16.643 | 50.362 | 1.00 41.13 | A |
| ATOM | 100 | CG | LYS | A | 24 | 44.450 | 15.943 | 49.835 | 1.00 41.13 | A |
| ATOM | 101 | CD | LYS | A | 24 | 44.684 | 14.486 | 49.469 | 1.00 41.13 | A |
| ATOM | 102 | CE | LYS | A | 24 | 43.406 | 13.866 | 48.908 | 1.00 41.13 | A |
| ATOM | 103 | NZ | LYS | A | 24 | 43.411 | 12.372 | 49.000 | 1.00 41.13 | A |
| ATOM | 104 | C | LYS | A | 24 | 44.595 | 18.021 | 52.144 | 1.00 27.17 | A |
| ATOM | 105 | O | LYS | A | 24 | 43.381 | 18.296 | 52.151 | 1.00 27.17 | A |
| ATOM | 106 | N | LYS | A | 25 | 45.274 | 17.696 | 53.248 | 1.00 23.70 | A |
| ATOM | 107 | CA | LYS | A | 25 | 44.588 | 17.631 | 54.536 | 1.00 23.70 | A |
| ATOM | 108 | CB | LYS | A | 25 | 45.565 | 17.431 | 55.704 | 1.00 36.11 | A |
| ATOM | 109 | CG | LYS | A | 25 | 44.843 | 17.459 | 57.063 | 1.00 36.11 | A |
| ATOM | 110 | CD | LYS | A | 25 | 45.789 | 17.520 | 58.266 | 1.00 36.11 | A |
| ATOM | 111 | CE | LYS | A | 25 | 46.615 | 18.813 | 58.323 | 1.00 36.11 | A |
| ATOM | 112 | NZ | LYS | A | 25 | 45.775 | 20.034 | 58.447 | 1.00 36.11 | A |
| ATOM | 113 | C | LYS | A | 25 | 43.811 | 18.928 | 54.762 | 1.00 23.70 | A |
| ATOM | 114 | O | LYS | A | 25 | 42.604 | 18.904 | 55.046 | 1.00 23.70 | A |
| ATOM | 115 | N | ASP | A | 26 | 44.509 | 20.055 | 54.620 | 1.00 27.62 | A |
| ATOM | 116 | CA | ASP | A | 26 | 43.892 | 21.359 | 54.822 | 1.00 27.62 | A |
| ATOM | 117 | CB | ASP | A | 26 | 44.909 | 22.477 | 54.572 | 1.00 48.95 | A |
| ATOM | 118 | CG | ASP | A | 26 | 45.908 | 22.639 | 55.721 | 1.00 48.95 | A |
| ATOM | 119 | OD1 | ASP | A | 26 | 46.897 | 23.399 | 55.548 | 1.00 48.95 | A |
| ATOM | 120 | OD2 | ASP | A | 26 | 45.706 | 22.016 | 56.791 | 1.00 48.95 | A |
| ATOM | 121 | C | ASP | A | 26 | 42.656 | 21.576 | 53.959 | 1.00 27.62 | A |
| ATOM | 122 | O | ASP | A | 26 | 41.662 | 22.114 | 54.448 | 1.00 27.62 | A |
| ATOM | 123 | N | ARG | A | 27 | 42.708 | 21.168 | 52.685 | 1.00 22.30 | A |
| ATOM | 124 | CA | ARG | A | 27 | 41.563 | 21.343 | 51.798 | 1.00 22.30 | A |
| ATOM | 125 | CB | ARG | A | 27 | 41.952 | 21.014 | 50.354 | 1.00 52.90 | A |
| ATOM | 126 | CG | ARG | A | 27 | 42.798 | 22.123 | 49.697 | 1.00 52.90 | A |
| ATOM | 127 | CD | ARG | A | 27 | 43.108 | 21.870 | 48.208 | 1.00 52.90 | A |
| ATOM | 128 | NE | ARG | A | 27 | 44.493 | 21.445 | 47.986 | 1.00 52.90 | A |
| ATOM | 129 | CZ | ARG | A | 27 | 44.883 | 20.184 | 47.786 | 1.00 52.90 | A |
| ATOM | 130 | NH1 | ARG | A | 27 | 43.994 | 19.196 | 47.771 | 1.00 52.90 | A |
| ATOM | 131 | NH2 | ARG | A | 27 | 46.169 | 19.908 | 47.600 | 1.00 52.90 | A |
| ATOM | 132 | C | ARG | A | 27 | 40.388 | 20.484 | 52.284 | 1.00 22.30 | A |
| ATOM | 133 | O | ARG | A | 27 | 39.249 | 20.970 | 52.381 | 1.00 22.30 | A |
| ATOM | 134 | N | LEU | A | 28 | 40.668 | 19.226 | 52.625 | 1.00 28.23 | A |
| ATOM | 135 | CA | LEU | A | 28 | 39.628 | 18.342 | 53.124 | 1.00 28.23 | A |
| ATOM | 136 | CB | LEU | A | 28 | 40.204 | 16.951 | 53.384 | 1.00 19.62 | A |
| ATOM | 137 | CG | LEU | A | 28 | 40.644 | 16.188 | 52.133 | 1.00 19.62 | A |
| ATOM | 138 | CD1 | LEU | A | 28 | 41.264 | 14.854 | 52.538 | 1.00 19.62 | A |
| ATOM | 139 | CD2 | LEU | A | 28 | 39.431 | 15.979 | 51.225 | 1.00 19.62 | A |
| ATOM | 140 | C | LEU | A | 28 | 39.108 | 18.939 | 54.421 | 1.00 28.23 | A |
| ATOM | 141 | O | LEU | A | 28 | 37.902 | 19.103 | 54.606 | 1.00 28.23 | A |
| ATOM | 142 | N | LEU | A | 29 | 40.041 | 19.271 | 55.310 | 1.00 32.81 | A |

FIGURE 2-2

```
ATOM    143  CA   LEU A  29      39.723  19.844  56.610  1.00 32.81      A
ATOM    144  CB   LEU A  29      41.009  20.264  57.301  1.00 30.88      A
ATOM    145  CG   LEU A  29      40.893  20.746  58.740  1.00 30.88      A
ATOM    146  CD1  LEU A  29      39.898  19.883  59.510  1.00 30.88      A
ATOM    147  CD2  LEU A  29      42.282  20.693  59.379  1.00 30.88      A
ATOM    148  C    LEU A  29      38.794  21.038  56.471  1.00 32.81      A
ATOM    149  O    LEU A  29      37.873  21.226  57.273  1.00 32.81      A
ATOM    150  N    ASN A  30      39.030  21.839  55.437  1.00 33.15      A
ATOM    151  CA   ASN A  30      38.206  23.010  55.202  1.00 33.15      A
ATOM    152  CB   ASN A  30      38.812  23.879  54.106  1.00 37.23      A
ATOM    153  CG   ASN A  30      38.967  25.325  54.527  1.00 37.23      A
ATOM    154  OD1  ASN A  30      39.241  26.196  53.706  1.00 37.23      A
ATOM    155  ND2  ASN A  30      38.805  25.587  55.813  1.00 37.23      A
ATOM    156  C    ASN A  30      36.791  22.614  54.813  1.00 33.15      A
ATOM    157  O    ASN A  30      35.847  23.304  55.156  1.00 33.15      A
ATOM    158  N    GLU A  31      36.643  21.499  54.106  1.00 45.74      A
ATOM    159  CA   GLU A  31      35.320  21.055  53.681  1.00 45.74      A
ATOM    160  CB   GLU A  31      35.443  20.018  52.573  1.00111.71      A
ATOM    161  CG   GLU A  31      36.048  20.569  51.302  1.00111.71      A
ATOM    162  CD   GLU A  31      36.235  19.500  50.255  1.00111.71      A
ATOM    163  OE1  GLU A  31      35.229  18.863  49.877  1.00111.71      A
ATOM    164  OE2  GLU A  31      37.385  19.292  49.813  1.00111.71      A
ATOM    165  C    GLU A  31      34.502  20.493  54.829  1.00 45.74      A
ATOM    166  O    GLU A  31      33.325  20.802  54.962  1.00 45.74      A
ATOM    167  N    TYR A  32      35.119  19.677  55.668  1.00 43.75      A
ATOM    168  CA   TYR A  32      34.393  19.110  56.790  1.00 43.75      A
ATOM    169  CB   TYR A  32      35.171  17.926  57.355  1.00 50.30      A
ATOM    170  CG   TYR A  32      35.296  16.793  56.364  1.00 50.30      A
ATOM    171  CD1  TYR A  32      36.534  16.445  55.823  1.00 50.30      A
ATOM    172  CE1  TYR A  32      36.646  15.423  54.881  1.00 50.30      A
ATOM    173  CD2  TYR A  32      34.168  16.089  55.941  1.00 50.30      A
ATOM    174  CE2  TYR A  32      34.264  15.069  55.001  1.00 50.30      A
ATOM    175  CZ   TYR A  32      35.506  14.740  54.471  1.00 50.30      A
ATOM    176  OH   TYR A  32      35.601  13.741  53.520  1.00 50.30      A
ATOM    177  C    TYR A  32      34.117  20.154  57.876  1.00 43.75      A
ATOM    178  O    TYR A  32      33.278  19.951  58.746  1.00 43.75      A
ATOM    179  N    LEU A  33      34.806  21.286  57.805  1.00 31.02      A
ATOM    180  CA   LEU A  33      34.628  22.343  58.785  1.00 31.02      A
ATOM    181  CB   LEU A  33      35.933  23.120  58.969  1.00 26.92      A
ATOM    182  CG   LEU A  33      36.988  22.548  59.905  1.00 26.92      A
ATOM    183  CD1  LEU A  33      38.137  23.523  59.973  1.00 26.92      A
ATOM    184  CD2  LEU A  33      36.399  22.324  61.291  1.00 26.92      A
ATOM    185  C    LEU A  33      33.529  23.327  58.397  1.00 31.02      A
ATOM    186  O    LEU A  33      32.846  23.877  59.266  1.00 31.02      A
ATOM    187  N    SER A  34      33.379  23.561  57.094  1.00 47.63      A
ATOM    188  CA   SER A  34      32.380  24.498  56.584  1.00 47.63      A
ATOM    189  CB   SER A  34      32.121  24.237  55.097  1.00 75.10      A
ATOM    190  OG   SER A  34      31.147  25.133  54.585  1.00 75.10      A
ATOM    191  C    SER A  34      31.053  24.459  57.353  1.00 47.63      A
ATOM    192  O    SER A  34      30.504  25.507  57.706  1.00 47.63      A
ATOM    193  N    PRO A  35      30.528  23.249  57.632  1.00 43.33      A
ATOM    194  CD   PRO A  35      31.030  21.949  57.157  1.00 63.21      A
ATOM    195  CA   PRO A  35      29.263  23.069  58.359  1.00 43.33      A
ATOM    196  CB   PRO A  35      29.049  21.559  58.317  1.00 63.21      A
ATOM    197  CG   PRO A  35      29.764  21.146  57.072  1.00 63.21      A
ATOM    198  C    PRO A  35      29.293  23.578  59.794  1.00 43.33      A
ATOM    199  O    PRO A  35      28.296  23.501  60.504  1.00 43.33      A
ATOM    200  N    LEU A  36      30.441  24.090  60.222  1.00 41.82      A
ATOM    201  CA   LEU A  36      30.587  24.589  61.587  1.00 41.82      A
ATOM    202  CB   LEU A  36      31.673  23.792  62.320  1.00 53.45      A
ATOM    203  CG   LEU A  36      31.335  23.115  63.659  1.00 53.45      A
ATOM    204  CD1  LEU A  36      32.514  22.238  64.077  1.00 53.45      A
ATOM    205  CD2  LEU A  36      31.026  24.153  64.741  1.00 53.45      A
ATOM    206  C    LEU A  36      30.925  26.078  61.636  1.00 41.82      A
ATOM    207  O    LEU A  36      31.226  26.612  62.700  1.00 41.82      A
ATOM    208  N    ASP A  37      30.878  26.750  60.489  1.00 34.90      A
ATOM    209  CA   ASP A  37      31.178  28.176  60.451  1.00 34.90      A
ATOM    210  CB   ASP A  37      30.202  28.950  61.337  1.00 88.32      A
ATOM    211  CG   ASP A  37      29.042  29.523  60.558  1.00 88.32      A
ATOM    212  OD1  ASP A  37      29.289  30.383  59.684  1.00 88.32      A
ATOM    213  OD2  ASP A  37      27.888  29.115  60.816  1.00 88.32      A
ATOM    214  C    ASP A  37      32.606  28.506  60.883  1.00 34.90      A
ATOM    215  O    ASP A  37      32.828  29.476  61.610  1.00 34.90      A
```

FIGURE 2-3

| ATOM | 216 | N   | ILE A | 38 | 33.570 | 27.702 | 60.442 | 1.00 | 28.88 | A |
| --- | --- | --- | --- | --- | --- | --- | --- | --- | --- | --- |
| ATOM | 217 | CA  | ILE A | 38 | 34.964 | 27.952 | 60.779 | 1.00 | 28.88 | A |
| ATOM | 218 | CB  | ILE A | 38 | 35.350 | 27.274 | 62.108 | 1.00 | 20.06 | A |
| ATOM | 219 | CG2 | ILE A | 38 | 35.702 | 25.822 | 61.878 | 1.00 | 20.06 | A |
| ATOM | 220 | CG1 | ILE A | 38 | 36.545 | 28.010 | 62.722 | 1.00 | 20.06 | A |
| ATOM | 221 | CD1 | ILE A | 38 | 37.305 | 27.243 | 63.816 | 1.00 | 20.06 | A |
| ATOM | 222 | C   | ILE A | 38 | 35.896 | 27.461 | 59.663 | 1.00 | 28.88 | A |
| ATOM | 223 | O   | ILE A | 38 | 35.651 | 26.422 | 59.041 | 1.00 | 28.88 | A |
| ATOM | 224 | N   | THR A | 39 | 36.959 | 28.215 | 59.399 | 1.00 | 29.25 | A |
| ATOM | 225 | CA  | THR A | 39 | 37.904 | 27.840 | 58.349 | 1.00 | 29.25 | A |
| ATOM | 226 | CB  | THR A | 39 | 38.426 | 29.068 | 57.605 | 1.00 | 9.47  | A |
| ATOM | 227 | OG1 | THR A | 39 | 39.300 | 29.807 | 58.477 | 1.00 | 9.47  | A |
| ATOM | 228 | CG2 | THR A | 39 | 37.291 | 29.959 | 57.169 | 1.00 | 9.47  | A |
| ATOM | 229 | C   | THR A | 39 | 39.127 | 27.121 | 58.923 | 1.00 | 29.25 | A |
| ATOM | 230 | O   | THR A | 39 | 39.458 | 27.278 | 60.101 | 1.00 | 29.25 | A |
| ATOM | 231 | N   | ALA A | 40 | 39.801 | 26.347 | 58.078 | 1.00 | 29.21 | A |
| ATOM | 232 | CA  | ALA A | 40 | 40.994 | 25.610 | 58.480 | 1.00 | 29.21 | A |
| ATOM | 233 | CB  | ALA A | 40 | 41.616 | 24.918 | 57.280 | 1.00 | 1.00  | A |
| ATOM | 234 | C   | ALA A | 40 | 42.010 | 26.565 | 59.080 | 1.00 | 29.21 | A |
| ATOM | 235 | O   | ALA A | 40 | 42.684 | 26.245 | 60.064 | 1.00 | 29.21 | A |
| ATOM | 236 | N   | ALA A | 41 | 42.129 | 27.740 | 58.476 | 1.00 | 28.55 | A |
| ATOM | 237 | CA  | ALA A | 41 | 43.087 | 28.719 | 58.972 | 1.00 | 28.55 | A |
| ATOM | 238 | CB  | ALA A | 41 | 43.012 | 30.003 | 58.145 | 1.00 | 30.67 | A |
| ATOM | 239 | C   | ALA A | 41 | 42.801 | 29.025 | 60.442 | 1.00 | 28.55 | A |
| ATOM | 240 | O   | ALA A | 41 | 43.675 | 28.890 | 61.309 | 1.00 | 28.55 | A |
| ATOM | 241 | N   | GLN A | 42 | 41.567 | 29.430 | 60.717 | 1.00 | 23.69 | A |
| ATOM | 242 | CA  | GLN A | 42 | 41.180 | 29.775 | 62.069 | 1.00 | 23.69 | A |
| ATOM | 243 | CB  | GLN A | 42 | 39.712 | 30.183 | 62.088 | 1.00 | 31.90 | A |
| ATOM | 244 | CG  | GLN A | 42 | 39.421 | 31.267 | 61.070 | 1.00 | 31.90 | A |
| ATOM | 245 | CD  | GLN A | 42 | 37.966 | 31.641 | 61.012 | 1.00 | 31.90 | A |
| ATOM | 246 | OE1 | GLN A | 42 | 37.092 | 30.776 | 60.997 | 1.00 | 31.90 | A |
| ATOM | 247 | NE2 | GLN A | 42 | 37.692 | 32.938 | 60.967 | 1.00 | 31.90 | A |
| ATOM | 248 | C   | GLN A | 42 | 41.417 | 28.596 | 62.988 | 1.00 | 23.69 | A |
| ATOM | 249 | O   | GLN A | 42 | 42.026 | 28.730 | 64.058 | 1.00 | 23.69 | A |
| ATOM | 250 | N   | PHE A | 43 | 40.949 | 27.429 | 62.561 | 1.00 | 20.02 | A |
| ATOM | 251 | CA  | PHE A | 43 | 41.099 | 26.232 | 63.368 | 1.00 | 20.02 | A |
| ATOM | 252 | CB  | PHE A | 43 | 40.441 | 25.042 | 62.665 | 1.00 | 21.86 | A |
| ATOM | 253 | CG  | PHE A | 43 | 40.607 | 23.738 | 63.394 | 1.00 | 21.86 | A |
| ATOM | 254 | CD1 | PHE A | 43 | 40.118 | 23.582 | 64.692 | 1.00 | 21.86 | A |
| ATOM | 255 | CD2 | PHE A | 43 | 41.250 | 22.659 | 62.778 | 1.00 | 21.86 | A |
| ATOM | 256 | CE1 | PHE A | 43 | 40.264 | 22.368 | 65.375 | 1.00 | 21.86 | A |
| ATOM | 257 | CE2 | PHE A | 43 | 41.402 | 21.441 | 63.448 | 1.00 | 21.86 | A |
| ATOM | 258 | CZ  | PHE A | 43 | 40.907 | 21.293 | 64.754 | 1.00 | 21.86 | A |
| ATOM | 259 | C   | PHE A | 43 | 42.575 | 25.962 | 63.646 | 1.00 | 20.02 | A |
| ATOM | 260 | O   | PHE A | 43 | 42.946 | 25.641 | 64.776 | 1.00 | 20.02 | A |
| ATOM | 261 | N   | LYS A | 44 | 43.425 | 26.105 | 62.632 | 1.00 | 25.04 | A |
| ATOM | 262 | CA  | LYS A | 44 | 44.856 | 25.883 | 62.839 | 1.00 | 25.04 | A |
| ATOM | 263 | CB  | LYS A | 44 | 45.648 | 26.125 | 61.550 | 1.00 | 46.29 | A |
| ATOM | 264 | CG  | LYS A | 44 | 45.596 | 24.991 | 60.552 | 1.00 | 46.29 | A |
| ATOM | 265 | CD  | LYS A | 44 | 46.639 | 25.210 | 59.467 | 1.00 | 46.29 | A |
| ATOM | 266 | CE  | LYS A | 44 | 46.797 | 23.984 | 58.585 | 1.00 | 46.29 | A |
| ATOM | 267 | NZ  | LYS A | 44 | 48.034 | 24.060 | 57.757 | 1.00 | 46.29 | A |
| ATOM | 268 | C   | LYS A | 44 | 45.402 | 26.802 | 63.940 | 1.00 | 25.04 | A |
| ATOM | 269 | O   | LYS A | 44 | 46.092 | 26.334 | 64.861 | 1.00 | 25.04 | A |
| ATOM | 270 | N   | VAL A | 45 | 45.103 | 28.102 | 63.836 | 1.00 | 24.20 | A |
| ATOM | 271 | CA  | VAL A | 45 | 45.563 | 29.073 | 64.830 | 1.00 | 24.20 | A |
| ATOM | 272 | CB  | VAL A | 45 | 45.056 | 30.508 | 64.511 | 1.00 | 17.46 | A |
| ATOM | 273 | CG1 | VAL A | 45 | 45.349 | 31.440 | 65.670 | 1.00 | 17.46 | A |
| ATOM | 274 | CG2 | VAL A | 45 | 45.736 | 31.036 | 63.238 | 1.00 | 17.46 | A |
| ATOM | 275 | C   | VAL A | 45 | 45.053 | 28.665 | 66.213 | 1.00 | 24.20 | A |
| ATOM | 276 | O   | VAL A | 45 | 45.818 | 28.590 | 67.183 | 1.00 | 24.20 | A |
| ATOM | 277 | N   | LEU A | 46 | 43.755 | 28.398 | 66.294 | 1.00 | 22.98 | A |
| ATOM | 278 | CA  | LEU A | 46 | 43.144 | 27.979 | 67.542 | 1.00 | 22.98 | A |
| ATOM | 279 | CB  | LEU A | 46 | 41.701 | 27.570 | 67.277 | 1.00 | 18.73 | A |
| ATOM | 280 | CG  | LEU A | 46 | 40.618 | 28.396 | 67.970 | 1.00 | 18.73 | A |
| ATOM | 281 | CD1 | LEU A | 46 | 40.946 | 29.880 | 67.928 | 1.00 | 18.73 | A |
| ATOM | 282 | CD2 | LEU A | 46 | 39.276 | 28.083 | 67.296 | 1.00 | 18.73 | A |
| ATOM | 283 | C   | LEU A | 46 | 43.918 | 26.808 | 68.170 | 1.00 | 22.98 | A |
| ATOM | 284 | O   | LEU A | 46 | 44.198 | 26.809 | 69.374 | 1.00 | 22.98 | A |
| ATOM | 285 | N   | CYS A | 47 | 44.276 | 25.816 | 67.356 | 1.00 | 25.10 | A |
| ATOM | 286 | CA  | CYS A | 47 | 45.027 | 24.657 | 67.853 | 1.00 | 25.10 | A |
| ATOM | 287 | CB  | CYS A | 47 | 45.147 | 23.588 | 66.764 | 1.00 | 37.95 | A |
| ATOM | 288 | SG  | CYS A | 47 | 43.614 | 22.685 | 66.463 | 1.00 | 37.95 | A |

FIGURE 2-4

```
ATOM  289  C    CYS A  47      46.426  24.997  68.367  1.00 25.10      A
ATOM  290  O    CYS A  47      46.885  24.424  69.350  1.00 25.10      A
ATOM  291  N    SER A  48      47.113  25.920  67.703  1.00 26.62      A
ATOM  292  CA   SER A  48      48.460  26.286  68.128  1.00 26.62      A
ATOM  293  CB   SER A  48      49.082  27.220  67.100  1.00 43.10      A
ATOM  294  OG   SER A  48      49.034  26.614  65.824  1.00 43.10      A
ATOM  295  C    SER A  48      48.423  26.954  69.502  1.00 26.62      A
ATOM  296  O    SER A  48      49.246  26.667  70.385  1.00 26.62      A
ATOM  297  N    ILE A  49      47.459  27.850  69.678  1.00 23.50      A
ATOM  298  CA   ILE A  49      47.301  28.534  70.946  1.00 23.50      A
ATOM  299  CB   ILE A  49      46.226  29.642  70.852  1.00 14.67      A
ATOM  300  CG2  ILE A  49      45.970  30.242  72.234  1.00 14.67      A
ATOM  301  CG1  ILE A  49      46.683  30.720  69.857  1.00 14.67      A
ATOM  302  CD1  ILE A  49      45.560  31.560  69.315  1.00 14.67      A
ATOM  303  C    ILE A  49      46.906  27.512  72.016  1.00 23.50      A
ATOM  304  O    ILE A  49      47.507  27.476  73.092  1.00 23.50      A
ATOM  305  N    ARG A  50      45.916  26.669  71.726  1.00 25.93      A
ATOM  306  CA   ARG A  50      45.505  25.671  72.713  1.00 25.93      A
ATOM  307  CB   ARG A  50      44.391  24.766  72.189  1.00 51.02      A
ATOM  308  CG   ARG A  50      44.109  23.617  73.147  1.00 51.02      A
ATOM  309  CD   ARG A  50      42.736  23.006  72.969  1.00 51.02      A
ATOM  310  NE   ARG A  50      42.773  21.759  72.211  1.00 51.02      A
ATOM  311  CZ   ARG A  50      41.765  20.890  72.165  1.00 51.02      A
ATOM  312  NH1  ARG A  50      40.645  21.142  72.839  1.00 51.02      A
ATOM  313  NH2  ARG A  50      41.872  19.772  71.449  1.00 51.02      A
ATOM  314  C    ARG A  50      46.678  24.791  73.124  1.00 25.93      A
ATOM  315  O    ARG A  50      46.873  24.491  74.307  1.00 25.93      A
ATOM  316  N    CYS A  51      47.459  24.373  72.138  1.00 40.32      A
ATOM  317  CA   CYS A  51      48.597  23.523  72.411  1.00 40.32      A
ATOM  318  CB   CYS A  51      49.253  23.092  71.107  1.00 66.88      A
ATOM  319  SG   CYS A  51      50.555  21.891  71.373  1.00 66.88      A
ATOM  320  C    CYS A  51      49.609  24.233  73.303  1.00 40.32      A
ATOM  321  O    CYS A  51      50.189  23.621  74.192  1.00 40.32      A
ATOM  322  N    ALA A  52      49.805  25.528  73.076  1.00 38.59      A
ATOM  323  CA   ALA A  52      50.757  26.304  73.866  1.00 38.59      A
ATOM  324  CB   ALA A  52      51.221  27.516  73.067  1.00 22.10      A
ATOM  325  C    ALA A  52      50.193  26.770  75.209  1.00 38.59      A
ATOM  326  O    ALA A  52      50.948  27.036  76.145  1.00 38.59      A
ATOM  327  N    ALA A  53      48.869  26.876  75.291  1.00 28.02      A
ATOM  328  CA   ALA A  53      48.184  27.343  76.498  1.00 28.02      A
ATOM  329  CB   ALA A  53      48.779  26.719  77.746  1.00  8.31      A
ATOM  330  C    ALA A  53      48.266  28.857  76.597  1.00 28.02      A
ATOM  331  O    ALA A  53      47.250  29.519  76.808  1.00 28.02      A
ATOM  332  N    CYS A  54      49.475  29.399  76.451  1.00 17.61      A
ATOM  333  CA   CYS A  54      49.706  30.850  76.508  1.00 17.61      A
ATOM  334  CB   CYS A  54      49.977  31.291  77.939  1.00 33.17      A
ATOM  335  SG   CYS A  54      49.981  33.078  78.102  1.00 33.17      A
ATOM  336  C    CYS A  54      50.918  31.140  75.628  1.00 17.61      A
ATOM  337  O    CYS A  54      51.918  30.424  75.698  1.00 17.61      A
ATOM  338  N    ILE A  55      50.856  32.185  74.811  1.00 19.43      A
ATOM  339  CA   ILE A  55      51.969  32.434  73.889  1.00 19.43      A
ATOM  340  CB   ILE A  55      51.881  31.396  72.727  1.00 24.10      A
ATOM  341  CG2  ILE A  55      50.660  31.703  71.856  1.00 24.10      A
ATOM  342  CG1  ILE A  55      53.142  31.411  71.865  1.00 24.10      A
ATOM  343  CD1  ILE A  55      53.142  30.324  70.750  1.00 24.10      A
ATOM  344  C    ILE A  55      51.977  33.858  73.309  1.00 19.43      A
ATOM  345  O    ILE A  55      50.928  34.492  73.181  1.00 19.43      A
ATOM  346  N    THR A  56      53.157  34.359  72.957  1.00 31.11      A
ATOM  347  CA   THR A  56      53.253  35.704  72.396  1.00 31.11      A
ATOM  348  CB   THR A  56      54.633  36.338  72.605  1.00 27.01      A
ATOM  349  OG1  THR A  56      55.611  35.560  71.903  1.00 27.01      A
ATOM  350  CG2  THR A  56      54.995  36.395  74.081  1.00 27.01      A
ATOM  351  C    THR A  56      53.041  35.598  70.898  1.00 31.11      A
ATOM  352  O    THR A  56      53.252  34.532  70.306  1.00 31.11      A
ATOM  353  N    PRO A  57      52.621  36.701  70.257  1.00 39.22      A
ATOM  354  CD   PRO A  57      52.134  37.964  70.836  1.00 28.66      A
ATOM  355  CA   PRO A  57      52.392  36.688  68.816  1.00 39.22      A
ATOM  356  CB   PRO A  57      51.892  38.098  68.541  1.00 28.66      A
ATOM  357  CG   PRO A  57      51.148  38.419  69.793  1.00 28.66      A
ATOM  358  C    PRO A  57      53.653  36.357  68.038  1.00 39.22      A
ATOM  359  O    PRO A  57      53.606  35.641  67.037  1.00 39.22      A
ATOM  360  N    VAL A  58      54.788  36.878  68.485  1.00 41.76      A
ATOM  361  CA   VAL A  58      56.020  36.585  67.778  1.00 41.76      A
```

FIGURE 2-5

```
ATOM    362  CB  VAL A  58      57.233  37.319  68.397  1.00 36.94      A
ATOM    363  CG1 VAL A  58      58.538  36.680  67.928  1.00 36.94      A
ATOM    364  CG2 VAL A  58      57.211  38.777  67.969  1.00 36.94      A
ATOM    365  C   VAL A  58      56.263  35.086  67.800  1.00 41.76      A
ATOM    366  O   VAL A  58      56.427  34.469  66.748  1.00 41.76      A
ATOM    367  N   GLU A  59      56.259  34.497  68.994  1.00 42.87      A
ATOM    368  CA  GLU A  59      56.506  33.068  69.117  1.00 42.87      A
ATOM    369  CB  GLU A  59      56.554  32.665  70.588  1.00 79.89      A
ATOM    370  CG  GLU A  59      57.670  31.681  70.885  1.00 79.89      A
ATOM    371  CD  GLU A  59      59.000  32.113  70.274  1.00 79.89      A
ATOM    372  OE1 GLU A  59      59.378  33.295  70.431  1.00 79.89      A
ATOM    373  OE2 GLU A  59      59.672  31.269  69.641  1.00 79.89      A
ATOM    374  C   GLU A  59      55.466  32.235  68.374  1.00 42.87      A
ATOM    375  O   GLU A  59      55.738  31.096  67.974  1.00 42.87      A
ATOM    376  N   LEU A  60      54.280  32.802  68.171  1.00 30.72      A
ATOM    377  CA  LEU A  60      53.229  32.075  67.468  1.00 30.72      A
ATOM    378  CB  LEU A  60      51.842  32.625  67.818  1.00 25.76      A
ATOM    379  CG  LEU A  60      50.703  31.829  67.164  1.00 25.76      A
ATOM    380  CD1 LEU A  60      50.673  30.422  67.744  1.00 25.76      A
ATOM    381  CD2 LEU A  60      49.367  32.514  67.412  1.00 25.76      A
ATOM    382  C   LEU A  60      53.399  32.115  65.953  1.00 30.72      A
ATOM    383  O   LEU A  60      53.043  31.160  65.262  1.00 30.72      A
ATOM    384  N   LYS A  61      53.919  33.223  65.429  1.00 59.73      A
ATOM    385  CA  LYS A  61      54.104  33.322  63.988  1.00 59.73      A
ATOM    386  CB  LYS A  61      54.420  34.768  63.560  1.00 50.33      A
ATOM    387  CG  LYS A  61      55.814  35.288  63.899  1.00 50.33      A
ATOM    388  CD  LYS A  61      56.731  35.255  62.677  1.00 50.33      A
ATOM    389  CE  LYS A  61      58.029  36.018  62.915  1.00 50.33      A
ATOM    390  NZ  LYS A  61      58.852  35.406  63.994  1.00 50.33      A
ATOM    391  C   LYS A  61      55.208  32.364  63.560  1.00 59.73      A
ATOM    392  O   LYS A  61      55.184  31.844  62.448  1.00 59.73      A
ATOM    393  N   LYS A  62      56.168  32.113  64.445  1.00 50.25      A
ATOM    394  CA  LYS A  62      57.237  31.190  64.112  1.00 50.25      A
ATOM    395  CB  LYS A  62      58.297  31.165  65.212  1.00 70.74      A
ATOM    396  CG  LYS A  62      59.040  32.475  65.350  1.00 70.74      A
ATOM    397  CD  LYS A  62      60.177  32.384  66.357  1.00 70.74      A
ATOM    398  CE  LYS A  62      60.894  33.727  66.474  1.00 70.74      A
ATOM    399  NZ  LYS A  62      62.121  33.639  67.314  1.00 70.74      A
ATOM    400  C   LYS A  62      56.609  29.812  63.953  1.00 50.25      A
ATOM    401  O   LYS A  62      56.801  29.144  62.938  1.00 50.25      A
ATOM    402  N   VAL A  63      55.837  29.404  64.953  1.00 44.77      A
ATOM    403  CA  VAL A  63      55.168  28.107  64.944  1.00 44.77      A
ATOM    404  CB  VAL A  63      54.325  27.922  66.226  1.00 51.34      A
ATOM    405  CG1 VAL A  63      53.707  26.543  66.249  1.00 51.34      A
ATOM    406  CG2 VAL A  63      55.200  28.130  67.455  1.00 51.34      A
ATOM    407  C   VAL A  63      54.268  27.913  63.720  1.00 44.77      A
ATOM    408  O   VAL A  63      54.313  26.872  63.072  1.00 44.77      A
ATOM    409  N   LEU A  64      53.447  28.908  63.405  1.00 32.87      A
ATOM    410  CA  LEU A  64      52.553  28.821  62.248  1.00 32.87      A
ATOM    411  CB  LEU A  64      51.406  29.836  62.367  1.00 41.38      A
ATOM    412  CG  LEU A  64      50.173  29.587  63.236  1.00 41.38      A
ATOM    413  CD1 LEU A  64      49.310  28.505  62.617  1.00 41.38      A
ATOM    414  CD2 LEU A  64      50.606  29.195  64.630  1.00 41.38      A
ATOM    415  C   LEU A  64      53.296  29.101  60.948  1.00 32.87      A
ATOM    416  O   LEU A  64      52.736  28.918  59.870  1.00 32.87      A
ATOM    417  N   SER A  65      54.548  29.548  61.047  1.00 42.60      A
ATOM    418  CA  SER A  65      55.333  29.889  59.859  1.00 42.60      A
ATOM    419  CB  SER A  65      55.719  28.626  59.081  1.00 59.96      A
ATOM    420  OG  SER A  65      56.738  27.908  59.759  1.00 59.96      A
ATOM    421  C   SER A  65      54.534  30.841  58.960  1.00 42.60      A
ATOM    422  O   SER A  65      54.162  30.501  57.833  1.00 42.60      A
ATOM    423  N   VAL A  66      54.266  32.037  59.473  1.00 37.30      A
ATOM    424  CA  VAL A  66      53.515  33.026  58.721  1.00 37.30      A
ATOM    425  CB  VAL A  66      51.992  32.916  59.032  1.00 65.92      A
ATOM    426  CG1 VAL A  66      51.434  31.630  58.447  1.00 65.92      A
ATOM    427  CG2 VAL A  66      51.754  32.927  60.533  1.00 65.92      A
ATOM    428  C   VAL A  66      54.004  34.436  59.024  1.00 37.30      A
ATOM    429  O   VAL A  66      54.865  34.641  59.894  1.00 37.30      A
ATOM    430  N   ASP A  67      53.455  35.396  58.285  1.00 42.15      A
ATOM    431  CA  ASP A  67      53.787  36.812  58.429  1.00 42.15      A
ATOM    432  CB  ASP A  67      53.186  37.587  57.243  1.00 69.98      A
ATOM    433  CG  ASP A  67      53.562  39.059  57.239  1.00 69.98      A
ATOM    434  OD1 ASP A  67      54.770  39.367  57.146  1.00 69.98      A
```

FIGURE 2-6

| | | | | | | | | | |
|---|---|---|---|---|---|---|---|---|---|
| ATOM | 435 | OD2 | ASP A | 67 | 52.644 | 39.908 | 57.321 | 1.00 69.98 | A |
| ATOM | 436 | C | ASP A | 67 | 53.194 | 37.304 | 59.753 | 1.00 42.15 | A |
| ATOM | 437 | O | ASP A | 67 | 52.018 | 37.047 | 60.046 | 1.00 42.15 | A |
| ATOM | 438 | N | LEU A | 68 | 54.006 | 37.995 | 60.551 | 1.00 43.19 | A |
| ATOM | 439 | CA | LEU A | 68 | 53.542 | 38.516 | 61.836 | 1.00 43.19 | A |
| ATOM | 440 | CB | LEU A | 68 | 54.655 | 39.303 | 62.521 | 1.00 28.99 | A |
| ATOM | 441 | CG | LEU A | 68 | 54.292 | 39.876 | 63.890 | 1.00 28.99 | A |
| ATOM | 442 | CD1 | LEU A | 68 | 53.785 | 38.755 | 64.802 | 1.00 28.99 | A |
| ATOM | 443 | CD2 | LEU A | 68 | 55.507 | 40.546 | 64.507 | 1.00 28.99 | A |
| ATOM | 444 | C | LEU A | 68 | 52.320 | 39.416 | 61.645 | 1.00 43.19 | A |
| ATOM | 445 | O | LEU A | 68 | 51.379 | 39.404 | 62.452 | 1.00 43.19 | A |
| ATOM | 446 | N | GLY A | 69 | 52.338 | 40.186 | 60.563 | 1.00 24.15 | A |
| ATOM | 447 | CA | GLY A | 69 | 51.236 | 41.076 | 60.276 | 1.00 24.15 | A |
| ATOM | 448 | C | GLY A | 69 | 49.977 | 40.315 | 59.920 | 1.00 24.15 | A |
| ATOM | 449 | O | GLY A | 69 | 48.871 | 40.711 | 60.307 | 1.00 24.15 | A |
| ATOM | 450 | N | ALA A | 70 | 50.122 | 39.227 | 59.172 | 1.00 34.42 | A |
| ATOM | 451 | CA | ALA A | 70 | 48.949 | 38.434 | 58.799 | 1.00 34.42 | A |
| ATOM | 452 | CB | ALA A | 70 | 49.316 | 37.387 | 57.762 | 1.00 25.53 | A |
| ATOM | 453 | C | ALA A | 70 | 48.412 | 37.758 | 60.053 | 1.00 34.42 | A |
| ATOM | 454 | O | ALA A | 70 | 47.199 | 37.606 | 60.225 | 1.00 34.42 | A |
| ATOM | 455 | N | LEU A | 71 | 49.321 | 37.356 | 60.933 | 1.00 33.80 | A |
| ATOM | 456 | CA | LEU A | 71 | 48.905 | 36.718 | 62.166 | 1.00 33.80 | A |
| ATOM | 457 | CB | LEU A | 71 | 50.117 | 36.208 | 62.948 | 1.00 27.48 | A |
| ATOM | 458 | CG | LEU A | 71 | 49.810 | 35.500 | 64.269 | 1.00 27.48 | A |
| ATOM | 459 | CD1 | LEU A | 71 | 48.665 | 34.512 | 64.089 | 1.00 27.48 | A |
| ATOM | 460 | CD2 | LEU A | 71 | 51.069 | 34.784 | 64.748 | 1.00 27.48 | A |
| ATOM | 461 | C | LEU A | 71 | 48.136 | 37.726 | 63.003 | 1.00 33.80 | A |
| ATOM | 462 | O | LEU A | 71 | 47.015 | 37.459 | 63.446 | 1.00 33.80 | A |
| ATOM | 463 | N | THR A | 72 | 48.730 | 38.895 | 63.203 | 1.00 29.00 | A |
| ATOM | 464 | CA | THR A | 72 | 48.082 | 39.914 | 64.008 | 1.00 29.00 | A |
| ATOM | 465 | CB | THR A | 72 | 48.895 | 41.210 | 64.002 | 1.00 31.46 | A |
| ATOM | 466 | OG1 | THR A | 72 | 50.117 | 40.983 | 64.719 | 1.00 31.46 | A |
| ATOM | 467 | CG2 | THR A | 72 | 48.106 | 42.349 | 64.663 | 1.00 31.46 | A |
| ATOM | 468 | C | THR A | 72 | 46.657 | 40.181 | 63.555 | 1.00 29.00 | A |
| ATOM | 469 | O | THR A | 72 | 45.741 | 40.242 | 64.384 | 1.00 29.00 | A |
| ATOM | 470 | N | ARG A | 73 | 46.460 | 40.333 | 62.249 | 1.00 39.42 | A |
| ATOM | 471 | CA | ARG A | 73 | 45.120 | 40.580 | 61.728 | 1.00 39.42 | A |
| ATOM | 472 | CB | ARG A | 73 | 45.136 | 40.709 | 60.204 | 1.00 68.23 | A |
| ATOM | 473 | CG | ARG A | 73 | 45.743 | 41.993 | 59.689 | 1.00 68.23 | A |
| ATOM | 474 | CD | ARG A | 73 | 45.392 | 42.203 | 58.226 | 1.00 68.23 | A |
| ATOM | 475 | NE | ARG A | 73 | 46.042 | 43.386 | 57.676 | 1.00 68.23 | A |
| ATOM | 476 | CZ | ARG A | 73 | 47.361 | 43.536 | 57.580 | 1.00 68.23 | A |
| ATOM | 477 | NH1 | ARG A | 73 | 48.180 | 42.576 | 57.999 | 1.00 68.23 | A |
| ATOM | 478 | NH2 | ARG A | 73 | 47.868 | 44.651 | 57.064 | 1.00 68.23 | A |
| ATOM | 479 | C | ARG A | 73 | 44.207 | 39.423 | 62.117 | 1.00 39.42 | A |
| ATOM | 480 | O | ARG A | 73 | 43.056 | 39.630 | 62.507 | 1.00 39.42 | A |
| ATOM | 481 | N | MET A | 74 | 44.733 | 38.207 | 62.006 | 1.00 34.55 | A |
| ATOM | 482 | CA | MET A | 74 | 43.972 | 37.006 | 62.342 | 1.00 34.55 | A |
| ATOM | 483 | CB | MET A | 74 | 44.764 | 35.751 | 61.921 | 1.00 18.52 | A |
| ATOM | 484 | CG | MET A | 74 | 44.122 | 34.405 | 62.282 | 1.00 18.52 | A |
| ATOM | 485 | SD | MET A | 74 | 42.438 | 34.164 | 61.672 | 1.00 18.52 | A |
| ATOM | 486 | CE | MET A | 74 | 42.765 | 32.941 | 60.397 | 1.00 18.52 | A |
| ATOM | 487 | C | MET A | 74 | 43.651 | 36.973 | 63.840 | 1.00 34.55 | A |
| ATOM | 488 | O | MET A | 74 | 42.504 | 36.704 | 64.235 | 1.00 34.55 | A |
| ATOM | 489 | N | LEU A | 75 | 44.656 | 37.247 | 64.675 | 1.00 29.89 | A |
| ATOM | 490 | CA | LEU A | 75 | 44.429 | 37.251 | 66.115 | 1.00 29.89 | A |
| ATOM | 491 | CB | LEU A | 75 | 45.728 | 37.581 | 66.870 | 1.00 15.40 | A |
| ATOM | 492 | CG | LEU A | 75 | 46.720 | 36.410 | 66.867 | 1.00 15.40 | A |
| ATOM | 493 | CD1 | LEU A | 75 | 48.069 | 36.851 | 67.405 | 1.00 15.40 | A |
| ATOM | 494 | CD2 | LEU A | 75 | 46.141 | 35.244 | 67.689 | 1.00 15.40 | A |
| ATOM | 495 | C | LEU A | 75 | 43.349 | 38.277 | 66.422 | 1.00 29.89 | A |
| ATOM | 496 | O | LEU A | 75 | 42.408 | 37.996 | 67.171 | 1.00 29.89 | A |
| ATOM | 497 | N | ASP A | 76 | 43.477 | 39.456 | 65.811 | 1.00 31.44 | A |
| ATOM | 498 | CA | ASP A | 76 | 42.508 | 40.524 | 66.013 | 1.00 31.44 | A |
| ATOM | 499 | CB | ASP A | 76 | 42.846 | 41.722 | 65.136 | 1.00 97.34 | A |
| ATOM | 500 | CG | ASP A | 76 | 43.324 | 42.895 | 65.948 | 1.00 97.34 | A |
| ATOM | 501 | OD1 | ASP A | 76 | 42.531 | 43.382 | 66.781 | 1.00 97.34 | A |
| ATOM | 502 | OD2 | ASP A | 76 | 44.484 | 43.322 | 65.770 | 1.00 97.34 | A |
| ATOM | 503 | C | ASP A | 76 | 41.096 | 40.053 | 65.734 | 1.00 31.44 | A |
| ATOM | 504 | O | ASP A | 76 | 40.204 | 40.244 | 66.555 | 1.00 31.44 | A |
| ATOM | 505 | N | ARG A | 77 | 40.898 | 39.416 | 64.586 | 1.00 31.21 | A |
| ATOM | 506 | CA | ARG A | 77 | 39.576 | 38.914 | 64.217 | 1.00 31.21 | A |
| ATOM | 507 | CB | ARG A | 77 | 39.600 | 38.275 | 62.818 | 1.00 77.50 | A |

FIGURE 2-7

| | | | | | | | | | | |
|---|---|---|---|---|---|---|---|---|---|---|
| ATOM | 508 | CG | ARG | A | 77 | 40.061 | 39.194 | 61.696 | 1.00 77.50 | A |
| ATOM | 509 | CD | ARG | A | 77 | 39.341 | 38.870 | 60.393 | 1.00 77.50 | A |
| ATOM | 510 | NE | ARG | A | 77 | 39.526 | 37.486 | 59.971 | 1.00 77.50 | A |
| ATOM | 511 | CZ | ARG | A | 77 | 40.620 | 37.019 | 59.375 | 1.00 77.50 | A |
| ATOM | 512 | NH1 | ARG | A | 77 | 41.645 | 37.829 | 59.120 | 1.00 77.50 | A |
| ATOM | 513 | NH2 | ARG | A | 77 | 40.687 | 35.734 | 59.032 | 1.00 77.50 | A |
| ATOM | 514 | C | ARG | A | 77 | 39.088 | 37.878 | 65.233 | 1.00 31.21 | A |
| ATOM | 515 | O | ARG | A | 77 | 37.913 | 37.885 | 65.628 | 1.00 31.21 | A |
| ATOM | 516 | N | LEU | A | 78 | 39.998 | 36.994 | 65.654 | 1.00 31.76 | A |
| ATOM | 517 | CA | LEU | A | 78 | 39.657 | 35.945 | 66.608 | 1.00 31.76 | A |
| ATOM | 518 | CB | LEU | A | 78 | 40.786 | 34.916 | 66.696 | 1.00 22.72 | A |
| ATOM | 519 | CG | LEU | A | 78 | 41.060 | 34.145 | 65.394 | 1.00 22.72 | A |
| ATOM | 520 | CD1 | LEU | A | 78 | 42.129 | 33.095 | 65.622 | 1.00 22.72 | A |
| ATOM | 521 | CD2 | LEU | A | 78 | 39.769 | 33.474 | 64.917 | 1.00 22.72 | A |
| ATOM | 522 | C | LEU | A | 78 | 39.318 | 36.488 | 67.993 | 1.00 31.76 | A |
| ATOM | 523 | O | LEU | A | 78 | 38.544 | 35.876 | 68.730 | 1.00 31.76 | A |
| ATOM | 524 | N | VAL | A | 79 | 39.889 | 37.632 | 68.355 | 1.00 25.81 | A |
| ATOM | 525 | CA | VAL | A | 79 | 39.568 | 38.209 | 69.649 | 1.00 25.81 | A |
| ATOM | 526 | CB | VAL | A | 79 | 40.581 | 39.316 | 70.056 | 1.00 14.52 | A |
| ATOM | 527 | CG1 | VAL | A | 79 | 40.103 | 40.047 | 71.328 | 1.00 14.52 | A |
| ATOM | 528 | CG2 | VAL | A | 79 | 41.977 | 38.675 | 70.305 | 1.00 14.52 | A |
| ATOM | 529 | C | VAL | A | 79 | 38.159 | 38.766 | 69.514 | 1.00 25.81 | A |
| ATOM | 530 | O | VAL | A | 79 | 37.359 | 38.688 | 70.447 | 1.00 25.81 | A |
| ATOM | 531 | N | CYS | A | 80 | 37.834 | 39.297 | 68.338 | 1.00 30.46 | A |
| ATOM | 532 | CA | CYS | A | 80 | 36.488 | 39.825 | 68.103 | 1.00 30.46 | A |
| ATOM | 533 | CB | CYS | A | 80 | 36.381 | 40.469 | 66.724 | 1.00 75.62 | A |
| ATOM | 534 | SG | CYS | A | 80 | 37.191 | 42.062 | 66.616 | 1.00 75.62 | A |
| ATOM | 535 | C | CYS | A | 80 | 35.454 | 38.718 | 68.217 | 1.00 30.46 | A |
| ATOM | 536 | O | CYS | A | 80 | 34.404 | 38.925 | 68.802 | 1.00 30.46 | A |
| ATOM | 537 | N | LYS | A | 81 | 35.747 | 37.541 | 67.666 | 1.00 26.41 | A |
| ATOM | 538 | CA | LYS | A | 81 | 34.797 | 36.430 | 67.728 | 1.00 26.41 | A |
| ATOM | 539 | CB | LYS | A | 81 | 35.261 | 35.250 | 66.870 | 1.00 27.80 | A |
| ATOM | 540 | CG | LYS | A | 81 | 35.336 | 35.482 | 65.354 | 1.00 27.80 | A |
| ATOM | 541 | CD | LYS | A | 81 | 35.801 | 34.183 | 64.666 | 1.00 27.80 | A |
| ATOM | 542 | CE | LYS | A | 81 | 36.220 | 34.388 | 63.206 | 1.00 27.80 | A |
| ATOM | 543 | NZ | LYS | A | 81 | 35.067 | 34.552 | 62.277 | 1.00 27.80 | A |
| ATOM | 544 | C | LYS | A | 81 | 34.639 | 35.935 | 69.157 | 1.00 26.41 | A |
| ATOM | 545 | O | LYS | A | 81 | 33.690 | 35.219 | 69.473 | 1.00 26.41 | A |
| ATOM | 546 | N | GLY | A | 82 | 35.574 | 36.306 | 70.025 | 1.00 28.59 | A |
| ATOM | 547 | CA | GLY | A | 82 | 35.512 | 35.847 | 71.401 | 1.00 28.59 | A |
| ATOM | 548 | C | GLY | A | 82 | 36.158 | 34.482 | 71.602 | 1.00 28.59 | A |
| ATOM | 549 | O | GLY | A | 82 | 35.887 | 33.804 | 72.591 | 1.00 28.59 | A |
| ATOM | 550 | N | TRP | A | 83 | 37.019 | 34.067 | 70.679 | 1.00 24.24 | A |
| ATOM | 551 | CA | TRP | A | 83 | 37.678 | 32.764 | 70.797 | 1.00 24.24 | A |
| ATOM | 552 | CB | TRP | A | 83 | 37.796 | 32.088 | 69.410 | 1.00 17.27 | A |
| ATOM | 553 | CG | TRP | A | 83 | 36.457 | 31.894 | 68.722 | 1.00 17.27 | A |
| ATOM | 554 | CD2 | TRP | A | 83 | 36.236 | 31.502 | 67.365 | 1.00 17.27 | A |
| ATOM | 555 | CE2 | TRP | A | 83 | 34.838 | 31.467 | 67.158 | 1.00 17.27 | A |
| ATOM | 556 | CE3 | TRP | A | 83 | 37.083 | 31.178 | 66.297 | 1.00 17.27 | A |
| ATOM | 557 | CD1 | TRP | A | 83 | 35.215 | 32.073 | 69.273 | 1.00 17.27 | A |
| ATOM | 558 | NE1 | TRP | A | 83 | 34.237 | 31.819 | 68.338 | 1.00 17.27 | A |
| ATOM | 559 | CZ2 | TRP | A | 83 | 34.272 | 31.124 | 65.935 | 1.00 17.27 | A |
| ATOM | 560 | CZ3 | TRP | A | 83 | 36.514 | 30.839 | 65.077 | 1.00 17.27 | A |
| ATOM | 561 | CH2 | TRP | A | 83 | 35.120 | 30.816 | 64.911 | 1.00 17.27 | A |
| ATOM | 562 | C | TRP | A | 83 | 39.061 | 32.899 | 71.428 | 1.00 24.24 | A |
| ATOM | 563 | O | TRP | A | 83 | 39.547 | 31.973 | 72.083 | 1.00 24.24 | A |
| ATOM | 564 | N | VAL | A | 84 | 39.688 | 34.058 | 71.231 | 1.00 30.33 | A |
| ATOM | 565 | CA | VAL | A | 84 | 41.014 | 34.326 | 71.777 | 1.00 30.33 | A |
| ATOM | 566 | CB | VAL | A | 84 | 42.046 | 34.570 | 70.659 | 1.00 10.78 | A |
| ATOM | 567 | CG1 | VAL | A | 84 | 43.398 | 34.887 | 71.274 | 1.00 10.78 | A |
| ATOM | 568 | CG2 | VAL | A | 84 | 42.144 | 33.354 | 69.763 | 1.00 10.78 | A |
| ATOM | 569 | C | VAL | A | 84 | 40.982 | 35.570 | 72.654 | 1.00 30.33 | A |
| ATOM | 570 | O | VAL | A | 84 | 40.268 | 36.530 | 72.359 | 1.00 30.33 | A |
| ATOM | 571 | N | GLU | A | 85 | 41.785 | 35.552 | 73.712 | 1.00 30.48 | A |
| ATOM | 572 | CA | GLU | A | 85 | 41.883 | 36.651 | 74.671 | 1.00 30.48 | A |
| ATOM | 573 | CB | GLU | A | 85 | 41.482 | 36.121 | 76.051 | 1.00 48.81 | A |
| ATOM | 574 | CG | GLU | A | 85 | 41.723 | 37.057 | 77.224 | 1.00 48.81 | A |
| ATOM | 575 | CD | GLU | A | 85 | 41.513 | 36.359 | 78.567 | 1.00 48.81 | A |
| ATOM | 576 | OE1 | GLU | A | 85 | 41.467 | 37.055 | 79.610 | 1.00 48.81 | A |
| ATOM | 577 | OE2 | GLU | A | 85 | 41.399 | 35.110 | 78.581 | 1.00 48.81 | A |
| ATOM | 578 | C | GLU | A | 85 | 43.322 | 37.187 | 74.715 | 1.00 30.48 | A |
| ATOM | 579 | O | GLU | A | 85 | 44.273 | 36.401 | 74.689 | 1.00 30.48 | A |
| ATOM | 580 | N | ARG | A | 86 | 43.486 | 38.511 | 74.775 | 1.00 26.85 | A |

FIGURE 2-8

| ATOM | 581 | CA | ARG A | 86 | 44.830 | 39.118 | 74.855 | 1.00 | 26.85 | A |
|------|-----|-----|-------|----|--------|--------|--------|------|-------|---|
| ATOM | 582 | CB | ARG A | 86 | 44.903 | 40.444 | 74.097 | 1.00 | 38.70 | A |
| ATOM | 583 | CG | ARG A | 86 | 44.744 | 40.394 | 72.600 | 1.00 | 38.70 | A |
| ATOM | 584 | CD | ARG A | 86 | 44.769 | 41.827 | 72.082 | 1.00 | 38.70 | A |
| ATOM | 585 | NE | ARG A | 86 | 44.228 | 41.997 | 70.733 | 1.00 | 38.70 | A |
| ATOM | 586 | CZ | ARG A | 86 | 44.744 | 41.439 | 69.642 | 1.00 | 38.70 | A |
| ATOM | 587 | NH1 | ARG A | 86 | 45.820 | 40.656 | 69.729 | 1.00 | 38.70 | A |
| ATOM | 588 | NH2 | ARG A | 86 | 44.201 | 41.687 | 68.456 | 1.00 | 38.70 | A |
| ATOM | 589 | C | ARG A | 86 | 45.162 | 39.426 | 76.315 | 1.00 | 26.85 | A |
| ATOM | 590 | O | ARG A | 86 | 44.304 | 39.887 | 77.059 | 1.00 | 26.85 | A |
| ATOM | 591 | N | LEU A | 87 | 46.401 | 39.183 | 76.724 | 1.00 | 25.04 | A |
| ATOM | 592 | CA | LEU A | 87 | 46.815 | 39.474 | 78.097 | 1.00 | 25.04 | A |
| ATOM | 593 | CB | LEU A | 87 | 47.118 | 38.184 | 78.858 | 1.00 | 36.39 | A |
| ATOM | 594 | CG | LEU A | 87 | 45.922 | 37.372 | 79.349 | 1.00 | 36.39 | A |
| ATOM | 595 | CD1 | LEU A | 87 | 46.416 | 36.090 | 79.986 | 1.00 | 36.39 | A |
| ATOM | 596 | CD2 | LEU A | 87 | 45.134 | 38.181 | 80.360 | 1.00 | 36.39 | A |
| ATOM | 597 | C | LEU A | 87 | 48.053 | 40.366 | 78.090 | 1.00 | 25.04 | A |
| ATOM | 598 | O | LEU A | 87 | 48.894 | 40.291 | 77.174 | 1.00 | 25.04 | A |
| ATOM | 599 | N | PRO A | 88 | 48.185 | 41.237 | 79.101 | 1.00 | 41.37 | A |
| ATOM | 600 | CD | PRO A | 88 | 47.257 | 41.606 | 80.178 | 1.00 | 36.25 | A |
| ATOM | 601 | CA | PRO A | 88 | 49.370 | 42.099 | 79.109 | 1.00 | 41.37 | A |
| ATOM | 602 | CB | PRO A | 88 | 49.106 | 43.057 | 80.271 | 1.00 | 36.25 | A |
| ATOM | 603 | CG | PRO A | 88 | 47.602 | 43.063 | 80.385 | 1.00 | 36.25 | A |
| ATOM | 604 | C | PRO A | 88 | 50.613 | 41.257 | 79.333 | 1.00 | 41.37 | A |
| ATOM | 605 | O | PRO A | 88 | 50.626 | 40.363 | 80.192 | 1.00 | 41.37 | A |
| ATOM | 606 | N | ASN A | 89 | 51.642 | 41.530 | 78.540 | 1.00 | 40.92 | A |
| ATOM | 607 | CA | ASN A | 89 | 52.890 | 40.806 | 78.668 | 1.00 | 40.92 | A |
| ATOM | 608 | CB | ASN A | 89 | 53.757 | 40.990 | 77.426 | 1.00 | 48.54 | A |
| ATOM | 609 | CG | ASN A | 89 | 54.948 | 40.063 | 77.424 | 1.00 | 48.54 | A |
| ATOM | 610 | OD1 | ASN A | 89 | 55.520 | 39.784 | 78.482 | 1.00 | 48.54 | A |
| ATOM | 611 | ND2 | ASN A | 89 | 55.334 | 39.581 | 76.244 | 1.00 | 48.54 | A |
| ATOM | 612 | C | ASN A | 89 | 53.612 | 41.376 | 79.881 | 1.00 | 40.92 | A |
| ATOM | 613 | O | ASN A | 89 | 54.057 | 42.526 | 79.864 | 1.00 | 40.92 | A |
| ATOM | 614 | N | PRO A | 90 | 53.727 | 40.578 | 80.955 | 1.00 | 44.27 | A |
| ATOM | 615 | CD | PRO A | 90 | 53.271 | 39.176 | 80.997 | 1.00 | 40.09 | A |
| ATOM | 616 | CA | PRO A | 90 | 54.381 | 40.941 | 82.216 | 1.00 | 44.27 | A |
| ATOM | 617 | CB | PRO A | 90 | 54.617 | 39.586 | 82.875 | 1.00 | 40.09 | A |
| ATOM | 618 | CG | PRO A | 90 | 53.392 | 38.836 | 82.477 | 1.00 | 40.09 | A |
| ATOM | 619 | C | PRO A | 90 | 55.668 | 41.769 | 82.115 | 1.00 | 44.27 | A |
| ATOM | 620 | O | PRO A | 90 | 55.866 | 42.688 | 82.911 | 1.00 | 44.27 | A |
| ATOM | 621 | N | ASN A | 91 | 56.544 | 41.462 | 81.158 | 1.00 | 69.68 | A |
| ATOM | 622 | CA | ASN A | 91 | 57.785 | 42.226 | 81.060 | 1.00 | 69.68 | A |
| ATOM | 623 | CB | ASN A | 91 | 59.005 | 41.288 | 81.081 | 1.00 | 76.88 | A |
| ATOM | 624 | CG | ASN A | 91 | 59.169 | 40.493 | 79.797 | 1.00 | 76.88 | A |
| ATOM | 625 | OD1 | ASN A | 91 | 59.444 | 41.050 | 78.732 | 1.00 | 76.88 | A |
| ATOM | 626 | ND2 | ASN A | 91 | 59.008 | 39.179 | 79.896 | 1.00 | 76.88 | A |
| ATOM | 627 | C | ASN A | 91 | 57.897 | 43.179 | 79.876 | 1.00 | 69.68 | A |
| ATOM | 628 | O | ASN A | 91 | 58.384 | 44.303 | 80.029 | 1.00 | 69.68 | A |
| ATOM | 629 | N | ASP A | 92 | 57.447 | 42.745 | 78.702 | 1.00 | 97.47 | A |
| ATOM | 630 | CA | ASP A | 92 | 57.533 | 43.585 | 77.513 | 1.00 | 97.47 | A |
| ATOM | 631 | CB | ASP A | 92 | 56.898 | 42.886 | 76.310 | 1.00 | 77.46 | A |
| ATOM | 632 | CG | ASP A | 92 | 57.184 | 43.608 | 75.009 | 1.00 | 77.46 | A |
| ATOM | 633 | OD1 | ASP A | 92 | 56.846 | 44.808 | 74.915 | 1.00 | 77.46 | A |
| ATOM | 634 | OD2 | ASP A | 92 | 57.749 | 42.980 | 74.087 | 1.00 | 77.46 | A |
| ATOM | 635 | C | ASP A | 92 | 56.869 | 44.941 | 77.721 | 1.00 | 97.47 | A |
| ATOM | 636 | O | ASP A | 92 | 57.351 | 45.956 | 77.222 | 1.00 | 97.47 | A |
| ATOM | 637 | N | LYS A | 93 | 55.758 | 44.951 | 78.451 | 1.00 | 79.22 | A |
| ATOM | 638 | CA | LYS A | 93 | 55.035 | 46.187 | 78.735 | 1.00 | 79.22 | A |
| ATOM | 639 | CB | LYS A | 93 | 55.964 | 47.188 | 79.439 | 1.00 | 105.99 | A |
| ATOM | 640 | CG | LYS A | 93 | 56.461 | 46.727 | 80.813 | 1.00 | 105.99 | A |
| ATOM | 641 | CD | LYS A | 93 | 57.584 | 47.619 | 81.345 | 1.00 | 105.99 | A |
| ATOM | 642 | CE | LYS A | 93 | 57.140 | 49.067 | 81.530 | 1.00 | 105.99 | A |
| ATOM | 643 | NZ | LYS A | 93 | 56.095 | 49.203 | 82.577 | 1.00 | 105.99 | A |
| ATOM | 644 | C | LYS A | 93 | 54.434 | 46.831 | 77.481 | 1.00 | 79.22 | A |
| ATOM | 645 | O | LYS A | 93 | 53.643 | 47.770 | 77.575 | 1.00 | 79.22 | A |
| ATOM | 646 | N | ARG A | 94 | 54.812 | 46.328 | 76.309 | 1.00 | 101.34 | A |
| ATOM | 647 | CA | ARG A | 94 | 54.298 | 46.854 | 75.047 | 1.00 | 101.34 | A |
| ATOM | 648 | CB | ARG A | 94 | 55.382 | 47.656 | 74.312 | 1.00 | 133.25 | A |
| ATOM | 649 | CG | ARG A | 94 | 55.380 | 49.164 | 74.590 | 1.00 | 133.25 | A |
| ATOM | 650 | CD | ARG A | 94 | 55.552 | 49.481 | 76.072 | 1.00 | 133.25 | A |
| ATOM | 651 | NE | ARG A | 94 | 55.707 | 50.913 | 76.325 | 1.00 | 133.25 | A |
| ATOM | 652 | CZ | ARG A | 94 | 55.877 | 51.447 | 77.533 | 1.00 | 133.25 | A |
| ATOM | 653 | NH1 | ARG A | 94 | 55.911 | 50.670 | 78.610 | 1.00 | 133.25 | A |

FIGURE 2-9

```
ATOM    654  NH2 ARG A  94      56.026  52.759  77.663  1.00133.25       A
ATOM    655  C   ARG A  94      53.808  45.722  74.152  1.00101.34       A
ATOM    656  O   ARG A  94      53.294  45.965  73.060  1.00101.34       A
ATOM    657  N   GLY A  95      53.974  44.486  74.618  1.00 68.05       A
ATOM    658  CA  GLY A  95      53.537  43.336  73.846  1.00 68.05       A
ATOM    659  C   GLY A  95      52.361  42.639  74.503  1.00 68.05       A
ATOM    660  O   GLY A  95      51.963  42.995  75.611  1.00 68.05       A
ATOM    661  N   VAL A  96      51.799  41.644  73.826  1.00 32.70       A
ATOM    662  CA  VAL A  96      50.662  40.914  74.378  1.00 32.70       A
ATOM    663  CB  VAL A  96      49.384  41.151  73.540  1.00 46.59       A
ATOM    664  CG1 VAL A  96      49.061  42.631  73.489  1.00 46.59       A
ATOM    665  CG2 VAL A  96      49.576  40.582  72.134  1.00 46.59       A
ATOM    666  C   VAL A  96      50.880  39.401  74.464  1.00 32.70       A
ATOM    667  O   VAL A  96      51.871  38.864  73.975  1.00 32.70       A
ATOM    668  N   LEU A  97      49.938  38.729  75.112  1.00 23.07       A
ATOM    669  CA  LEU A  97      49.964  37.282  75.251  1.00 23.07       A
ATOM    670  CB  LEU A  97      50.225  36.883  76.703  1.00 46.89       A
ATOM    671  CG  LEU A  97      51.491  37.474  77.318  1.00 46.89       A
ATOM    672  CD1 LEU A  97      51.666  36.944  78.730  1.00 46.89       A
ATOM    673  CD2 LEU A  97      52.692  37.111  76.456  1.00 46.89       A
ATOM    674  C   LEU A  97      48.570  36.839  74.831  1.00 23.07       A
ATOM    675  O   LEU A  97      47.575  37.517  75.125  1.00 23.07       A
ATOM    676  N   VAL A  98      48.492  35.724  74.120  1.00 29.54       A
ATOM    677  CA  VAL A  98      47.199  35.243  73.682  1.00 29.54       A
ATOM    678  CB  VAL A  98      47.075  35.216  72.143  1.00 16.38       A
ATOM    679  CG1 VAL A  98      47.126  36.631  71.597  1.00 16.38       A
ATOM    680  CG2 VAL A  98      48.186  34.384  71.553  1.00 16.38       A
ATOM    681  C   VAL A  98      46.968  33.859  74.208  1.00 29.54       A
ATOM    682  O   VAL A  98      47.908  33.076  74.396  1.00 29.54       A
ATOM    683  N   LYS A  99      45.699  33.575  74.453  1.00 22.55       A
ATOM    684  CA  LYS A  99      45.273  32.289  74.960  1.00 22.55       A
ATOM    685  CB  LYS A  99      45.310  32.298  76.491  1.00 25.06       A
ATOM    686  CG  LYS A  99      44.402  33.337  77.130  1.00 25.06       A
ATOM    687  CD  LYS A  99      44.394  33.234  78.669  1.00 25.06       A
ATOM    688  CE  LYS A  99      43.619  32.009  79.172  1.00 25.06       A
ATOM    689  NZ  LYS A  99      42.150  32.101  78.900  1.00 25.06       A
ATOM    690  C   LYS A  99      43.841  32.074  74.469  1.00 22.55       A
ATOM    691  O   LYS A  99      43.173  33.020  74.042  1.00 22.55       A
ATOM    692  N   LEU A 100      43.369  30.837  74.507  1.00 21.07       A
ATOM    693  CA  LEU A 100      42.010  30.576  74.080  1.00 21.07       A
ATOM    694  CB  LEU A 100      41.818  29.095  73.759  1.00 18.76       A
ATOM    695  CG  LEU A 100      42.598  28.488  72.578  1.00 18.76       A
ATOM    696  CD1 LEU A 100      41.992  27.126  72.253  1.00 18.76       A
ATOM    697  CD2 LEU A 100      42.526  29.400  71.343  1.00 18.76       A
ATOM    698  C   LEU A 100      41.053  30.956  75.195  1.00 21.07       A
ATOM    699  O   LEU A 100      41.399  30.864  76.387  1.00 21.07       A
ATOM    700  N   THR A 101      39.857  31.412  74.827  1.00 17.16       A
ATOM    701  CA  THR A 101      38.858  31.711  75.849  1.00 17.16       A
ATOM    702  CB  THR A 101      37.775  32.645  75.357  1.00  7.57       A
ATOM    703  OG1 THR A 101      37.178  32.067  74.189  1.00  7.57       A
ATOM    704  CG2 THR A 101      38.361  34.025  75.019  1.00  7.57       A
ATOM    705  C   THR A 101      38.243  30.341  76.029  1.00 17.16       A
ATOM    706  O   THR A 101      38.624  29.393  75.332  1.00 17.16       A
ATOM    707  N   THR A 102      37.292  30.210  76.943  1.00 17.61       A
ATOM    708  CA  THR A 102      36.710  28.892  77.142  1.00 17.61       A
ATOM    709  CB  THR A 102      35.924  28.813  78.492  1.00 19.84       A
ATOM    710  OG1 THR A 102      34.558  29.190  78.309  1.00 19.84       A
ATOM    711  CG2 THR A 102      36.566  29.748  79.500  1.00 19.84       A
ATOM    712  C   THR A 102      35.861  28.546  75.929  1.00 17.61       A
ATOM    713  O   THR A 102      35.781  27.387  75.529  1.00 17.61       A
ATOM    714  N   GLY A 103      35.266  29.560  75.313  1.00 30.04       A
ATOM    715  CA  GLY A 103      34.470  29.318  74.121  1.00 30.04       A
ATOM    716  C   GLY A 103      35.353  28.847  72.972  1.00 30.04       A
ATOM    717  O   GLY A 103      34.990  27.928  72.224  1.00 30.04       A
ATOM    718  N   GLY A 104      36.517  29.479  72.829  1.00 27.12       A
ATOM    719  CA  GLY A 104      37.445  29.106  71.777  1.00 27.12       A
ATOM    720  C   GLY A 104      37.986  27.703  71.976  1.00 27.12       A
ATOM    721  O   GLY A 104      38.169  26.959  71.005  1.00 27.12       A
ATOM    722  N   ALA A 105      38.244  27.330  73.228  1.00 31.63       A
ATOM    723  CA  ALA A 105      38.762  25.993  73.512  1.00 31.63       A
ATOM    724  CB  ALA A 105      39.180  25.866  74.977  1.00  1.17       A
ATOM    725  C   ALA A 105      37.679  24.976  73.191  1.00 31.63       A
ATOM    726  O   ALA A 105      37.965  23.900  72.667  1.00 31.63       A
```

FIGURE 2-10

```
ATOM    727  N   ALA A 106      36.435  25.327  73.509  1.00 15.93       A
ATOM    728  CA  ALA A 106      35.304  24.439  73.238  1.00 15.93       A
ATOM    729  CB  ALA A 106      34.008  25.061  73.734  1.00 34.73       A
ATOM    730  C   ALA A 106      35.218  24.191  71.739  1.00 15.93       A
ATOM    731  O   ALA A 106      35.118  23.049  71.291  1.00 15.93       A
ATOM    732  N   ILE A 107      35.265  25.264  70.964  1.00 24.47       A
ATOM    733  CA  ILE A 107      35.198  25.144  69.516  1.00 24.47       A
ATOM    734  CB  ILE A 107      35.361  26.531  68.844  1.00 27.19       A
ATOM    735  CG2 ILE A 107      35.734  26.378  67.377  1.00 27.19       A
ATOM    736  CG1 ILE A 107      34.070  27.324  69.009  1.00 27.19       A
ATOM    737  CD1 ILE A 107      34.170  28.743  68.513  1.00 27.19       A
ATOM    738  C   ILE A 107      36.300  24.211  69.023  1.00 24.47       A
ATOM    739  O   ILE A 107      36.071  23.338  68.179  1.00 24.47       A
ATOM    740  N   CYS A 108      37.497  24.390  69.565  1.00 23.24       A
ATOM    741  CA  CYS A 108      38.627  23.572  69.145  1.00 23.24       A
ATOM    742  CB  CYS A 108      39.869  23.955  69.948  1.00 44.34       A
ATOM    743  SG  CYS A 108      41.387  23.261  69.295  1.00 44.34       A
ATOM    744  C   CYS A 108      38.307  22.095  69.336  1.00 23.24       A
ATOM    745  O   CYS A 108      38.444  21.286  68.411  1.00 23.24       A
ATOM    746  N   GLU A 109      37.864  21.755  70.543  1.00 34.17       A
ATOM    747  CA  GLU A 109      37.525  20.379  70.867  1.00 34.17       A
ATOM    748  CB  GLU A 109      37.121  20.269  72.342  1.00 54.06       A
ATOM    749  CG  GLU A 109      36.882  18.841  72.820  1.00 54.06       A
ATOM    750  CD  GLU A 109      38.027  17.892  72.469  1.00 54.06       A
ATOM    751  OE1 GLU A 109      39.195  18.212  72.790  1.00 54.06       A
ATOM    752  OE2 GLU A 109      37.755  16.822  71.876  1.00 54.06       A
ATOM    753  C   GLU A 109      36.407  19.868  69.965  1.00 34.17       A
ATOM    754  O   GLU A 109      36.491  18.775  69.423  1.00 34.17       A
ATOM    755  N   GLN A 110      35.371  20.672  69.781  1.00 31.70       A
ATOM    756  CA  GLN A 110      34.263  20.243  68.954  1.00 31.70       A
ATOM    757  CB  GLN A 110      33.130  21.268  69.050  1.00 54.33       A
ATOM    758  CG  GLN A 110      31.790  20.641  69.442  1.00 54.33       A
ATOM    759  CD  GLN A 110      31.943  19.486  70.440  1.00 54.33       A
ATOM    760  OE1 GLN A 110      32.444  19.662  71.559  1.00 54.33       A
ATOM    761  NE2 GLN A 110      31.515  18.295  70.026  1.00 54.33       A
ATOM    762  C   GLN A 110      34.680  19.988  67.498  1.00 31.70       A
ATOM    763  O   GLN A 110      34.241  19.008  66.885  1.00 31.70       A
ATOM    764  N   CYS A 111      35.535  20.852  66.947  1.00 20.80       A
ATOM    765  CA  CYS A 111      35.990  20.679  65.572  1.00 20.80       A
ATOM    766  CB  CYS A 111      36.893  21.841  65.156  1.00 32.98       A
ATOM    767  SG  CYS A 111      35.999  23.387  64.796  1.00 32.98       A
ATOM    768  C   CYS A 111      36.731  19.352  65.412  1.00 20.80       A
ATOM    769  O   CYS A 111      36.511  18.632  64.443  1.00 20.80       A
ATOM    770  N   HIS A 112      37.606  19.025  66.360  1.00 36.28       A
ATOM    771  CA  HIS A 112      38.344  17.761  66.308  1.00 36.28       A
ATOM    772  CB  HIS A 112      39.294  17.635  67.504  1.00 32.43       A
ATOM    773  CG  HIS A 112      40.594  18.365  67.339  1.00 32.43       A
ATOM    774  CD2 HIS A 112      41.170  19.340  68.085  1.00 32.43       A
ATOM    775  ND1 HIS A 112      41.493  18.072  66.334  1.00 32.43       A
ATOM    776  CE1 HIS A 112      42.566  18.830  66.470  1.00 32.43       A
ATOM    777  NE2 HIS A 112      42.397  19.608  67.525  1.00 32.43       A
ATOM    778  C   HIS A 112      37.379  16.570  66.330  1.00 36.28       A
ATOM    779  O   HIS A 112      37.537  15.610  65.575  1.00 36.28       A
ATOM    780  N   GLN A 113      36.373  16.642  67.194  1.00 32.58       A
ATOM    781  CA  GLN A 113      35.416  15.556  67.321  1.00 32.58       A
ATOM    782  CB  GLN A 113      34.575  15.737  68.585  1.00 64.21       A
ATOM    783  CG  GLN A 113      35.383  15.675  69.869  1.00 64.21       A
ATOM    784  CD  GLN A 113      34.518  15.624  71.116  1.00 64.21       A
ATOM    785  OE1 GLN A 113      35.030  15.690  72.236  1.00 64.21       A
ATOM    786  NE2 GLN A 113      33.203  15.501  70.933  1.00 64.21       A
ATOM    787  C   GLN A 113      34.493  15.334  66.133  1.00 32.58       A
ATOM    788  O   GLN A 113      34.194  14.193  65.793  1.00 32.58       A
ATOM    789  N   LEU A 114      34.050  16.406  65.487  1.00 43.53       A
ATOM    790  CA  LEU A 114      33.124  16.267  64.370  1.00 43.53       A
ATOM    791  CB  LEU A 114      32.095  17.399  64.416  1.00 83.39       A
ATOM    792  CG  LEU A 114      31.191  17.440  65.658  1.00 83.39       A
ATOM    793  CD1 LEU A 114      30.424  18.760  65.725  1.00 83.39       A
ATOM    794  CD2 LEU A 114      30.231  16.258  65.615  1.00 83.39       A
ATOM    795  C   LEU A 114      33.801  16.262  63.022  1.00 43.53       A
ATOM    796  O   LEU A 114      33.144  16.383  61.995  1.00 43.53       A
ATOM    797  N   VAL A 115      35.113  16.094  63.016  1.00 22.15       A
ATOM    798  CA  VAL A 115      35.867  16.129  61.768  1.00 22.15       A
ATOM    799  CB  VAL A 115      36.511  17.528  61.597  1.00 22.88       A
```

FIGURE 2-11

```
ATOM    800  CG1 VAL A 115      37.978  17.412  61.200  1.00 22.88      A
ATOM    801  CG2 VAL A 115      35.728  18.329  60.572  1.00 22.88      A
ATOM    802  C   VAL A 115      36.948  15.064  61.712  1.00 22.15      A
ATOM    803  O   VAL A 115      37.257  14.522  60.642  1.00 22.15      A
ATOM    804  N   GLY A 116      37.522  14.779  62.873  1.00 30.44      A
ATOM    805  CA  GLY A 116      38.581  13.797  62.966  1.00 30.44      A
ATOM    806  C   GLY A 116      38.384  12.527  62.163  1.00 30.44      A
ATOM    807  O   GLY A 116      39.139  12.257  61.224  1.00 30.44      A
ATOM    808  N   GLN A 117      37.363  11.749  62.511  1.00 39.45      A
ATOM    809  CA  GLN A 117      37.117  10.483  61.823  1.00 39.45      A
ATOM    810  CB  GLN A 117      35.899   9.783  62.424  1.00 99.18      A
ATOM    811  CG  GLN A 117      36.100   8.289  62.577  1.00 99.18      A
ATOM    812  CD  GLN A 117      37.439   7.956  63.222  1.00 99.18      A
ATOM    813  OE1 GLN A 117      37.735   8.397  64.336  1.00 99.18      A
ATOM    814  NE2 GLN A 117      38.259   7.179  62.520  1.00 99.18      A
ATOM    815  C   GLN A 117      36.947  10.619  60.317  1.00 39.45      A
ATOM    816  O   GLN A 117      37.662   9.982  59.543  1.00 39.45      A
ATOM    817  N   ASP A 118      36.004  11.453  59.901  1.00 47.18      A
ATOM    818  CA  ASP A 118      35.759  11.662  58.480  1.00 47.18      A
ATOM    819  CB  ASP A 118      34.688  12.740  58.281  1.00 77.40      A
ATOM    820  CG  ASP A 118      33.306  12.275  58.704  1.00 77.40      A
ATOM    821  OD1 ASP A 118      32.401  13.127  58.810  1.00 77.40      A
ATOM    822  OD2 ASP A 118      33.121  11.057  58.923  1.00 77.40      A
ATOM    823  C   ASP A 118      37.032  12.053  57.733  1.00 47.18      A
ATOM    824  O   ASP A 118      37.314  11.517  56.663  1.00 47.18      A
ATOM    825  N   LEU A 119      37.796  12.985  58.300  1.00 42.24      A
ATOM    826  CA  LEU A 119      39.032  13.447  57.675  1.00 42.24      A
ATOM    827  CB  LEU A 119      39.676  14.561  58.515  1.00 15.97      A
ATOM    828  CG  LEU A 119      41.092  14.941  58.055  1.00 15.97      A
ATOM    829  CD1 LEU A 119      41.020  15.406  56.612  1.00 15.97      A
ATOM    830  CD2 LEU A 119      41.684  16.010  58.936  1.00 15.97      A
ATOM    831  C   LEU A 119      40.015  12.295  57.531  1.00 42.24      A
ATOM    832  O   LEU A 119      40.662  12.137  56.496  1.00 42.24      A
ATOM    833  N   HIS A 120      40.129  11.507  58.594  1.00 39.36      A
ATOM    834  CA  HIS A 120      41.026  10.365  58.619  1.00 39.36      A
ATOM    835  CB  HIS A 120      40.947   9.655  59.959  1.00 36.14      A
ATOM    836  CG  HIS A 120      41.656   8.342  59.971  1.00 36.14      A
ATOM    837  CD2 HIS A 120      41.204   7.084  59.763  1.00 36.14      A
ATOM    838  ND1 HIS A 120      43.015   8.233  60.172  1.00 36.14      A
ATOM    839  CE1 HIS A 120      43.369   6.963  60.089  1.00 36.14      A
ATOM    840  NE2 HIS A 120      42.289   6.245  59.842  1.00 36.14      A
ATOM    841  C   HIS A 120      40.619   9.377  57.549  1.00 39.36      A
ATOM    842  O   HIS A 120      41.449   8.780  56.865  1.00 39.36      A
ATOM    843  N   GLN A 121      39.317   9.191  57.436  1.00 35.35      A
ATOM    844  CA  GLN A 121      38.738   8.281  56.467  1.00 35.35      A
ATOM    845  CB  GLN A 121      37.223   8.336  56.618  1.00 61.52      A
ATOM    846  CG  GLN A 121      36.466   7.174  56.059  1.00 61.52      A
ATOM    847  CD  GLN A 121      35.049   7.152  56.584  1.00 61.52      A
ATOM    848  OE1 GLN A 121      34.827   7.055  57.798  1.00 61.52      A
ATOM    849  NE2 GLN A 121      34.077   7.253  55.679  1.00 61.52      A
ATOM    850  C   GLN A 121      39.149   8.675  55.047  1.00 35.35      A
ATOM    851  O   GLN A 121      39.795   7.907  54.335  1.00 35.35      A
ATOM    852  N   GLU A 122      38.779   9.885  54.643  1.00 27.29      A
ATOM    853  CA  GLU A 122      39.096  10.380  53.309  1.00 27.29      A
ATOM    854  CB  GLU A 122      38.586  11.815  53.155  1.00 50.77      A
ATOM    855  CG  GLU A 122      38.783  12.414  51.772  1.00 50.77      A
ATOM    856  CD  GLU A 122      38.039  11.659  50.681  1.00 50.77      A
ATOM    857  OE1 GLU A 122      38.145  12.066  49.499  1.00 50.77      A
ATOM    858  OE2 GLU A 122      37.349  10.663  51.004  1.00 50.77      A
ATOM    859  C   GLU A 122      40.597  10.318  52.996  1.00 27.29      A
ATOM    860  O   GLU A 122      40.991   9.922  51.895  1.00 27.29      A
ATOM    861  N   LEU A 123      41.436  10.693  53.956  1.00 37.09      A
ATOM    862  CA  LEU A 123      42.871  10.675  53.718  1.00 37.09      A
ATOM    863  CB  LEU A 123      43.628  11.267  54.915  1.00 42.11      A
ATOM    864  CG  LEU A 123      43.574  12.766  55.229  1.00 42.11      A
ATOM    865  CD1 LEU A 123      44.474  13.051  56.431  1.00 42.11      A
ATOM    866  CD2 LEU A 123      44.036  13.575  54.027  1.00 42.11      A
ATOM    867  C   LEU A 123      43.406   9.269  53.443  1.00 37.09      A
ATOM    868  O   LEU A 123      44.435   9.106  52.775  1.00 37.09      A
ATOM    869  N   THR A 124      42.710   8.256  53.948  1.00 47.34      A
ATOM    870  CA  THR A 124      43.165   6.881  53.779  1.00 47.34      A
ATOM    871  CB  THR A 124      43.280   6.189  55.147  1.00 51.95      A
ATOM    872  OG1 THR A 124      41.992   6.173  55.778  1.00 51.95      A
```

FIGURE 2-12

```
ATOM    873  CG2 THR A 124      44.263   6.935  56.040  1.00 51.95           A
ATOM    874  C   THR A 124      42.293   6.006  52.885  1.00 47.34           A
ATOM    875  O   THR A 124      42.402   4.785  52.926  1.00 47.34           A
ATOM    876  N   LYS A 125      41.441   6.612  52.070  1.00 44.88           A
ATOM    877  CA  LYS A 125      40.572   5.821  51.209  1.00 44.88           A
ATOM    878  CB  LYS A 125      39.633   6.732  50.411  1.00 45.55           A
ATOM    879  CG  LYS A 125      40.317   7.559  49.354  1.00 45.55           A
ATOM    880  CD  LYS A 125      39.353   8.555  48.745  1.00 45.55           A
ATOM    881  CE  LYS A 125      40.063   9.392  47.694  1.00 45.55           A
ATOM    882  NZ  LYS A 125      39.217  10.513  47.202  1.00 45.55           A
ATOM    883  C   LYS A 125      41.338   4.899  50.257  1.00 44.88           A
ATOM    884  O   LYS A 125      40.821   3.854  49.864  1.00 44.88           A
ATOM    885  N   ASN A 126      42.561   5.276  49.886  1.00 32.03           A
ATOM    886  CA  ASN A 126      43.366   4.455  48.979  1.00 32.03           A
ATOM    887  CB  ASN A 126      44.005   5.313  47.885  1.00 55.44           A
ATOM    888  CG  ASN A 126      42.987   6.043  47.047  1.00 55.44           A
ATOM    889  OD1 ASN A 126      42.162   5.422  46.370  1.00 55.44           A
ATOM    890  ND2 ASN A 126      43.034   7.377  47.082  1.00 55.44           A
ATOM    891  C   ASN A 126      44.480   3.711  49.709  1.00 32.03           A
ATOM    892  O   ASN A 126      45.527   3.426  49.124  1.00 32.03           A
ATOM    893  N   LEU A 127      44.280   3.411  50.986  1.00 29.87           A
ATOM    894  CA  LEU A 127      45.289   2.680  51.736  1.00 29.87           A
ATOM    895  CB  LEU A 127      45.969   3.586  52.759  1.00 41.10           A
ATOM    896  CG  LEU A 127      46.688   4.836  52.259  1.00 41.10           A
ATOM    897  CD1 LEU A 127      47.585   5.351  53.383  1.00 41.10           A
ATOM    898  CD2 LEU A 127      47.524   4.516  51.029  1.00 41.10           A
ATOM    899  C   LEU A 127      44.689   1.482  52.465  1.00 29.87           A
ATOM    900  O   LEU A 127      43.617   1.576  53.065  1.00 29.87           A
ATOM    901  N   THR A 128      45.381   0.350  52.410  1.00 63.04           A
ATOM    902  CA  THR A 128      44.919  -0.845  53.102  1.00 63.04           A
ATOM    903  CB  THR A 128      45.728  -2.087  52.685  1.00 36.80           A
ATOM    904  OG1 THR A 128      47.102  -1.913  53.074  1.00 36.80           A
ATOM    905  CG2 THR A 128      45.638  -2.304  51.164  1.00 36.80           A
ATOM    906  C   THR A 128      45.161  -0.595  54.585  1.00 63.04           A
ATOM    907  O   THR A 128      45.999   0.232  54.951  1.00 63.04           A
ATOM    908  N   ALA A 129      44.435  -1.301  55.440  1.00 39.48           A
ATOM    909  CA  ALA A 129      44.606  -1.125  56.875  1.00 39.48           A
ATOM    910  CB  ALA A 129      43.749  -2.128  57.639  1.00 39.02           A
ATOM    911  C   ALA A 129      46.072  -1.277  57.271  1.00 39.48           A
ATOM    912  O   ALA A 129      46.544  -0.596  58.179  1.00 39.48           A
ATOM    913  N   ASP A 130      46.797  -2.160  56.589  1.00 50.74           A
ATOM    914  CA  ASP A 130      48.206  -2.371  56.912  1.00 50.74           A
ATOM    915  CB  ASP A 130      48.738  -3.631  56.229  1.00 98.04           A
ATOM    916  CG  ASP A 130      48.257  -4.899  56.900  1.00 98.04           A
ATOM    917  OD1 ASP A 130      47.035  -5.156  56.873  1.00 98.04           A
ATOM    918  OD2 ASP A 130      49.100  -5.633  57.461  1.00 98.04           A
ATOM    919  C   ASP A 130      49.060  -1.179  56.519  1.00 50.74           A
ATOM    920  O   ASP A 130      49.963  -0.781  57.265  1.00 50.74           A
ATOM    921  N   GLU A 131      48.771  -0.618  55.347  1.00 61.99           A
ATOM    922  CA  GLU A 131      49.500   0.543  54.848  1.00 61.99           A
ATOM    923  CB  GLU A 131      49.018   0.905  53.432  1.00 35.87           A
ATOM    924  CG  GLU A 131      49.255  -0.199  52.383  1.00 35.87           A
ATOM    925  CD  GLU A 131      48.725   0.156  50.991  1.00 35.87           A
ATOM    926  OE1 GLU A 131      47.518   0.469  50.867  1.00 35.87           A
ATOM    927  OE2 GLU A 131      49.514   0.116  50.019  1.00 35.87           A
ATOM    928  C   GLU A 131      49.285   1.720  55.805  1.00 61.99           A
ATOM    929  O   GLU A 131      50.210   2.494  56.061  1.00 61.99           A
ATOM    930  N   VAL A 132      48.066   1.835  56.338  1.00 41.47           A
ATOM    931  CA  VAL A 132      47.716   2.899  57.282  1.00 41.47           A
ATOM    932  CB  VAL A 132      46.227   2.827  57.703  1.00 27.86           A
ATOM    933  CG1 VAL A 132      45.971   3.746  58.890  1.00 27.86           A
ATOM    934  CG2 VAL A 132      45.345   3.243  56.550  1.00 27.86           A
ATOM    935  C   VAL A 132      48.566   2.789  58.541  1.00 41.47           A
ATOM    936  O   VAL A 132      49.214   3.755  58.958  1.00 41.47           A
ATOM    937  N   ALA A 133      48.551   1.607  59.146  1.00 41.81           A
ATOM    938  CA  ALA A 133      49.327   1.358  60.351  1.00 41.81           A
ATOM    939  CB  ALA A 133      49.198  -0.103  60.759  1.00 40.85           A
ATOM    940  C   ALA A 133      50.790   1.700  60.096  1.00 41.81           A
ATOM    941  O   ALA A 133      51.426   2.374  60.904  1.00 41.81           A
ATOM    942  N   THR A 134      51.320   1.232  58.970  1.00 46.90           A
ATOM    943  CA  THR A 134      52.712   1.497  58.633  1.00 46.90           A
ATOM    944  CB  THR A 134      53.106   0.851  57.293  1.00 46.04           A
ATOM    945  OG1 THR A 134      53.111  -0.574  57.439  1.00 46.04           A
```

FIGURE 2-13

```
ATOM    946  CG2 THR A 134      54.494    1.324   56.857  1.00 46.04      A
ATOM    947  C   THR A 134      52.957    2.992   58.538  1.00 46.90      A
ATOM    948  O   THR A 134      53.908    3.518   59.130  1.00 46.90      A
ATOM    949  N   LEU A 135      52.097    3.668   57.784  1.00 53.07      A
ATOM    950  CA  LEU A 135      52.206    5.109   57.611  1.00 53.07      A
ATOM    951  CB  LEU A 135      50.997    5.629   56.838  1.00 28.73      A
ATOM    952  CG  LEU A 135      50.926    7.133   56.591  1.00 28.73      A
ATOM    953  CD1 LEU A 135      52.240    7.647   56.003  1.00 28.73      A
ATOM    954  CD2 LEU A 135      49.763    7.405   55.650  1.00 28.73      A
ATOM    955  C   LEU A 135      52.295    5.803   58.972  1.00 53.07      A
ATOM    956  O   LEU A 135      53.204    6.601   59.214  1.00 53.07      A
ATOM    957  N   GLU A 136      51.361    5.484   59.863  1.00 44.05      A
ATOM    958  CA  GLU A 136      51.360    6.088   61.186  1.00 44.05      A
ATOM    959  CB  GLU A 136      50.082    5.723   61.938  1.00 46.25      A
ATOM    960  CG  GLU A 136      48.848    6.270   61.250  1.00 46.25      A
ATOM    961  CD  GLU A 136      47.720    6.554   62.208  1.00 46.25      A
ATOM    962  OE1 GLU A 136      46.624    6.927   61.737  1.00 46.25      A
ATOM    963  OE2 GLU A 136      47.932    6.413   63.433  1.00 46.25      A
ATOM    964  C   GLU A 136      52.583    5.692   62.000  1.00 44.05      A
ATOM    965  O   GLU A 136      53.122    6.497   62.768  1.00 44.05      A
ATOM    966  N   TYR A 137      53.034    4.457   61.836  1.00 42.24      A
ATOM    967  CA  TYR A 137      54.205    4.012   62.572  1.00 42.24      A
ATOM    968  CB  TYR A 137      54.504    2.545   62.263  1.00 52.94      A
ATOM    969  CG  TYR A 137      55.858    2.111   62.761  1.00 52.94      A
ATOM    970  CD1 TYR A 137      56.111    1.973   64.123  1.00 52.94      A
ATOM    971  CE1 TYR A 137      57.379    1.636   64.586  1.00 52.94      A
ATOM    972  CD2 TYR A 137      56.904    1.897   61.870  1.00 52.94      A
ATOM    973  CE2 TYR A 137      58.174    1.560   62.316  1.00 52.94      A
ATOM    974  CZ  TYR A 137      58.410    1.431   63.674  1.00 52.94      A
ATOM    975  OH  TYR A 137      59.679    1.099   64.109  1.00 52.94      A
ATOM    976  C   TYR A 137      55.402    4.876   62.180  1.00 42.24      A
ATOM    977  O   TYR A 137      56.093    5.425   63.039  1.00 42.24      A
ATOM    978  N   LEU A 138      55.631    4.995   60.874  1.00 37.69      A
ATOM    979  CA  LEU A 138      56.745    5.780   60.351  1.00 37.69      A
ATOM    980  CB  LEU A 138      56.878    5.554   58.836  1.00 52.05      A
ATOM    981  CG  LEU A 138      57.143    4.104   58.390  1.00 52.05      A
ATOM    982  CD1 LEU A 138      57.126    4.020   56.870  1.00 52.05      A
ATOM    983  CD2 LEU A 138      58.482    3.626   58.933  1.00 52.05      A
ATOM    984  C   LEU A 138      56.611    7.275   60.657  1.00 37.69      A
ATOM    985  O   LEU A 138      57.566    7.900   61.111  1.00 37.69      A
ATOM    986  N   LEU A 139      55.437    7.849   60.411  1.00 53.38      A
ATOM    987  CA  LEU A 139      55.238    9.264   60.696  1.00 53.38      A
ATOM    988  CB  LEU A 139      53.782    9.674   60.428  1.00 22.81      A
ATOM    989  CG  LEU A 139      53.510   10.039   58.957  1.00 22.81      A
ATOM    990  CD1 LEU A 139      52.025   10.086   58.665  1.00 22.81      A
ATOM    991  CD2 LEU A 139      54.167   11.368   58.656  1.00 22.81      A
ATOM    992  C   LEU A 139      55.615    9.570   62.144  1.00 53.38      A
ATOM    993  O   LEU A 139      56.289   10.569   62.424  1.00 53.38      A
ATOM    994  N   LYS A 140      55.196    8.708   63.065  1.00 46.77      A
ATOM    995  CA  LYS A 140      55.517    8.912   64.473  1.00 46.77      A
ATOM    996  CB  LYS A 140      54.854    7.830   65.324  1.00 58.30      A
ATOM    997  CG  LYS A 140      53.336    7.886   65.328  1.00 58.30      A
ATOM    998  CD  LYS A 140      52.751    6.751   66.144  1.00 58.30      A
ATOM    999  CE  LYS A 140      51.240    6.713   66.029  1.00 58.30      A
ATOM   1000  NZ  LYS A 140      50.658    5.553   66.765  1.00 58.30      A
ATOM   1001  C   LYS A 140      57.035    8.900   64.696  1.00 46.77      A
ATOM   1002  O   LYS A 140      57.559    9.669   65.503  1.00 46.77      A
ATOM   1003  N   LYS A 141      57.736    8.025   63.980  1.00 52.29      A
ATOM   1004  CA  LYS A 141      59.183    7.927   64.102  1.00 52.29      A
ATOM   1005  CB  LYS A 141      59.733    6.906   63.103  1.00 78.01      A
ATOM   1006  CG  LYS A 141      59.234    5.485   63.304  1.00 78.01      A
ATOM   1007  CD  LYS A 141      59.917    4.803   64.483  1.00 78.01      A
ATOM   1008  CE  LYS A 141      61.401    4.570   64.211  1.00 78.01      A
ATOM   1009  NZ  LYS A 141      61.626    3.676   63.039  1.00 78.01      A
ATOM   1010  C   LYS A 141      59.822    9.283   63.831  1.00 52.29      A
ATOM   1011  O   LYS A 141      60.721    9.710   64.561  1.00 52.29      A
ATOM   1012  N   VAL A 142      59.351    9.962   62.785  1.00 48.93      A
ATOM   1013  CA  VAL A 142      59.889   11.268   62.410  1.00 48.93      A
ATOM   1014  CB  VAL A 142      59.205   11.796   61.126  1.00 31.55      A
ATOM   1015  CG1 VAL A 142      59.666   13.211   60.816  1.00 31.55      A
ATOM   1016  CG2 VAL A 142      59.540   10.881   59.962  1.00 31.55      A
ATOM   1017  C   VAL A 142      59.792   12.321   63.522  1.00 48.93      A
ATOM   1018  O   VAL A 142      60.540   13.297   63.520  1.00 48.93      A
```

FIGURE 2-14

```
ATOM   1019  N    LEU A 143      58.877  12.129  64.466  1.00 67.04      A
ATOM   1020  CA   LEU A 143      58.737  13.062  65.583  1.00 67.04      A
ATOM   1021  CB   LEU A 143      57.302  13.053  66.120  1.00 42.71      A
ATOM   1022  CG   LEU A 143      56.178  13.434  65.151  1.00 42.71      A
ATOM   1023  CD1  LEU A 143      54.823  13.233  65.821  1.00 42.71      A
ATOM   1024  CD2  LEU A 143      56.355  14.874  64.714  1.00 42.71      A
ATOM   1025  C    LEU A 143      59.695  12.601  66.682  1.00 67.04      A
ATOM   1026  O    LEU A 143      60.170  11.461  66.660  1.00 67.04      A
ATOM   1027  N    PRO A 144      59.987  13.467  67.667  1.00135.51      A
ATOM   1028  CD   PRO A 144      60.809  13.066  68.823  1.00 96.05      A
ATOM   1029  CA   PRO A 144      59.495  14.840  67.835  1.00135.51      A
ATOM   1030  CB   PRO A 144      60.165  15.287  69.135  1.00 96.05      A
ATOM   1031  CG   PRO A 144      60.316  14.001  69.895  1.00 96.05      A
ATOM   1032  C    PRO A 144      59.851  15.747  66.656  1.00135.51      A
ATOM   1033  O    PRO A 144      58.923  16.371  66.093  1.00135.51      A
ATOM   1034  OXT  PRO A 144      61.053  15.826  66.317  1.00 96.05      A
ATOM   1035  CB   ASN B   9      51.205   2.213  67.233  1.00135.37      B
ATOM   1036  CG   ASN B   9      50.539   1.403  66.123  1.00135.37      B
ATOM   1037  OD1  ASN B   9      50.453   0.173  66.194  1.00135.37      B
ATOM   1038  ND2  ASN B   9      50.060   2.096  65.091  1.00135.37      B
ATOM   1039  C    ASN B   9      48.981   2.335  68.349  1.00 66.09      B
ATOM   1040  O    ASN B   9      48.315   1.572  67.640  1.00 66.09      B
ATOM   1041  N    ASN B   9      50.712   0.757  69.190  1.00 66.09      B
ATOM   1042  CA   ASN B   9      50.471   2.096  68.577  1.00 66.09      B
ATOM   1043  N    GLU B  10      48.458   3.398  68.949  1.00129.71      B
ATOM   1044  CA   GLU B  10      47.050   3.722  68.781  1.00129.71      B
ATOM   1045  CB   GLU B  10      46.538   4.558  69.965  1.00111.04      B
ATOM   1046  CG   GLU B  10      47.613   5.022  70.946  1.00111.04      B
ATOM   1047  CD   GLU B  10      48.429   6.195  70.432  1.00111.04      B
ATOM   1048  OE1  GLU B  10      49.073   6.062  69.369  1.00111.04      B
ATOM   1049  OE2  GLU B  10      48.425   7.253  71.099  1.00111.04      B
ATOM   1050  C    GLU B  10      46.817   4.471  67.472  1.00129.71      B
ATOM   1051  O    GLU B  10      47.241   5.619  67.314  1.00129.71      B
ATOM   1052  N    ILE B  11      46.165   3.803  66.523  1.00 72.20      B
ATOM   1053  CA   ILE B  11      45.859   4.430  65.249  1.00 72.20      B
ATOM   1054  CB   ILE B  11      45.047   3.482  64.321  1.00 44.08      B
ATOM   1055  CG2  ILE B  11      44.363   4.273  63.215  1.00 44.08      B
ATOM   1056  CG1  ILE B  11      45.981   2.447  63.685  1.00 44.08      B
ATOM   1057  CD1  ILE B  11      47.045   3.052  62.771  1.00 44.08      B
ATOM   1058  C    ILE B  11      45.030   5.664  65.570  1.00 72.20      B
ATOM   1059  O    ILE B  11      43.859   5.559  65.931  1.00 72.20      B
ATOM   1060  N    ILE B  12      45.659   6.830  65.468  1.00 83.43      B
ATOM   1061  CA   ILE B  12      44.990   8.093  65.740  1.00 83.43      B
ATOM   1062  CB   ILE B  12      45.914   9.042  66.517  1.00 57.67      B
ATOM   1063  CG2  ILE B  12      46.291   8.415  67.849  1.00 57.67      B
ATOM   1064  CG1  ILE B  12      47.169   9.336  65.696  1.00 57.67      B
ATOM   1065  CD1  ILE B  12      48.155  10.247  66.400  1.00 57.67      B
ATOM   1066  C    ILE B  12      44.614   8.733  64.410  1.00 83.43      B
ATOM   1067  O    ILE B  12      45.108   8.318  63.361  1.00 83.43      B
ATOM   1068  N    PRO B  13      43.734   9.751  64.430  1.00 40.24      B
ATOM   1069  CD   PRO B  13      43.092  10.404  65.582  1.00 21.06      B
ATOM   1070  CA   PRO B  13      43.332  10.404  63.178  1.00 40.24      B
ATOM   1071  CB   PRO B  13      42.435  11.547  63.657  1.00 21.06      B
ATOM   1072  CG   PRO B  13      41.867  11.005  64.948  1.00 21.06      B
ATOM   1073  C    PRO B  13      44.567  10.892  62.428  1.00 40.24      B
ATOM   1074  O    PRO B  13      45.298  11.766  62.903  1.00 40.24      B
ATOM   1075  N    LEU B  14      44.806  10.306  61.262  1.00 44.39      B
ATOM   1076  CA   LEU B  14      45.969  10.670  60.479  1.00 44.39      B
ATOM   1077  CB   LEU B  14      45.908   9.983  59.117  1.00 19.34      B
ATOM   1078  CG   LEU B  14      47.107  10.215  58.191  1.00 19.34      B
ATOM   1079  CD1  LEU B  14      48.395   9.890  58.927  1.00 19.34      B
ATOM   1080  CD2  LEU B  14      46.967   9.347  56.941  1.00 19.34      B
ATOM   1081  C    LEU B  14      46.076  12.185  60.314  1.00 44.39      B
ATOM   1082  O    LEU B  14      47.176  12.743  60.347  1.00 44.39      B
ATOM   1083  N    GLY B  15      44.932  12.848  60.153  1.00 31.14      B
ATOM   1084  CA   GLY B  15      44.931  14.292  59.983  1.00 31.14      B
ATOM   1085  C    GLY B  15      45.771  14.999  61.030  1.00 31.14      B
ATOM   1086  O    GLY B  15      46.495  15.959  60.725  1.00 31.14      B
ATOM   1087  N    ARG B  16      45.673  14.531  62.272  1.00 41.91      B
ATOM   1088  CA   ARG B  16      46.440  15.101  63.382  1.00 41.91      B
ATOM   1089  CB   ARG B  16      45.947  14.523  64.716  1.00 51.45      B
ATOM   1090  CG   ARG B  16      44.787  15.262  65.386  1.00 51.45      B
ATOM   1091  CD   ARG B  16      43.456  15.229  64.609  1.00 51.45      B
```

FIGURE 2-15

```
ATOM   1092  NE   ARG B  16      43.346  16.273  63.581  1.00 51.45      B
ATOM   1093  CZ   ARG B  16      42.194  16.797  63.167  1.00 51.45      B
ATOM   1094  NH1  ARG B  16      41.052  16.376  63.696  1.00 51.45      B
ATOM   1095  NH2  ARG B  16      42.186  17.736  63.228  1.00 51.45      B
ATOM   1096  C    ARG B  16      47.945  14.811  63.223  1.00 41.91      B
ATOM   1097  O    ARG B  16      48.793  15.676  63.462  1.00 41.91      B
ATOM   1098  N    LEU B  17      48.272  13.588  62.820  1.00 38.48      B
ATOM   1099  CA   LEU B  17      49.667  13.186  62.634  1.00 38.48      B
ATOM   1100  CB   LEU B  17      49.747  11.706  62.251  1.00 42.44      B
ATOM   1101  CG   LEU B  17      50.527  10.781  63.183  1.00 42.44      B
ATOM   1102  CD1  LEU B  17      50.582   9.383  62.577  1.00 42.44      B
ATOM   1103  CD2  LEU B  17      51.933  11.312  63.380  1.00 42.44      B
ATOM   1104  C    LEU B  17      50.318  14.027  61.541  1.00 38.48      B
ATOM   1105  O    LEU B  17      51.416  14.560  61.722  1.00 38.48      B
ATOM   1106  N    ILE B  18      49.639  14.127  60.398  1.00 33.51      B
ATOM   1107  CA   ILE B  18      50.131  14.919  59.273  1.00 33.51      B
ATOM   1108  CB   ILE B  18      49.089  14.986  58.154  1.00 35.12      B
ATOM   1109  CG2  ILE B  18      49.478  16.025  57.131  1.00 35.12      B
ATOM   1110  CG1  ILE B  18      48.953  13.616  57.505  1.00 35.12      B
ATOM   1111  CD1  ILE B  18      47.936  13.574  56.392  1.00 35.12      B
ATOM   1112  C    ILE B  18      50.407  16.335  59.768  1.00 33.51      B
ATOM   1113  O    ILE B  18      51.434  16.926  59.430  1.00 33.51      B
ATOM   1114  N    HIS B  19      49.488  16.865  60.579  1.00 26.80      B
ATOM   1115  CA   HIS B  19      49.634  18.207  61.131  1.00 26.80      B
ATOM   1116  CB   HIS B  19      48.402  18.596  61.953  1.00 38.93      B
ATOM   1117  CG   HIS B  19      48.514  19.943  62.609  1.00 38.93      B
ATOM   1118  CD2  HIS B  19      47.842  21.101  62.391  1.00 38.93      B
ATOM   1119  ND1  HIS B  19      49.422  20.212  63.613  1.00 38.93      B
ATOM   1120  CE1  HIS B  19      49.305  21.474  63.985  1.00 38.93      B
ATOM   1121  NE2  HIS B  19      48.354  22.035  63.259  1.00 38.93      B
ATOM   1122  C    HIS B  19      50.883  18.324  62.010  1.00 26.80      B
ATOM   1123  O    HIS B  19      51.666  19.259  61.852  1.00 26.80      B
ATOM   1124  N    MET B  20      51.063  17.394  62.943  1.00 28.60      B
ATOM   1125  CA   MET B  20      52.232  17.433  63.821  1.00 28.60      B
ATOM   1126  CB   MET B  20      52.227  16.259  64.820  1.00 39.32      B
ATOM   1127  CG   MET B  20      51.096  16.297  65.880  1.00 39.32      B
ATOM   1128  SD   MET B  20      50.911  14.776  66.939  1.00 39.32      B
ATOM   1129  CE   MET B  20      49.664  13.868  66.026  1.00 39.32      B
ATOM   1130  C    MET B  20      53.509  17.374  62.981  1.00 28.60      B
ATOM   1131  O    MET B  20      54.360  18.257  63.067  1.00 28.60      B
ATOM   1132  N    VAL B  21      53.645  16.337  62.165  1.00 44.11      B
ATOM   1133  CA   VAL B  21      54.831  16.202  61.328  1.00 44.11      B
ATOM   1134  CB   VAL B  21      54.750  14.920  60.419  1.00 25.48      B
ATOM   1135  CG1  VAL B  21      55.871  14.909  59.369  1.00 25.48      B
ATOM   1136  CG2  VAL B  21      54.851  13.667  61.296  1.00 25.48      B
ATOM   1137  C    VAL B  21      55.024  17.453  60.472  1.00 44.11      B
ATOM   1138  O    VAL B  21      56.147  17.951  60.365  1.00 44.11      B
ATOM   1139  N    ASN B  22      53.941  17.967  59.880  1.00 30.47      B
ATOM   1140  CA   ASN B  22      54.033  19.161  59.038  1.00 30.47      B
ATOM   1141  CB   ASN B  22      52.663  19.551  58.476  1.00 26.19      B
ATOM   1142  CG   ASN B  22      52.696  20.880  57.708  1.00 26.19      B
ATOM   1143  OD1  ASN B  22      53.363  21.014  56.676  1.00 26.19      B
ATOM   1144  ND2  ASN B  22      51.965  21.867  58.218  1.00 26.19      B
ATOM   1145  C    ASN B  22      54.592  20.317  59.851  1.00 30.47      B
ATOM   1146  O    ASN B  22      55.460  21.061  59.377  1.00 30.47      B
ATOM   1147  N    GLN B  23      54.082  20.460  61.073  1.00 46.49      B
ATOM   1148  CA   GLN B  23      54.518  21.507  61.988  1.00 46.49      B
ATOM   1149  CB   GLN B  23      53.941  21.261  63.380  1.00 78.77      B
ATOM   1150  CG   GLN B  23      52.673  22.015  63.661  1.00 78.77      B
ATOM   1151  CD   GLN B  23      52.923  23.495  63.762  1.00 78.77      B
ATOM   1152  OE1  GLN B  23      53.721  23.937  64.588  1.00 78.77      B
ATOM   1153  NE2  GLN B  23      52.247  24.277  62.921  1.00 78.77      B
ATOM   1154  C    GLN B  23      56.030  21.474  62.075  1.00 46.49      B
ATOM   1155  O    GLN B  23      56.717  22.470  61.805  1.00 46.49      B
ATOM   1156  N    LYS B  24      56.541  20.310  62.463  1.00 34.97      B
ATOM   1157  CA   LYS B  24      57.976  20.100  62.603  1.00 34.97      B
ATOM   1158  CB   LYS B  24      58.270  18.647  62.982  1.00 37.02      B
ATOM   1159  CG   LYS B  24      59.722  18.264  62.762  1.00 37.02      B
ATOM   1160  CD   LYS B  24      60.128  16.985  63.486  1.00 37.02      B
ATOM   1161  CE   LYS B  24      61.567  16.611  63.127  1.00 37.02      B
ATOM   1162  NZ   LYS B  24      62.174  15.628  64.082  1.00 37.02      B
ATOM   1163  C    LYS B  24      58.729  20.448  61.322  1.00 34.97      B
ATOM   1164  O    LYS B  24      59.758  21.123  61.355  1.00 34.97      B
```

FIGURE 2-16

```
ATOM   1165  N    LYS B  25      58.220  19.976  60.193  1.00 37.64      B
ATOM   1166  CA   LYS B  25      58.855  20.255  58.919  1.00 37.64      B
ATOM   1167  CB   LYS B  25      57.990  19.746  57.762  1.00 42.01      B
ATOM   1168  CG   LYS B  25      58.655  19.922  56.407  1.00 42.01      B
ATOM   1169  CD   LYS B  25      57.650  20.235  55.311  1.00 42.01      B
ATOM   1170  CE   LYS B  25      57.095  21.642  55.459  1.00 42.01      B
ATOM   1171  NZ   LYS B  25      56.097  21.963  54.394  1.00 42.01      B
ATOM   1172  C    LYS B  25      59.075  21.761  58.752  1.00 37.64      B
ATOM   1173  O    LYS B  25      60.199  22.200  58.489  1.00 37.64      B
ATOM   1174  N    ASP B  26      58.001  22.542  58.907  1.00 35.53      B
ATOM   1175  CA   ASP B  26      58.088  23.994  58.748  1.00 35.53      B
ATOM   1176  CB   ASP B  26      56.699  24.640  58.880  1.00 56.04      B
ATOM   1177  CG   ASP B  26      55.787  24.341  57.681  1.00 56.04      B
ATOM   1178  OD1  ASP B  26      56.233  24.520  56.522  1.00 56.04      B
ATOM   1179  OD2  ASP B  26      54.618  23.937  57.897  1.00 56.04      B
ATOM   1180  C    ASP B  26      59.072  24.629  59.739  1.00 35.53      B
ATOM   1181  O    ASP B  26      59.735  25.614  59.417  1.00 35.53      B
ATOM   1182  N    ARG B  27      59.171  24.070  60.940  1.00 25.58      B
ATOM   1183  CA   ARG B  27      60.101  24.602  61.926  1.00 25.58      B
ATOM   1184  CB   ARG B  27      60.023  23.818  63.245  1.00 59.09      B
ATOM   1185  CG   ARG B  27      61.276  23.954  64.121  1.00 59.09      B
ATOM   1186  CD   ARG B  27      61.081  23.472  65.571  1.00 59.09      B
ATOM   1187  NE   ARG B  27      60.843  22.034  65.700  1.00 59.09      B
ATOM   1188  CZ   ARG B  27      59.642  21.475  65.865  1.00 59.09      B
ATOM   1189  NH1  ARG B  27      58.546  22.230  65.922  1.00 59.09      B
ATOM   1190  NH2  ARG B  27      59.537  20.154  65.991  1.00 59.09      B
ATOM   1191  C    ARG B  27      61.492  24.460  61.333  1.00 25.58      B
ATOM   1192  O    ARG B  27      62.217  25.445  61.145  1.00 25.58      B
ATOM   1193  N    LEU B  28      61.866  23.221  61.031  1.00 30.74      B
ATOM   1194  CA   LEU B  28      63.173  22.958  60.454  1.00 30.74      B
ATOM   1195  CB   LEU B  28      63.303  21.490  60.060  1.00 25.37      B
ATOM   1196  CG   LEU B  28      63.317  20.479  61.204  1.00 25.37      B
ATOM   1197  CD1  LEU B  28      63.329  19.085  60.628  1.00 25.37      B
ATOM   1198  CD2  LEU B  28      64.532  20.705  62.088  1.00 25.37      B
ATOM   1199  C    LEU B  28      63.402  23.826  59.227  1.00 30.74      B
ATOM   1200  O    LEU B  28      64.450  24.468  59.100  1.00 30.74      B
ATOM   1201  N    LEU B  29      62.422  23.843  58.323  1.00 35.92      B
ATOM   1202  CA   LEU B  29      62.519  24.635  57.097  1.00 35.92      B
ATOM   1203  CB   LEU B  29      61.193  24.617  56.335  1.00 29.83      B
ATOM   1204  CG   LEU B  29      61.253  25.212  54.924  1.00 29.83      B
ATOM   1205  CD1  LEU B  29      62.079  24.314  54.024  1.00 29.83      B
ATOM   1206  CD2  LEU B  29      59.859  25.341  54.356  1.00 29.83      B
ATOM   1207  C    LEU B  29      62.892  26.083  57.422  1.00 35.92      B
ATOM   1208  O    LEU B  29      63.767  26.675  56.783  1.00 35.92      B
ATOM   1209  N    ASN B  30      62.232  26.652  58.423  1.00 32.28      B
ATOM   1210  CA   ASN B  30      62.519  28.018  58.811  1.00 32.28      B
ATOM   1211  CB   ASN B  30      61.609  28.440  59.960  1.00 55.71      B
ATOM   1212  CG   ASN B  30      60.475  29.325  59.501  1.00 55.71      B
ATOM   1213  OD1  ASN B  30      59.407  29.356  60.118  1.00 55.71      B
ATOM   1214  ND2  ASN B  30      60.699  30.064  58.418  1.00 55.71      B
ATOM   1215  C    ASN B  30      63.977  28.170  59.215  1.00 32.28      B
ATOM   1216  O    ASN B  30      64.655  29.106  58.790  1.00 32.28      B
ATOM   1217  N    GLU B  31      64.464  27.248  60.034  1.00 28.98      B
ATOM   1218  CA   GLU B  31      65.840  27.315  60.492  1.00 28.98      B
ATOM   1219  CB   GLU B  31      66.158  26.172  61.453  1.00 46.83      B
ATOM   1220  CG   GLU B  31      65.361  26.133  62.739  1.00 46.83      B
ATOM   1221  CD   GLU B  31      65.784  24.959  63.607  1.00 46.83      B
ATOM   1222  OE1  GLU B  31      66.487  24.059  63.085  1.00 46.83      B
ATOM   1223  OE2  GLU B  31      65.410  24.926  64.799  1.00 46.83      B
ATOM   1224  C    GLU B  31      66.794  27.222  59.319  1.00 28.98      B
ATOM   1225  O    GLU B  31      67.678  28.054  59.159  1.00 28.98      B
ATOM   1226  N    TYR B  32      66.628  26.193  58.503  1.00 35.77      B
ATOM   1227  CA   TYR B  32      67.506  26.014  57.362  1.00 35.77      B
ATOM   1228  CB   TYR B  32      67.223  24.672  56.668  1.00 40.71      B
ATOM   1229  CG   TYR B  32      67.928  23.494  57.302  1.00 40.71      B
ATOM   1230  CD1  TYR B  32      67.209  22.441  57.873  1.00 40.71      B
ATOM   1231  CE1  TYR B  32      67.861  21.338  58.449  1.00 40.71      B
ATOM   1232  CD2  TYR B  32      69.319  23.426  57.323  1.00 40.71      B
ATOM   1233  CE2  TYR B  32      69.984  22.339  57.896  1.00 40.71      B
ATOM   1234  CZ   TYR B  32      69.251  21.296  58.455  1.00 40.71      B
ATOM   1235  OH   TYR B  32      69.918  20.213  58.998  1.00 40.71      B
ATOM   1236  C    TYR B  32      67.432  27.148  56.346  1.00 35.77      B
ATOM   1237  O    TYR B  32      68.383  27.342  55.581  1.00 35.77      B
```

FIGURE 2-17

```
ATOM   1238  N    LEU B  33      66.326  27.896  56.335  1.00 52.15      B
ATOM   1239  CA   LEU B  33      66.170  28.996  55.380  1.00 52.15      B
ATOM   1240  CB   LEU B  33      64.707  29.153  54.940  1.00 25.90      B
ATOM   1241  CG   LEU B  33      64.061  28.198  53.921  1.00 25.90      B
ATOM   1242  CD1  LEU B  33      62.616  28.613  53.731  1.00 25.90      B
ATOM   1243  CD2  LEU B  33      64.793  28.219  52.587  1.00 25.90      B
ATOM   1244  C    LEU B  33      66.662  30.348  55.878  1.00 52.15      B
ATOM   1245  O    LEU B  33      67.086  31.182  55.077  1.00 52.15      B
ATOM   1246  N    SER B  34      66.601  30.563  57.191  1.00 35.65      B
ATOM   1247  CA   SER B  34      67.018  31.829  57.809  1.00 35.65      B
ATOM   1248  CB   SER B  34      67.164  31.619  59.319  1.00 47.51      B
ATOM   1249  OG   SER B  34      66.819  32.791  60.039  1.00 47.51      B
ATOM   1250  C    SER B  34      68.309  32.458  57.222  1.00 35.65      B
ATOM   1251  O    SER B  34      68.354  33.664  56.930  1.00 35.65      B
ATOM   1252  N    PRO B  35      69.377  31.657  57.061  1.00 45.02      B
ATOM   1253  CD   PRO B  35      69.647  30.355  57.695  1.00 42.17      B
ATOM   1254  CA   PRO B  35      70.609  32.218  56.502  1.00 45.02      B
ATOM   1255  CB   PRO B  35      71.662  31.150  56.828  1.00 42.17      B
ATOM   1256  CG   PRO B  35      70.878  29.894  56.944  1.00 42.17      B
ATOM   1257  C    PRO B  35      70.562  32.579  55.012  1.00 45.02      B
ATOM   1258  O    PRO B  35      71.604  32.831  54.400  1.00 45.02      B
ATOM   1259  N    LEU B  36      69.365  32.614  54.428  1.00 41.85      B
ATOM   1260  CA   LEU B  36      69.230  32.985  53.021  1.00 41.85      B
ATOM   1261  CB   LEU B  36      68.741  31.794  52.198  1.00 42.76      B
ATOM   1262  CG   LEU B  36      69.454  30.458  52.439  1.00 42.76      B
ATOM   1263  CD1  LEU B  36      69.045  29.466  51.351  1.00 42.76      B
ATOM   1264  CD2  LEU B  36      70.964  30.649  52.427  1.00 42.76      B
ATOM   1265  C    LEU B  36      68.256  34.160  52.893  1.00 41.85      B
ATOM   1266  O    LEU B  36      67.936  34.610  51.785  1.00 41.85      B
ATOM   1267  N    ASP B  37      67.811  34.663  54.043  1.00 46.79      B
ATOM   1268  CA   ASP B  37      66.872  35.782  54.107  1.00 46.79      B
ATOM   1269  CB   ASP B  37      67.464  37.026  53.442  1.00 96.46      B
ATOM   1270  CG   ASP B  37      68.133  37.952  54.441  1.00 96.46      B
ATOM   1271  OD1  ASP B  37      67.437  38.425  55.365  1.00 96.46      B
ATOM   1272  OD2  ASP B  37      69.348  38.206  54.308  1.00 96.46      B
ATOM   1273  C    ASP B  37      65.527  35.446  53.483  1.00 46.79      B
ATOM   1274  O    ASP B  37      64.991  36.195  52.653  1.00 46.79      B
ATOM   1275  N    ILE B  38      64.986  34.303  53.889  1.00 41.11      B
ATOM   1276  CA   ILE B  38      63.697  33.859  53.396  1.00 41.11      B
ATOM   1277  CB   ILE B  38      63.835  32.886  52.230  1.00 28.68      B
ATOM   1278  CG2  ILE B  38      62.540  32.872  51.436  1.00 28.68      B
ATOM   1279  CG1  ILE B  38      64.997  33.300  51.337  1.00 28.68      B
ATOM   1280  CD1  ILE B  38      65.143  32.438  50.104  1.00 28.68      B
ATOM   1281  C    ILE B  38      62.980  33.113  54.499  1.00 41.11      B
ATOM   1282  O    ILE B  38      63.599  32.360  55.253  1.00 41.11      B
ATOM   1283  N    THR B  39      61.674  33.319  54.592  1.00 26.87      B
ATOM   1284  CA   THR B  39      60.885  32.625  55.594  1.00 26.87      B
ATOM   1285  CB   THR B  39      59.815  33.541  56.153  1.00 31.96      B
ATOM   1286  OG1  THR B  39      58.964  33.981  55.084  1.00 31.96      B
ATOM   1287  CG2  THR B  39      60.466  34.752  56.837  1.00 31.96      B
ATOM   1288  C    THR B  39      60.231  31.447  54.893  1.00 26.87      B
ATOM   1289  O    THR B  39      60.110  31.455  53.659  1.00 26.87      B
ATOM   1290  N    ALA B  40      59.819  30.431  55.651  1.00 35.79      B
ATOM   1291  CA   ALA B  40      59.178  29.267  55.030  1.00 35.79      B
ATOM   1292  CB   ALA B  40      58.996  28.135  56.047  1.00  6.71      B
ATOM   1293  C    ALA B  40      57.836  29.700  54.459  1.00 35.79      B
ATOM   1294  O    ALA B  40      57.346  29.121  53.490  1.00 35.79      B
ATOM   1295  N    ALA B  41      57.266  30.742  55.056  1.00 35.78      B
ATOM   1296  CA   ALA B  41      55.986  31.284  54.616  1.00 35.78      B
ATOM   1297  CB   ALA B  41      55.616  32.512  55.465  1.00 11.87      B
ATOM   1298  C    ALA B  41      56.106  31.679  53.151  1.00 35.78      B
ATOM   1299  O    ALA B  41      55.376  31.179  52.281  1.00 35.78      B
ATOM   1300  N    GLN B  42      57.050  32.575  52.890  1.00 33.53      B
ATOM   1301  CA   GLN B  42      57.291  33.061  51.538  1.00 33.53      B
ATOM   1302  CB   GLN B  42      58.394  34.107  51.569  1.00 34.68      B
ATOM   1303  CG   GLN B  42      58.068  35.300  52.437  1.00 34.68      B
ATOM   1304  CD   GLN B  42      59.279  36.195  52.665  1.00 34.68      B
ATOM   1305  OE1  GLN B  42      59.133  37.359  53.034  1.00 34.68      B
ATOM   1306  NE2  GLN B  42      60.485  35.647  52.460  1.00 34.68      B
ATOM   1307  C    GLN B  42      57.679  31.915  50.613  1.00 33.53      B
ATOM   1308  O    GLN B  42      57.219  31.847  49.470  1.00 33.53      B
ATOM   1309  N    PHE B  43      58.514  31.013  51.123  1.00 29.03      B
ATOM   1310  CA   PHE B  43      58.974  29.872  50.343  1.00 29.03      B
```

FIGURE 2-18

```
ATOM   1311  CB  PHE B  43      59.971  29.047  51.145  1.00 37.88      B
ATOM   1312  CG  PHE B  43      60.544  27.894  50.377  1.00 37.88      B
ATOM   1313  CD1 PHE B  43      61.275  28.114  49.210  1.00 37.88      B
ATOM   1314  CD2 PHE B  43      60.350  26.583  50.808  1.00 37.88      B
ATOM   1315  CE1 PHE B  43      61.804  27.041  48.479  1.00 37.88      B
ATOM   1316  CE2 PHE B  43      60.876  25.501  50.082  1.00 37.88      B
ATOM   1317  CZ  PHE B  43      61.603  25.732  48.918  1.00 37.88      B
ATOM   1318  C   PHE B  43      57.814  28.983  49.908  1.00 29.03      B
ATOM   1319  O   PHE B  43      57.734  28.566  48.746  1.00 29.03      B
ATOM   1320  N   LYS B  44      56.912  28.698  50.841  1.00 36.68      B
ATOM   1321  CA  LYS B  44      55.768  27.851  50.532  1.00 36.68      B
ATOM   1322  CB  LYS B  44      54.913  27.635  51.792  1.00 86.09      B
ATOM   1323  CG  LYS B  44      55.545  26.659  52.801  1.00 86.09      B
ATOM   1324  CD  LYS B  44      54.913  26.748  54.194  1.00 86.09      B
ATOM   1325  CE  LYS B  44      53.467  26.253  54.234  1.00 86.09      B
ATOM   1326  NZ  LYS B  44      53.345  24.763  54.191  1.00 86.09      B
ATOM   1327  C   LYS B  44      54.947  28.466  49.399  1.00 36.68      B
ATOM   1328  O   LYS B  44      54.622  27.786  48.431  1.00 36.68      B
ATOM   1329  N   VAL B  45      54.629  29.750  49.508  1.00 34.37      B
ATOM   1330  CA  VAL B  45      53.860  30.406  48.471  1.00 34.37      B
ATOM   1331  CB  VAL B  45      53.622  31.876  48.816  1.00 27.32      B
ATOM   1332  CG1 VAL B  45      52.980  32.594  47.631  1.00 27.32      B
ATOM   1333  CG2 VAL B  45      52.717  31.968  50.026  1.00 27.32      B
ATOM   1334  C   VAL B  45      54.569  30.301  47.119  1.00 34.37      B
ATOM   1335  O   VAL B  45      53.952  29.895  46.119  1.00 34.37      B
ATOM   1336  N   LEU B  46      55.856  30.660  47.079  1.00 34.02      B
ATOM   1337  CA  LEU B  46      56.630  30.574  45.837  1.00 34.02      B
ATOM   1338  CB  LEU B  46      58.097  30.928  46.089  1.00 41.81      B
ATOM   1339  CG  LEU B  46      58.407  32.358  46.526  1.00 41.81      B
ATOM   1340  CD1 LEU B  46      59.911  32.538  46.588  1.00 41.81      B
ATOM   1341  CD2 LEU B  46      57.793  33.356  45.548  1.00 41.81      B
ATOM   1342  C   LEU B  46      56.552  29.178  45.203  1.00 34.02      B
ATOM   1343  O   LEU B  46      56.477  29.056  43.982  1.00 34.02      B
ATOM   1344  N   CYS B  47      56.575  28.130  46.025  1.00 34.11      B
ATOM   1345  CA  CYS B  47      56.495  26.762  45.509  1.00 34.11      B
ATOM   1346  CB  CYS B  47      56.771  25.748  46.620  1.00 73.82      B
ATOM   1347  SG  CYS B  47      58.491  25.691  47.144  1.00 73.82      B
ATOM   1348  C   CYS B  47      55.132  26.467  44.897  1.00 34.11      B
ATOM   1349  O   CYS B  47      55.030  25.800  43.861  1.00 34.11      B
ATOM   1350  N   SER B  48      54.086  26.972  45.540  1.00 30.53      B
ATOM   1351  CA  SER B  48      52.727  26.757  45.068  1.00 30.53      B
ATOM   1352  CB  SER B  48      51.734  27.371  46.055  1.00 28.82      B
ATOM   1353  OG  SER B  48      51.984  26.926  47.380  1.00 28.82      B
ATOM   1354  C   SER B  48      52.546  27.394  43.693  1.00 30.53      B
ATOM   1355  O   SER B  48      51.934  26.811  42.791  1.00 30.53      B
ATOM   1356  N   ILE B  49      53.083  28.596  43.537  1.00 27.84      B
ATOM   1357  CA  ILE B  49      52.971  29.298  42.275  1.00 27.84      B
ATOM   1358  CB  ILE B  49      53.401  30.771  42.439  1.00 22.70      B
ATOM   1359  CG2 ILE B  49      53.243  31.526  41.113  1.00 22.70      B
ATOM   1360  CG1 ILE B  49      52.528  31.421  43.526  1.00 22.70      B
ATOM   1361  CD1 ILE B  49      53.047  32.738  44.026  1.00 22.70      B
ATOM   1362  C   ILE B  49      53.820  28.599  41.224  1.00 27.84      B
ATOM   1363  O   ILE B  49      53.382  28.402  40.092  1.00 27.84      B
ATOM   1364  N   ARG B  50      55.027  28.203  41.607  1.00 18.56      B
ATOM   1365  CA  ARG B  50      55.925  27.512  40.687  1.00 18.56      B
ATOM   1366  CB  ARG B  50      57.239  27.200  41.396  1.00 82.28      B
ATOM   1367  CG  ARG B  50      58.304  26.600  40.514  1.00 82.28      B
ATOM   1368  CD  ARG B  50      59.495  26.222  41.356  1.00 82.28      B
ATOM   1369  NE  ARG B  50      60.697  25.996  40.562  1.00 82.28      B
ATOM   1370  CZ  ARG B  50      61.877  25.682  41.088  1.00 82.28      B
ATOM   1371  NH1 ARG B  50      62.002  25.555  42.405  1.00 82.28      B
ATOM   1372  NH2 ARG B  50      62.933  25.507  40.303  1.00 82.28      B
ATOM   1373  C   ARG B  50      55.271  26.206  40.213  1.00 18.56      B
ATOM   1374  O   ARG B  50      55.241  25.893  39.014  1.00 18.56      B
ATOM   1375  N   CYS B  51      54.740  25.444  41.160  1.00 43.60      B
ATOM   1376  CA  CYS B  51      54.107  24.186  40.819  1.00 43.60      B
ATOM   1377  CB  CYS B  51      53.584  23.504  42.081  1.00 84.70      B
ATOM   1378  SG  CYS B  51      52.553  22.064  41.740  1.00 84.70      B
ATOM   1379  C   CYS B  51      52.961  24.398  39.826  1.00 43.60      B
ATOM   1380  O   CYS B  51      52.780  23.612  38.889  1.00 43.60      B
ATOM   1381  N   ALA B  52      52.198  25.470  40.029  1.00 31.36      B
ATOM   1382  CA  ALA B  52      51.059  25.776  39.172  1.00 31.36      B
ATOM   1383  CB  ALA B  52      50.083  26.633  39.920  1.00 17.44      B
```

FIGURE 2-19

```
ATOM   1384  C    ALA B  52      51.455  26.474  37.881  1.00 31.36      B
ATOM   1385  O    ALA B  52      50.676  26.510  36.931  1.00 31.36      B
ATOM   1386  N    ALA B  53      52.660  27.037  37.857  1.00 34.68      B
ATOM   1387  CA   ALA B  53      53.156  27.743  36.688  1.00 34.68      B
ATOM   1388  CB   ALA B  53      52.944  26.903  35.440  1.00 31.90      B
ATOM   1389  C    ALA B  53      52.467  29.083  36.518  1.00 34.68      B
ATOM   1390  O    ALA B  53      53.118  30.111  36.368  1.00 34.68      B
ATOM   1391  N    CYS B  54      51.142  29.058  36.567  1.00 32.06      B
ATOM   1392  CA   CYS B  54      50.316  30.245  36.368  1.00 32.06      B
ATOM   1393  CB   CYS B  54      50.058  30.370  34.872  1.00 58.96      B
ATOM   1394  SG   CYS B  54      49.247  31.838  34.359  1.00 58.96      B
ATOM   1395  C    CYS B  54      49.008  30.003  37.137  1.00 32.06      B
ATOM   1396  O    CYS B  54      48.354  28.979  36.949  1.00 32.06      B
ATOM   1397  N    ILE B  55      48.605  30.936  37.990  1.00 18.46      B
ATOM   1398  CA   ILE B  55      47.404  30.692  38.777  1.00 18.46      B
ATOM   1399  CB   ILE B  55      47.762  29.766  39.974  1.00 12.62      B
ATOM   1400  CG2  ILE B  55      48.683  30.502  40.950  1.00 12.62      B
ATOM   1401  CG1  ILE B  55      46.510  29.340  40.734  1.00 12.62      B
ATOM   1402  CD1  ILE B  55      46.796  28.230  41.760  1.00 12.62      B
ATOM   1403  C    ILE B  55      46.739  31.963  39.302  1.00 18.46      B
ATOM   1404  O    ILE B  55      47.411  32.961  39.598  1.00 18.46      B
ATOM   1405  N    THR B  56      45.416  31.925  39.415  1.00 29.52      B
ATOM   1406  CA   THR B  56      44.670  33.066  39.924  1.00 29.52      B
ATOM   1407  CB   THR B  56      43.196  32.976  39.544  1.00 27.79      B
ATOM   1408  OG1  THR B  56      42.613  31.853  40.213  1.00 27.79      B
ATOM   1409  CG2  THR B  56      43.041  32.806  38.039  1.00 27.79      B
ATOM   1410  C    THR B  56      44.765  33.030  41.443  1.00 29.52      B
ATOM   1411  O    THR B  56      44.974  31.964  42.033  1.00 29.52      B
ATOM   1412  N    PRO B  57      44.620  34.194  42.094  1.00 30.29      B
ATOM   1413  CD   PRO B  57      44.561  35.518  41.456  1.00 29.70      B
ATOM   1414  CA   PRO B  57      44.687  34.318  43.555  1.00 30.29      B
ATOM   1415  CB   PRO B  57      44.508  35.812  43.782  1.00 29.70      B
ATOM   1416  CG   PRO B  57      45.119  36.410  42.535  1.00 29.70      B
ATOM   1417  C    PRO B  57      43.600  33.502  44.250  1.00 30.29      B
ATOM   1418  O    PRO B  57      43.823  32.925  45.321  1.00 30.29      B
ATOM   1419  N    VAL B  58      42.420  33.461  43.641  1.00 38.22      B
ATOM   1420  CA   VAL B  58      41.319  32.713  44.221  1.00 38.22      B
ATOM   1421  CB   VAL B  58      39.996  32.966  43.435  1.00 66.42      B
ATOM   1422  CG1  VAL B  58      40.088  32.407  42.020  1.00 66.42      B
ATOM   1423  CG2  VAL B  58      38.828  32.372  44.192  1.00 66.42      B
ATOM   1424  C    VAL B  58      41.668  31.219  44.260  1.00 38.22      B
ATOM   1425  O    VAL B  58      41.516  30.572  45.295  1.00 38.22      B
ATOM   1426  N    GLU B  59      42.153  30.673  43.149  1.00 36.09      B
ATOM   1427  CA   GLU B  59      42.534  29.262  43.114  1.00 36.09      B
ATOM   1428  CB   GLU B  59      42.827  28.833  41.678  1.00 40.02      B
ATOM   1429  CG   GLU B  59      41.640  28.926  40.734  1.00 40.02      B
ATOM   1430  CD   GLU B  59      40.609  27.810  40.936  1.00 40.02      B
ATOM   1431  OE1  GLU B  59      39.800  27.876  41.895  1.00 40.02      B
ATOM   1432  OE2  GLU B  59      40.614  26.858  40.122  1.00 40.02      B
ATOM   1433  C    GLU B  59      43.776  29.002  43.991  1.00 36.09      B
ATOM   1434  O    GLU B  59      43.998  27.881  44.455  1.00 36.09      B
ATOM   1435  N    LEU B  60      44.583  30.038  44.207  1.00 32.50      B
ATOM   1436  CA   LEU B  60      45.781  29.912  45.022  1.00 32.50      B
ATOM   1437  CB   LEU B  60      46.677  31.135  44.833  1.00 29.62      B
ATOM   1438  CG   LEU B  60      47.978  31.130  45.642  1.00 29.62      B
ATOM   1439  CD1  LEU B  60      48.835  29.920  45.253  1.00 29.62      B
ATOM   1440  CD2  LEU B  60      48.732  32.435  45.385  1.00 29.62      B
ATOM   1441  C    LEU B  60      45.375  29.789  46.486  1.00 32.50      B
ATOM   1442  O    LEU B  60      45.877  28.939  47.220  1.00 32.50      B
ATOM   1443  N    LYS B  61      44.460  30.654  46.895  1.00 35.36      B
ATOM   1444  CA   LYS B  61      43.933  30.674  48.248  1.00 35.36      B
ATOM   1445  CB   LYS B  61      42.790  31.688  48.315  1.00 67.16      B
ATOM   1446  CG   LYS B  61      41.883  31.550  49.515  1.00 67.16      B
ATOM   1447  CD   LYS B  61      40.659  32.433  49.367  1.00 67.16      B
ATOM   1448  CE   LYS B  61      39.915  32.122  48.078  1.00 67.16      B
ATOM   1449  NZ   LYS B  61      39.618  30.668  47.968  1.00 67.16      B
ATOM   1450  C    LYS B  61      43.424  29.285  48.645  1.00 35.36      B
ATOM   1451  O    LYS B  61      43.628  28.835  49.778  1.00 35.36      B
ATOM   1452  N    LYS B  62      42.746  28.613  47.719  1.00 56.38      B
ATOM   1453  CA   LYS B  62      42.237  27.275  47.991  1.00 56.38      B
ATOM   1454  CB   LYS B  62      41.448  26.744  46.794  1.00 56.12      B
ATOM   1455  CG   LYS B  62      40.146  27.469  46.524  1.00 56.12      B
ATOM   1456  CD   LYS B  62      39.429  26.878  45.313  1.00 56.12      B
```

FIGURE 2-20

```
ATOM   1457  CE  LYS B  62      38.081  27.546  45.070  1.00 56.12           B
ATOM   1458  NZ  LYS B  62      38.199  29.033  44.949  1.00 56.12           B
ATOM   1459  C   LYS B  62      43.414  26.342  48.275  1.00 56.38           B
ATOM   1460  O   LYS B  62      43.404  25.595  49.257  1.00 56.38           B
ATOM   1461  N   VAL B  63      44.424  26.396  47.407  1.00 37.26           B
ATOM   1462  CA  VAL B  63      45.607  25.567  47.549  1.00 37.26           B
ATOM   1463  CB  VAL B  63      46.641  25.874  46.440  1.00 20.35           B
ATOM   1464  CG1 VAL B  63      48.013  25.281  46.813  1.00 20.35           B
ATOM   1465  CG2 VAL B  63      46.160  25.301  45.125  1.00 20.35           B
ATOM   1466  C   VAL B  63      46.268  25.784  48.899  1.00 37.26           B
ATOM   1467  O   VAL B  63      46.497  24.837  49.652  1.00 37.26           B
ATOM   1468  N   LEU B  64      46.568  27.037  49.203  1.00 37.82           B
ATOM   1469  CA  LEU B  64      47.230  27.377  50.454  1.00 37.82           B
ATOM   1470  CB  LEU B  64      47.786  28.800  50.381  1.00 50.74           B
ATOM   1471  CG  LEU B  64      49.053  29.018  49.560  1.00 50.74           B
ATOM   1472  CD1 LEU B  64      48.961  28.277  48.243  1.00 50.74           B
ATOM   1473  CD2 LEU B  64      49.241  30.520  49.342  1.00 50.74           B
ATOM   1474  C   LEU B  64      46.334  27.258  51.680  1.00 37.82           B
ATOM   1475  O   LEU B  64      46.819  27.268  52.814  1.00 37.82           B
ATOM   1476  N   SER B  65      45.031  27.149  51.454  1.00 47.27           B
ATOM   1477  CA  SER B  65      44.083  27.052  52.552  1.00 47.27           B
ATOM   1478  CB  SER B  65      44.261  25.729  53.302  1.00 79.02           B
ATOM   1479  OG  SER B  65      44.033  24.624  52.444  1.00 79.02           B
ATOM   1480  C   SER B  65      44.288  28.227  53.504  1.00 47.27           B
ATOM   1481  O   SER B  65      44.569  28.037  54.697  1.00 47.27           B
ATOM   1482  N   VAL B  66      44.168  29.444  52.970  1.00 24.67           B
ATOM   1483  CA  VAL B  66      44.321  30.652  53.790  1.00 24.67           B
ATOM   1484  CB  VAL B  66      45.750  31.269  53.701  1.00 43.56           B
ATOM   1485  CG1 VAL B  66      46.801  30.190  53.939  1.00 43.56           B
ATOM   1486  CG2 VAL B  66      45.948  31.969  52.346  1.00 43.56           B
ATOM   1487  C   VAL B  66      43.329  31.753  53.407  1.00 24.67           B
ATOM   1488  O   VAL B  66      42.554  31.620  52.453  1.00 24.67           B
ATOM   1489  N   ASP B  67      43.361  32.840  54.169  1.00 57.77           B
ATOM   1490  CA  ASP B  67      42.490  33.980  53.924  1.00 57.77           B
ATOM   1491  CB  ASP B  67      42.546  34.932  55.127  1.00 65.50           B
ATOM   1492  CG  ASP B  67      41.804  36.236  54.883  1.00 65.50           B
ATOM   1493  OD1 ASP B  67      40.948  36.273  53.973  1.00 65.50           B
ATOM   1494  OD2 ASP B  67      42.067  37.222  55.607  1.00 65.50           B
ATOM   1495  C   ASP B  67      42.931  34.702  52.645  1.00 57.77           B
ATOM   1496  O   ASP B  67      44.105  35.057  52.504  1.00 57.77           B
ATOM   1497  N   LEU B  68      41.990  34.912  51.722  1.00 50.58           B
ATOM   1498  CA  LEU B  68      42.274  35.584  50.450  1.00 50.58           B
ATOM   1499  CB  LEU B  68      40.999  35.779  49.625  1.00 44.31           B
ATOM   1500  CG  LEU B  68      41.160  36.605  48.337  1.00 44.31           B
ATOM   1501  CD1 LEU B  68      42.422  36.198  47.587  1.00 44.31           B
ATOM   1502  CD2 LEU B  68      39.943  36.407  47.453  1.00 44.31           B
ATOM   1503  C   LEU B  68      42.934  36.933  50.637  1.00 50.58           B
ATOM   1504  O   LEU B  68      43.783  37.332  49.832  1.00 50.58           B
ATOM   1505  N   GLY B  69      42.528  37.647  51.682  1.00 44.91           B
ATOM   1506  CA  GLY B  69      43.132  38.936  51.957  1.00 44.91           B
ATOM   1507  C   GLY B  69      44.561  38.698  52.404  1.00 44.91           B
ATOM   1508  O   GLY B  69      45.481  39.391  51.975  1.00 44.91           B
ATOM   1509  N   ALA B  70      44.753  37.705  53.264  1.00 46.62           B
ATOM   1510  CA  ALA B  70      46.083  37.374  53.750  1.00 46.62           B
ATOM   1511  CB  ALA B  70      46.016  36.136  54.632  1.00 21.93           B
ATOM   1512  C   ALA B  70      46.988  37.106  52.552  1.00 46.62           B
ATOM   1513  O   ALA B  70      48.123  37.609  52.482  1.00 46.62           B
ATOM   1514  N   LEU B  71      46.472  36.304  51.619  1.00 61.44           B
ATOM   1515  CA  LEU B  71      47.207  35.931  50.411  1.00 61.44           B
ATOM   1516  CB  LEU B  71      46.366  35.019  49.505  1.00 24.15           B
ATOM   1517  CG  LEU B  71      47.104  34.526  48.251  1.00 24.15           B
ATOM   1518  CD1 LEU B  71      48.421  33.875  48.657  1.00 24.15           B
ATOM   1519  CD2 LEU B  71      46.241  33.525  47.488  1.00 24.15           B
ATOM   1520  C   LEU B  71      47.581  37.168  49.631  1.00 61.44           B
ATOM   1521  O   LEU B  71      48.746  37.375  49.281  1.00 61.44           B
ATOM   1522  N   THR B  72      46.570  37.984  49.357  1.00 48.36           B
ATOM   1523  CA  THR B  72      46.765  39.213  48.612  1.00 48.36           B
ATOM   1524  CB  THR B  72      45.493  40.033  48.585  1.00 28.65           B
ATOM   1525  OG1 THR B  72      44.508  39.340  47.811  1.00 28.65           B
ATOM   1526  CG2 THR B  72      45.754  41.376  47.959  1.00 28.65           B
ATOM   1527  C   THR B  72      47.891  40.078  49.160  1.00 48.36           B
ATOM   1528  O   THR B  72      48.725  40.552  48.394  1.00 48.36           B
ATOM   1529  N   ARG B  73      47.922  40.289  50.473  1.00 34.07           B
```

FIGURE 2-21

| ATOM | 1530 | CA | ARG B | 73 | 48.982 | 41.104 | 51.045 | 1.00 | 34.07 | B |
|---|---|---|---|---|---|---|---|---|---|---|
| ATOM | 1531 | CB | ARG B | 73 | 48.726 | 41.380 | 52.527 | 1.00 | 63.70 | B |
| ATOM | 1532 | CG | ARG B | 73 | 47.497 | 42.242 | 52.771 | 1.00 | 63.70 | B |
| ATOM | 1533 | CD | ARG B | 73 | 47.368 | 42.666 | 54.223 | 1.00 | 63.70 | B |
| ATOM | 1534 | NE | ARG B | 73 | 46.082 | 43.311 | 54.459 | 1.00 | 63.70 | B |
| ATOM | 1535 | CZ | ARG B | 73 | 44.910 | 42.685 | 54.372 | 1.00 | 63.70 | B |
| ATOM | 1536 | NH1 | ARG B | 73 | 44.867 | 41.394 | 54.063 | 1.00 | 63.70 | B |
| ATOM | 1537 | NH2 | ARG B | 73 | 43.777 | 43.350 | 54.578 | 1.00 | 63.70 | B |
| ATOM | 1538 | C | ARG B | 73 | 50.321 | 40.417 | 50.853 | 1.00 | 34.07 | B |
| ATOM | 1539 | O | ARG B | 73 | 51.337 | 41.084 | 50.649 | 1.00 | 34.07 | B |
| ATOM | 1540 | N | MET B | 74 | 50.332 | 39.087 | 50.902 | 1.00 | 33.57 | B |
| ATOM | 1541 | CA | MET B | 74 | 51.578 | 38.358 | 50.699 | 1.00 | 33.57 | B |
| ATOM | 1542 | CB | MET B | 74 | 51.405 | 36.866 | 51.030 | 1.00 | 28.43 | B |
| ATOM | 1543 | CG | MET B | 74 | 52.644 | 36.005 | 50.727 | 1.00 | 28.43 | B |
| ATOM | 1544 | SD | MET B | 74 | 54.177 | 36.471 | 51.632 | 1.00 | 28.43 | B |
| ATOM | 1545 | CE | MET B | 74 | 54.311 | 35.010 | 52.755 | 1.00 | 28.43 | B |
| ATOM | 1546 | C | MET B | 74 | 52.020 | 38.524 | 49.240 | 1.00 | 33.57 | B |
| ATOM | 1547 | O | MET B | 74 | 53.196 | 38.799 | 48.958 | 1.00 | 33.57 | B |
| ATOM | 1548 | N | LEU B | 75 | 51.075 | 38.370 | 48.313 | 1.00 | 27.16 | B |
| ATOM | 1549 | CA | LEU B | 75 | 51.396 | 38.502 | 46.892 | 1.00 | 27.16 | B |
| ATOM | 1550 | CB | LEU B | 75 | 50.148 | 38.291 | 46.017 | 1.00 | 20.11 | B |
| ATOM | 1551 | CG | LEU B | 75 | 49.595 | 36.867 | 46.001 | 1.00 | 20.11 | B |
| ATOM | 1552 | CD1 | LEU B | 75 | 48.347 | 36.813 | 45.155 | 1.00 | 20.11 | B |
| ATOM | 1553 | CD2 | LEU B | 75 | 50.657 | 35.910 | 45.471 | 1.00 | 20.11 | B |
| ATOM | 1554 | C | LEU B | 75 | 51.986 | 39.873 | 46.617 | 1.00 | 27.16 | B |
| ATOM | 1555 | O | LEU B | 75 | 52.999 | 39.991 | 45.930 | 1.00 | 27.16 | B |
| ATOM | 1556 | N | ASP B | 76 | 51.353 | 40.911 | 47.155 | 1.00 | 33.17 | B |
| ATOM | 1557 | CA | ASP B | 76 | 51.846 | 42.262 | 46.954 | 1.00 | 33.17 | B |
| ATOM | 1558 | CB | ASP B | 76 | 50.982 | 43.275 | 47.703 | 1.00 | 123.73 | B |
| ATOM | 1559 | CG | ASP B | 76 | 49.670 | 43.555 | 46.993 | 1.00 | 123.73 | B |
| ATOM | 1560 | OD1 | ASP B | 76 | 48.815 | 42.646 | 46.923 | 1.00 | 123.73 | B |
| ATOM | 1561 | OD2 | ASP B | 76 | 49.496 | 44.687 | 46.494 | 1.00 | 123.73 | B |
| ATOM | 1562 | C | ASP B | 76 | 53.291 | 42.350 | 47.428 | 1.00 | 33.17 | B |
| ATOM | 1563 | O | ASP B | 76 | 54.157 | 42.870 | 46.715 | 1.00 | 33.17 | B |
| ATOM | 1564 | N | ARG B | 77 | 53.559 | 41.819 | 48.620 | 1.00 | 43.84 | B |
| ATOM | 1565 | CA | ARG B | 77 | 54.909 | 41.858 | 49.165 | 1.00 | 43.84 | B |
| ATOM | 1566 | CB | ARG B | 77 | 54.921 | 41.315 | 50.599 | 1.00 | 55.30 | B |
| ATOM | 1567 | CG | ARG B | 77 | 54.155 | 42.179 | 51.599 | 1.00 | 55.30 | B |
| ATOM | 1568 | CD | ARG B | 77 | 54.376 | 41.708 | 53.035 | 1.00 | 55.30 | B |
| ATOM | 1569 | NE | ARG B | 77 | 53.743 | 40.420 | 53.322 | 1.00 | 55.30 | B |
| ATOM | 1570 | CZ | ARG B | 77 | 52.461 | 40.262 | 53.657 | 1.00 | 55.30 | B |
| ATOM | 1571 | NH1 | ARG B | 77 | 51.651 | 41.314 | 53.758 | 1.00 | 55.30 | B |
| ATOM | 1572 | NH2 | ARG B | 77 | 51.979 | 39.042 | 53.885 | 1.00 | 55.30 | B |
| ATOM | 1573 | C | ARG B | 77 | 55.873 | 41.072 | 48.282 | 1.00 | 43.84 | B |
| ATOM | 1574 | O | ARG B | 77 | 57.025 | 41.475 | 48.103 | 1.00 | 43.84 | B |
| ATOM | 1575 | N | LEU B | 78 | 55.399 | 39.961 | 47.717 | 1.00 | 32.40 | B |
| ATOM | 1576 | CA | LEU B | 78 | 56.241 | 39.139 | 46.849 | 1.00 | 32.40 | B |
| ATOM | 1577 | CB | LEU B | 78 | 55.617 | 37.750 | 46.628 | 1.00 | 31.07 | B |
| ATOM | 1578 | CG | LEU B | 78 | 55.564 | 36.814 | 47.857 | 1.00 | 31.07 | B |
| ATOM | 1579 | CD1 | LEU B | 78 | 54.824 | 35.526 | 47.494 | 1.00 | 31.07 | B |
| ATOM | 1580 | CD2 | LEU B | 78 | 56.975 | 36.482 | 48.350 | 1.00 | 31.07 | B |
| ATOM | 1581 | C | LEU B | 78 | 56.474 | 39.827 | 45.513 | 1.00 | 32.40 | B |
| ATOM | 1582 | O | LEU B | 78 | 57.538 | 39.671 | 44.903 | 1.00 | 32.40 | B |
| ATOM | 1583 | N | VAL B | 79 | 55.486 | 40.585 | 45.046 | 1.00 | 62.46 | B |
| ATOM | 1584 | CA | VAL B | 79 | 55.641 | 41.298 | 43.781 | 1.00 | 62.46 | B |
| ATOM | 1585 | CB | VAL B | 79 | 54.293 | 41.884 | 43.283 | 1.00 | 32.18 | B |
| ATOM | 1586 | CG1 | VAL B | 79 | 54.531 | 42.947 | 42.220 | 1.00 | 32.18 | B |
| ATOM | 1587 | CG2 | VAL B | 79 | 53.434 | 40.766 | 42.690 | 1.00 | 32.18 | B |
| ATOM | 1588 | C | VAL B | 79 | 56.663 | 42.418 | 43.981 | 1.00 | 62.46 | B |
| ATOM | 1589 | O | VAL B | 79 | 57.467 | 42.702 | 43.089 | 1.00 | 62.46 | B |
| ATOM | 1590 | N | CYS B | 80 | 56.637 | 43.037 | 45.160 | 1.00 | 54.33 | B |
| ATOM | 1591 | CA | CYS B | 80 | 57.575 | 44.102 | 45.483 | 1.00 | 54.33 | B |
| ATOM | 1592 | CB | CYS B | 80 | 57.187 | 44.772 | 46.795 | 1.00 | 78.30 | B |
| ATOM | 1593 | SG | CYS B | 80 | 55.867 | 45.974 | 46.623 | 1.00 | 78.30 | B |
| ATOM | 1594 | C | CYS B | 80 | 59.008 | 43.589 | 45.585 | 1.00 | 54.33 | B |
| ATOM | 1595 | O | CYS B | 80 | 59.944 | 44.286 | 45.207 | 1.00 | 54.33 | B |
| ATOM | 1596 | N | LYS B | 81 | 59.189 | 42.376 | 46.096 | 1.00 | 65.17 | B |
| ATOM | 1597 | CA | LYS B | 81 | 60.530 | 41.825 | 46.217 | 1.00 | 65.17 | B |
| ATOM | 1598 | CB | LYS B | 81 | 60.546 | 40.660 | 47.213 | 1.00 | 59.31 | B |
| ATOM | 1599 | CG | LYS B | 81 | 59.864 | 40.991 | 48.543 | 1.00 | 59.31 | B |
| ATOM | 1600 | CD | LYS B | 81 | 60.115 | 39.938 | 49.612 | 1.00 | 59.31 | B |
| ATOM | 1601 | CE | LYS B | 81 | 61.515 | 40.062 | 50.192 | 1.00 | 59.31 | B |
| ATOM | 1602 | NZ | LYS B | 81 | 61.815 | 39.005 | 51.206 | 1.00 | 59.31 | B |

FIGURE 2-22

| ATOM | 1603 | C | LYS | B | 81 | 61.015 | 41.367 | 44.847 | 1.00 | 65.17 | B |
| ATOM | 1604 | O | LYS | B | 81 | 62.185 | 41.025 | 44.674 | 1.00 | 65.17 | B |
| ATOM | 1605 | N | GLY | B | 82 | 60.111 | 41.364 | 43.871 | 1.00 | 29.81 | B |
| ATOM | 1606 | CA | GLY | B | 82 | 60.480 | 40.967 | 42.522 | 1.00 | 29.81 | B |
| ATOM | 1607 | C | GLY | B | 82 | 60.550 | 39.472 | 42.261 | 1.00 | 29.81 | B |
| ATOM | 1608 | O | GLY | B | 82 | 61.260 | 39.037 | 41.346 | 1.00 | 29.81 | B |
| ATOM | 1609 | N | TRP | B | 83 | 59.821 | 38.681 | 43.045 | 1.00 | 33.85 | B |
| ATOM | 1610 | CA | TRP | B | 83 | 59.829 | 37.232 | 42.860 | 1.00 | 33.85 | B |
| ATOM | 1611 | CB | TRP | B | 83 | 59.997 | 36.524 | 44.208 | 1.00 | 51.71 | B |
| ATOM | 1612 | CG | TRP | B | 83 | 61.213 | 36.946 | 44.993 | 1.00 | 51.71 | B |
| ATOM | 1613 | CD2 | TRP | B | 83 | 61.436 | 36.753 | 46.399 | 1.00 | 51.71 | B |
| ATOM | 1614 | CE2 | TRP | B | 83 | 62.729 | 37.244 | 46.689 | 1.00 | 51.71 | B |
| ATOM | 1615 | CE3 | TRP | B | 83 | 60.670 | 36.212 | 47.440 | 1.00 | 51.71 | B |
| ATOM | 1616 | CD1 | TRP | B | 83 | 62.347 | 37.532 | 44.504 | 1.00 | 51.71 | B |
| ATOM | 1617 | NE1 | TRP | B | 83 | 63.262 | 37.713 | 45.517 | 1.00 | 51.71 | B |
| ATOM | 1618 | CZ2 | TRP | B | 83 | 63.274 | 37.209 | 47.979 | 1.00 | 51.71 | B |
| ATOM | 1619 | CZ3 | TRP | B | 83 | 61.215 | 36.178 | 48.727 | 1.00 | 51.71 | B |
| ATOM | 1620 | CH2 | TRP | B | 83 | 62.504 | 36.674 | 48.980 | 1.00 | 51.71 | B |
| ATOM | 1621 | C | TRP | B | 83 | 58.539 | 36.744 | 42.180 | 1.00 | 33.85 | B |
| ATOM | 1622 | O | TRP | B | 83 | 58.519 | 35.684 | 41.540 | 1.00 | 33.85 | B |
| ATOM | 1623 | N | VAL | B | 84 | 57.471 | 37.527 | 42.324 | 1.00 | 31.00 | B |
| ATOM | 1624 | CA | VAL | B | 84 | 56.173 | 37.203 | 41.741 | 1.00 | 31.00 | B |
| ATOM | 1625 | CB | VAL | B | 84 | 55.127 | 36.956 | 42.847 | 1.00 | 24.28 | B |
| ATOM | 1626 | CG1 | VAL | B | 84 | 53.739 | 36.784 | 42.239 | 1.00 | 24.28 | B |
| ATOM | 1627 | CG2 | VAL | B | 84 | 55.508 | 35.728 | 43.645 | 1.00 | 24.28 | B |
| ATOM | 1628 | C | VAL | B | 84 | 55.692 | 38.346 | 40.832 | 1.00 | 31.00 | B |
| ATOM | 1629 | O | VAL | B | 84 | 55.840 | 39.529 | 41.162 | 1.00 | 31.00 | B |
| ATOM | 1630 | N | GLU | B | 85 | 55.104 | 37.971 | 39.697 | 1.00 | 29.82 | B |
| ATOM | 1631 | CA | GLU | B | 85 | 54.621 | 38.920 | 38.706 | 1.00 | 29.82 | B |
| ATOM | 1632 | CB | GLU | B | 85 | 55.355 | 38.673 | 37.394 | 1.00 | 50.76 | B |
| ATOM | 1633 | CG | GLU | B | 85 | 55.113 | 39.708 | 36.331 | 1.00 | 50.76 | B |
| ATOM | 1634 | CD | GLU | B | 85 | 55.596 | 39.248 | 34.968 | 1.00 | 50.76 | B |
| ATOM | 1635 | OE1 | GLU | B | 85 | 55.594 | 40.076 | 34.030 | 1.00 | 50.76 | B |
| ATOM | 1636 | OE2 | GLU | B | 85 | 55.968 | 38.057 | 34.838 | 1.00 | 50.76 | B |
| ATOM | 1637 | C | GLU | B | 85 | 53.123 | 38.759 | 38.489 | 1.00 | 29.82 | B |
| ATOM | 1638 | O | GLU | B | 85 | 52.605 | 37.638 | 38.516 | 1.00 | 29.82 | B |
| ATOM | 1639 | N | ARG | B | 86 | 52.425 | 39.875 | 38.280 | 1.00 | 29.70 | B |
| ATOM | 1640 | CA | ARG | B | 86 | 50.976 | 39.854 | 38.034 | 1.00 | 29.70 | B |
| ATOM | 1641 | CB | ARG | B | 86 | 50.269 | 40.980 | 38.782 | 1.00 | 41.84 | B |
| ATOM | 1642 | CG | ARG | B | 86 | 50.075 | 40.752 | 40.245 | 1.00 | 41.84 | B |
| ATOM | 1643 | CD | ARG | B | 86 | 49.029 | 41.718 | 40.769 | 1.00 | 41.84 | B |
| ATOM | 1644 | NE | ARG | B | 86 | 48.848 | 41.623 | 42.215 | 1.00 | 41.84 | B |
| ATOM | 1645 | CZ | ARG | B | 86 | 49.639 | 42.211 | 43.108 | 1.00 | 41.84 | B |
| ATOM | 1646 | NH1 | ARG | B | 86 | 50.674 | 42.947 | 42.705 | 1.00 | 41.84 | B |
| ATOM | 1647 | NH2 | ARG | B | 86 | 49.388 | 42.069 | 44.404 | 1.00 | 41.84 | B |
| ATOM | 1648 | C | ARG | B | 86 | 50.657 | 40.015 | 36.548 | 1.00 | 29.70 | B |
| ATOM | 1649 | O | ARG | B | 86 | 51.264 | 40.826 | 35.857 | 1.00 | 29.70 | B |
| ATOM | 1650 | N | LEU | B | 87 | 49.688 | 39.242 | 36.071 | 1.00 | 43.02 | B |
| ATOM | 1651 | CA | LEU | B | 87 | 49.270 | 39.303 | 34.673 | 1.00 | 43.02 | B |
| ATOM | 1652 | CB | LEU | B | 87 | 49.695 | 38.047 | 33.922 | 1.00 | 34.18 | B |
| ATOM | 1653 | CG | LEU | B | 87 | 51.161 | 37.829 | 33.616 | 1.00 | 34.18 | B |
| ATOM | 1654 | CD1 | LEU | B | 87 | 51.319 | 36.505 | 32.877 | 1.00 | 34.18 | B |
| ATOM | 1655 | CD2 | LEU | B | 87 | 51.673 | 38.999 | 32.779 | 1.00 | 34.18 | B |
| ATOM | 1656 | C | LEU | B | 87 | 47.760 | 39.421 | 34.522 | 1.00 | 43.02 | B |
| ATOM | 1657 | O | LEU | B | 87 | 46.993 | 38.931 | 35.356 | 1.00 | 43.02 | B |
| ATOM | 1658 | N | PRO | B | 88 | 47.313 | 40.072 | 33.440 | 1.00 | 39.72 | B |
| ATOM | 1659 | CD | PRO | B | 88 | 48.111 | 40.752 | 32.405 | 1.00 | 25.30 | B |
| ATOM | 1660 | CA | PRO | B | 88 | 45.875 | 40.230 | 33.190 | 1.00 | 39.72 | B |
| ATOM | 1661 | CB | PRO | B | 88 | 45.827 | 41.092 | 31.934 | 1.00 | 25.30 | B |
| ATOM | 1662 | CG | PRO | B | 88 | 47.171 | 41.810 | 31.941 | 1.00 | 25.30 | B |
| ATOM | 1663 | C | PRO | B | 88 | 45.366 | 38.830 | 32.885 | 1.00 | 39.72 | B |
| ATOM | 1664 | O | PRO | B | 88 | 45.949 | 38.145 | 32.047 | 1.00 | 39.72 | B |
| ATOM | 1665 | N | ASN | B | 89 | 44.308 | 38.378 | 33.546 | 1.00 | 30.26 | B |
| ATOM | 1666 | CA | ASN | B | 89 | 43.803 | 37.044 | 33.242 | 1.00 | 30.26 | B |
| ATOM | 1667 | CB | ASN | B | 89 | 42.859 | 36.566 | 34.338 | 1.00 | 30.59 | B |
| ATOM | 1668 | CG | ASN | B | 89 | 42.274 | 35.195 | 34.046 | 1.00 | 30.59 | B |
| ATOM | 1669 | OD1 | ASN | B | 89 | 41.576 | 34.630 | 34.885 | 1.00 | 30.59 | B |
| ATOM | 1670 | ND2 | ASN | B | 89 | 42.551 | 34.653 | 32.860 | 1.00 | 30.59 | B |
| ATOM | 1671 | C | ASN | B | 89 | 43.057 | 37.126 | 31.921 | 1.00 | 30.26 | B |
| ATOM | 1672 | O | ASN | B | 89 | 42.085 | 37.870 | 31.796 | 1.00 | 30.26 | B |
| ATOM | 1673 | N | PRO | B | 90 | 43.514 | 36.382 | 30.903 | 1.00 | 32.35 | B |
| ATOM | 1674 | CD | PRO | B | 90 | 44.768 | 35.613 | 30.819 | 1.00 | 35.64 | B |
| ATOM | 1675 | CA | PRO | B | 90 | 42.838 | 36.419 | 29.600 | 1.00 | 32.35 | B |

FIGURE 2-23

```
ATOM   1676  CB   PRO B  90      43.831  35.716  28.674  1.00 35.64      B
ATOM   1677  CG   PRO B  90      44.529  34.757  29.595  1.00 35.64      B
ATOM   1678  C    PRO B  90      41.447  35.783  29.559  1.00 32.35      B
ATOM   1679  O    PRO B  90      40.638  36.132  28.699  1.00 32.35      B
ATOM   1680  N    ASN B  91      41.159  34.868  30.482  1.00 36.98      B
ATOM   1681  CA   ASN B  91      39.855  34.199  30.506  1.00 36.98      B
ATOM   1682  CB   ASN B  91      39.987  32.760  31.023  1.00 38.48      B
ATOM   1683  CG   ASN B  91      41.044  31.963  30.280  1.00 38.48      B
ATOM   1684  OD1  ASN B  91      41.044  31.897  29.043  1.00 38.48      B
ATOM   1685  ND2  ASN B  91      41.957  31.346  31.035  1.00 38.48      B
ATOM   1686  C    ASN B  91      38.844  34.932  31.381  1.00 36.98      B
ATOM   1687  O    ASN B  91      37.744  34.426  31.623  1.00 36.98      B
ATOM   1688  N    ASP B  92      39.215  36.112  31.872  1.00 42.26      B
ATOM   1689  CA   ASP B  92      38.317  36.880  32.720  1.00 42.26      B
ATOM   1690  CB   ASP B  92      38.276  36.281  34.124  1.00 70.87      B
ATOM   1691  CG   ASP B  92      37.060  36.723  34.903  1.00 70.87      B
ATOM   1692  OD1  ASP B  92      35.939  36.530  34.389  1.00 70.87      B
ATOM   1693  OD2  ASP B  92      37.219  37.259  36.021  1.00 70.87      B
ATOM   1694  C    ASP B  92      38.739  38.342  32.787  1.00 42.26      B
ATOM   1695  O    ASP B  92      39.629  38.724  33.555  1.00 42.26      B
ATOM   1696  N    LYS B  93      38.070  39.141  31.966  1.00 54.34      B
ATOM   1697  CA   LYS B  93      38.290  40.575  31.834  1.00 54.34      B
ATOM   1698  CB   LYS B  93      36.934  41.265  31.649  1.00 66.28      B
ATOM   1699  CG   LYS B  93      37.001  42.673  31.085  1.00 66.28      B
ATOM   1700  CD   LYS B  93      35.604  43.180  30.748  1.00 66.28      B
ATOM   1701  CE   LYS B  93      35.651  44.550  30.100  1.00 66.28      B
ATOM   1702  NZ   LYS B  93      36.332  45.540  30.977  1.00 66.28      B
ATOM   1703  C    LYS B  93      39.071  41.265  32.951  1.00 54.34      B
ATOM   1704  O    LYS B  93      40.190  41.728  32.736  1.00 54.34      B
ATOM   1705  N    ARG B  94      38.496  41.326  34.145  1.00 36.91      B
ATOM   1706  CA   ARG B  94      39.159  42.004  35.251  1.00 36.91      B
ATOM   1707  CB   ARG B  94      38.131  42.845  36.008  1.00 45.25      B
ATOM   1708  CG   ARG B  94      37.482  43.880  35.114  1.00 45.25      B
ATOM   1709  CD   ARG B  94      36.332  44.580  35.794  1.00 45.25      B
ATOM   1710  NE   ARG B  94      35.640  45.503  34.893  1.00 45.25      B
ATOM   1711  CZ   ARG B  94      36.204  46.569  34.325  1.00 45.25      B
ATOM   1712  NH1  ARG B  94      37.482  46.864  34.554  1.00 45.25      B
ATOM   1713  NH2  ARG B  94      35.481  47.351  33.531  1.00 45.25      B
ATOM   1714  C    ARG B  94      39.944  41.126  36.221  1.00 36.91      B
ATOM   1715  O    ARG B  94      40.325  41.576  37.303  1.00 36.91      B
ATOM   1716  N    GLY B  95      40.207  39.882  35.838  1.00 47.16      B
ATOM   1717  CA   GLY B  95      40.967  39.010  36.717  1.00 47.16      B
ATOM   1718  C    GLY B  95      42.467  39.094  36.477  1.00 47.16      B
ATOM   1719  O    GLY B  95      42.920  39.707  35.516  1.00 47.16      B
ATOM   1720  N    VAL B  96      43.250  38.491  37.360  1.00 27.95      B
ATOM   1721  CA   VAL B  96      44.698  38.490  37.197  1.00 27.95      B
ATOM   1722  CB   VAL B  96      45.409  39.413  38.197  1.00 23.13      B
ATOM   1723  CG1  VAL B  96      44.808  40.802  38.149  1.00 23.13      B
ATOM   1724  CG2  VAL B  96      45.330  38.820  39.583  1.00 23.13      B
ATOM   1725  C    VAL B  96      45.252  37.101  37.433  1.00 27.95      B
ATOM   1726  O    VAL B  96      44.616  36.253  38.054  1.00 27.95      B
ATOM   1727  N    LEU B  97      46.445  36.872  36.915  1.00 27.10      B
ATOM   1728  CA   LEU B  97      47.118  35.605  37.107  1.00 27.10      B
ATOM   1729  CB   LEU B  97      47.356  34.880  35.778  1.00 15.99      B
ATOM   1730  CG   LEU B  97      46.199  34.238  35.001  1.00 15.99      B
ATOM   1731  CD1  LEU B  97      46.712  33.848  33.610  1.00 15.99      B
ATOM   1732  CD2  LEU B  97      45.656  33.011  35.748  1.00 15.99      B
ATOM   1733  C    LEU B  97      48.455  35.975  37.718  1.00 27.10      B
ATOM   1734  O    LEU B  97      48.999  37.058  37.447  1.00 27.10      B
ATOM   1735  N    VAL B  98      48.972  35.098  38.567  1.00 24.64      B
ATOM   1736  CA   VAL B  98      50.268  35.346  39.165  1.00 24.64      B
ATOM   1737  CB   VAL B  98      50.197  35.434  40.709  1.00 17.53      B
ATOM   1738  CG1  VAL B  98      49.701  36.806  41.128  1.00 17.53      B
ATOM   1739  CG2  VAL B  98      49.287  34.345  41.244  1.00 17.53      B
ATOM   1740  C    VAL B  98      51.187  34.211  38.772  1.00 24.64      B
ATOM   1741  O    VAL B  98      50.752  33.060  38.629  1.00 24.64      B
ATOM   1742  N    LYS B  99      52.452  34.550  38.569  1.00 25.92      B
ATOM   1743  CA   LYS B  99      53.450  33.565  38.216  1.00 25.92      B
ATOM   1744  CB   LYS B  99      53.527  33.410  36.707  1.00 28.24      B
ATOM   1745  CG   LYS B  99      54.279  34.520  36.008  1.00 28.24      B
ATOM   1746  CD   LYS B  99      54.341  34.259  34.515  1.00 28.24      B
ATOM   1747  CE   LYS B  99      55.558  34.910  33.911  1.00 28.24      B
ATOM   1748  NZ   LYS B  99      56.805  34.299  34.459  1.00 28.24      B
```

FIGURE 2-24

| | | | | | | | | | | |
|---|---|---|---|---|---|---|---|---|---|---|
| ATOM | 1749 | C | LYS | B | 99 | 54.768 | 34.084 | 38.783 | 1.00 25.92 | B |
| ATOM | 1750 | O | LYS | B | 99 | 54.852 | 35.237 | 39.226 | 1.00 25.92 | B |
| ATOM | 1751 | N | LEU | B | 100 | 55.791 | 33.242 | 38.801 | 1.00 23.47 | B |
| ATOM | 1752 | CA | LEU | B | 100 | 57.064 | 33.678 | 39.342 | 1.00 23.47 | B |
| ATOM | 1753 | CB | LEU | B | 100 | 57.900 | 32.476 | 39.796 | 1.00 16.95 | B |
| ATOM | 1754 | CG | LEU | B | 100 | 57.355 | 31.635 | 40.952 | 1.00 16.95 | B |
| ATOM | 1755 | CD1 | LEU | B | 100 | 58.353 | 30.573 | 41.322 | 1.00 16.95 | B |
| ATOM | 1756 | CD2 | LEU | B | 100 | 57.101 | 32.522 | 42.152 | 1.00 16.95 | B |
| ATOM | 1757 | C | LEU | B | 100 | 57.823 | 34.449 | 38.279 | 1.00 23.47 | B |
| ATOM | 1758 | O | LEU | B | 100 | 57.671 | 34.181 | 37.082 | 1.00 23.47 | B |
| ATOM | 1759 | N | THR | B | 101 | 58.616 | 35.421 | 38.724 | 1.00 21.01 | B |
| ATOM | 1760 | CA | THR | B | 101 | 59.438 | 36.222 | 37.833 | 1.00 21.01 | B |
| ATOM | 1761 | CB | THR | B | 101 | 59.763 | 37.573 | 38.446 | 1.00 28.80 | B |
| ATOM | 1762 | OG1 | THR | B | 101 | 60.482 | 37.365 | 39.667 | 1.00 28.80 | B |
| ATOM | 1763 | CG2 | THR | B | 101 | 58.494 | 38.341 | 38.742 | 1.00 28.80 | B |
| ATOM | 1764 | C | THR | B | 101 | 60.723 | 35.427 | 37.750 | 1.00 21.01 | B |
| ATOM | 1765 | O | THR | B | 101 | 60.891 | 34.459 | 38.488 | 1.00 21.01 | B |
| ATOM | 1766 | N | THR | B | 102 | 61.629 | 35.826 | 36.865 | 1.00 29.71 | B |
| ATOM | 1767 | CA | THR | B | 102 | 62.906 | 35.124 | 36.717 | 1.00 29.71 | B |
| ATOM | 1768 | CB | THR | B | 102 | 63.881 | 35.908 | 35.818 | 1.00 48.84 | B |
| ATOM | 1769 | OG1 | THR | B | 102 | 63.233 | 36.248 | 34.585 | 1.00 48.84 | B |
| ATOM | 1770 | CG2 | THR | B | 102 | 65.122 | 35.070 | 35.528 | 1.00 48.84 | B |
| ATOM | 1771 | C | THR | B | 102 | 63.566 | 34.983 | 38.081 | 1.00 29.71 | B |
| ATOM | 1772 | O | THR | B | 102 | 63.982 | 33.898 | 38.477 | 1.00 29.71 | B |
| ATOM | 1773 | N | GLY | B | 103 | 63.654 | 36.107 | 38.783 | 1.00 40.41 | B |
| ATOM | 1774 | CA | GLY | B | 103 | 64.266 | 36.131 | 40.096 | 1.00 40.41 | B |
| ATOM | 1775 | C | GLY | B | 103 | 63.611 | 35.177 | 41.061 | 1.00 40.41 | B |
| ATOM | 1776 | O | GLY | B | 103 | 64.295 | 34.412 | 41.743 | 1.00 40.41 | B |
| ATOM | 1777 | N | GLY | B | 104 | 62.284 | 35.225 | 41.122 | 1.00 39.22 | B |
| ATOM | 1778 | CA | GLY | B | 104 | 61.557 | 34.341 | 42.015 | 1.00 39.22 | B |
| ATOM | 1779 | C | GLY | B | 104 | 61.868 | 32.872 | 41.781 | 1.00 39.22 | B |
| ATOM | 1780 | O | GLY | B | 104 | 62.178 | 32.140 | 42.717 | 1.00 39.22 | B |
| ATOM | 1781 | N | ALA | B | 105 | 61.798 | 32.437 | 40.528 | 1.00 35.18 | B |
| ATOM | 1782 | CA | ALA | B | 105 | 62.072 | 31.041 | 40.198 | 1.00 35.18 | B |
| ATOM | 1783 | CB | ALA | B | 105 | 61.925 | 30.811 | 38.696 | 1.00 1.00 | B |
| ATOM | 1784 | C | ALA | B | 105 | 63.470 | 30.649 | 40.644 | 1.00 35.18 | B |
| ATOM | 1785 | O | ALA | B | 105 | 63.693 | 29.529 | 41.104 | 1.00 35.18 | B |
| ATOM | 1786 | N | ALA | B | 106 | 64.403 | 31.585 | 40.497 | 1.00 35.53 | B |
| ATOM | 1787 | CA | ALA | B | 106 | 65.797 | 31.382 | 40.868 | 1.00 35.53 | B |
| ATOM | 1788 | CB | ALA | B | 106 | 66.624 | 32.565 | 40.420 | 1.00 9.21 | B |
| ATOM | 1789 | C | ALA | B | 106 | 65.901 | 31.217 | 42.368 | 1.00 35.53 | B |
| ATOM | 1790 | O | ALA | B | 106 | 66.643 | 30.370 | 42.855 | 1.00 35.53 | B |
| ATOM | 1791 | N | ILE | B | 107 | 65.162 | 32.039 | 43.102 | 1.00 27.57 | B |
| ATOM | 1792 | CA | ILE | B | 107 | 65.173 | 31.948 | 44.559 | 1.00 27.57 | B |
| ATOM | 1793 | CB | ILE | B | 107 | 64.166 | 32.933 | 45.212 | 1.00 42.27 | B |
| ATOM | 1794 | CG2 | ILE | B | 107 | 64.085 | 32.674 | 46.715 | 1.00 42.27 | B |
| ATOM | 1795 | CG1 | ILE | B | 107 | 64.598 | 34.377 | 44.951 | 1.00 42.27 | B |
| ATOM | 1796 | CD1 | ILE | B | 107 | 65.995 | 34.708 | 45.459 | 1.00 42.27 | B |
| ATOM | 1797 | C | ILE | B | 107 | 64.758 | 30.531 | 44.926 | 1.00 27.57 | B |
| ATOM | 1798 | O | ILE | B | 107 | 65.406 | 29.868 | 45.739 | 1.00 27.57 | B |
| ATOM | 1799 | N | CYS | B | 108 | 63.676 | 30.069 | 44.307 | 1.00 33.42 | B |
| ATOM | 1800 | CA | CYS | B | 108 | 63.186 | 28.726 | 44.581 | 1.00 33.42 | B |
| ATOM | 1801 | CB | CYS | B | 108 | 61.964 | 28.402 | 43.725 | 1.00 38.41 | B |
| ATOM | 1802 | SG | CYS | B | 108 | 60.451 | 28.849 | 44.535 | 1.00 38.41 | B |
| ATOM | 1803 | C | CYS | B | 108 | 64.243 | 27.673 | 44.343 | 1.00 33.42 | B |
| ATOM | 1804 | O | CYS | B | 108 | 64.538 | 26.873 | 45.231 | 1.00 33.42 | B |
| ATOM | 1805 | N | GLU | B | 109 | 64.810 | 27.668 | 43.142 | 1.00 37.97 | B |
| ATOM | 1806 | CA | GLU | B | 109 | 65.818 | 26.678 | 42.835 | 1.00 37.97 | B |
| ATOM | 1807 | CB | GLU | B | 109 | 66.343 | 26.854 | 41.412 | 1.00 73.89 | B |
| ATOM | 1808 | CG | GLU | B | 109 | 67.143 | 25.648 | 40.926 | 1.00 73.89 | B |
| ATOM | 1809 | CD | GLU | B | 109 | 66.377 | 24.325 | 41.060 | 1.00 73.89 | B |
| ATOM | 1810 | OE1 | GLU | B | 109 | 66.989 | 23.259 | 40.830 | 1.00 73.89 | B |
| ATOM | 1811 | OE2 | GLU | B | 109 | 65.167 | 24.344 | 41.391 | 1.00 73.89 | B |
| ATOM | 1812 | C | GLU | B | 109 | 66.959 | 26.763 | 43.843 | 1.00 37.97 | B |
| ATOM | 1813 | O | GLU | B | 109 | 67.442 | 25.740 | 44.323 | 1.00 37.97 | B |
| ATOM | 1814 | N | GLN | B | 110 | 67.365 | 27.985 | 44.182 | 1.00 42.51 | B |
| ATOM | 1815 | CA | GLN | B | 110 | 68.450 | 28.208 | 45.135 | 1.00 42.51 | B |
| ATOM | 1816 | CB | GLN | B | 110 | 68.719 | 29.709 | 45.300 | 1.00 63.33 | B |
| ATOM | 1817 | CG | GLN | B | 110 | 69.443 | 30.355 | 44.133 | 1.00 63.33 | B |
| ATOM | 1818 | CD | GLN | B | 110 | 70.799 | 30.905 | 44.534 | 1.00 63.33 | B |
| ATOM | 1819 | OE1 | GLN | B | 110 | 70.893 | 31.775 | 45.403 | 1.00 63.33 | B |
| ATOM | 1820 | NE2 | GLN | B | 110 | 71.861 | 30.397 | 43.904 | 1.00 63.33 | B |
| ATOM | 1821 | C | GLN | B | 110 | 68.151 | 27.597 | 46.501 | 1.00 42.51 | B |

FIGURE 2-25

```
ATOM   1822  O   GLN B 110      69.008  26.952  47.100  1.00 42.51      B
ATOM   1823  N   CYS B 111      66.941  27.806  47.004  1.00 43.30      B
ATOM   1824  CA  CYS B 111      66.581  27.247  48.294  1.00 43.30      B
ATOM   1825  CB  CYS B 111      65.213  27.750  48.721  1.00 38.30      B
ATOM   1826  SG  CYS B 111      65.269  29.469  49.201  1.00 38.30      B
ATOM   1827  C   CYS B 111      66.598  25.724  48.277  1.00 43.30      B
ATOM   1828  O   CYS B 111      67.238  25.104  49.124  1.00 43.30      B
ATOM   1829  N   HIS B 112      65.903  25.120  47.316  1.00 88.21      B
ATOM   1830  CA  HIS B 112      65.861  23.664  47.220  1.00 88.21      B
ATOM   1831  CB  HIS B 112      65.104  23.229  45.964  1.00 61.47      B
ATOM   1832  CG  HIS B 112      63.620  23.414  46.053  1.00 61.47      B
ATOM   1833  CD2 HIS B 112      62.772  24.180  45.327  1.00 61.47      B
ATOM   1834  ND1 HIS B 112      62.842  22.754  46.980  1.00 61.47      B
ATOM   1835  CE1 HIS B 112      61.578  23.106  46.822  1.00 61.47      B
ATOM   1836  NE2 HIS B 112      61.509  23.970  45.825  1.00 61.47      B
ATOM   1837  C   HIS B 112      67.269  23.098  47.172  1.00 88.21      B
ATOM   1838  O   HIS B 112      67.545  22.030  47.718  1.00 88.21      B
ATOM   1839  N   GLN B 113      68.156  23.843  46.522  1.00 61.47      B
ATOM   1840  CA  GLN B 113      69.546  23.451  46.343  1.00 61.47      B
ATOM   1841  CB  GLN B 113      70.184  24.349  45.280  1.00104.41      B
ATOM   1842  CG  GLN B 113      71.604  23.972  44.906  1.00104.41      B
ATOM   1843  CD  GLN B 113      71.674  22.689  44.100  1.00104.41      B
ATOM   1844  OE1 GLN B 113      71.223  21.631  44.548  1.00104.41      B
ATOM   1845  NE2 GLN B 113      72.245  22.775  42.902  1.00104.41      B
ATOM   1846  C   GLN B 113      70.410  23.483  47.607  1.00 61.47      B
ATOM   1847  O   GLN B 113      71.276  22.624  47.792  1.00 61.47      B
ATOM   1848  N   LEU B 114      70.184  24.468  48.472  1.00 73.58      B
ATOM   1849  CA  LEU B 114      70.991  24.592  49.680  1.00 73.58      B
ATOM   1850  CB  LEU B 114      71.600  25.997  49.761  1.00 50.36      B
ATOM   1851  CG  LEU B 114      71.926  26.724  48.445  1.00 50.36      B
ATOM   1852  CD1 LEU B 114      72.690  28.017  48.745  1.00 50.36      B
ATOM   1853  CD2 LEU B 114      72.742  25.817  47.529  1.00 50.36      B
ATOM   1854  C   LEU B 114      70.215  24.309  50.955  1.00 73.58      B
ATOM   1855  O   LEU B 114      70.520  24.869  52.006  1.00 73.58      B
ATOM   1856  N   VAL B 115      69.218  23.436  50.871  1.00 50.97      B
ATOM   1857  CA  VAL B 115      68.413  23.100  52.040  1.00 50.97      B
ATOM   1858  CB  VAL B 115      67.269  24.127  52.255  1.00 93.44      B
ATOM   1859  CG1 VAL B 115      66.397  23.698  53.419  1.00 93.44      B
ATOM   1860  CG2 VAL B 115      67.841  25.512  52.523  1.00 93.44      B
ATOM   1861  C   VAL B 115      67.797  21.717  51.894  1.00 50.97      B
ATOM   1862  O   VAL B 115      67.458  21.072  52.885  1.00 50.97      B
ATOM   1863  N   GLY B 116      67.657  21.265  50.653  1.00 40.00      B
ATOM   1864  CA  GLY B 116      67.062  19.964  50.401  1.00 40.00      B
ATOM   1865  C   GLY B 116      67.715  18.821  51.152  1.00 40.00      B
ATOM   1866  O   GLY B 116      67.045  18.088  51.892  1.00 40.00      B
ATOM   1867  N   GLN B 117      69.024  18.663  50.963  1.00 36.16      B
ATOM   1868  CA  GLN B 117      69.751  17.593  51.630  1.00 36.16      B
ATOM   1869  CB  GLN B 117      71.205  17.564  51.150  1.00 97.53      B
ATOM   1870  CG  GLN B 117      71.382  16.732  49.894  1.00 97.53      B
ATOM   1871  CD  GLN B 117      70.848  15.326  50.086  1.00 97.53      B
ATOM   1872  OE1 GLN B 117      71.406  14.542  50.853  1.00 97.53      B
ATOM   1873  NE2 GLN B 117      69.750  15.008  49.407  1.00 97.53      B
ATOM   1874  C   GLN B 117      69.685  17.695  53.149  1.00 36.16      B
ATOM   1875  O   GLN B 117      69.240  16.762  53.818  1.00 36.16      B
ATOM   1876  N   ASP B 118      70.115  18.831  53.689  1.00 45.11      B
ATOM   1877  CA  ASP B 118      70.094  19.051  55.128  1.00 45.11      B
ATOM   1878  CB  ASP B 118      70.466  20.497  55.422  1.00 63.00      B
ATOM   1879  CG  ASP B 118      71.856  20.847  54.934  1.00 63.00      B
ATOM   1880  OD1 ASP B 118      72.217  22.046  54.974  1.00 63.00      B
ATOM   1881  OD2 ASP B 118      72.587  19.919  54.514  1.00 63.00      B
ATOM   1882  C   ASP B 118      68.722  18.741  55.725  1.00 45.11      B
ATOM   1883  O   ASP B 118      68.607  18.024  56.720  1.00 45.11      B
ATOM   1884  N   LEU B 119      67.676  19.270  55.104  1.00 38.08      B
ATOM   1885  CA  LEU B 119      66.332  19.055  55.602  1.00 38.08      B
ATOM   1886  CB  LEU B 119      65.329  19.879  54.790  1.00 55.08      B
ATOM   1887  CG  LEU B 119      63.895  19.822  55.327  1.00 55.08      B
ATOM   1888  CD1 LEU B 119      63.893  20.275  56.778  1.00 55.08      B
ATOM   1889  CD2 LEU B 119      62.978  20.693  54.486  1.00 55.08      B
ATOM   1890  C   LEU B 119      65.954  17.586  55.549  1.00 38.08      B
ATOM   1891  O   LEU B 119      65.353  17.046  56.484  1.00 38.08      B
ATOM   1892  N   HIS B 120      66.312  16.934  54.452  1.00 37.90      B
ATOM   1893  CA  HIS B 120      65.982  15.534  54.284  1.00 37.90      B
ATOM   1894  CB  HIS B 120      66.324  15.107  52.866  1.00 44.03      B
```

FIGURE 2-26

```
ATOM   1895  CG   HIS B 120      65.762  13.777  52.491  1.00 44.03      B
ATOM   1896  CD2  HIS B 120      64.508  13.407  52.138  1.00 44.03      B
ATOM   1897  ND1  HIS B 120      66.519  12.626  52.477  1.00 44.03      B
ATOM   1898  CE1  HIS B 120      65.757  11.604  52.132  1.00 44.03      B
ATOM   1899  NE2  HIS B 120      64.531  12.050  51.921  1.00 44.03      B
ATOM   1900  C    HIS B 120      66.723  14.680  55.308  1.00 37.90      B
ATOM   1901  O    HIS B 120      66.182  13.704  55.831  1.00 37.90      B
ATOM   1902  N    GLN B 121      67.956  15.074  55.606  1.00 42.58      B
ATOM   1903  CA   GLN B 121      68.785  14.362  56.563  1.00 42.58      B
ATOM   1904  CB   GLN B 121      70.195  14.959  56.555  1.00 84.48      B
ATOM   1905  CG   GLN B 121      71.264  14.100  57.206  1.00 84.48      B
ATOM   1906  CD   GLN B 121      72.658  14.658  56.985  1.00 84.48      B
ATOM   1907  OE1  GLN B 121      73.047  14.951  55.852  1.00 84.48      B
ATOM   1908  NE2  GLN B 121      73.419  14.804  58.064  1.00 84.48      B
ATOM   1909  C    GLN B 121      68.168  14.467  57.957  1.00 42.58      B
ATOM   1910  O    GLN B 121      67.945  13.449  58.618  1.00 42.58      B
ATOM   1911  N    GLU B 122      67.885  15.696  58.392  1.00 47.08      B
ATOM   1912  CA   GLU B 122      67.299  15.949  59.709  1.00 47.08      B
ATOM   1913  CB   GLU B 122      67.150  17.456  59.935  1.00 73.03      B
ATOM   1914  CG   GLU B 122      68.154  18.027  60.913  1.00 73.03      B
ATOM   1915  CD   GLU B 122      67.966  17.476  62.312  1.00 73.03      B
ATOM   1916  OE1  GLU B 122      66.934  17.789  62.944  1.00 73.03      B
ATOM   1917  OE2  GLU B 122      68.847  16.722  62.777  1.00 73.03      B
ATOM   1918  C    GLU B 122      65.944  15.271  59.913  1.00 47.08      B
ATOM   1919  O    GLU B 122      65.693  14.664  60.959  1.00 47.08      B
ATOM   1920  N    LEU B 123      65.068  15.385  58.917  1.00 59.13      B
ATOM   1921  CA   LEU B 123      63.745  14.783  59.000  1.00 59.13      B
ATOM   1922  CB   LEU B 123      62.905  15.155  57.776  1.00 52.32      B
ATOM   1923  CG   LEU B 123      62.127  16.471  57.797  1.00 52.32      B
ATOM   1924  CD1  LEU B 123      61.355  16.622  56.488  1.00 52.32      B
ATOM   1925  CD2  LEU B 123      61.173  16.482  58.979  1.00 52.32      B
ATOM   1926  C    LEU B 123      63.787  13.266  59.117  1.00 59.13      B
ATOM   1927  O    LEU B 123      63.037  12.682  59.901  1.00 59.13      B
ATOM   1928  N    THR B 124      64.664  12.631  58.341  1.00 49.05      B
ATOM   1929  CA   THR B 124      64.768  11.174  58.341  1.00 49.05      B
ATOM   1930  CB   THR B 124      64.987  10.639  56.911  1.00 64.49      B
ATOM   1931  OG1  THR B 124      66.173  11.221  56.363  1.00 64.49      B
ATOM   1932  CG2  THR B 124      63.813  10.993  56.019  1.00 64.49      B
ATOM   1933  C    THR B 124      65.862  10.589  59.233  1.00 49.05      B
ATOM   1934  O    THR B 124      66.059   9.370  59.255  1.00 49.05      B
ATOM   1935  N    LYS B 125      66.560  11.444  59.978  1.00 66.45      B
ATOM   1936  CA   LYS B 125      67.642  10.982  60.843  1.00 66.45      B
ATOM   1937  CB   LYS B 125      68.193  12.143  61.671  1.00 68.58      B
ATOM   1938  CG   LYS B 125      67.284  12.598  62.794  1.00 68.58      B
ATOM   1939  CD   LYS B 125      67.964  13.659  63.645  1.00 68.58      B
ATOM   1940  CE   LYS B 125      67.083  14.099  64.803  1.00 68.58      B
ATOM   1941  NZ   LYS B 125      67.767  15.137  65.628  1.00 68.58      B
ATOM   1942  C    LYS B 125      67.248   9.835  61.778  1.00 66.45      B
ATOM   1943  O    LYS B 125      68.114   9.148  62.316  1.00 66.45      B
ATOM   1944  N    ASN B 126      65.950   9.628  61.973  1.00 53.40      B
ATOM   1945  CA   ASN B 126      65.480   8.560  62.853  1.00 53.40      B
ATOM   1946  CB   ASN B 126      64.369   9.077  63.777  1.00 70.54      B
ATOM   1947  CG   ASN B 126      64.877  10.066  64.818  1.00 70.54      B
ATOM   1948  OD1  ASN B 126      64.086  10.728  65.494  1.00 70.54      B
ATOM   1949  ND2  ASN B 126      66.196  10.162  64.958  1.00 70.54      B
ATOM   1950  C    ASN B 126      64.952   7.373  62.058  1.00 53.40      B
ATOM   1951  O    ASN B 126      64.430   6.418  62.632  1.00 53.40      B
ATOM   1952  N    LEU B 127      65.090   7.433  60.738  1.00 70.93      B
ATOM   1953  CA   LEU B 127      64.601   6.361  59.884  1.00 70.93      B
ATOM   1954  CB   LEU B 127      63.448   6.860  59.008  1.00 58.67      B
ATOM   1955  CG   LEU B 127      62.158   7.291  59.707  1.00 58.67      B
ATOM   1956  CD1  LEU B 127      61.174   7.793  58.668  1.00 58.67      B
ATOM   1957  CD2  LEU B 127      61.565   6.126  60.480  1.00 58.67      B
ATOM   1958  C    LEU B 127      65.671   5.771  58.985  1.00 70.93      B
ATOM   1959  O    LEU B 127      66.562   6.473  58.512  1.00 70.93      B
ATOM   1960  N    THR B 128      65.567   4.469  58.749  1.00 75.76      B
ATOM   1961  CA   THR B 128      66.500   3.769  57.884  1.00 75.76      B
ATOM   1962  CB   THR B 128      66.343   2.258  58.021  1.00 67.91      B
ATOM   1963  OG1  THR B 128      65.106   1.854  57.417  1.00 67.91      B
ATOM   1964  CG2  THR B 128      66.330   1.863  59.495  1.00 67.91      B
ATOM   1965  C    THR B 128      66.138   4.157  56.457  1.00 75.76      B
ATOM   1966  O    THR B 128      65.112   4.795  56.224  1.00 75.76      B
ATOM   1967  N    ALA B 129      66.970   3.767  55.502  1.00 76.39      B
```

FIGURE 2-27

```
ATOM   1968  CA   ALA B 129      66.711    4.090   54.107  1.00 76.39      B
ATOM   1969  CB   ALA B 129      67.891    3.657   53.249  1.00 63.22      B
ATOM   1970  C    ALA B 129      65.431    3.411   53.623  1.00 76.39      B
ATOM   1971  O    ALA B 129      64.695    3.960   52.801  1.00 76.39      B
ATOM   1972  N    ASP B 130      65.167    2.217   54.141  1.00 80.92      B
ATOM   1973  CA   ASP B 130      63.983    1.464   53.743  1.00 80.92      B
ATOM   1974  CB   ASP B 130      64.112    0.000   54.179  1.00118.02      B
ATOM   1975  CG   ASP B 130      65.261   -0.716   53.487  1.00118.02      B
ATOM   1976  OD1  ASP B 130      66.425   -0.317   53.701  1.00118.02      B
ATOM   1977  OD2  ASP B 130      65.002   -1.673   52.726  1.00118.02      B
ATOM   1978  C    ASP B 130      62.700    2.059   54.301  1.00 80.92      B
ATOM   1979  O    ASP B 130      61.682    2.108   53.609  1.00 80.92      B
ATOM   1980  N    GLU B 131      62.748    2.505   55.552  1.00 71.60      B
ATOM   1981  CA   GLU B 131      61.575    3.102   56.180  1.00 71.60      B
ATOM   1982  CB   GLU B 131      61.865    3.406   57.657  1.00 50.30      B
ATOM   1983  CG   GLU B 131      62.214    2.161   58.462  1.00 50.30      B
ATOM   1984  CD   GLU B 131      62.588    2.448   59.915  1.00 50.30      B
ATOM   1985  OE1  GLU B 131      63.536    3.232   60.154  1.00 50.30      B
ATOM   1986  OE2  GLU B 131      61.938    1.872   60.822  1.00 50.30      B
ATOM   1987  C    GLU B 131      61.216    4.376   55.416  1.00 71.60      B
ATOM   1988  O    GLU B 131      60.043    4.651   55.156  1.00 71.60      B
ATOM   1989  N    VAL B 132      62.242    5.133   55.038  1.00 47.01      B
ATOM   1990  CA   VAL B 132      62.070    6.375   54.292  1.00 47.01      B
ATOM   1991  CB   VAL B 132      63.434    7.031   53.979  1.00 59.53      B
ATOM   1992  CG1  VAL B 132      63.236    8.246   53.086  1.00 59.53      B
ATOM   1993  CG2  VAL B 132      64.131    7.427   55.273  1.00 59.53      B
ATOM   1994  C    VAL B 132      61.342    6.146   52.974  1.00 47.01      B
ATOM   1995  O    VAL B 132      60.407    6.873   52.640  1.00 47.01      B
ATOM   1996  N    ALA B 133      61.776    5.139   52.224  1.00 62.22      B
ATOM   1997  CA   ALA B 133      61.156    4.832   50.939  1.00 62.22      B
ATOM   1998  CB   ALA B 133      61.968    3.768   50.211  1.00 45.41      B
ATOM   1999  C    ALA B 133      59.713    4.364   51.122  1.00 62.22      B
ATOM   2000  O    ALA B 133      58.849    4.636   50.288  1.00 62.22      B
ATOM   2001  N    THR B 134      59.456    3.656   52.216  1.00 43.56      B
ATOM   2002  CA   THR B 134      58.112    3.162   52.507  1.00 43.56      B
ATOM   2003  CB   THR B 134      58.128    2.233   53.728  1.00 52.11      B
ATOM   2004  OG1  THR B 134      59.117    1.212   53.538  1.00 52.11      B
ATOM   2005  CG2  THR B 134      56.761    1.599   53.927  1.00 52.11      B
ATOM   2006  C    THR B 134      57.187    4.346   52.817  1.00 43.56      B
ATOM   2007  O    THR B 134      56.058    4.436   52.321  1.00 43.56      B
ATOM   2008  N    LEU B 135      57.696    5.246   53.652  1.00 41.37      B
ATOM   2009  CA   LEU B 135      56.980    6.439   54.067  1.00 41.37      B
ATOM   2010  CB   LEU B 135      57.849    7.243   55.030  1.00 38.54      B
ATOM   2011  CG   LEU B 135      57.203    8.484   55.640  1.00 38.54      B
ATOM   2012  CD1  LEU B 135      56.004    8.075   56.502  1.00 38.54      B
ATOM   2013  CD2  LEU B 135      58.238    9.217   56.471  1.00 38.54      B
ATOM   2014  C    LEU B 135      56.606    7.308   52.870  1.00 41.37      B
ATOM   2015  O    LEU B 135      55.540    7.938   52.855  1.00 41.37      B
ATOM   2016  N    GLU B 136      57.485    7.337   51.871  1.00 39.88      B
ATOM   2017  CA   GLU B 136      57.249    8.137   50.675  1.00 39.88      B
ATOM   2018  CB   GLU B 136      58.555    8.358   49.913  1.00 58.39      B
ATOM   2019  CG   GLU B 136      59.605    9.113   50.707  1.00 58.39      B
ATOM   2020  CD   GLU B 136      60.620    9.807   49.820  1.00 58.39      B
ATOM   2021  OE1  GLU B 136      61.445   10.575   50.363  1.00 58.39      B
ATOM   2022  OE2  GLU B 136      60.593    9.594   48.585  1.00 58.39      B
ATOM   2023  C    GLU B 136      56.216    7.504   49.749  1.00 39.88      B
ATOM   2024  O    GLU B 136      55.408    8.209   49.136  1.00 39.88      B
ATOM   2025  N    TYR B 137      56.234    6.178   49.643  1.00 45.26      B
ATOM   2026  CA   TYR B 137      55.280    5.506   48.778  1.00 45.26      B
ATOM   2027  CB   TYR B 137      55.630    4.021   48.626  1.00 69.50      B
ATOM   2028  CG   TYR B 137      54.622    3.258   47.795  1.00 69.50      B
ATOM   2029  CD1  TYR B 137      54.160    3.773   46.584  1.00 69.50      B
ATOM   2030  CE1  TYR B 137      53.193    3.106   45.841  1.00 69.50      B
ATOM   2031  CD2  TYR B 137      54.097    2.045   48.240  1.00 69.50      B
ATOM   2032  CE2  TYR B 137      53.130    1.366   47.502  1.00 69.50      B
ATOM   2033  CZ   TYR B 137      52.680    1.904   46.307  1.00 69.50      B
ATOM   2034  OH   TYR B 137      51.701    1.258   45.588  1.00 69.50      B
ATOM   2035  C    TYR B 137      53.876    5.668   49.349  1.00 45.26      B
ATOM   2036  O    TYR B 137      52.938    6.023   48.626  1.00 45.26      B
ATOM   2037  N    LEU B 138      53.736    5.414   50.648  1.00 35.44      B
ATOM   2038  CA   LEU B 138      52.442    5.545   51.307  1.00 35.44      B
ATOM   2039  CB   LEU B 138      52.543    5.088   52.765  1.00 36.43      B
ATOM   2040  CG   LEU B 138      52.936    3.625   52.990  1.00 36.43      B
```

FIGURE 2-28

```
ATOM  2041  CD1  LEU  B  138    52.990   3.326  54.486  1.00  36.43     B
ATOM  2042  CD2  LEU  B  138    51.929   2.716  52.305  1.00  36.43     B
ATOM  2043  C    LEU  B  138    51.940   6.996  51.242  1.00  35.44     B
ATOM  2044  O    LEU  B  138    50.769   7.244  50.932  1.00  35.44     B
ATOM  2045  N    LEU  B  139    52.823   7.952  51.534  1.00  33.21     B
ATOM  2046  CA   LEU  B  139    52.439   9.355  51.482  1.00  33.21     B
ATOM  2047  CB   LEU  B  139    53.616  10.259  51.872  1.00  38.76     B
ATOM  2048  CG   LEU  B  139    53.835  10.434  53.383  1.00  38.76     B
ATOM  2049  CD1  LEU  B  139    55.119  11.198  53.656  1.00  38.76     B
ATOM  2050  CD2  LEU  B  139    52.635  11.170  53.983  1.00  38.76     B
ATOM  2051  C    LEU  B  139    51.966   9.685  50.078  1.00  33.21     B
ATOM  2052  O    LEU  B  139    50.958  10.368  49.905  1.00  33.21     B
ATOM  2053  N    LYS  B  140    52.687   9.190  49.073  1.00  32.26     B
ATOM  2054  CA   LYS  B  140    52.315   9.437  47.679  1.00  32.26     B
ATOM  2055  CB   LYS  B  140    53.355   8.824  46.735  1.00  53.55     B
ATOM  2056  CG   LYS  B  140    54.738   9.452  46.831  1.00  53.55     B
ATOM  2057  CD   LYS  B  140    55.753   8.716  45.969  1.00  53.55     B
ATOM  2058  CE   LYS  B  140    57.152   9.289  46.159  1.00  53.55     B
ATOM  2059  NZ   LYS  B  140    58.197   8.604  45.334  1.00  53.55     B
ATOM  2060  C    LYS  B  140    50.926   8.875  47.350  1.00  32.26     B
ATOM  2061  O    LYS  B  140    50.256   9.370  46.446  1.00  32.26     B
ATOM  2062  N    LYS  B  141    50.496   7.846  48.085  1.00  46.02     B
ATOM  2063  CA   LYS  B  141    49.185   7.237  47.852  1.00  46.02     B
ATOM  2064  CB   LYS  B  141    49.103   5.840  48.479  1.00  51.68     B
ATOM  2065  CG   LYS  B  141    49.941   4.782  47.767  1.00  51.68     B
ATOM  2066  CD   LYS  B  141    49.637   3.365  48.258  1.00  51.68     B
ATOM  2067  CE   LYS  B  141    48.242   2.904  47.838  1.00  51.68     B
ATOM  2068  NZ   LYS  B  141    47.928   1.518  48.308  1.00  51.68     B
ATOM  2069  C    LYS  B  141    48.043   8.085  48.383  1.00  46.02     B
ATOM  2070  O    LYS  B  141    46.895   7.910  47.981  1.00  46.02     B
ATOM  2071  N    VAL  B  142    48.355   9.005  49.285  1.00  38.10     B
ATOM  2072  CA   VAL  B  142    47.328   9.864  49.855  1.00  38.10     B
ATOM  2073  CB   VAL  B  142    47.785  10.504  51.186  1.00  34.97     B
ATOM  2074  CG1  VAL  B  142    46.649  11.321  51.776  1.00  34.97     B
ATOM  2075  CG2  VAL  B  142    48.245   9.423  52.166  1.00  34.97     B
ATOM  2076  C    VAL  B  142    46.990  10.985  48.886  1.00  38.10     B
ATOM  2077  O    VAL  B  142    45.833  11.402  48.784  1.00  38.10     B
ATOM  2078  N    LEU  B  143    47.999  11.466  48.166  1.00  45.02     B
ATOM  2079  CA   LEU  B  143    47.790  12.565  47.231  1.00  45.02     B
ATOM  2080  CB   LEU  B  143    49.105  12.915  46.525  1.00  26.86     B
ATOM  2081  CG   LEU  B  143    50.062  13.627  47.486  1.00  26.86     B
ATOM  2082  CD1  LEU  B  143    51.383  13.934  46.802  1.00  26.86     B
ATOM  2083  CD2  LEU  B  143    49.394  14.906  47.974  1.00  26.86     B
ATOM  2084  C    LEU  B  143    46.668  12.370  46.211  1.00  45.02     B
ATOM  2085  O    LEU  B  143    45.824  13.256  46.035  1.00  45.02     B
ATOM  2086  N    PRO  B  144    46.643  11.220  45.521  1.00 136.81     B
ATOM  2087  CD   PRO  B  144    47.703  10.213  45.346  1.00 119.29     B
ATOM  2088  CA   PRO  B  144    45.570  11.019  44.543  1.00 136.81     B
ATOM  2089  CB   PRO  B  144    46.035   9.785  43.768  1.00 119.29     B
ATOM  2090  CG   PRO  B  144    47.535   9.845  43.895  1.00 119.29     B
ATOM  2091  C    PRO  B  144    44.224  10.792  45.237  1.00 136.81     B
ATOM  2092  O    PRO  B  144    43.451   9.933  44.760  1.00 136.81     B
ATOM  2093  OXT  PRO  B  144    43.955  11.484  46.244  1.00 119.29     B
ATOM  2094  O    HOH  S    1    48.178  40.496  68.629  1.00  35.76     S
ATOM  2095  O    HOH  S    2    46.684  40.021  43.558  1.00  29.93     S
ATOM  2096  O    HOH  S    3    34.364  30.965  80.945  1.00  25.52     S
ATOM  2097  O    HOH  S    4    40.671  32.039  57.247  1.00  33.95     S
ATOM  2098  O    HOH  S    5    54.783  40.457  73.829  1.00  29.99     S
ATOM  2099  O    HOH  S    6    44.763  28.859  75.845  1.00  18.35     S
ATOM  2100  O    HOH  S    7    68.120  36.357  49.261  1.00  38.62     S
ATOM  2101  O    HOH  S    8    41.008  40.210  74.710  1.00  29.13     S
ATOM  2102  O    HOH  S    9    58.797  33.370  61.148  1.00  34.94     S
ATOM  2103  O    HOH  S   10    51.657  20.370  74.794  1.00  34.89     S
ATOM  2104  O    HOH  S   11    34.356  12.998  61.568  1.00  19.59     S
ATOM  2105  O    HOH  S   12    31.589  17.449  58.590  1.00  33.06     S
ATOM  2106  O    HOH  S   13    51.809  23.559  46.413  1.00  42.58     S
ATOM  2107  O    HOH  S   14    41.787  36.216  41.713  1.00  34.36     S
END
```

FIGURE 2-29

Sequence 1: SlyA (Top)
Sequence 2: MarR (Bottom)
Identity score: 21.2 %

```
        10        20        30        40        50        60        70        80
MKLESPLGSDLARLVRIWRALIDHRLKPLELTQTHWVTLHNIHQLPPDQSQIQLAKAIGIEQPSLVRTLDQLEDKGLIS
LFNEIIPLGRLIHMVNQKKDRLLNEYLSPLDITAAQFKVLCSIRC AACITPVELKKVLSVDLGALTRMLDRLVCKGWVE 90       100       110       120       130       140       150       160
RQTCASDRRAKRIKLTEKAEPLIAEMEEVI HKTRGEILAGISSEEIELLIKLIAKLEHNIMELHSHD
RLPNPNDKRGVLVKLTTGGAAICEQCHQLVGQDLHQELTKNLTADEVATLEYLLKKV    LP
```

Figure 11

Sequence 1: SlyA (Top)
Sequence 2: MarR (Bottom)

Figure 12

METHODS FOR IDENTIFYING AND USING MARR FAMILY POLYPEPTIDE BINDING COMPOUNDS

RELATED APPLICATIONS

This application claims priority to U.S. Provisional Application Ser. No. 60/388,618, entitled "Methods for Identifying and Using MarR Family Polypeptide Binding Compounds," filed on Jun. 13, 2002; and U.S. Provisional Application Ser. No. 60/305,322, entitled "Methods for Identifying and Using MarR Family Polypeptide Binding Compounds," filed on Jul. 13, 2001. This application is related to U.S. patent application Ser. No. 10/196,655, entitled "Crystal Structure of a MarR Family Polypeptide," filed concurrently herewith; U.S. Provisional Application Ser. No. 60/388,622, entitled "Crystal Structure of a MarR Family Polypeptide," filed Jun. 13, 2002; and U.S. Provisional Application Ser. No. 60/305,404, entitled "Crystal Structure of a MarR Family Polypeptide," filed on Jul. 13, 2001. The entire contents each of the aforementioned applications are hereby incorporated herein by reference.

BACKGROUND OF THE INVENTION

The Mar phenotype in E. coli is attributed largely to the action of MarA, the expression of which is regulated by MarR (Alekshun, M. N. supra (1997)). MarA is a transcription factor that autoactivates expression of the marRAB operon and regulates the expression of a global network of more than 60 chromosomal genes (Martin, R. G. et at. J. Bact. 178, 2216–2223 (1996); Barbosa, T. M. & Levy, S. B. J. Bad. 182, 3467–3474 (2000)). Mar mutants in isolates of clinical origin have now been identified (Maneewannakul, K. & Levy, S. B. Antimicrob. Agents Chemoiher. 40, 1695–1698 (1996); Oethinger, M. et at. Antimicrob. Agents Chemother. 42, 2089–2094 (1998); Linde, H. J. et at. Antimicrob. Agents Chemother. 44, 1865–1868 (2000); Ziha-Zarifi, I., et at. Antimicrob. Agents Chemother. 43, 287–291 (1999); Koutsolioutsou, A et at. Antimicrob. Agents Chemother. 45, 38–43 (2001)). Constitutive overexpression of MarA or a MarA homolog in many, of these strains is a key contributor to the maintenance of the resistance phenotype, particularly with respect to the fluoroquinolones, and recent studies have documented the selection of Mar mutants, bearing mutations in MarR, MexR, or other homologous loci, in E. coli, Pseudomonas aeruginosa, and other organisms during antimicrobial chemotherapy (Oethinger, M supra; Linde, H. J. et at.; supra; Ziha-Zarifi, I. et al. supra; Kern, W. V., et at. Antimicrob. Agents Chemother. 44, 814–820 (2000)).

MarR is a regulator of multiple antibiotic resistance in Escherichia coli. It is the prototypic member of a family of regulatory proteins found in the Bacteria and the Archae that play important roles in the development of antibiotic resistance, a global health problem. In the absence of an appropriate stimulus, MarR negatively regulates expression of the marRAB operon (Cohen, S. P., et al. 1993. J. Bacteriol. 175: 1484–1492; Martin, R. G. and Rosner, J. L. 1995. Proc. Natl. Acad. Sci. 92: 5456–5460; Seoane, A. S. and Levy, S. B. 1995. J. Bacteriol. 177: 3414–3419, 1995). DNA footprinting experiments suggest that MarR dimerizes at two locations, sites I and II, within the mar operator (marO) (Martin and Rosner, 1995, supra). Site I is positioned among the −35 and −10 hexamers and site II spans the putative MarR ribosome binding site (reviewed in Alekshun, M. N. and Levy, S. B. 1997. Antimicrob. Agents Chemother. 10: 2067–2075).

MarR is a member of a newly recognized family of regulatory proteins (Alekshun, M. N. and Levy, S. B. 1997. Antimicrob. Agents Chemother. 10: 2067–2075. Sulavik, M. C., et al. 1995. Mol. Med. 1: 436–446) and many functional homologues have been identified in a variety of important human pathogens and have been found to regulate a variety of different processes. For example, some MarR homologues have been found to control expression of multiple antibiotic resistance operons, some regulate tissue-specific adhesive properties, some control expression of a cryptic hemolysin, some regulate protease production, and some regulate sporulation. Proteins of the MarR family control an assortment of biological functions including resistance to multiple antibiotics, organic solvents, household disinfectants, and oxidative stress agents, collectively termed the multiple antibiotic resistance (Mar) phenotype (Alekshun, M. N. & Levy, S. B. Trends Microbiol. 7, 410–413 (1999)). These proteins also regulate the synthesis of pathogenic factors in microbes that infect humans and plants (Miller, P. F. & Sulavik, M. C. Mol. Microbiol. 21, 441–448 (1996)). Insight into the three dimensional structure of MarR family proteins would be of great value in designing drugs that interact with this family of proteins and modulate MarR function, for example, antibiotic resistance and virulence.

SUMMARY OF THE INVENTION

The instant invention advances the prior art by providing the crystal structure of a MarR family polypeptide, MarR. The crystal structure of MarR provides the three-dimensional structure, as well as the shape and electronic properties of its active sites. It can be used in a comprehensive rational drug design program to develop novel chemotherapeutics targeted toward the MarR/MarA transcription system. The atomic coordinates of a MarR crystal structure cocrystallized with and without salicylate are given in FIG. 1 and FIG. 2, respectively.

In one embodiment, the invention pertains, at least in part, to methods for identifying a MarR family modulating compound. The method includes selecting a candidate MarR family modulating compound by performing rational drug design with the set of atomic coordinates in FIG. 1 or 2. The method may further include contacting the candidate MarR family modulating compound with the MarR family polypeptide, and determining the ability of the candidate MarR family modulating compound to modulate the MarR family polypeptide. The invention also pertains to compounds identified by these methods and methods of using the compounds to modulate MarR family polypeptides.

In another embodiment, the invention pertains, at least in part, to methods for identifying a MarR family modulating compound. The methods include determining the structure of a MarR family polypeptide using the structure of MarR and identifying a candidate MarR family modulating compound by performing rational drug design based on the structure. The method may further include the steps of contacting the candidate MarR family modulating compound with a MarR family peptide, and a nucleic acid molecule, and measuring the binding affinity of the MarR family polypeptide peptide with the nucleic acid molecule. The invention also pertains to compounds identified by these methods and methods of using the compounds to modulate polypeptides.

In yet another embodiment, the invention pertains, at least in part, to a method for identifying a MarR modulating compound. The method includes obtaining a set of atomic coordinates defining the three-dimensional structure of MarR and selecting a candidate MarR modulating compound by performing rational drug design with the three dimensional structure of MarR. The method may further include the steps of contacting the candidate MarR modulating compound with MarR, measuring the ability of the candidate MarR modulating compound to modulate the activity of MarR. The invention also pertains to compounds identified by these methods and methods for modulating MarR using the compounds of the invention.

In another embodiment, the invention pertains, at least in part, to a MarR modulating compound of the formula (I):

X-Y-Z  (I)

wherein X is an interacting moiety; Y is a hydrophobic moiety; and Z is a polar moiety.

The invention also pertains, at least in part, to methods for inhibiting expression of MarA, by contacting MarR with a MarR modulating compound of formula (I).

In yet another embodiment, the invention also pertains to methods for decreasing multidrug resistance in a microbe. The method includes contacting the microbe with a MarR modulating compound of formula(I).

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 1 shows the atomic coordinates of the MarR-salicylate co-crystal.

FIG. 2 shows the atomic coordinates of the MarR crystal without salicylate.

FIG. 11 shows a sequence comparison and alignment of MarR (SEQ ID NO. 2) and SlyA (SEQ ID NO. 6).

FIG. 12 shows structurally conserved regions of SIyA (SEQ ID NO. 6) and MarR (SEQ ID NO.2) as determined by COMPOSER.

DETAILED DESCRIPTION OF THE INVENTION

Figure 3:
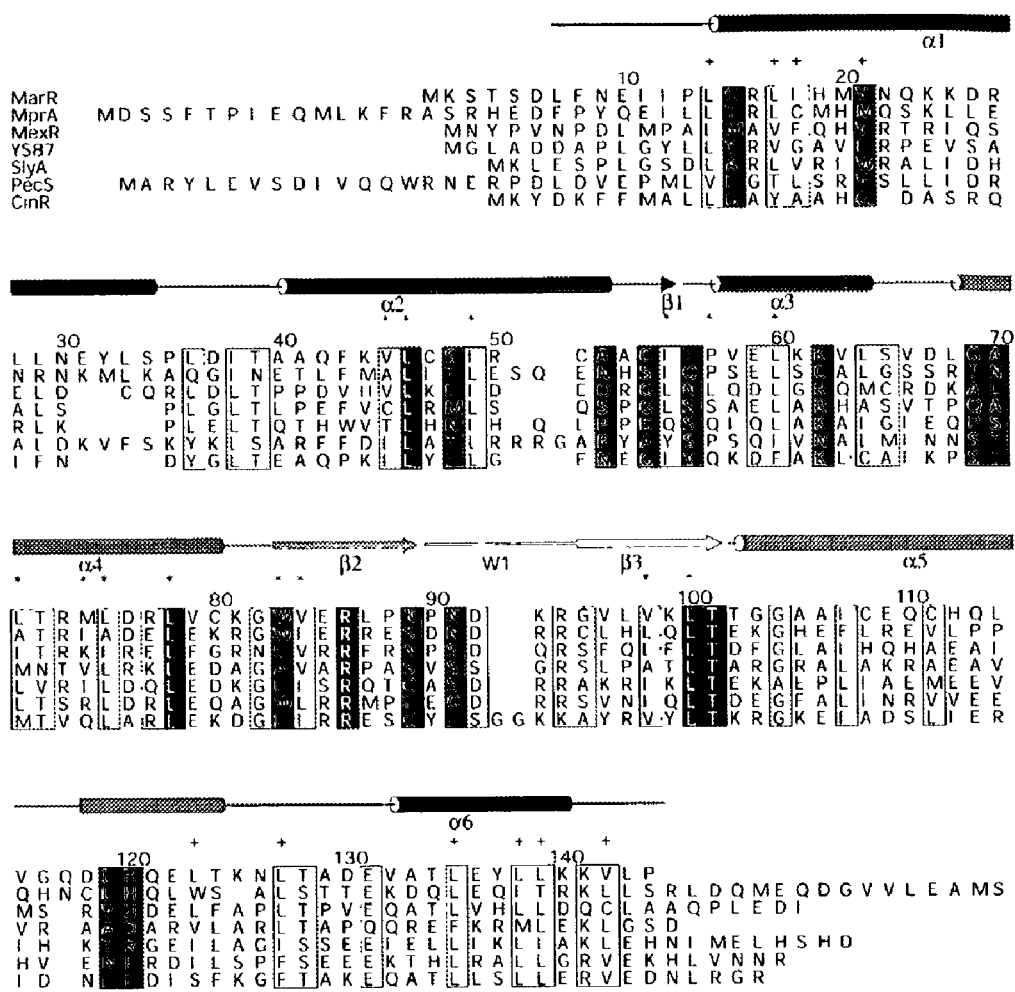
FIG. 3 shows the sequence alignment of MarR (SEQ ID NO. 2) with representative members of the MarR family. The representive members of the MarR family shown in FIG. 3 are MprA (SEQ ID NO. 3). MexR (SEQ ID NO. 4). Ys87 (SEQ ID NO. 5). SlvA (SEO ID NO. 6). PecS (SEO ID NO. 7). and CinR (SEQ ID NO. 8).

Chemotherapeutic intervention for the treatment and prevention of disease is predicated upon the ability of small molecules (drugs) to infiltrate a biological system and to interact with the components of the biological system (e.g. proteins, RNA, DNA, membranes, etc.) in a manner that modulates their normal function. Rational drug design attempts to formulate drug design hypotheses that specify and optimize the physical contacts between the drug and target. Koshland has used a lock and key analogy to characterize drug-target interactions; a specific "key" (drug) interacts only with its respective molecular "lock" (target) (Koshland, D. E., Jr. *Angew. Chem.* 1994, 106, 2468–2472). This model asserts that an appropriate degree of shape and electronic complimentarily between the drug and target must occur to produce productive drug-target interactions-those that cause a desired pharmacological response. The specific location on the "lock" or target is referred to as the active or catalytic site. The three dimensional shape and electronic properties of the active site form the basis for rational drug design and provides information toward the systematic chemical modifications of potential drugs.

In one embodiment, the invention pertains to methods for identifying MarR family modulating compounds using the three-dimensional structure of a MarR family polypeptide. The method includes selecting a candidate MarR family modulating compound by performing rational drug design with the atomic coordinates of a MarR family polypeptide. The method may also include contacting the candidate MarR family modulating compound with MarR family polypeptide; and determining the ability of said candidate MarR family modulating compound to a modulate MarR family polypeptide. In one embodiment, the MarR family polypeptide is MarR. The atomic coordinates of MarR in the presence and absence of salicylate are given in FIGS. 1 and 2, respectively.

MarR Family Polypeptides and Nucleic Acid Molecules

The term "MarR family polypeptide" includes molecules related to MarR, e.g., having certain shared structural and functional features. MarR family polypeptides also include those which are structural homologs of MarR. The structural homologs include those having a crystallized form which are structurally similar to that of crystallized MarR. Generally, it is believed that there is a strong relationship between the tertiary structure of a protein and its function within the biological system. Furthermore, it is known that a protein's overall tertiary structure is related to its primary amino acid sequence. Therefore, it has been demonstrated that proteins with similar amino acid make up and sequence will possess similar overall structure and will likely share similar function. MarR family members, in addition to having similarity to MarR, may bind to DNA and regulate transcription. While some MarR family members negatively control transcription (e.g., MarR), others have positive/activator functions (e.g., SlyA, BadR, NhhD, and MexR). MarR family polypeptides comprise DNA and protein binding domains. In addition, MarR family polypeptides can interact with a variety of structurally unrelated compounds that regulate their activity.

Exemplary MarR family members are taught in the art and can be found, e.g., in Sulavik et al. (1995. *Molecular Medicine*. 1:436), Miller and Sulavik (1996. *Molecular Microbiology*. 21:441) in which alignments of MarR and related proteins are shown, or through the use of BLAST searches and other techniques known in the art. Exemplary MarR family polypeptides are also illustrated in the following chart:

MarR Family Polypeptides

| Gram-negative | Gram-positive | Acid-fast |
|---|---|---|
| *Escherichia coli* | *Bacillus subtilus* | *Mycobacterium tuberculosis* |
| MarR | YdcH | 14.7 kD |
| SlyA | YhbI | Rv1404 |
| EmrR (MprA) | YkmA | Rv0737 |
| PapX | YkoM | Rv0042c |
| PrsX | Orf7 | Yz08 (15.6 kD) |
| HpcR | YfiV | *Mycobacterium leprae* |
| Ec17kD | YetL | |
| *Slamonella typhimurium* | YdgJ | Yz08 (15.6 kD) |
| | YwoH | |
| MarR | YwaE | Archaea |
| SlyA | YwhA | *Methanobacterium thermoautotrophicum* |
| EmrR | Hpr | |
| | YybA | MTH313 |
| *Pseudomonas aeruginosa* | YxaD | |
| | YsmB | |
| MexR | YusO | *Sulfolobus solfataricus* |
| | YpoP | |
| *Erwinia chrysanthemi* | YkvE | Lrs14 |
| PecS | | *Archaeoglobus fulgidus* |
| | | CinR |
| *Rhodopseudomonas palustris* | *Bacillus firmus* | |
| BadR | Orf7 | Purple non-sulfur *Rhodobacter capsulatus* |
| *Burkheldaria pseudomallei* | *Staphylococcus sciuri* | PetP |
| OrfE | Orf145 | *Sinorhizobium meliloti* |
| | Orf141 | SlyA (E293909) |
| | *Butyrivibrio fibrisolvens* | |
| | CinR | |
| | *Sphingomonas aromaticivorans* | |
| | Orf158 | |
| | *Rhodococcus rhodochrous* | |
| | NhhD | |
| | *Streptomyces peucetius* | |
| | Orf1 | |

Preferably, a MarR family polypeptide is MarR. Other preferred MarR family polypeptides include: EmrR, Ec17kD, and MexR.

In a further embodiment, the MarR family polypeptide has a winged-helix structure, such as the three dimensional structure of MarR.

FIG. 3 shows a sequence alignment of MarR with representative MarR family polypeptides. The MarR secondary structure elements were identified in its crystal structure and are illustrated in FIG. 3 (e.g., as tubes for α-helices (α) and arrows for β-sheets (β) and the single wing region (W1)). The numbering in FIG. 3 is according to the MarR primary sequence. Furthermore, residues that are identical in all homologs are colored in red, highly conserved amino acids are colored in yellow, and moderately conserved residues are colored in blue. The MarR family polypeptides used for the alignment were from the following organisms: MarR, *E. coli*; MprA (EmrR), *E. coli*; MexR, *Pseudomonas aeruginosa*; YS87, *Mycobacterium tuberculosis*; SlyA, *Salmonella typhimurium*; PecS, *Erwinia chrysanthemi*; CinR, *Butyrivibrio fibrisolvens*.

In a further embodiment, the MarR family polypeptide comprises, consists essentially of, or consists of the polypeptide sequence shown in Sequence Listing SEQ ID NO:1. Other MarR family polypeptides of interest include EmrR, YS87, PecS, CinR, SlyA, Ec17kD, MexR.

In another embodiment, the MarR family polypeptide is found, for example, in one of the following organisms *Escherichia coli, Salmonella typhimurium, Salmonella enterica, Enterobacter cloacae, Enterobacter aerogenes, Erwinia chrysanthemi, Yrsinia pestis, Yersinia enterocolitica, Kluyvera cryocrescens, Edwardsiella tarda, Pseudomonas aeruginosa, Vibrio cholera, Xanthomonas axonopodis, Xanthomonas campestris, Ralstonia solanacearum, Burkholderia pseudomallei, Burkholderia cepacia, Vogesella indigofera, Mesorhizobium loti, Agrobacterium tumefaciens, Sinorhizobium meliloti, Brucella melitensis, Caulobacter crescentus, Bacillus anthracis, Bacillus subtilis, Bacillus halodurans, Listeria monocytogenes, Listeria innocua, Listeria welshimeri, Staphylococcus sciuri, Streptococcus criceti, Streptococcus pneumoniae, Clostridium perfringens, Clostridium difficile, Streptomyces coelicolor, Streptomyces avermitilis, Mycobacterium tuberculosis, Mycobacterium leprae, Corynebacterium glutamicum, Thermotoga maritima, Methanosarcina acetivorans, Methanosarcina mazei,* and *Sulfolobus solfataricus.*

In another embodiment, the MarR family polypeptide is from an organism belonging to one of the following biological classifications: Enterobacteriaceae, Enterobacter, Yersinia, Kluyvera, Edwardsiella, Xanthomonas group, Xanthomonadales, Pseudomonaceae/Moraxellaceae group, Pseudomonadaceae, Vibrionaceae group, Burkholderia/Oxalobacter/Ralstonia group, Ralstonia group, Burkholderia group, Neisseriaceae, Vogesella, Rhizobiaceae group, Phyllobacteriaceae, Mesorhizobium, Rhizobiaceae, Sinorhizobium, Brucellaceae, Brucella, Caulobacter group, Firmicutes, Bacillus/Clostridium group, Bacilli, Bacillales, Bacillus, Bacillaceae, *Bacillus cereus* group, Listeria, Listeriaceae, Staphylococcaceae, Staphylococcus, Streptococcus, Lactobacillales, Streptococcaceae, Clostridium, Clostridiaceae, Clostridiales, Clostridia, Actinomycetales, Actinobacteria, Actinobacteridae, Streptomyces, Streptomycineae, Streptomycetaceae, Corynebacterineae, Mycobacterium, Mycobacteriaceae, Corynebacteriaceae, Corynebacterium, Nostocales, Nostocaceae, Nostoc, Thermotogae, Thermotogales, Thermotogaceae; Thermotoga, Methanosarcina, Euryarchaeota, Methanococci; Methanosarcinales, Methanosarcinaceae, Crenarchaeota, Thermoprotei; Sulfolobales, Sulfolobaceae, Sulfolobus, Proteobacteria, Pectobacterium, Cyanobacteria, or Archaea.

In one embodiment, the MarR family polypeptides of the invention are naturally occurring. In another embodiment, the subject crystal structures can be generated using non-naturally occurring forms of MarR family polypeptides, e.g. mutants or synthetic forms of MarR family polypeptides not found in nature.

In one embodiment, the MarR family polypeptide comprises one or more conservative mutations as compared to the wild type protein for the particular MarR family polypeptide. The term "MarR family polypeptide" also includes fragments of MarR family polypeptides which minimally retain at least a portion of the tertiary structure of the MarR family protein.

MarR family member polypeptide sequences are "structurally related" to one or more known MarR family members, preferably to MarR. This structural relatedness is shown by sequence similarity between two MarR family polypeptide sequences or between two MarR family nucleotide sequences. Sequence similarity can be shown, e.g., by optimally aligning MarR family member sequences using an alignment program for purposes of comparison and comparing corresponding positions. To determine the degree of similarity between sequences, they will be aligned for optimal comparison purposes (e.g., gaps may be introduced in the sequence of one protein or nucleic acid molecule for optimal alignment with the other protein or nucleic acid molecules). The amino acid residues or bases and corresponding amino acid positions or bases are then compared. When a position in one sequence is occupied by the same amino acid residue or by the same base as the corresponding position in the other sequence, then the molecules are identical at that position. If amino acid residues are not identical, they may be similar. An amino acid residue is "similar" to another amino acid residue if the two amino acid residues are members of the same family of residues having similar side chains. Families of amino acid residues having similar side chains have been defined in the art (see, for example, Altschul et al. 1990. *J. Mol. Biol.* 215:403) including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan). The degree (percentage) of identity or similarity between sequences, therefore, can be calculated as a function of the number of identical or similar positions shared by two sequences (i.e., % homology=# of identical or similar positions/total # of positions×100). Alignment strategies are well known in the art; see, for example, Altschul et al. supra for optimal sequence alignment.

MarR family polypeptides share some amino acid sequence similarity with MarR. The nucleic acid and amino acid sequences of MarR as well as other MarR family polypeptides are available in the art. For example, the nucleic acid and amino acid sequence of MarR can be found, e.g., on GeneBank (accession number M96235 or in Cohen et al. 1993. J. Bacteriol. 175:1484, or in SEQ ID NO:1).

The nucleic acid and protein sequences of MarR can be used as "query sequences" to perform a search against databases (e.g., either public or private) to, for example, identify other MarR family members having related sequences. Such searches can be performed, e.g., using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to MarR family nucleic acid molecules. BLAST protein searches can be performed with the XBLAST program, score=50, wordlength=3 to obtain amino acid sequences homologous to MarR protein molecules of the invention. To obtain gapped alignments for comparison purposes, Gapped BLAST can be utilized as described in Altschul et al., (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

MarR family members can also be identified as being structurally similiar based on their ability to specifically hybridize to the complement of nucleic acid sequences specifying MarR. Such stringent conditions are known to those skilled in the art and can be found e.g., in *Current Protocols in Molecular Biology*, John Wiley & Sons, N.Y. (1989), 6.3.1–6.3.6. A preferred, non-limiting example of stringent hybridization conditions are hybridization in 6×sodium chloride/sodium citrate (SSC) at about 45° C., followed by one or more washes in 0.2×SSC, 0.1% SDS at 50–65° C. Conditions for hybridizations are largely dependent on the melting temperature that is observed for half of the molecules of a substantially pure population of a double-stranded nucleic acid. The melting temperature is the temperature in °C. at which half the molecules of a given sequence are melted or single-stranded. For nucleic acids of sequence 11 to 23 bases, the melting temperature can be estimated in degrees C. as 2(number of A+T residues)+4 (number of C+G residues). Hybridization or annealing of nucleic acid molecules should be conducted at a temperature lower than the melting temperature, e.g., 15° C., 20° C., 25° C. or 30° C. lower than the melting temperature. The effect of salt concentration (in M of NaCl) can also be calculated, see for example, Brown, A., "Hybridization" pp. 503–506, in *The Encyclopedia of Molec. Biol.*, J. Kendrew, Ed., Blackwell, Oxford (1994).

Preferably, the nucleic acid sequence of a MarR family member identified in this way is at least about 10%, 20%, more preferably at least about 30%, more preferably at least about 40% identical and most preferably at least about 50%, or 60% identical or more with a MarR nucleotide sequence. Preferably, MarR family members have an amino acid sequence at least about 20%, more preferably at least about 30%, more preferably at least about 40% identical and most preferably at least about 50%, or 60% or more identical with a MarR amino acid sequence. However, it will be understood that the level of sequence similarity among microbial regulators of gene transcription, even though members of the same family, is not necessarily high. This is particularly true in the case of divergent genomes where the level of sequence identity may be low, e.g., less than 20% (e.g., *B. burgdorferi* as compared e.g., to *B. subtilis*). For example, the level of amino acid sequence homology between MarR and Pecs is about 31% and the level of amino acid sequence homology between MarR and PapX is about 28% when determined as described above. Accordingly, structural similarity among MarR family members can also be determined based on "three-dimensional correspondence" of amino acid residues.

The language "three-dimensional correspondence" includes residues which spatially correspond, e.g., are in the same functional position of a MarR family protein member as determined, e.g., by x-ray crystallography, but which may not correspond when aligned using a linear alignment program. The language "three-dimensional correspondence" also includes residues which perform the same function, e.g., bind to DNA or bind the same cofactor, as determined, e.g., by mutational analysis. Thus, MarR family members can be identified based on functional homology and sequence homology, e.g., as described in the art (Li et al. 2001. EMBO Journal 20:4854).

Preferred MarR family polypeptides include: MarR, EmrR, Ec17kD, MexR, PapX, SlyA, Hpr, PecS, Hpr, MprA, or (EmrR). In a more preferred embodiment, a MarR family polypeptide is selected from the group consisting of: MarR, EmrR, Ec17kD, and MexR. In a particularly preferred embodiment, a MarR family polypeptide is MarR.

In addition to sharing structural similarity, MarR family members have a MarR family polypeptide activity, i.e., they bind to DNA and regulate transcription. Some MarR family members positively regulate transcription (e.g., SlyA, BadR, NhhD, or MexR), while others negatively regulate transcription (e.g., MarR). While all MarR family members bind to DNA and regulate transcription, the different loci controlled by each family member regulate different processes in microbes. For example, MarR family polypeptides can control the expression of microbial loci involved in: regulation of antibiotic resistance [e.g., MarR (Cohen et al. 1993. J. Bacteriol. 175:1484), EmrR (Lomovskaya and Lewis. 1992. Proc. Natl. Acad. Sci. 89:8938), and Ec17kD (Sulavik et al. 1995. Mol. Med. 1:436), and MexR (Poole et al. 1996. Antimicrob. Agents. Chemother. 40:2021)], regulation of tissue-specific adhesive properties [e.g., PapX (Marklund et al., 1992. Mol. Microbiol. 6:2225)], regulation of expression of a cryptic hemolysin [e.g., SlyA (Ludwig et al. 1995 249:4740)], regulation of protease production [e.g., Hpr from *B. subtilis* (Perago and Hoch. 1988. J. Bacteriol. 170:2560) and PecS from *Erwinia chrysanthemi* (Reverchon et al., 1994. Mol. Microbiol. 11:1127)] and regulation of sporulation [e.g., Hpr (Perego and Hoch. 1988. J. Bacteriol. 170:2560)], regulation of the breakdown of plant materials [e.g., CinR (Dalymple and Swadling 1997 Microbiology)] sensing of phenolic compounds [(e.g., Sulvik et al. 1995. Mol. Med. 1:436], and repress marRAB expression when introduced into *E. coli* [e.g., Ec17kd (Marklund et al. 1992. Mol. Microbiol. 6:2225) and MprA (EmrR) (del Castillo et al., 1991. J. Bacteriol. 173:3924)]. The activity of MarR family polypeptides is antagonized by salicylate (Lomovskaya et al., 1995. J. Bacteriol. 177:2328; Sulavik et al. 1995. Mol. Med. 1:436).

Preferred MarR family polypeptide activities include regulation of multiple drug resistance and/or regulation of virulence.

In addition to full length MarR family polypeptide fragments MarR family polypeptide which are useful in making crystals are also within the scope of the invention. Accordingly, MarR family polypeptides for use in the instant screening assays can be full length MarR family member proteins or fragments thereof. Thus, a MarR family polypeptide can comprise, consist essentially of, or consist of an amino acid sequence derived from the full length amino acid sequence of a MarR family member. For example, in one embodiment, a polypeptide comprising a MarR family polypeptide DNA interacting domain or a polypeptide comprising a MarR family member protein interacting domain can be used.

In addition, naturally or non-naturally occurring variants of these polypeptides and nucleic acid molecules which retain the same functional activity, e.g., the ability to bind to DNA and regulate transcription. Such variants can be made, e.g., by mutation using techniques which are known in the art. Alternatively, variants can be chemically synthesized.

For example, it will be understood that the MarR family polypeptides described herein, are also meant to include equivalents thereof. For instance, mutant forms of MarR family polypeptides which are functionally equivalent, (e.g., have the ability to bind to DNA and to regulate transcription from an operon) can be made using techniques which are well known in the art. Mutations can include, e.g., at least one of a discrete point mutation which can give rise to a substitution, or by at least one deletion or insertion. For example, random mutagenesis can be used. Mutations can be made, e.g., by random mutagenesis or using cassette mutagenesis. For the former, the entire coding region of a molecule is mutagenized by one of several methods (chemical, PCR, doped oligonucleotide synthesis) and that collection of randomly mutated molecules is subjected to selection or screening procedures. In the latter, discrete regions of a protein, corresponding either to defined structural or functional determinants (e.g., the first or second helix of a helix-turn-helix domain) are subjected to saturating or semi-random mutagenesis and these mutagenized cassettes are re-introduced into the context of the otherwise wild type allele. In one embodiment, PCR mutagenesis can be used. For example, Megaprimer PCR can be used (O. H. Landt, Gene 96:125–128).

In addition, other portions of the above described polypeptides suitable for use in the claimed assays, such as those which retain their function (e.g., the ability to bind to DNA, to regulate transcription from an operon) or those which are critical for binding to regulatory molecules (such as compounds) can be easily determined by one of ordinary skill in the art (e.g, using standard truncation or mutagenesis techniques) and used in the instant assays. Exemplary techniques are described by Gallegos et al. (1996. J. Bacteriol. 178:6427).

It shall be understood that the instant invention also pertains to isolated MarR family member polypeptides, portions thereof, and the nucleic acid molecules encoding them, including naturally occurring and mutant forms.

Preparation of MarR Family Polypeptides

Preferred MarR family polypeptides for use in screening assays are synthesized, isolated or recombinant polypeptides. In one embodiment, MarR family polypeptides can be made from nucleic acid molecules. Nucleic acid molecules encoding MarR family polypeptides can be used to produce MarR family polypeptides. For example, nucleic acid molecules encoding a MarR family polypeptide can be isolated (e.g., isolated from the sequences which naturally flank it in the genome and from cellular components) and can be used to produce a MarR family polypeptide. In one embodiment, a nucleic acid molecule which has been (1) amplified in vitro by, for example, polymerase chain reaction (PCR); (2) recombinantly produced by cloning, or (3) purified, as by cleavage and gel separation; or (4) synthesized by, for example, chemical synthesis can be used to produce MarR family polypeptides. The term "nucleic acid" refers to polynucleotides such as deoxyribonucleic acid (DNA) and ribonucleic acid (RNA).

Nucleic acid molecules specifying MarR family polypeptides can be placed in a vector. The term "vector" refers to a nucleic acid molecule capable of transporting another nucleic acid molecule to which it has been linked. The term "expression vector" includes any vector, (e.g., a plasmid, cosmid or phage chromosome) containing a gene construct in a form suitable for expression by a cell (e.g., linked to a promoter). In the present specification, "plasmid" and "vector" are used interchangeably, as a plasmid is a commonly used form of vector. Moreover, the invention is intended to include other vectors which serve equivalent functions.

Exemplary expression vectors for expression of a gene encoding a MarR family polypeptide and capable of replication in a bacterium, such a bacterium from a genus selected from the group consisting of: *Escherichia, Bacillus, Streptomyces, Streptococcus*, or in a cell of a simple eukaryotic fungus such as a *Saccharomyces* or, *Pichia*, or in a cell of a eukaryotic organism such as an insect, a bird, a mammal, or a plant, are known in the art. Such vectors may carry functional replication-specifying sequences (replicons) both for a host for expression, for example a *Streptomyces*, and for a host, for example, *E. coli*, for genetic manipulations and vector construction. See e.g. U.S. Pat. No. 4,745,056. Suitable vectors for a variety of organisms are described in Ausubel, F. et al., *Short Protocols in Molecular Biology*, Wiley, New York (1995), and for example, for Pichia, can be obtained from Invitrogen (Carlsbad, Calif.).

Useful expression control sequences, include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. A useful translational enhancer sequence is described in U.S. Pat. No. 4,820,639.

It should be understood that the design of the expression vector may depend on such factors as the choice of the host cell to be transformed and/or the type of protein desired to be expressed.

"Transcriptional regulatory sequence" is a generic term to refer to DNA sequences, such as initiation signals, enhancers, operators, and promoters, which induce or control transcription of nucleic acid sequences with which they are operably linked. It will also be understood that a recombinant gene encoding a MarR family polypeptide can be under the control of transcriptional regulatory sequences which are the same or which are different from those sequences which control transcription of the naturally-occurring MarR family gene. Exemplary regulatory sequences are described in Goeddel; *Gene Expression Technology: Methods in Enzymology* 185, Academic Press, San Diego, Calif. (1990). For instance, any of a wide variety of expression control sequences, that control the expression of a DNA sequence when operatively linked to it, may be used in these vectors to express DNA sequences encoding the MarR family proteins of this invention.

Appropriate vectors are widely available commercially and it is within the knowledge and discretion of one of ordinary skill in the art to choose a vector which is appropriate for use with a given microbial cell. The sequences encoding MarR family polypeptides can be introduced into a cell on a self-replicating vector or may be introduced into the chromosome of a microbe using homologous recombination or by an insertion element such as a transposon.

Such vectors can be introduced into cells using standard techniques, e.g., transformation or transfection. The terms "transformation" and "transfection" mean the introduction of a nucleic acid, e.g., an expression vector, into a recipient or "host" cell. The term "transduction" means transfer of a nucleic acid sequence, preferably DNA, from a donor to a recipient cell, by means of infection with a virus previously grown in the donor, preferably a bacteriophage. Nucleic acids can also be introduced into microbial cells by transformation using calcium chloride or electroporation.

"Cells," "host cells," "recipient cells, are terms used interchangeably herein. It is understood that such terms refer not only to the particular subject cell but to the progeny or potential progeny of such a cell. In preferred embodiments, cells used to express MarR family polypeptides for purification, e.g., host cells, comprise a mutation which renders any endogenous MarR family polypeptide nonfunctional or causes the endogenous polypeptide to not be expressed. In other embodiments, mutations may also be made in other related genes of the host cell, such that there will be no interference from the endogenous host loci.

Purification of a MarR family polypeptides, e.g., recombinantly expressed polypeptides, can be accomplished using techniques known in the art. For example, if the MarR family polypeptide is expressed in a form that is secreted from cells, the medium can be collected. Alternatively, if the MarR family polypeptide is expressed in a form that is retained by cells, the host cells can be lysed to release the MarR family polypeptide. Such spent medium or cell lysate can be used to concentrate and purify the MarR family polypeptide. For example, the medium or lysate can be passed over a column, e.g., a column to which antibodies specific for the MarR family member polypeptide have been bound. Alternatively, such antibodies can be specific for a non-MarR family member polypeptide which has been fused to the MarR family polypeptide (e.g., as a tag) to facilitate purification of the MarR family member polypeptide. Other means of purifying MarR family member polypeptides are known in the art.

Architecture of the MarR-Salicylate Co-Crystal Structure

The term "three dimensional structure" includes both pictorial representations of MarR family polypeptides (e.g., such as those shown for MarR in the Figures) as well as atomic coordinates (e.g., such as those given in FIG. 1 for MarR-salicylate cocrystal, or in FIG. 2 for MarR) and other renditions of the shape, size, or symmetry of a MarR family polypeptide of interest. In a further embodiment, the three dimensional structure of the crystallized MarR family polypeptide is determined to a resolution of 5 Å or better, 3 Å or better, 2.5 Å or better, or, advantageously, 2.3 Å or better. The three dimensional structure of MarR, a MarR family polypeptide, is described in greater detail below.

Figure 4:
FIG. 4 is a ribbon representation of the salicylate containing MarR dimer with the two-fold axis near vertical. There are two salicylate molecules per monomer and each is represented by a stick model.

The salicylate containing MarR consists of a dimer with approximate overall dimensions of 50×55×45 Å, as shown in FIG. 4. There is one monomer in the asymmetric unit of the crystal with the dimer composed of subunits related by a crystallographic two-fold rotation. The dimeric structure is consistent with the results of earlier in vitro experiments suggesting that MarR binds the mar operator (marO) as a dimer (Martin, R. G. et al. supra (1996); Martin, R. G. & Rosner, J. L. Proc. *Natl. Acad. Sci. U.S.A.* 92, 5456–5460 (1995)). Another family member, MprA (EmrR) (FIG. 3) is also believed to function as a dimer (Brooun, A., et al. *J. Bact.* 181, 5131–5133 (1999)).

Figure 5:
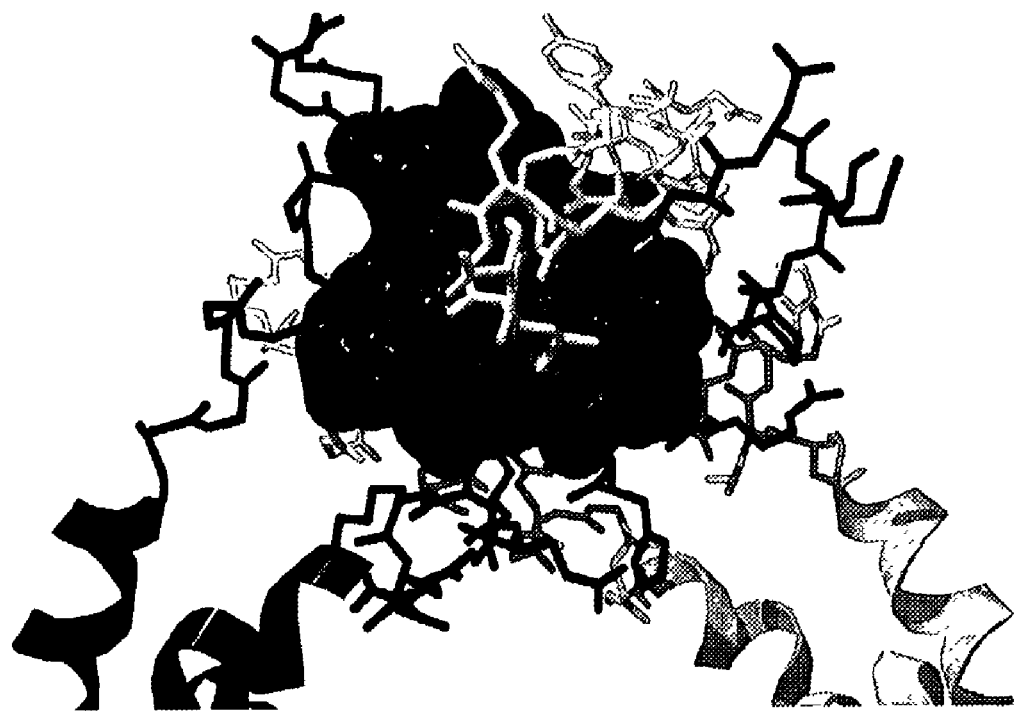
FIG. 5 is a representation of the N-/C-terminal domain represented by a surface (red) around the van der Waals radii of the side chain atoms only of the hydrophobic core residues. The main chain and other residues of the domain are shown in yellow for one subunit and blue for the other. Helices leading to and from the domain are shown in ribbon representation.

Each MarR salicylate subunit is an α/β protein with approximate dimensions of 35×25×60 Å and can be divided into two domains as shown in FIG. 4. FIG. 4 is a ribbon representation of the co-crystal structure of the MarR dimer viewed with the subunit 2-fold axis near vertical. The N- and C-terminal regions are closely juxtaposed and intertwine with the equivalent regions of the second subunit to form a domain that holds the subunits together (FIG. 5). This N-/C-terminal domain is linked to the remainder of the protein by two long antiparallel helices in each subunit.

Figure 6:
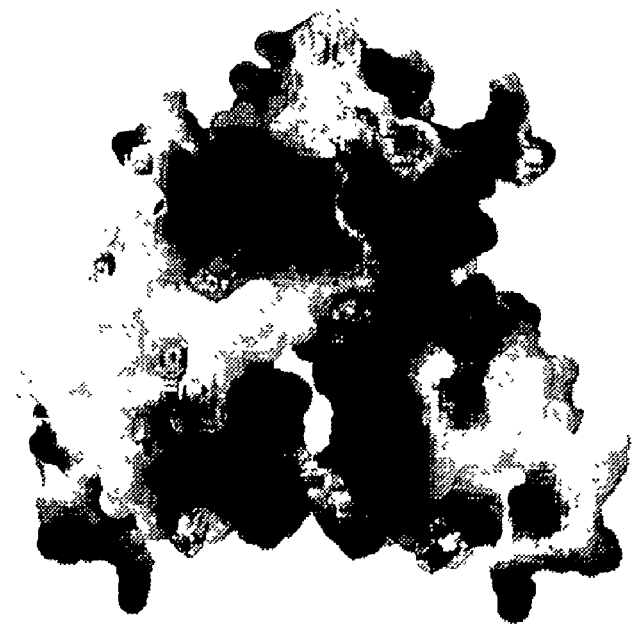
FIG. 6 is an electrostatic surface representation of the MarR dimer.
Figure 7:
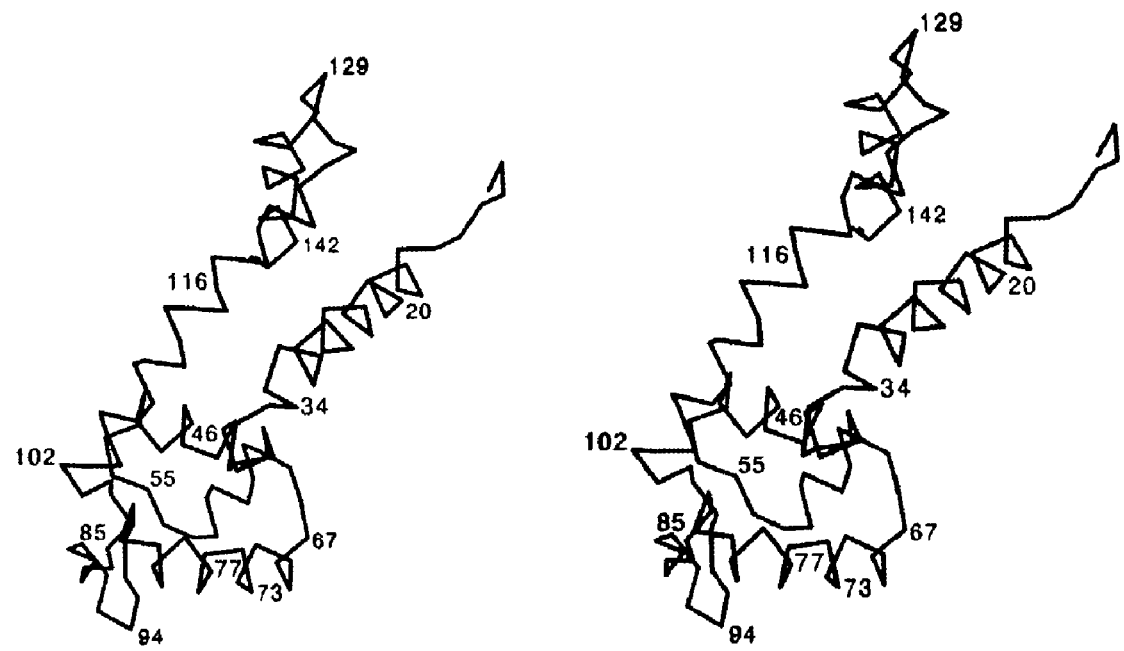
FIG. 7 is a Cα trace of a MarR subunit in stereo representation.

These helices lead to a globular domain that is likely to be responsible for DNA binding (see below). Although the globular DNA-binding domains of the dimer are adjacent to one another, they make minimal contact with each other and are situated to function independently. The overall organization of the N-/C-terminal domain and the two DNA-binding domains results in the formation of an approximately 6 Å wide channel through the center of the dimer (FIGS. 6 and 7). The electrostatic surface potential is consistent with the putative DNA-binding regions being strongly electropositive, as observed in other such winged-helix DNA-binding proteins (Gajiwala, K. S. & Burley, S. K. *Curr. Opin. Str. Biol.* 10, 110–116 (2000)).

Genetic and biochemical data have previously identified the N-terminus of MarR to be important for mediating protein-protein contacts between repressor subunits and have demonstrated that the C-terminus is important for protein function (Alekshun, M. N., et al. *Mol. Microbiol.* 35, 1394–404 (2000); Linde, H. J. et al. supra). The present structure shows that α-helices in the N- and C-terminal regions of each monomer fold around and interdigitate with those of the other subunit to form a well-packed hydrophobic core (FIG. 5) burying a surface area of 3,570 Å$^2$ (the total buried surface area for the whole dimer is 3,700 Å$^2$). The dimer is further stabilized in this region by several intermolecular hydrogen bonds, notably that between the ε-amino group of Lys 24 and the main chain carbonyl oxygen of Pro 144' in the C-terminus of the second subunit and that between the main chain carbonyl oxygen of Glu 10 and the side chain amino group of Lys 140'.

Figure 8:
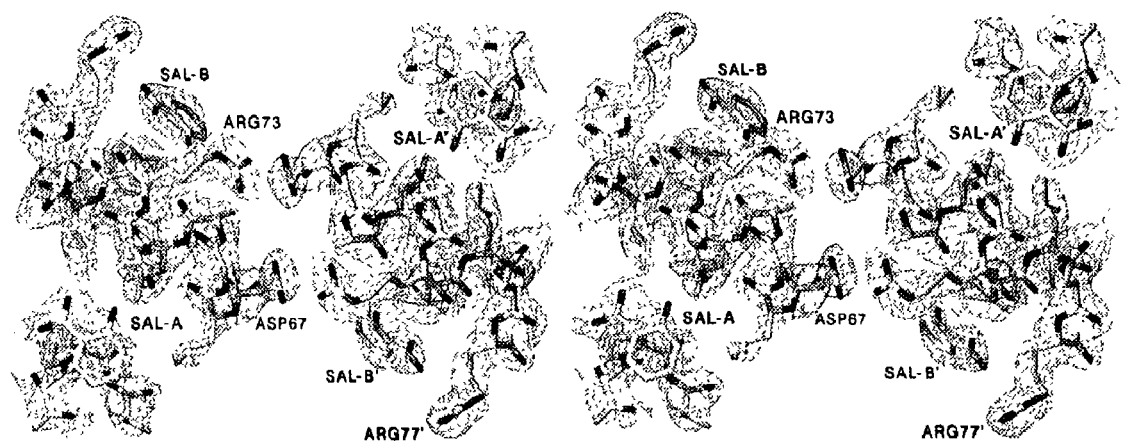
FIG. 8 is a diagram which shows interactions between the DNA-binding domains of the dimer in the region of the Arg 73–Asp 67' salt bridges. The stereo view is coincident with the 2-fold rotation axis of the dimer. Electron density shown is a $2F_O–F_C$ map contoured at 1σ.

While the DNA-binding lobe of each subunit also forms a well-packed hydrophobic core, the only interactions between these lobes of the two subunits are salt bridges formed between Asp 67 and Arg 73' and the reciprocal pair (FIG. 8). These salt bridges stabilize the relationship between the two lobes of the dimer in the crystal form of the protein but if disrupted by other interactions, such as might occur during the binding of MarR to marO, the two lobes would be able to act independently. Relative movement of the lobes would require distortion of the helices that link them to the N-/C-terminal domain. The long linker helix region encompassing residues 103–126 (α5/α5') appears poorly ordered in the region of Gly 116, as is the loop (residues 128–131) that connects this helix to the C-terminal helix (α6/α6'). It is possible that flexibility at these sites in MarR helps to accommodate relative shifts of the two lobes of the dimer that might occur on binding to DNA.

Architecture of the MarR Crystal Structure

The MarR without salicylate structure is a dimer and both subunits of the dimer are in the asymmetric unit. These individual subunits are joined by protein-protein interactions mediated by amino acids within both the N- and C-termini of the monomers. Like the MarR-salicylate structure, MarR without salicylate is an α/β protein. The MarR without salicylate structure is, however, conformationally different from the salicylate bound protein in that the caliper created by the dimer is more closed in the form of the protein without salicylate. Thus, the channel through the center of the dimer has been lost.

Figure 9:
FIG. 9 shows a ribbon representation of the MarR dimer with the two-fold axis near vertical.

The overall architecture of the MarR without salicylate structure is comparable to that of the salicylate bound protein. The presumed DNA binding lobes or domains are linked to the remainder of the protein by two long α-helices. The positioning of the two DNA binding lobes in the MarR without salicylate structure is fixed by hydrogen bonds between the two lobes. This arrangement is believed to be mediated by interactions between Asp 67 and Arg 77'. In addition, Asp 26 is involved in hydrogen bonds with the side chains of Lys 44 and Lys 25. Together, the presumed recognition helices within the DNA binds lobes overlap by approximately one helical turn. FIG. 9 shows a ribbon representation of the MarR dimer with the two-fold axis near vertical.

The DNA Binding Domain

Previous studies have shown the region spanning amino acids 61–121 in MarR to be required for its DNA binding activity (Alekshun, M. N et al., supra, (2000)). In the crystal structure, amino acids 55–100 [β1-α3-α4-β2-W1 (wing)-β3] adopt the winged-helix fold (Clark, K. L. et al. *Nature* 364, 412–420 (1993)). The overall topology [H1 (α2)-S1 (β1)-H2 (α3)-H3 (α4, recognition helix)-S2 (β2)-W1-S3 (β3)] of this region is similar to other winged-helix DNA binding proteins (the terminology applied for these and subsequent structural elements is according to Gajiwala and Burley, supra (2000)) except that a third strand of sheet present in most members of the group appears to be represented in this MarR structure only by an interaction with Ile 55 (β1). The presence of this residue as the third component in the sheet interaction is similar to that observed in OmpR (Martinez-Hackert, E. & Stock, A. M. *Structure* 5, 109–124 (1997)), a winged helix protein, where Leu 180 interacts with the two strands of the antiparallel sheet that forms part of the "wing" in this transcription factor.

Within the winged-helix family of DNA-binding proteins, there are multiple modes of DNA binding. Members such as HNF-3γ use the recognition helix (H3) of the motif as the primary determinant for DNA-protein interactions in the major groove, and a wing region(s) (W1) to form minor groove or phosphodiester backbone nucleoprotein contacts (Clark, K. L. et al. supra (1993)). Others, such as hRFX1, use W1 to interact with the major groove and the H3 helix makes only a single minor groove contact (Gajiwala, K. S. et al. *Nature* 403, 916–921 (2000)). The juxtaposition of the DNA-binding lobes in the present structure does not allow for modeling of the whole dimer onto a B-DNA representation of the operator. However, since mutations in both α4 (H3) and W1 affect the DNA binding activity of MarR it is expected that amino acids from each of these regions would contribute to the DNA binding activity of the protein. For example, mutations in α4, including an R73C change, abolish MarR DNA binding activity in whole cells and in vitro(Alekshun, M. N et al., supra, (2000)). In the present crystal structure, it is the side chain of Arg 73 that is hydrogen bonded to Asp 67' of the other subunit, an interaction that stabilizes the relative orientation of the two DNA-binding lobes. Also, an R94C mutation at the tip of W1 is inactive in a whole cell assay while a G95S "super-repressor" mutation increases the DNA binding activity of MarR 30-fold in vitro (Alekshun, M. N et al., supra, (2000); Alekshun, M. N. & Levy, S. B. *J. Bact.* 181, 3303–3306 (1999)). In the absence of protein-DNA co-crystal structures, the precise mechanism by which these mutations affect the DNA binding activity of the protein is uncertain.

Footprinting experiments have suggested that MarR binds as a dimer at two separate but very similar sites in marO, the protein protects ~21-bp of DNA on both strands at a single site, and does not bend its target (Martin, R. G. et al., supra (1996); Martin, R. G. et al. *Proc. Natl. Acad Sci. U.S.A.* 92, 5456–5460 (1995)). Each MarR binding site is composed of two half-sites whose organization is such that they are on different faces of the DNA double helix (Alekshun, M. N. et al. *Mol. Microbiol.* 35, 1394–404 (2000)), an arrangement that is very similar to the hRFX1 binding site (Gajiwala, K. S. et al. *Nature* 403, 916–921 (2000)). For MarR to bind as a dimer, with each winged-helix DNA binding domain contacting one half-site on B-DNA, geometric constraints suggest only a few possible modes of binding. One scenario, involving the binding of a single dimer to one MarR binding site, would require reorientation of the DNA binding lobes so that each could reach one half-site. This would be analogous to the binding of an E2F-DP heterodimer (a eukaryotic transcription factor in which each subunit also has a winged-helix DNA binding domain) to its cognate binding site (Zheng, N. et al. *Genes Dev.* 13, 666–74. (1999)). A second scenario would involve the binding of two dimers, on opposite faces of the double helix, to a single MarR binding site. This model would be analogous to the binding of DtxR (a bacterial protein with a winged-helix DNA binding domain) to its target, although in DtxR the half-sites are on the same face of the DNA helix (Pohl, E. et al. *J. Biol. Chem.* 273, 22420–22427 (1998); White, A. et al. *Nature* 394, 502–506 (1998)).

The term "appropriate conditions" include those conditions which result in the formation of a crystal which can by analyzed to a resolution of 5.0 Å or less. The crystals may be formed using suitable art recognized techniques, such as hanging droplet vapor diffusion. In one embodiment, the temperature of crystallization of the MarR family polypeptide is from about 1° C. to about 30° C., from about 10° C. to about 25° C., from about 15° C. to about 20° C., or abut 17° C. In a further embodiment, the conditions are selected such that crystals of said MarR family polypeptide grow within an acceptable time and reach dimensions which are suitable for structural determination, e.g., by using X-ray diffraction. In one embodiment, the acceptable time is 8 weeks or less, 6 weeks or less, 4 weeks or less, or 3 weeks or less. In an embodiment, the dimensions of the crystal are approximately 0.1 mm or greater per side, 0.2 mm or greater per said, or approximately 0.3 mm per side or greater.

In a further embodiment, the appropriate conditions include a cocrystallization agent which interacts with the protein such that the three dimensional structure of the protein can be determined.

The term "cocrystallization agent" includes substances which can be crystallized with the MarR family polypeptide such that the three dimensional structure can be determined. In an embodiment, the coocrystallization agent is a MarR family polypeptide modulator. The term "MarR family polypeptide modulator" includes compounds which interact with MarR family polypeptides, either to inhibit or enhance the activity of the MarR family polypeptides, such that they alter its activity in its non-crystallized form. In one embodiment, the MarR family polypeptide modulator is a MarR inhibitor (e.g., salicylate, plombagin, or DNP). In an embodiment, the concentration of the salicylate is about 100 mM or less, 150 mM or less, 200 mM or less, or 250 mM or less.

The crystal structure or MarR has been solved using crystals grown in the presence and in the absence of high concentrations (250 mM) of sodium salicylate. This agent, at millimolar concentrations, is known to inhibit MarR activity both in vitro and in whole cells (Alekshun, M. N. supra (1999)). It is routinely used as a model inhibitor of MarR to induce MarA expression in *E. coli* and *S. typhimurium* (Cohen, S. P. et al. *J. Bact.* 175, 7856–7862 (1993); Sulavik, M. C. et al. *J. Bact.* 179, 1857–1866 (1997)) and thus, to confer a Mar phenotype (Alekshun, M. N. supra (1999)). In one example, salicylate was included in the current crystal growth conditions to provide stable crystals. In another example, the crystal structure of MarR was determined using MarR without salicylate.

Electron density that is consistent with bound salicylate is apparent at two sites on each subunit in the present structure. These sites are on the surface of the molecule on either side of the proposed DNA-binding helix α4 (H3). In one site (SAL-A), the salicylate hydroxyl is hydrogen bonded to the hydroxyl side chain of Thr 72 in the α4 (H3) helix and the salicylate carboxylate hydrogen bonds to the guanidinium group of Arg 86. In the other site (SAL-B), the salicylate hydroxyl hydrogen bonds to the backbone carbonyl of Ala 70 and its carboxyl hydrogen bonds to Arg 77. In each of these sites, the salicylate ring sits over a hydrophobic side chain in the pocket; Pro 57 in SAL-A and Met 74 in SAL-B and other surface hydrophobes are also located laterally within 3.5 Å of the unsubstituted side of the ring. Although SAL-B is solvent exposed, SAL-A packs in the crystal with Val 96 of a symmetry mate situated 3.6 Å above the salicylate ring and adjacent to the SAL-A site of this symmetry mate. Since both SAL-A and SAL-B are close to the DNA binding helix, they may be positioned to influence DNA binding.

The crystal structure of MarR was solved by multiwavelength anomalous dispersion methods using protein containing selenomethionine. Diffraction data were collected to 2.3 Å from crystals of both seleno and native protein.

Use of the MarR Crystal Structure to Model the Structures of Other MarR Family Polypeptides In one embodiment, the invention pertains to a method for determining the structure of a MarR family polypeptide comprising analyzing the sequence of the related polypeptide and then modeling its structure based on the structure of MarR. The invention also pertains to the use of the MarR family polypeptide structures in the methods described below, e.g., for the identification of MarR family polypeptide modulating compounds.

Given the sequence-structure relationship described, the MarR crystal structure (described below) in the presence or absence of a MarR family polypeptide modulating compound can be used as a template to generate a computational three-dimensional model of any of the other members of the MarR protein family. In another embodiment, both crystals can be compared and the resulting information (including information regarding the binding site of the MarR family modulator) can be used. The resulting structure(s) can be subjected to the entire complement of computational approaches discussed and demonstrated above. Computer software packages such as COMPOSER (SYBYL. Tripos, Inc. 1699 Hanley Rd. St. Louis, Mo. 63144; Sutcliffe, M. J. et al. *Protein Eng.* 1987, 1, 385–392), MODELLER (Accelrys, Inc. 9685 Scranton Road San Diego, Calif. 92121–3752 U.S.A.; Sali, A. B. *J. Mol. Biol.* 1993, 234, 779–815) are widely utilized. The process of generating a structure as described is known as homology modeling or comparative molecular modeling. Generically, the process includes overall protein sequence alignment, determination of structurally conserved regions (SCR's), transposition of the template structure onto the undetermined sequence, loop building and refinement. As an example of how the MarR structure can be used for this purpose, a three-dimensional model of SlyA was generated as described in the appended examples.

Design of MarR Family Modulating Compounds Using Rational Drug Design Techniques The term "MarR family modulating compound" includes small molecules and other chemical entities which are capable of modulating, e.g., increasing or decreasing or otherwise altering the activity of a MarR family polypeptide or its down stream products, e.g., a MarR modulating compound may modulate the binding of MarR to DNA (e.g., the marO operon) or otherwise alter the expression of MarA. In one embodiment, the MarR family modulating compound is a MarR activator that enhances the binding of MarR to DNA (e.g., the marO operon), such that MarA expression is reduced.

The term "MarR family modulating compound candidate" includes compounds which are being screened or otherwise tested (e.g., computationally or in the laboratory) to determine whether or not they modulate MarR or a MarR family polypeptide.

The term "rational drug design" includes both computer aided and non-computer techniques where a protein is analyzed for active sites, and then modulating compound candidates are designed to interact with the particular spatial and electrochemical requirements of the particular site.

The term "active site" includes regions of a protein where a MarR family modulating compound physically interacts with a MarR family polypeptide. Any portion of the surface of a MarR family polypeptide can be considered an active site region or locus. In one embodiment, the portion of the MarR family protein immediately adjacent to the binding site of a MarR family modulating compound (e.g., a salicylate moiety) is referred to as the active site for the MarR family polypeptide. Other active sites include the DNA binding regions and regions necessary for interactions with other biological components, e.g., DNA or protein.

The term "interacts" includes interactions between the MarR family polypeptide and the MarR family modulating compound which result in modulation of a MarR family associated activity, e.g., expression of MarA when the MarR family polypeptide is MarR. The term also includes interactions which are determined by the shape and electronic complementarity between the MarR family polypeptide and the MarR family modulating compound. The term "interact" includes detectable interactions between molecules. The term interact is also meant to include "binding" interactions between molecules. Exemplary interactions include protein-protein and protein-nucleic acid interactions.

Specific knowledge of the three-dimensional shape and electronic properties of the MarR family polypeptide's active site provides information on how a MarR family modulating compound candidate may be modified to optimize interactions with a MarR family polypeptide. Several computer programs may be used to graphically depict the shape and electronic properties of the active site. These include, but are not restricted to CoMFA, (See Podlogar, B. L.; et al. *Drug Des. Discov.* 2000, 17, 4–12. and references therein), GRID (See GRID: Molecular Discovery Ltd., 4 Chandos St., London, W1A 3AQ, Goodford, P. J. et al. *J. Med. Chem.* 1985, 28, 849–857), and LIG BUILDER (See LIGBUILDER: Wang, R. et al. *J. Mol. Model.* 2000, 6, 498–516).

In these approaches, the active site is postulated and then placed within a three-dimensional lattice of evenly distributed grid points. A small molecular fragment or atom is placed on each lattice point, and a mathematical evaluation is made to determine the electronic and spatial properties at that point. After each lattice point within the active site is thus defined, the spatial and electronic "values" are contoured to generate maps or graphical representations that indicate the locations within the active site that are capable of accommodating additional "atomic bulk" and whether the atomic bulk should be charge positive, negative or neutral. It is the general theory that "filling" the active site with appropriate "atomic bulk" will optimize the drug-target interaction, thereby producing the maximal pharmacological response.

For example, the program LigBuilder was used to characterize one of the MarR active sites (SAL-A) in terms of its spatial and electronic properties. The results from this program represent a collection of colored crosses that depict an "inverse cast" of the MarR active site. Each cross represents a point where a mathematical determination was made. The shape of the inverse cast is dependent upon the van der Waals radii of the target's atoms constituting the active site as defined by the crystal structure of MarR. The colors indicate where the active site prefers positive or negative charge complemetarity. For example, arginine # 86 of MarR is positively charged at physiologic pH. Consequently, atoms or atom fragments that are negatively charged would produce the optimal complimentarily about that point, which is correctly depicted by the LigBuilder program.

Once the active site has been graphically defined, the spatial and electronic representations of a MarR family modulating compound candidate can be fit or docked within the target active site. Specific modifications of an initial candidate can be made electronically, and then tested to determine whether the complementarity between the active site and the modulating compound candidate has been increased.

To demonstrate the use of the crystal structure for docking, the coordinates of the salicylate (a MarR modulator, which, in one embodiment, can be cocrystalized with MarR) were artificially removed from the MarR active site. Using this newly created empty active site as input, the program FLEXX is able to predict the proper binding orientation of salicylate with MarR (FLEXX Module, in SYBYL. Tripos, Inc. 1699 Hanley Rd. St. Louis, Mo. 63144. Rarey, M. et al. *J. Mol. Bio.* 1996, 261, 470–489). The result of this docking experiment is shown in green, which can be compared to the original salicylate orientation as determined crystallographically. As shown, the dominant molecular interactions between the cocrystalized salicylate molecule and the active site residues are predicted by the docking algorithm, e.g. the carboxylate and hydroxyl groups. The greatest variation between the computationally predicted docking and that determined by experiment occurs at the 4- and 5-positions of the aromatic ring. These correspond to the regions of the cocrystalized salicylate molecule with the largest crystallographic b-factors, and indicate that the carboxylate and hydroxyl groups of the salicylate moiety create the primary interactions within the active site. These two major interactions create a hinge point where the aromatic ring pivots within the active site.

As used in a drug discovery program, small modifications of the salicylate molecule can be made computationally, and then subjected to the identical FLEXX docking as demonstrated above for salicylate. The score of the modified salicylate can be compared to the original to ascertain the modification's benefit to overall target site complimentarily. This is a time consuming process, and is typically utilized only as part of the lead optimization process in an active drug discovery program. A variant of this approach is the automated application to large virtual libraries of potential drug candidates, known as automated ligand docking (Muegge, I.; Rarey, M. Small Molecule Docking and Scoring. *Reviews in Computational Chemistry*; Wiley: New York, 2000). This approach is typically employed as a part of the lead identification or screening process of a drug discovery program, since a large number of modulating compound candidates can quickly be assessed for active site complimentarily. Programs available include, but are not restricted to DOCK (DOCK Suite of Programs: Reagents of the University of California: DesJarlais et al. *J. Med. Chem.* 1988, 31, 722–729), AUTO_DOCK (AUTO_DOCK: Olson, A. J., SCRIPPS, La Jolla, Calif. Goodsell, D. S., et al. *J. Mol. Recognit.* 1996, 9), GLIDE, and FLEXX (FLEXX Module, SYBYL. Tripos, Inc.; Rarey, M. et al. *J. Mol. Bio.* 1996, 261, 470–489). Each requires an electronic representation of a library of potential drug candidates. Early versions of these approaches treated the drug candidate as a rigid body, wherein conformational flexibility was neglected. Algorithmic improvements and increases in computational speed now allow the flexibility of a potential candidate to be included. Based on the relative values of these scores, a virtual library of structures can be quickly screened for members that would produce the best interaction within the active site. As such, large libraries, originating from commercial vendors, from proprietary template enumeration or other sources, can be culled to eliminate compounds that are not promising (data reduction) and/or prioritized to highlight compounds warranting further consideration. Compounds with better overall docking scores will be placed higher on the list.

Each of the techniques described above are included as rational drug design methods. Other rational drug design techniques include de novo drug design which utilizes the structure of the protein to generate molecules to dock within the active site. In this approach, a "seed" atom, or seed-molecule with pre-defined attachment points is placed within the active site. Programs are available to systematically "grow" chemical modifications at the attachment points resulting in novel molecules. Through an iterative process of growing and assessing the complimentarily of the new structures, productive attachments can be saved, while unproductive attachments are discarded. Subsequent redefinition of the seed based on productive attachments can produce large number of drug candidates for the specified target. This is an unbiased approach since the resulting compound is not taken from a pre-existing virtual library, and is often used to generate compounds that would otherwise not be considered based on current proprietary knowledge or chemist's intuition. For example, this approach was applied to one of the MarR active sites using the program LigBuilder to produce a list of novel potential drug candidates. The compounds generated by LigBuilder are merely representative of one class of compounds which may be useful as MarR family protein modulating compounds. The invention also pertains to other compounds which may interact with other portions and thus have little or no structural similarity to these compounds.

Rational drug design also may involve the identification of pharmacophoric elements. In drug design, important functional groups are referred to as pharmacophoric elements and are useful for productive drug-target interaction. For example, for MarR salicylate site A (SAL-A), certain interactions between the salicylate moiety and the MarR active site may be attributable to the two main functional groups of the salicylate moiety, namely the carboxylate and the hydroxyl groups. At this site, the carboxylate creates a charge-charge interaction with arginine #86, and the hydroxyl group interacts strongly with threonine #72 by virtue of hydrogen bonding. Furthermore, the absence of either of these elements may diminish the degree of complemintarity. The collection of pharmacophoric elements and their mutual spatial disposition within the active site defines the pharmacophore of the active site (See, e.g., WO 97/27219). In one embodiment, a MarR family modulating compound of the invention interacts with an amino acid corresponding (e.g., linearly or three dimensionally) to arginine at position #86 of SEQ ID NO:1 and/or threonine at position #72 SEQ ID NO:1.

For MarR, the carboxylate and hydroxyl groups of an inhibitor are separated by a distance of about 1.5 Å. As such, any compound with a similar functional groups thus positioned will possess the pharmacophore for MarR. Such information can be deduced from a known collection of compounds that demonstrate interaction with MarR. However, the crystal structure of MarR and its active site can be used to define a series of testable pharmacophore hypothesis. Programs, such as CoMFA, GRID and LigBuilder are instrumental in defining these hypotheses in a manner similar to that detailed by Clackson. In one embodiment, a MarR family modulating compound of the invention comprises a carboxylate and a hydroxyl group separated by a distance of 1.5 Angstroms.

In one embodiment, a known drug candidate is co-crystallized in the active site (e.g., salicylate, plumbagin, or DNP for MarR), since the exact coordinates of the pharmacophore can be determined. In another embodiment, the MarR family member is crystalized without a cocrystalizing agent. In another embodiment, the crystal structures of the MarR family member in the presence and absence of the co-crystallizing agent are compared to determine the effect of binding of the cocrystalizing agent. Thus, with or without a co-crystallizing compound, the pharmacophore can be used as a search query to identify structures from virtual libraries of commercial (known) or hypothetical structures. Programs including, but not restricted to UNITY (UNITY Module, in SYBYL. Tripos, Inc. 1699 Hanley Rd. St. Louis, Mo. 63144), CATALYST (CATALYST, Accelrys, Inc. 9685 Scranton Road San Diego, Calif. 92121–3752 U.S.A. Sprague, P. W. *Comput.-Assisted Lead Find Optim., [Eur. Symp. Quant. Struct.-Act. Relat.]* 1997, 225–240) may be used for this purpose (Greer, J. et al. *J. Med. Chem.* 1994, 37, 1035–1054; WO 99/45389). The pharmacophore elements can also be used as the seeds for de novo design. LigBuilder was applied to the active site of MarR using the carboxylate and hydroxyl groups as "seed" groups to approximate the pharmacophore hypothesis. Common among these structures are the actual elements of the pharmacophore as expected, but in nearly all of the structures examined, another hydrogen bond acceptor was present, indicating the possibility of yet another pharmacophoric element in the pharmacophore.

In another embodiment, the invention pertains to a method for identifying a MarR family modulating compound using the three-dimensional structure of a MarR family polypeptide. The method includes selecting a candidate MarR family modulating compound by performing rational drug design with the set of atomic coordinates in FIG. 1 and/or FIG. 2 using computer aided techniques, as described herein. In one embodiment, the method also includes contacting the candidate MarR family modulating compound with a MarR family peptide, and a nucleic acid molecule, and then measuring the binding affinity of the MarR family polypeptide peptide with the nucleic acid molecule, such that MarR family modulating compounds are identified. In one embodiment, the nucleic acid molecule is a nucleic acid molecule to which a particular MarR family member is known to bind. For example, for MarR, the nucleic acid used for the binding acid may be, for example, marO.

In a further embodiment, the MarR family modulating compound is a MarR activator that acts, e.g., to inhibit the expression of MarA.

The invention also pertains to a method of identifying a MarR family member modulating compound. The method includes obtaining a set of atomic coordinates defining the three-dimensional structure of MarR or a MarR family polypeptide; selecting a candidate MarR family modulating compound by performing rational drug design with said three dimensional structure of the MarR family polypeptide; contacting said candidate MarR family modulating compound with MarR family polypeptide; and measuring the ability of the candidate MarR family modulating compound to modulate the activity of the MarR family polypeptide, thus identifying a MarR modulating compound.

In one embodiment, the rational drug design is aided by a computer program described supra. In one embodiment, the MarR family polypeptide is MarR and has the polypeptide sequence given in SEQ ID NO. 1 and has the atomic coordinates given in FIG. 1, when cocrystallized with salicylate or FIG. 2, when crystallized without.

In another embodiment, the invention pertains to compounds generated by the methods of the invention, described above. For example, the invention pertains to the MarR family modulating compounds and MarR modulating compounds generated by the rational drug design techniques described above. Examples of MarR modulating compounds include those of the formula(I):

X-Y-Z         (I)

wherein
   X is an interacting moiety;
   Y is a hydrophobic moiety; and
   Z is a polar moiety.

The term "interacting moiety" includes moieties which are capable of interacting with a MarR family member. Preferably, such interacting moieties interact with Thr 72 of SEQ ID. 1 or an amino acid molecule that corresponds to Thr 72 in a MarR family polypeptide. In a further embodiment, the interacting moiety is capable of interacting by hydrogen bonding. Examples of interacting moieties include, but are not limited to, hydroxyl, thiol, sulfanyl, sulfonyl, amino, carbonyl, alkyl, and acyl moieties. The term "interacting moiety" includes moieties which allow the MarR modulating compound to perform its intended function, e.g., modulate MarR family member activity. In a further embodiment, the interacting moiety is hydroxy, thiol, or amino.

The term "hydrophobic moiety" includes moieties which are capable of interacting with the MarR family polypeptide such that the compound is capable of performing its intended function, e.g., modulate MarR. In certain embodiments, the hydrophobic moiety may be substituted with substituents capable of hydrogen bonding such as, but not limited to, hydroxy, thiol, carbonyl, amino, carboxylate, or thiol. Examples of hydrophobic moieties include, but are not limited to, substituted and unsubstituted alkyl, alkenyl, alkynyl, and aryl moieties.

In certain embodiments, the hydrophobic moiety is aryl. The aryl moiety may be cyclic, bicyclic or tricyclic. Preferably, the hydrophobic moiety is selected such that it is capable of interacting with MarR, such that its activity is modulated. In a further embodiment, the MarR family modulating compound is selected such that it is capable of interacting with hydrophobic or neutral amino acid residues, such as, but not limited to, Pro 57 or Met 74 or an amino acid residue corresponding to these amino acids of SEQ ID NO:1.

The term "polar moiety" includes moieties which are capable of interacting with MarR family polypeptide such that the activity of the MarR family polypeptide is modulated. In one embodiment, the polar moiety interacts with Arg 86 or Arg 77 or an amino acid residue corresponding to these amino acids of SEQ ID NO:1. In one embodiment, polar moiety is negatively charged. Examples of polar moieties include carboxylate and isoteres thereof. Other examples include, but are not limited to, phosphate, phosphite, sulfate, sulfite, nitrate, nitrite, nitro, hydroxy, oxalate, and perchlororate.

In one embodiment, the MarR family modulating compound is a MarR inhibitor. In another embodiment, the polar moiety and the interacting moiety are separated by a distance of about 1.5 Angstroms.

In a further embodiment, the MarR modulating compound is of the formula:

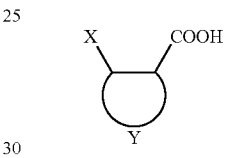

wherein Y is a substituted or unsubstituted cyclic or bicyclic moiety, and pharmaceutically acceptable salts and esters thereof. In a further embodiment, X is hydroxyl. In another further embodiment, Y is monocyclic or bicyclic, optionally substituted with a hydrophilic substituent. Examples of MarR modulating compounds include those listed below.

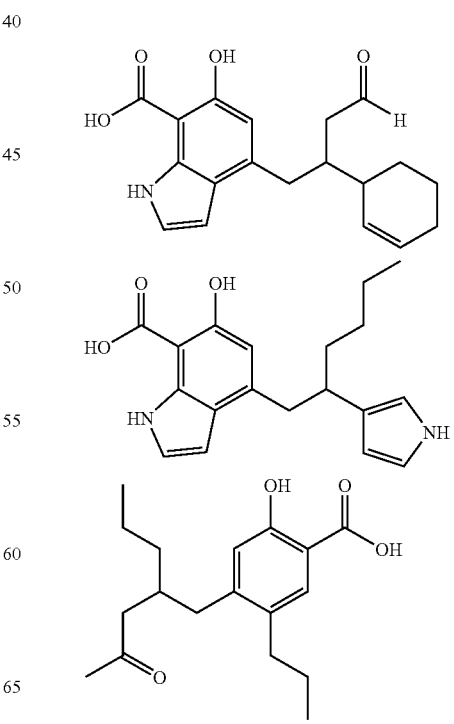

-continued
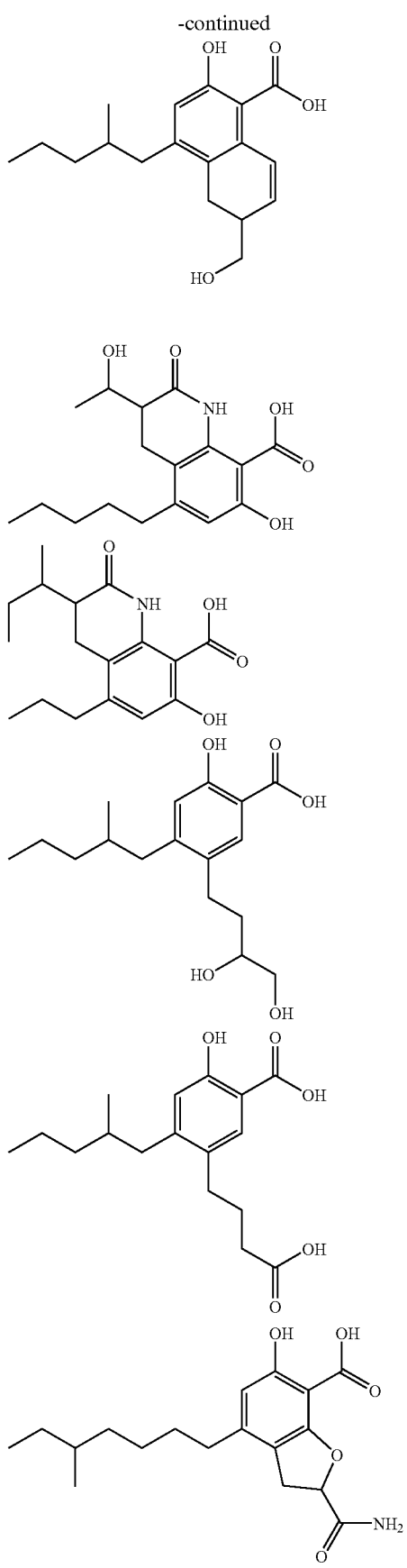
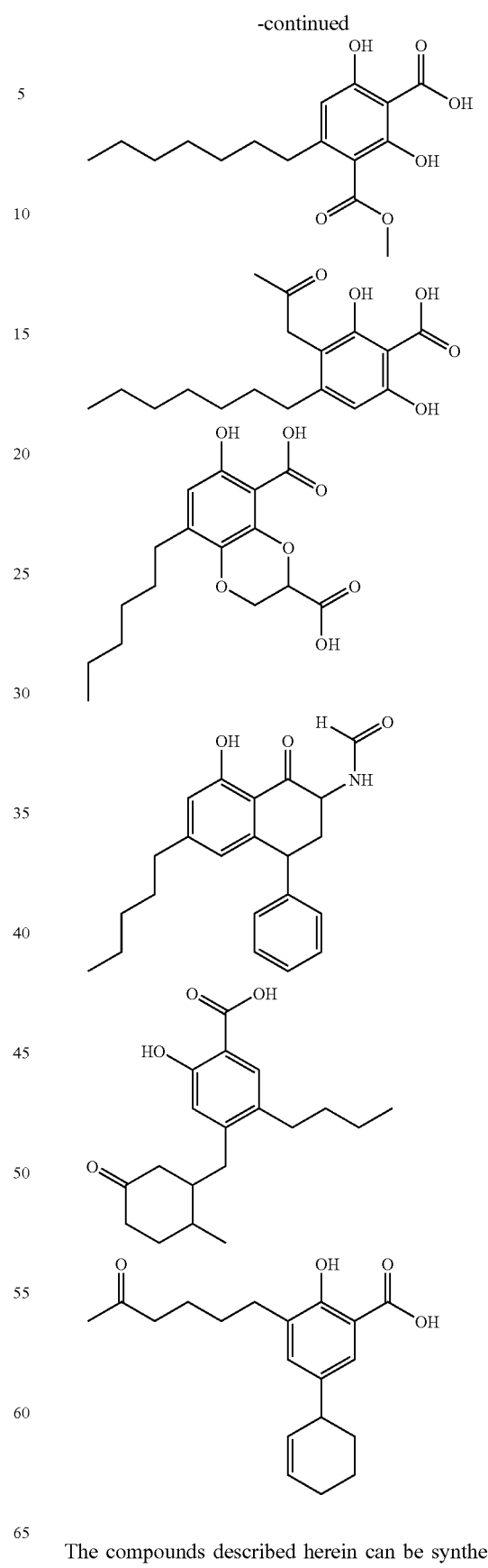
The compounds described herein can be synthesized by methods known in the art. An ordinarily skilled artisan will be able to consult the chemical literature and will be able to synthesize the compounds described herein.

The term "alkenyl" includes unsaturated aliphatic groups, including straight-chain alkenyl groups, branched-chain alkenyl groups, cycloalkenyl (alicyclic) groups, alkenyl substituted cycloalkyl or cycloalkenyl groups, and cycloalkenyl substituted alkyl or alkenyl groups. The term alkenyl further includes alkenyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkenyl group has 10 or fewer carbon atoms in its backbone (e.g., $C_1$–$C_{10}$ for straight chain, $C_3$–$C_{10}$ for branched chain), and more preferably 6 or fewer. Likewise, preferred cycloalkenyl groups have from 4–7 carbon atoms in their ring structure, and more preferably have 5 or 6 carbons in the ring structure, e.g., cyclopentene or cyclohexene.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 10 or fewer carbon atoms in its backbone (e.g., $C_1$–$C_{10}$ for straight chain, $C_3$–$C_{10}$ for branched chain), and more preferably 6 or fewer. Likewise, preferred cycloalkyls have from 4–7 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively. Examples of substituents of alkynyl groups include, for example alkyl, alkenyl (e.g., cycloalkenyl, e.g., cyclohenxenyl), and aryl groups.

Unless the number of carbons is otherwise specified, "lower alkyl" includes an alkyl group, as defined above, but having from one to three carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl" or "polycyclic radical" refer to two or more cyclic rings (e.g., cycloalkyls, cycloalkenyls, aryls and/or heterocyclyls) in which two or more carbons are common to two adjoining rings, e.g:, the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "alkylsulfinyl" include groups which have one or more sulfinyl (SO) linkages, typically 1 to about 5 or 6 sulfinyl linkages. Advantageous alkylsulfinyl groups include groups having 1 to about 12 carbon atoms, preferably from 1 to about 6 carbon atoms.

The term "alkylsulfonyl" includes groups which have one or more sulfonyl ($SO_2$) linkages, typically 1 to about 5 or 6 sulfonyl linkages. Advantageous alkylsulfonyl groups include groups having 1 to about 12 carbon atoms, preferably from 1 to about 6 carbon atoms.

The term "alkanoyl" includes groups having 1 to about 4 or 5 carbonyl groups. The term "aroyl" includes aryl groups, such as phenyl and other carbocyclic aryls, which have carbonyl substituents. The term "alkaroyl" includes aryl groups with alkylcarbonyl substituents, e.g., phenylacetyl.

The invention also includes a method for inhibiting expression of MarA. The method includes contacting MarR with a MarR inhibiting compound. In an embodiment, the MarR inhibiting compound is of the formula(I):

X-Y-Z   (I)

wherein X is an interacting moiety, Y is a hydrophobic moiety; and Z is a polar moiety, and acceptable salts thereof. In an embodiment, the MarR inhibiting compound inhibits the binding of MarR to DNA (e.g., the marO operon).

Figure 10:
FIG. 10 is a computer model of MarR interacting with DNA.

Biological systems generally function through carefully choreographed interactions of their respective components. The operative mechanisms for many disease states implicate protein-protein interactions as key. For transcription factors, such as MarR, protein-DNA and protein-RNA interactions control the regulation events for the biological system. The drug design approaches discussed above are targeted in part to disrupt the interaction between MarR and the mar operon. Knowledge of the three dimensional structure of the MarR-marO complex can provide clues as to the key interactions (pharmacophore) made between them. A computer model of an interaction between MarR and DNA is shown in FIG. 10.

The invention also pertains to a method for decreasing multidrug resistance in a microbe, e.g., $E.\ coli$. The invention includes contacting $E.\ coli$ with a MarR inhibiting compound, such that said multidrug resistance in $E.\ coli$ is decreased. In an embodiment, the MarR inhibiting compound is of the formula(I):

X-Y-Z   (I)

wherein X is an interacting moiety; Y is a hydrophobic moiety; and Z is a polar moiety, and acceptable salts thereof.

The invention also pertains to methods for modulating activity of a MarR family polypeptide. The method includes contacting a MarR family polypeptide with a MarR family modulating compound identified by any method described herein (e.g., the computer modeling techniques, etc.). The invention also pertains to any compound discovered using techniques described herein.

The invention is further illustrated by the following examples, which should not be construed as further limiting. The contents of all references, pending patent applications and published patents, cited throughout this application are hereby expressly incorporated by reference.

EXEMPLIFICATION OF THE INVENTION

Example 1: Crystallization of MarR with Salicylate

Protein Production and Purification

Native and selenomethionine (Se-Met) containing MarR was prepared from $E.\ coli$ BL21(DE3) (Novagen) bearing pMarR-WT, a wild type MarR expression vector that has been previously described (Alekshun, M. N. & Levy, S. B. $J.\ Bact.$ 181, 4669–4672 (1999)). Native MarR was produced in whole cells according to previous methods (Alekshun, M. N. & Levy, S. B. $J.\ Bact.$ 181, 4669–4672 (1999)). Se-Met MarR was produced by diluting an overnight culture of $E.\ coli$ BL21(DE3)+pMarR-WT 1:1000 in M9 medium supplemented with 2 mM $MgSO_4$, 0.2% glucose, 0.1 mM $CaCl_2$, 0.00005% thiamine, 0.04 mg ml$^{-1}$ each of the following amino acids phenylalanine, leucine, isoleucine, valine, serine, threonine, tyrosine, histidine, lysine, aspartic acid, glutamic acid, tryptophan, and tryptophan, and kanamycin (Miller, J. H. In $Experiments\ in\ Molecular\ Genetics$. (Cold Spring Harbor Laboratories, Cold Spring Harbor, N.Y.; 1972). This culture was grown at 37° C. to an OD600≈0.6 and 100 mg each of amino acids threonine, lysine-hydrochloride, phenylalanine, 50 mg each of amino acids leucine, isoleucine, and valine (single letter abbreviations), and 60 mg L-(+)-selenomethionine (Sigma) were then added. The culture was grown for 15 min at 37° C.; IPTG was subsequently added to a final concentration of 1 mM and protein production was allowed to proceed for 14.5 hr at 37° C. Cell pellets were collected and processed as previously described (Alekshun, M. N. & Levy, S. B. $J.\ Bact.$ 181, 4669–4672 (1999)).

Frozen cell pellets containing native or Se-Met MarR were resuspended in 100 mM sodium phosphate buffer (pH 7.4) containing a bacterial protease inhibitor cocktail (Sigma) and sonicated on ice. All buffers contained 2 mM DTT when Se-Met MarR was prepared. Insoluble matter was removed by centrifugation at 4° C. at 30,000×g for 40 min. The supernatant was passed over prepacked 5 ml SP-sepharose HiTrap columns (Amersham Pharmacia Biotech) previously equilibrated with 10 mM sodium phosphate buffer (pH 7.4). The column was washed with 50 ml of 10 mM sodium phosphate buffer (pH 7.4) and the pure proteins were eluted with a linear gradient (0–0.5 M) of NaCl in 10 mM sodium phosphate buffer (pH 7.4). Protein containing fractions were dialyzed vs. 10 mM HEPES (pH 7.4), 200 mM NaCl, and 1 mM DTT, or 2 mM DTT in the case of Se-Met MarR, and the protein in these samples was judged to be greater than 99% pure via SDS-PAGE and electrospray ionization mass spectrophotometry. The latter also demonstrated that more than 95% of the three methionine residues in Se-Met MarR were substituted with selenomethionine.

Crystallization:

MarR crystals were originally grown in 18% PEG MME 5000, 200 mM ammonium sulfate, 100 mM citrate buffer (pH 5.6) but showed anisotropic disorder in the diffraction data that made them unsuitable for structure determination. To stabilize the protein, the citrate was substituted by the known inhibitor salicylate. Crystals of the MarR-salicylate complex were grown at 17° C. by hanging droplet vapor diffusion. 6 μl of a 11.4 mg ml$^{-1}$ protein solution in 200 mM NaCl, 20 mM HEPES (pH 7.4), and 10 mM DTT were added to 2 μl of reservoir buffer (18% PEG MME 5000, 50 mM ammonium sulfate, 250 mM sodium salicylate, 10 mM DTT, and 15% glycerol, pH 5.5), and 0.8 μl 15% heptanetriol. The droplets were equilibrated with 1 ml of reservoir buffer. Crystals grew within 1 week reaching dimensions of approximately 0.3 mm per side.

X-ray Data Collection, Structure Determination, and Refinement:

Diffraction data were collected at the Brookhaven National Synchrotron Light Source, beamline X8C. Crystals were flash frozen in mother liquor at the beam line before data collection. All data were processed and reduced using DENZO and SCALEPACK (Otwinowski, Z. In $CCP4\ Proceedings$. 56–62 (Daresbury Laboratory, Warrington, UK, 1993). The space group of the MarR-salicylate co-crystals was determined to be I4$_1$22 with one molecule in the asymmetric unit and with unit cell dimensions of a=b=62.0 Å, c=132.9 Å, α=β=γ=90° for both the native and the selenoprotein. Data were collected on the selenoprotein crystals at three wavelengths to enable MAD phasing. Phases were determined from the MAD data using the program SOLVE (Terwilliger, T. C. & Berendzen, J. $Acta\ Crystallogr.\ D.$ 55, 849–861 (1999)). This showed two selenium sites per asymmetric unit, with the third selenomethionine, at the N-terminus, apparently disordered. Maps were solvent-flattened using the program DM and the model was built into density using the program O (Collaborative Computational Project, Number 4. *Acta Crystallogr. D.* 50, 760–763 (1994); Jones, T. A. et al. *Acta Crystallogr. A* 47, 110–119 (1991)). Model and refinement parameters for salicylate were obtained from the Hetero Compound Information Center (Kleywegt, G. J. & Jones, T. A. *Acta Crystallogr. D.* 54, 1119–1131 (1998)). Model refinement was performed using CNS and cycles of rebuilding and refinement continued to give the final model (Brunger, A. T. et al. *Acta Crystallogr. D.* 54, 905–921 (1998)). Model quality was assessed by sa-omit, Fo-Fc, maps generated over the whole molecule omitting no more than 7% of the structure at a time. The model extends from residue 6 to the C-terminus at residue 144. In common with several other transcription factors (e.g. TetR, (1A6I), ArgR (1B4B) and TreR (1BYK)), MarR shows relatively high thermal mobility throughout the structure, as reflected by the B-factors. Certain regions appear to be particularly mobile, including the extended structure at the N-terminus, the tip of the "wing" (residues 91–94), parts of the α5 helix, especially around Gly 116 and the connecting loop (128–131) between the α5 and the C-terminal α6 helix. Consistent with the high B-factors, the molecule shows few well-ordered solvent molecules. PROCHECK reports overall g-factors of 0.25 (dihedrals) and 0.55 (main chain covalent forces) and shows that 91% of the residues fall within the most favored region of the Ramachandran plot, with only residue Ala 53 in a disallowed region. This residue is located at the start of the loop connecting the α2 and α3 helices.

The coordinates of the MarR-salicylate cocrystal are shown in FIG. 1. Data collection, phasing and refinement statistics for the MarR-sal cocrystal structure is shown in Table 1.

TABLE 1

| Data set | Native | Se-met edge | e-met peak | e-met remote |
|---|---|---|---|---|
| Wavelength (Å) | 1.072 | 0.9795 | 0.9793 | 0.9500 |
| Resolution range (Å) | 50–2.3 | 50–2.3 | 50–2.3 | 50–2.3 |
| Measured reflections | 56,495 | 84,173 | 96,582 | 87,365 |
| Unique reflections | 6,069 | 5,534 | 5,564 | 5,472 |
| Completeness (%) overall (final shell) | 99.5(100) | 91.3(99.8) | 91.7(99.8) | 90.4(99.7) |
| <I/σI> (final shell) | 21.1(12.0) | 12.2(7.2) | 12.0(7.0) | 12.9(7.9) |
| $R_{merge}$ (%) (final shell) | 6.0(20.0) | 6.4(29.7) | 5.7(30.3) | 4.9(25.5) |
| Rano (%) | | 4.9 | 5.0 | 3.5 |
| Overall FOM (centric/acentric) | 0.59/0.71 | | | |
| Resolution | 50–2.3 | | | |
| Rfree | 28.7% | | | |
| Rcryst | 24.7% | | | |
| Atoms/AU | | | | |
| Protein | 1078 | | | |
| Salicylate | 20 | | | |
| Water | 18 | | | |
| Average B (Å$^2$) | | | | |
| main chain | 49.7 | | | |
| side chain | 59.2 | | | |
| salicylate | 42.7 | | | |
| water | 50.0 | | | |
| R.m.s. deviation | | | | |
| Bonds (Å) | 0.009 | | | |
| Angles (°) | 1.3 | | | |

Example 2: Crystallization of MarR

MarR was produced and purified as described in Example 1.

Crystallization:

Crystals of MarR were grown by hanging droplet vapor diffusion. 3 µl of a 10 mg ml$^{-1}$ 2:1 (mol:mol) DNA-protein solution in 200 mM NaCl, 20 mM HEPES, pH 7.4, 20 mM TRIS-HCl, pH 8.0, and 2 mM MgCl$_2$ was added to 1 µl of reservoir buffer (23% PEG MME 5000, 100 mM sodium citrate, 200 mM ammonium sulfate, 10 mM DTT, 10% glycerol, 5% Isopropanol, pH 5.6), and 0.4 µl 15% heptanetriol. The droplets were equilibrated with 0.5 ml of reservoir buffer.

X-ray Data Collection, Structure Determination, and Refinement:

Diffraction data were collected at the Brookhaven National Synchrotron Light Source, beamline X8C. Crystals were flash frozen in mother liquor at the beam line before data collection. All data were processed and reduced using DENZO and SCALEPACK (Otwinowski, Z. In *CCP4 Proceedings*. 56–62 (Daresbury Laboratory, Warrington, UK, 1993).

The coordinates of the MarR crystal without salicylate are shown in FIG. 2. Data collection, phasing, and refinement statistics for the MarR co-crystal structure is shown in Table 2.

TABLE 2

| | |
|---|---|
| Space group | C222 |
| Unit cell (Å) | a = 65.8, b = 137.7, c = 96.4 |
| Resolution | 50–2.7 |
| Rfree | 26.7% |
| Rcryst | 23.2% |
| Atoms/AU | |
| Protein | 2093 |
| Water | 14 |
| Average B (Å$^2$) | |
| main chain | 40.0 |
| side chain | 48.0 |
| Water | 32.6 |
| R.m.s. deviation | |
| Bonds (Å) | 0.009 |
| Angles (°) | 1.3 |

Example 3: Use of the Crystal Structure of MarR to Model Other MarR Family Polypeptides The amino acid sequences of MarR and SlyA are shown in FIG. 11. This alignment is generated automatically using the subroutines in COMPOSER, however it can be generated by a variety of other programs. FIG. 12 shows the results of the COMPOSER program in identifying the structurally conserved regions (SCRs).

The amino acids colored magenta are the regions of MarR and SlyA where the amino acid sequences are predicted to exhibit the same tertiary structure. These predictions are based on a knowledge base of information derived from the compilation of known crystal structures. Specifically, statistical correlations are made for protein tertiary structure with the respective amino acid sequences, and it was found that the correlations could be used in a predictive manner.

Figures 13A, 13B:
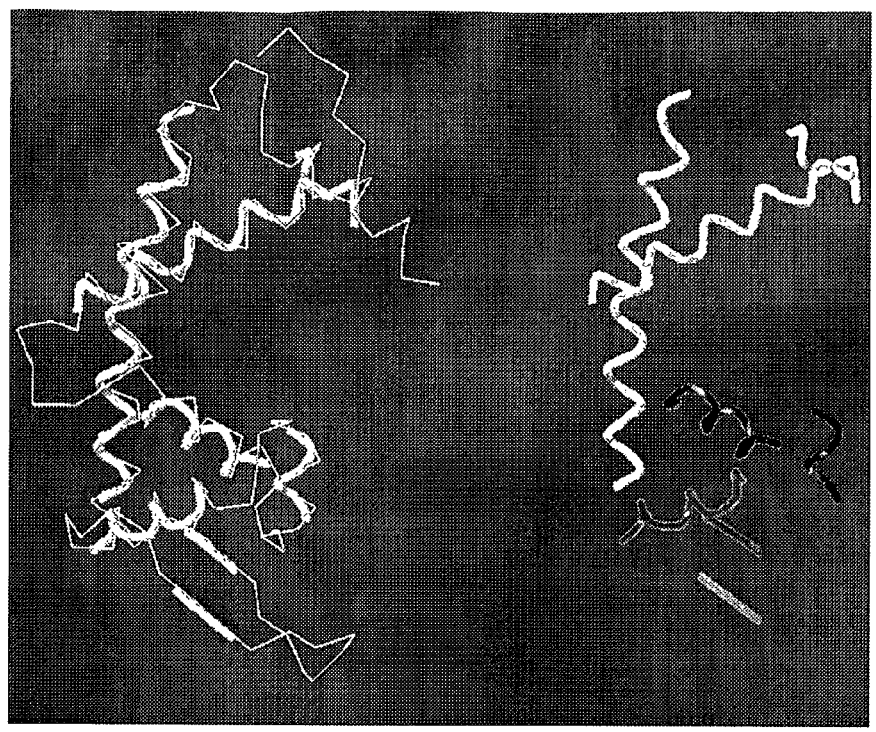
FIG. 13*a* represents the SCRs of MarR derived from the MarR crystal structure. The basic framework of SlyA is shown in FIG. 13*b*.

In the comparative molecular modeling process, the three-dimensional coordinates of the MarR backbone in the SCRs were directly transposed to create a general framework for SlyA as seen in FIGS. 13a and 13b. FIG. 13a is the C$_\alpha$-trace of MarR with the SCRs highlighted as orange tubes. The SCRs were "extracted" in their same mutual orientation to produce the basic framework of SlyA, which is shown in FIG. 13b. The process at this point generally includes only the backbone chain coordinates; the sidechains are added computationally to the SCR's on the left to create the SlyA protein. This model can, in all respects, be subjected to the identical regimen of computational protocols as the bona fide MarR crystal structure (Podlogar, B. L. et al. *J. Med. Chem.* 1997, 40, 3453–3455).

Figure 14:
FIG. 14 shows a $C_\alpha$-tube representations of MarR from the crystal structure and its homology with a model of SlyA.

The regions in yellow (FIG. 12) are the "loops" that connect the SCRs. Loop regions, in general, exhibit the greatest variation among members in the same family. As such, no logical template for their construction is available. Again, use is made of the vast knowledge contained in the database of determined protein structures to construct the loop regions. FIG. 14 shows the fully constructed SlyA structure (purple) in comparison to the template protein, MarR.

Example 4: Use of the Computer Modeling to Characterize the MarR Active Site

For example, the program LigBuilder was used to characterize the MarR active site in terms of its spatial and electronic properties. The results represent a collection of colored crosses that depict an "inverse cast" of the MarR active site. Each cross represents a point where a mathematical determination was made. The shape of the inverse cast is dependent upon the van der Waals radii of the target's atoms constituting the active site as defined by the crystal structure of MarR. The colors indicate where the active site prefers positive or negative charge complemetarity. For example, arginine # 86 of MarR is positively charged at physiologic pH. Consequently, atoms or atom fragments that are negatively charged would produce the optimal complimentarily about that point, which is correctly depicted by the LigBuilder program.

Once the active site has been graphically defined, the spatial and electronic representations of a MarR modulating compound candidate can be fit or docked within the target active site. Specific modifications of an initial candidate can be made electronically, and then tested to determine whether the complementarity between the active site and the modulating compound candidate has been increased. To demonstrate the use of the crystal structure for docking, the coordinates of the salicylate were artificially removed from the MarR active site. Using this newly created empty active site as input, the program FLEXX is able to predict the proper binding orientation of salicylate with MarR (FLEXX Module, in SYBYL. Tripos, Inc. 1699 Hanley Rd. St. Louis, Mo. 63144. Rarey, M. et al. *J. Mol. Bio.* 1996, 261, 470–489). The result of this docking experiment can be compared to the original salicylate orientation as determined crystallographically. The dominant molecular interactions between the salicylate and the active site residues may be predicted by the docking algorithm, e.g. the carboxylate and hydroxyl groups.

Example 5: Use of Rational Drug Design to Identify MarR Modulating Compounds

One method of rational drug design techniques includes de novo drug design which utilizes the structure of the protein to generate molecules to dock within the active site. In this approach, a "seed" atom, or seed-molecule with pre-defined attachment points is placed within the active site. Programs are available to systematically "grow" chemical modifications at the attachment points resulting in novel molecules. Through an iterative process of growing and assessing the complimentarily of the new structures, productive attachments can be saved, while unproductive attachments are discarded. Subsequent redefinition of the seed based on productive attachments can produce large number of drug candidates for the specified target. This is an unbiased approach since the result is not taken from a pre-existing virtual library, and is often used to generate compounds that would otherwise not be considered based on current proprietary knowledge or chemist's intuition.

This approach was applied to the MarR protein using the program LigBuilder to produce a list of novel potential drug candidates.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

All patents, patent applications, and literature references cited herein are hereby expressly incorporated by reference. The entire contents of Alekshun et al. "The Crystal Structure of MarR a Regulator of Multiple Antibiotic Resistance at 2.3 Å resolution," *Nature Structural Biology* 8(8) is hereby incorporated herein by reference.

The invention claimed is:

1. A MarR modulating compound of the formula:

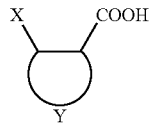

wherein

X is an interacting moiety;

wherein the interacting moiety is selected from the group consisting of hydroxyl, thiol, sulfanyl, sulfonyl, amino, carbonyl, alkyl, and acyl moieties Y is a substituted or unsubstituted indole and pharmaceutically acceptable salts and esters thereof; and wherein X and a carboxylate group of said formula are separated by a distance of about 1.5 Å.

2. The MarR modulating compound of claim 1, wherein said MarR modulating compound is

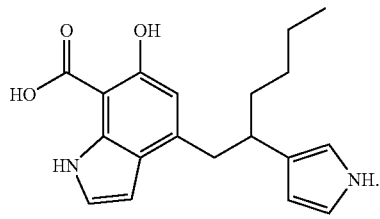

3. The MarR modulating compound of claim 1, wherein said compound is:

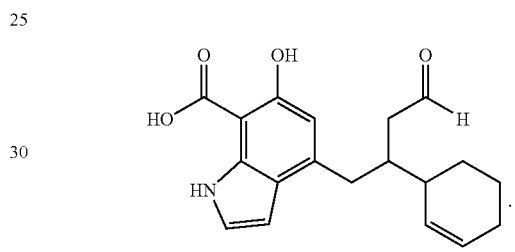

4. The MarR modulating compound of claim 1, wherein said interacting moiety is capable of hydrogen bonding.

5. The MarR modulating compound of claim 4, wherein said interacting moiety interacts with an amino acid, wherein the amino acid is Asn at position 72 of SEQ ID. 1.

6. The MarR modulating compound of claim 4, wherein said interacting moiety interacts with an amino acid, wherein the amino acid is Asn at position 70 of SEQ IID No. 1.

7. The MarR modulating compound of claim 1, wherein said MarR modulating compound is a MarR inhibitor.

* * * * *

UNITED STATES PATENT AND TRADEMARK OFFICE
CERTIFICATE OF CORRECTION

PATENT NO. : 7,075,582 B2
APPLICATION NO. : 10/196672
DATED : July 11, 2006
INVENTOR(S) : Alekshun et al.

It is certified that error appears in the above-identified patent and that said Letters Patent is hereby corrected as shown below:

On the Title page, and item 45

[*] Notice: Subject to any disclaimer, the term of this patent is extended or adjusted under 35 USC 154(b) by (328) days Delete the phrase "by 328" and insert -- by 236 days--

Signed and Sealed this

Sixteenth Day of January, 2007

JON W. DUDAS
*Director of the United States Patent and Trademark Office*

SEQUENCE LISTING

<160> NUMBER OF SEQ ID NOS: 1
<210> SEQ ID NO 1
<211> LENGTH: 125
<212> TYPE: PRT
<213> ORGANISM: Escherichia coli

<400> SEQUENCE: 1

Met Val Asn Gln Lys Lys Asp Arg Leu Leu Asn Glu Tyr Leu Ser Pro
 1               5                  10                  15

Leu Asp Ile Thr Ala Ala Gln Phe Lys Val Leu Cys Ser Ile Arg Cys
            20                  25                  30

```
Ala Ala Cys Ile Thr Pro Val Glu Leu Lys Lys Val Leu Ser Val Asp
        35              40                  45

Leu Gly Ala Leu Thr Arg Met Leu Asp Arg Leu Val Cys Lys Gly Trp
    50              55                  60

Val Glu Arg Leu Pro Asn Pro Asn Asp Lys Arg Gly Val Leu Val Lys
65              70                  75                      80

Leu Thr Thr Gly Gly Ala Ala Ile Cys Glu Gln Cys His Gln Leu Val
            85                  90                  95

Gly Gln Asp Leu His Gln Glu Leu Thr Lys Asn Leu Thr Ala Asp Glu
            100                 105                 110

Val Ala Thr Leu Glu Tyr Leu Leu Lys Lys Val Leu Pro
        115                 120                 125
```